(12) United States Patent
Miyoshi et al.

(10) Patent No.: US 6,187,809 B1
(45) Date of Patent: Feb. 13, 2001

(54) TRICYCLIC COMPOUNDS AND DRUG COMPOSITIONS CONTAINING THE SAME

(75) Inventors: Shiro Miyoshi, Sizuoka; Kohei Ogawa, Shizuoka, both of (JP)

(73) Assignee: Asahi Kasei Kogyo Kabushiki Kaisha, Osaka (JP)

( * ) Notice: Under 35 U.S.C. 154(b), the term of this patent shall be extended for 0 days.

(21) Appl. No.: 09/472,937

(22) Filed: Dec. 28, 1999

Related U.S. Application Data

(62) Division of application No. 09/101,232, filed as application No. PCT/JP96/03689 on Dec. 18, 1996, now Pat. No. 6,037,362.

(30) Foreign Application Priority Data

Jan. 10, 1996 (JP) ........................................... 8-2576

(51) Int. Cl.[7] ...................... A61K 31/343; A61K 31/381; C07D 307/91; C07D 333/76
(52) U.S. Cl. ............................ 514/443; 514/468; 548/48; 548/460
(58) Field of Search ..................... 549/48, 460; 514/443, 514/468

(56) References Cited

FOREIGN PATENT DOCUMENTS

| | | |
|---|---|---|
| 26 51 572 | 5/1982 | (DE) . |
| 0 023 385 | 2/1981 | (EP) . |
| 0 171 702 | 2/1986 | (EP) . |
| 0 455 006 | 11/1991 | (EP) . |
| 0 659 737 | 6/1995 | (EP) . |
| 52-89632 | 7/1977 | (JP) . |
| 53-111029 | 9/1978 | (JP) . |
| 54-73751 | 6/1979 | (JP) . |
| 55-53262 * | 4/1980 | (JP) . |
| 58-41860 * | 3/1983 | (JP) . |
| 61-63667 | 4/1986 | (JP) . |
| 8-165276 * | 6/1996 | (JP) . |
| 94/29290 * | 12/1994 | (WO) . |
| 95/29159 * | 11/1995 | (WO) . |

OTHER PUBLICATIONS

Takeshi Negoro et al., "Bromochlorination of Alkenes with Dichlorobromate (1-) Ion. V.", Bull. Chem. Soc., Japan, vol. 59, No. 11, 1996, pp. 3519–3522.

* cited by examiner

*Primary Examiner*—Fiona T. Powers
(74) *Attorney, Agent, or Firm*—Young & Thompson

(57) ABSTRACT

Compounds having a β-3 adrenaline receptor agonist and are useful as drugs for the treatment and prevention of diabetes, obesity, hyperlipemia, etc., represented by a general formula (I) and salts thereof, and a process for producing these, and their intermediates, wherein R represents hydrogen or methyl; $R^1$ represents hydrogen, halogen, hydroxy, benzyloxy, amino, or hydroxymethyl; $R^2$ represents hydrogen, hydroxymethyl, $NHR^3$, $SO_2NR^4R^4$, or nitro; $R^6$ represents hydrogen or lower alkyl; and X represents nitrogen, $R^9$ represents hydrogen, one of $R^7$ and $R^8$ represent hydrogen, and the other thereof represents hydrogen, amino, acetylamino, or hydroxy.

16 Claims, No Drawings

TRICYCLIC COMPOUNDS AND DRUG COMPOSITIONS CONTAINING THE SAME

CROSS-REFERENCE TO RELATED APPLICATIONS

This application is a division of application Ser. No. 09/101,232, filed Aug. 5, 1998, now U.S. Pat. No. 6,037,362 which was the 35 USC 371 national phase of International application PCT/JP96/03689 filed on Dec. 18, 1996, which designated the United States.

FIELD OF THE INVENTION

The present invention relates to novel tricyclic compounds and to drug compositions containing such tricyclic compounds.

BACKGROUND OF THE INVENTION

In the past, it was accepted that β-adrenaline receptors are classified into two groups β1 and β2, wherein the stimulation by β1 induces an increase in the cardiac rate and the stimulation by β2 brings about relaxation in the smooth muscle tissue and lowering of blood pressure. Arch et al discovered a compound which exhibits scarce activities to β1 and β2 but emphasizes lipolysis of fatty cells, wherefrom they have made clear the existence of a third receptor [Nature, 309, 163–165 (1984)]. Afterwards, the primary structure thereof was clarified [Emorine et al: Science, Vol. 245, 1118–1121 (1989)] and the receptor was named as β3.

Recently, it has been shown that compounds exhibiting a β3 activity are useful as a drug for preventive treatment of diabetes, obesity, hyperlipemia, digestive diseases and depression [int. J. Obesity 8 (suppl. 1), 93–102 (1984); Nature, 309, 163–165(1984); U.S. Pat. No. 5,120,766; Brit. J. Pharmacol., 103, 1351–1356 (1991); Eur. J. Pharmacol., 219, 193–201 (1992)].

Various compounds with correlation to β3 have been reported in the literatures, for example, a compound (BRL 37344) having the following molecular structure

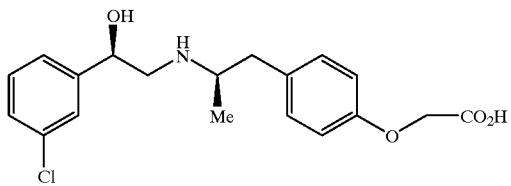

as disclosed in EP 023 385 and in Drugs of the Future. Vol. 16, 797–800 (1991); a compound (CL316, 243) having the following molecular structure

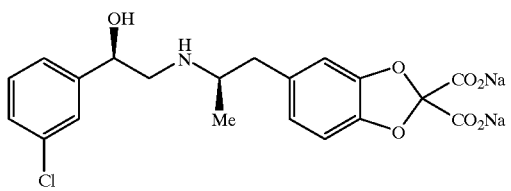

as disclosed in EP 0 455 006 and J. Med. Chem., Vol. 35, 3081–3084 (1992); a compound having the following molecular structure

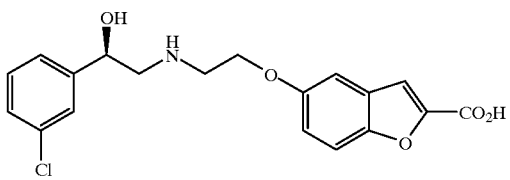

as disclosed in WO9429290; and a compound having the following molecular structure

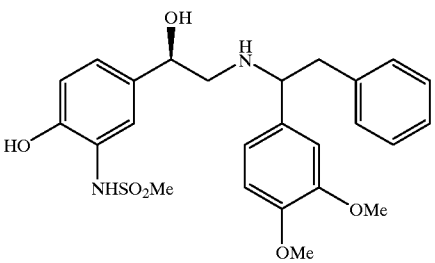

as disclosed in EP 0 659 737 in Example 1 thereof. All these compounds have molecular structures different clearly from that of the compound according to the present invention.

There was known a compound exhibiting a function for increasing the myocardial contraction strength and for antagonizing obesity represented by the following structural formula

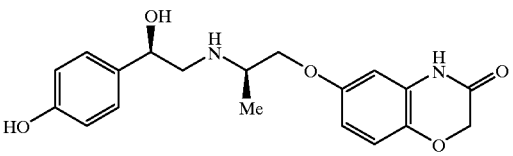

as disclosed in EP 171 702, which is distinguished from the compound according to the present invention in that it has a strong pharmacological activity onto the heart and has a molecular structure quite different from that of the compound according to the present invention.

Further, a compound exhibiting an α, β-blocking activity, namely, a function of lowering the blood pressure, represented by the following structural formula

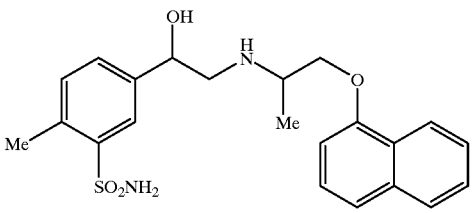

is disclosed in Japanese Patent Kokais Sho 55-53262 and Sho 58-41860 and a compound exhibiting a vasodilatoric function represented by the following structural formula

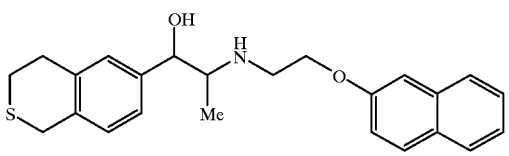

is disclosed in DE 2 651 572. They are different from the compound according to the present invention in the molecular structure and in function.

There is a demand for a novel and effective medicament or pharmacevtic composition which can be used for therapuetic treatment and preventive treatment of diseases correlating to β3, such as diabetes, obesity and hyperlipemia.

DISCLOSURE OF THE INVENTION

The inventors in sound research responding to the existing demand, by synthesizing various compounds and examining their functions reached the discovery that novel tricyclic compounds represented by the general formula (I) given below had β3-activities with functions for lowering blood sugar value and for lipolysis, which has led to the completion of the present invention.

Thus, the present invention consists in a compound represented by the general formula (I) or a salt thereof:

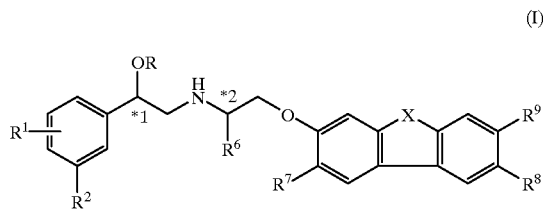

in which R represents hydrogen atom or methyl, $R^1$ stands for hydrogen atom, halogen atom, hydroxy, benzyloxy, amino or hydroxymethyl, $R^2$ stands for hydrogen atom, hydroxymethyl, $NHR^3$, $SO_2NR^4R^{4'}$ or nitro, herein $R^3$ is hydrogen atom, methyl, $SO_2R^5$, formyl or $CONHR^{6'}$, with $R^5$ being a lower alkyl, benzyl or $NR^4R^{4'}$ and $R^{6'}$ being hydrogen atom or lower alkyl, and $R^4$ and $R^{4'}$ may be identical with or different from each other and stand each for hydrogen atom, lower alkyl or benzyl, $R^6$ represents hydrogen atom or lower alkyl, X stands for a secondary nitrogen atom, oxygen atom, sulfur atom or methylene and, in case X is secondary nitrogen atom, oxygen atom or sulfur atom, $R^9$ stands for hydrogen atom and either one of $R^7$ and $R^8$ is hydrogen atom and the other one is hydrogen atom, amino, acetylamino or hydroxy, or, in case X is methylene, both $R^7$ and $R^8$ are hydrogen atom and $R^9$ stands for hydrogen atom, amino, acetylamino or hydroxy, *1 indicates an asymmetric carbon atom and *2 indicates that the carbon atom is asymmetric provided that $R^6$ is lower alkyl.

According to the present invention, there may be exemplified for the halogen atom fluorine atom, chlorine atom, bromine atom or iodine atom, among them, fluorine atom and chlorine atom are preferred. In the context of the present invention, "lower alkyl" means a straight or branched chain saturated hydrocarbon having 1–4 carbon atoms, such as methyl, ethyl, n-propyl, i-propyl, n-butyl, i-butyl, s-butyl and t-butyl.

In the formula (I), R may preferably be hydrogen atom, while R may favorably be also methyl for reason of providing more higher selectivity.

$R^1$ stands for hydrogen atom, halogen atom, hydroxy, benzyloxy, amino or hydroxymethyl. A preferred example of the compound represented by the general formula (I) is one in which $R^1$ denotes hydrogen atom. Also preferred example of the compound represented by the general formula (I) is one in which $R^1$ denotes amino or hydroxymethyl group. A further preferred example of the compound represented by the general formula (I) is one in which $R^1$ denotes halogen atom or hydroxyl or benzyloxy group.

$R^2$ stands for hydrogen atom, hydroxymethyl, $NHR^3$, $SO_2NR^4R^{4'}$ or nitro. A preferred example of the compound represented by the general formula (I) is one in which $R^2$ is hydrogen atom. Also preferred example of the compound represented by the general formula (I) is one in which $R^2$ is hydroxymethyl or nitro group. A further preferred example of the compound represented by the general formula (I) is one in which $R^2$ stands for $NHR^3$ or $SO_2NR^4R'$. $R^3$ in the group $NHR^3$ may be hydrogen atom, methyl, $SO_2R^5$, formyl or $CONHR^{6'}$, wherein preference is given especially to $NHR^3$ which is $NH_2$, NHNe, $NHSO_2R^5$ and $NHCONHR^{6'}$, among which $NHSO_2R^5$ is more preferable. In the group $NHSO_2R^5$, $R^5$ stands for lower alkyl, benzyl or $NR^4R^4$. $R^4$ and $R^{4'}$ may either be identical with or different from each other and may stand each for hydrogen atom, lower alkyl or benzyl, wherein either one of $R^4$ and $R^{4'}$ is preferably hydrogen.

Concrete examples of $NR^4R^{4'}$ include amino, methylamino, ethylamino, propylamino, benzylamino, dimethylamino, diethylamino, dipropylamino, methylethylamino, methylpropylamino and methylbenzylamino, among which preference is given to methylamino and dimethylamino. Therefore, preferred concrete examples of $NHSO_2R^5$ include $NHSO_2Me$, $NHSO_2Et$, $NHSO_2CH_2Ph$, $NHSO_2NH_2$, $NHSO_2NHMe$, $NHSO_2NHEt$, $NHSO_2NMe_2$, $NHSO_2NEt_2$, $NHSO_2NMeEt$ and $NHSO_2NMeCH_2Ph$. $R^{6'}$ in the group $NHCONHR^{6'}$ is hydrogen atom or lower alkyl. Concrete examples of $NHCONHR^{6'}$ include $NHCONH_2$, NHCONHMe, NHCONHEt and NHCONHPr. Concerning the group $SONR^4R^{4'}$ for the group $R^2$, the groups $R^4$ and $R^{4'}$ have the same meanings as given above and may either be identical with or different from each other and may stand each for hydrogen atom, lower alkyl or benzyl, wherein it is preferable that either one of $R^4$ and $R^{4'}$ is hydrogen atom. Therefore, concrete examples of the group $SO_2NR^4R^{4'}$ include $SO_2NH_2$, $SO_2NHMe$, $SO_2NHEt$, $SO_2NMe_2$, $SO_2NEt_2$, $SO_2NHCH_2Ph$ and $SO_2NMeCH_2Ph$.

$R^6$ represents hydrogen atom or lower alkyl. Preferred examples include hydrogen atom, methyl and ethyl. Here, preference is given to the case where it stands for hydrogen atom.

X stands for secondary nitrogen atom, oxygen atom, sulfur atom or methylene. A preferred example of the compound is one in which X is secondary nitrogen atom, namely, the tricyclic skeleton is constituted of carbazole group. Here, the groups $R^7$, $R^8$ and $R^9$ have the meanings as given previously.

The symbol *1 in the general formula (I) indicates an asymmetric carbon atom and, in case $R^6$ is lower alkyl, the symbol *2 also indicates an asymmetric carbon atom. In this case, the compound of the general formula (I) may be present in four isomers,namely, (R,R), (R,S), (S,S) and (S,R) represented by the sequence of (*1, *2). In case $R^6$ is hydrogen atom, two isomers are possible. The present invention encompasses not only each optically pure isomer, but also mixtures of two voluntarily selected isomer, of three voluntarily selected isomers and of all four isomers. From the point of view of development of the pharmacological activity, an asymmetric carbon atom (*1) in the ethanolamino chain may preferably have an absolute configuration (R). Concerning the asymmetric carbon atom (*1) for N-[5-[2-[2-(9H-carbazol-2-yloxy)ethylamino]-1-hydroxyethyl]-2-hydroxyphenyl]methanesulfonamide, especially preferred examples are R-hydroxy compounds.

For the compound according to the present invention, there are very favorable groups of combinations of the substituent groups. In the following, the symbols $R^6$, X, $R^7$, $R^8$, $R^9$, *1 and *2 for the general formula (1) have the meanings as defined above, so long as no special mention is made.

When $R^2$ in the general formula (I) for the compound according to the present invention represents hydroxymethyl, $NHR^3$, $SO_2NR^4R^{4'}$ or nitro, it is preferable that the group $R^1$ is in the 4- or 5-position, wherein preference is given to the case where $R^1$ is in 4-position. When $R^2$ is hydrogen atom, it is more preferable that $R^1$ is in the 2-position.

Preferred examples of the compound represented by the general formula (I) or the salt thereof according to the present invention are those in which the combination of the substituent groups in the general formula (I) is such that "R represents hydrogen atom, $R^1$ stands for hydrogen atom, a halogen atom, hydroxy, benzyloxy, amino or hydroxymethyl and $R^2$ stands for hydrogen atom, hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^4$ being lower alkyl, benzyl or $NR^4R^{4'}$ and $R^4$ and $R^{4'}$ may be identical with or different from each other and stand each for hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents hydrogen atom, $R^1$ stands for hydrogen atom, fluorine atom, chlorine atom, hydroxy or benzyloxy and $R^2$ stands for hydroxymethyl, $NHR^3$, $SO_2NR^4R^{4'}$ or nitro, wherein $R^3$ is hydrogen atom, methyl, $SO_2R^5$, formyl or $CONHR^{6'}$ and either one of $R^4$ and $R^{4'}$ is hydrogen atom and the other one is hydrogen atom, lower alkyl or benzyl, with $R^5$ being lower alkyl, benzyl or dimethylamino and $R^{6'}$ being the same as given above".

Also preferred examples of the compound represented by the general formula (I) or the salt thereof according to the present invention are those in which the combination of the substituent groups in the general formula (I) is such that "R represents hydrogen atom, $R^1$ stands for hydrogen atom, halogen atom, hydroxy or benzyloxy and $R^2$ stands for hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or $NR^4R^{4'}$ and $R^4$ and $R^{4'}$ may be identical with or different from each other and stand each for hydrogen atom, a lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents hydrogen atom, $R^1$ stands for hydrogen atom, fluorine atom, chlorine atom, hydroxy or benzyloxy and $R^2$ stands for hydroxymethyl, $NHR^3$, $SO_2NR^4R^4$ or nitro, wherein $R^3$ is hydrogen atom, methyl, $SO_2R^5$, formyl or $CONHR^{6'}$ and either one of $R^4$ and $R^{4'}$ is hydrogen atom and the other one is hydrogen atom, lower alkyl, benzyl, with $R^5$ being a lower alkyl, benzyl or dimethylamino and $R^{6'}$ being the same as given above".

Also preferred examples of the compound represented by the general formula (I) or the salt thereof according to the present invention are those in which the combination of the substituent groups in the general formula (I) is such that "R and $R^1$ represent each hydrogen and $R^2$ stands for hydroxymethyl, $NHR^3$ or $SO_2NR^4R^{4'}$, wherein $R^3$ is hydrogen atom, methyl, $SO_2R^5$, formyl or $CONHR^{6'}$ with $R^5$ being lower alkyl, benzyl or $NR^4R^{4'}$ and $R^4$ and $R^{4'}$ may be identical with or different from each other and stand each for hydrogen atom, lower alkyl or benzyl, and $R^{6'}$ being the same as given above".

Also preferred examples of the compound represented by the general formula (I) or the salt thereof according to the present invention are those in which the combination of the substituent groups in the general formula (I) is such that "R and $R^1$ represent each hydrogen atom and $R^2$ stands for hydroxymethyl, $NHR^3$ or $SO_2NR^4R^{4'}$, wherein $R^{3'}$ is hydrogen atom, methyl, $SO_2R^5$, formyl or $CONHR^{6'}$ and either one of $R^4$ and $R^{4'}$ is hydrogen atom and the other one is hydrogen atom, lower alkyl or benzyl, with $R^5$ being lower alkyl, benzyl or dimethylamino and $R^{6'}$ being the same as given above".

Also preferred examples of the compound represented by the general formula (I) or the salt thereof according to the present invention are those in which the combination of the substituent groups in the general formula (I) is such that "R represents hydrogen atom, $R^1$ stands for halogen atom or hydroxy and $R^2$ stands for $NHSO_2R^5$ or $SO_2NR^4R^{4'}$, wherein $R^5$ is lower alkyl, benzyl or $NR^4R^{4'}$ and $R^4$ and $R^{4'}$ may be identical with or different from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents hydrogen atom, $R^1$ stands for fluorine atom, chlorine atom or hydroxy and $R^2$ stands for $NHSO_2R^5$ or $SO_2NR^4R^{4'}$, wherein either one of $R^4$ and $R^{4'}$ is hydrogen atom and the other one is hydrogen atom, lower alkyl or benzyl and $R^5$ is lower alkyl, benzyl or dimethylamino".

Also preferred examples of the compound represented by the general formula (I) or the salt thereof according to the present invention are those in which the combination of the substituent groups in the general formula (I) is such that "R and $R^2$ represent each hydrogen atom and $R^1$ stands for hydrogen atom, halogen atom or hydroxy".

Also preferred examples of the compound represented by the general formula (I) or the salt thereof according to the present invention are those in which the combination of the substituent groups in the general formula (I) is such that "R and $R^2$ represent each hydrogen atom and $R^1$ stands for hydrogen atom, fluorine atom, chlorine atom or hydroxy".

Also preferred examples of the compound represented by the general formula (I) or the salt thereof according to the present invention are those in which the combination of the substituent groups in the general formula (I) is such that "R represents hydrogen atom, $R^1$ stands for hydrogen atom, halogen atom, hydroxy, amino or hydroxymethyl and $R^2$ stands for $NHR^3$ or $SO_2NR^4R^{4'}$, wherein $R^3$ is $SO_2R^5$, with $R^5$ being lower alkyl, benzyl or $NR^4R^{4'}$, and $R^4$ and $R^{4'}$ may be identical with or different from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents methyl, $R^1$ stands for hydrogen atom, halogen atom, hydroxy, benzyloxy, amino or hydroxymethyl and $R^2$ stands for hydrogen atom, hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or $NR^4R^{4'}$, and $R^4$ and $R^{4'}$ may be identical with or different from each other and stand each for hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl, $R^1$ stands for hydrogen atom, fluorine atom, chlorine atom, hydroxy or benzyloxy and $R^2$ stands for hydrogen atom, hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or $NR^4R^{4'}$, and either one of $R^4$ and $R^{4'}$ is hydrogen atom and the other one is hydrogen atom, lover alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl, $R^{1'}$ stands for hydrogen atom, halogen atom, hydroxy or benzyloxy and $R^2$ stands for hydroxymethyl, $NHR^3$, $SO_2NR^4R^4$ or nitro, wherein $R^3$ is hydrogen atom, methyl, $SO_2R^5$, formyl or $CONHR^{6'}$, with $R^3$ being lower alkyl, benzyl or $N^4R^{4'}$, and $R^4$ and $R^{4'}$ may be identical with or different from each other and stand each for hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl, $R^1$ stands for hydrogen atom, bromine atom, choline atom, hydroxy or benzyloxy and $R^2$ stands for hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or dimethylamino, and either one of $R^4$ and $R^{4'}$ is hydrogen atom and the other one is hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl. $R^1$ stands for hydrogen atom and $R^2$ stands for hydroxymethyl, $NHR^3$, $SO_2NR^4R^{4'}$, wherein $R^3$ is hydrogen atom, methyl, $SO_2R^5$, formyl or $CONHR^{6'}$, with $R^5$ being lower alkyl, benzyl or $N^4R^{4'}$, and $R^4$ and $R^{4'}$ may be identical with or different from each other and stand each for hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl, $R^1$ stands for hydrogen atom and $R^2$ stands for hydroxymethyl, $NHR^3$ or $SO_2NR^4R^{4'}$, wherein $R^3$ is hydrogen atom, methyl, $SO_2R^5$, formyl or $CONHR^{6'}$, with $R^5$ being lower alkyl, benzyl or dimethylamino, and either one of $R^4$ and $R^4$ is hydrogen atom and the other one is hydrogen atom, lower alkyl or benzyl and $R^{6'}$ has the meaning as given above".

Also preferred examples of the compound represented by the general formula (I) or the salt thereof according to the present invention are those in which the combination of the substituent groups in the general formula (I) is such that "R represents methyl, $R^1$ stands for halogen atom or hydroxy and R2 stands for $NHSO_2R^5$ or $SO_2NR^4R^{4'}$, wherein $R^5$ is lower alkyl, benzyl or $NR^4$ $R^{4'}$, and $R^4$ and $R^{4'}$ may be identical with or diffrent from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents methyl, $R^1$ stands for fluorine atom, chlorine atom or hydroxy and $R^2$ stands for $NHSO_2R^5$ or $SO_2NR^4R^{4'}$, wherein either one of $R^4$ and $R^{4'}$ is hydrogen atom and the other one is hydrogen atom, lower alkyl or benzyl and $R^5$ is lower alkyl, benzyl or dimethylamino".

Also preferred examples of the compound represented by the general formula (I) or the salt thereof according to the present invention are those in which the combination of the substituent groups in the general formula (I) is such that "R represents methyl, $R^1$ stands for hydrogen atom, a halogen atom or hydroxy and $R^2$ stands for hydrogen atom".

Also preferred examples of the compound represented by the general formula (I) or the salt thereof according to the present invention are those in which the combination of the substituent groups in the general formula (I) is such that "R represents methyl, $R^1$ stands for hydrogen atom, fluorine atom, chlorine atom or hydroxy and $R^2$ stands for hydrogen atom".

Also preferred examples of the compound represented by the general formula (I) or the salt thereof according to the present invention are those in which the combination of the substituent groups in the general formula (I) is such that "R represents methyl, $R^1$ stands for hydrogen atom, halogen atom, hydroxy, amino or hydroxyrmethyl and $R^2$ stands for $NHR^3$ or $SO_2NR^4R^{4'}$, wherein $R^3$ is $SO_2R^5$, with $R^5$ being lower alkyl, benzyl or $NR^4$ $R^{4'}$, and $R^4$ and $R^4$ may be identical with or different from each other and stand each for hydrogen atom, lower alkyl or benzyl".

Concrete examples of the compound represented by the general formula (I) according to the present invention include (R)-N-[5-[2-[2-(9H-carbazol-2-yloxy)ethylamino]-1-hydroxyethyl1-hydroxy,phenyl]methanesulfonamide, (S)-N-[5-[2-[2-(9H-carbazol-2-yloxy)ethylaminol]-1-hydroxyethyl]-2hydroxyphenyl]methanesulfonamide, N-[5-[2-[2-(9H-carbazol-2-yloxy)ethylamino]-1-hydroxyethyl]-2hydroxyphenyl]methanesulfonamide, N-[5-[2-[2-(3-hydroxy-9H-carbazol-2-yloxy)ethylamino]-1-hydroxyethyl]-2-hydroxyphenyl]methanesulfonamide, N-[5-[2-[2-(3-amino-9H-carbazol-2-yloxy)ethylamino]-1-hydroxyethyl]-2-hydroxyphenyl]methanesulfonamide, N-[5-[2-[2-(6-amino-9H-carbazol-2-yloxy)ethylamino]-1-hydroxyethyl]2-hydroxyphenyl]methanesulfonamide, N-[5-[2-[2-(6-hydroxy-9H-carbazol-2-yloxy)ethylamino]-1-hydroxyethyl]-2-hydroxyphenyl]methanesulfonamide, (R)-N-[3-[2-[2-(9H-carbazol-2-yloxy)ethylamino]-1-hdroxyethyl]phenyl]methanesulfonamide, (S)-N-[3-[2-[2-(9H-carbazol-2-yloxy)ethylamino]-1-hydroxyethyl]phenyl]methanesulfonamide, N-[3-[2-[2-(9H-carbazol-2-yloxy)ethylamino]-1-hydroxyethyl]phenyl]methanesulfonamide, N-methyl-3-[2-[2-(9H-carbazol-2-yloxy)ethylamino]-1-hydroxyethyl]benzenesulfonamide, N-methyl-[5-[2[-2-(2-(9H-carbazol-2-yloxy)ethylamino]-1-hydroxyethyl]-2-hydroxy]benzenesulfonamide, (R)-N-[5-[2-[2-(dibenzofuran-3-yloxy)ethylamino]-1-hydroxyethyl]-2-hydroxyphenyl]methanesulfonamide, (S)-N-[5-[2-[2-(dibenzofuran-3-yloxy)ethylamino]-1-hydroxyethyl]-2-hydroxyphenyl]methanesulfonamide, N-[5-[2-[2-(dibenzofuran-3-yloxy)ethylamino]-1-hydroxy,ethyl]-2-hydroxyphenl]methanesulfonamide, N-[5-[2-[2-(9H-carbazol-2-yloxy)ethylamino]-1-hydroxyethyl]-2-(benzyloxy)phenyl]methanesulfonamide, N-[5-[2-[2-(9H-carbazol-2-yloxy)ethylamino]-1-hydroxyethyl]-2-chlorophenyl]methanesulfonamide, N-[5-[2-[2-(9H-carbazol-2-yloxy)ethylamino]-1-hydroxyethl]-2-fluorophenyl]methanesulfonamide, N-[3-[2-[2-(dibenzofuran-3-yloxy)ethylamino]-1-hydroxyethyl]phenyl]methanesulfonamide, N-[5-[2-[2-(7-acetylaminofluoren-2-yloxy)ethylamino]-1-hydroxyethyl]2-hydroxyphenyl]methanesulfonamide, N-[5-[2-[2-(7-aminofluoren-2-yloxy)ethylamino]-1-hydroxyethyl]-2-hydroxyphenyl]methanesulfonamide, N-[3-[2-[2-(7-acetylaminofluoren-2-yloxy)ethylaminol]-1-hydroxyethl]phenyl]methanesulfonamide, N-[3-[2-[2-(7-aminofluoren-2-yloxy)ethylamino]-1-hydroxyethyl]phenyl]methanesulfonamide, N-[5-[2-[2-(9H-carbazol-2-yloxy)ethylamino]-1-hydroxyethyl]-2-hydroxyphenyl]formamide, N-[3-[2-[2-(9H-carbazol-2-yloxy)ethylamino]-1-hydroxyethyl]phenyl]formamide, N-[3-[2-[[1-(9H-carbazol-2-yloxy)propan-2R-yl]amino]-1-hydroxyethyl]phenyl]methanesulfonamide, 2-[N-[2-(9H-carbazol-2-yloxy)ethyl]amino]-1-(4-hydroxy-3-nitrophenyl) ethanol, 2-[N-[2-(9H-carbazol-2-yloxy)ethyl]amino]-1-(3-amino-4-hydroxyphenyl)-ethanol, N-[5-[2-[2-(9H-carbazol-2-yloxy)ethylamino]-1-hydroxyethyl]-2-(benzyloxy),pheny]urea, N-[5-[2-[2-(9H-carbazol-2-yloxy)ethylamino]-1-hydroxyethyl]-2-hydrovphenyl]urea, N-[5-[2-[2-(9H-carbazol-2-yloxy)ethylamino]-1-hydroxyethyl]-2-(benzyloxy)phenyl]formamide, N'-[5-[2-[2-(9H-carbazol-2-yloxy)ethylamino]-1-hydroxyethyl]-2-(benzyloxy)phenyl]-N,N-dimethylsulfamide, N'-[5-[2-[2-(9H-carbazol-2-yloxy)ethylamino]-1-hydroxyethyl]-2-hydroxy,phenyl]-N,N-dimethylsulfamide, 2-[N-[2-(9H-carbazol-2-yloxy)ethyl]amino]-1-[3-(methylamino)-4-(benzyloxy)phenyl]ethanol, 2-[N-[2-(9H-carbazol-2-yloxy)ethyl]amino]-1-[3-(methylamino)-4-hydroxyphenyl]ethanol, N-[5-[2-[2-(9H-carbazol-2-yloxy) ethbylamino]-1-hydrox)ethyl]-2-hydroxyphenyl]-2-propanesulfonamide, 2-[N-[2-(9H-carbazol-2-yloxy)ethyl]amino]-1-(3-nitrophenyl)ethanol, N'-[3-[2-[2-(9H-carbazol-2-yloxy)ethylaminol]-1-hydroxyethyl]phenyl]-N,N-dimethylsulfamide, 2-[N-[2-(9H-carbazol-2-yloxy)ethyl]amino]-1-(3-aminophenyl)ethanol, 2-[N-[2-(9H-carbazol-2-yloxy)ethyl]amino]-1-[3-(hydroxymethyl)-4-hydroxyphenyl]ethanol, N-[5-[2-[2-(9H-carbazol-2-yloxy)ethylamino]-1-hydroxyethyl]-3-hydroxyphenyl]methanesulfonamide, N-[3-[2-[2-(9H-carbazol-2-yloxy)ethylamino]-1-hydroxyethyl]-2-hydroxyphenyl]methanesulfonamide, N-[3-[2-[2-(9H-carbazol-2-yloxy)ethylamino]-1-hdroxyethyl]-4-hydroxphenyl]methanesulfonamide, (R)-N'-[5-[2-[2-(9H-carbazol-2-yloxy)ethylamino]-1-hydroxyethyl]-2-hydroxyphenyl]-N,N-dimethylsulfamide, (S)-N'-[5-[2-[2-(9H-carbazol-2-yloxy)ethylamino]-1-hydroxyethyl]-2-hydroxyphenyl]-N,N-dimethylsulfamide, N-[3-[2-[2-(6-acetylamino-9H-carbazol-2-yloxy)ethylamino]-1-hydroxyethyl]phenyl]methanesulfonamide, N-[5-[2-[2-(6-acetylamino-9H-carbazol-2-yloxy)ethylamino]-1-hydroxyethyl]-2-hydroxyphenyl]methanesulfonamide, (R)-N-[5-[2-[2-(9H-carbazol-2-yloxy)ethylamino]-1-hydroxethyl]-2-fluorophenyl]methanesulfonamide, (S)-N-[5-[2-[2-(9H-carbazol-2-yloxy)ethylamino]-1-hydroxyethyl]-2-fluorophenyl]methanesulfonamide, (R)-N-[5-[2-[2-(9H-carbazol-2-yloxy)ethylamino]-1-hydroxyethyl)-2chlorophenyl]methanesulfonamide, (S)-N-[5-[2-[2-(9H-carbazol-2-yloxy)ethlamino]-1-hydroxyethyl]-2-chlorophenyl]methanesulfonamide, N,N-dimethyl-[5-[2-[2-(9H-carbazol-2-yloxy)ethlamino]-1-hydroxyethyl]-2-hydroxy]benzenesulfonamide, N-[5-[2-[2-(9H-carbazol-2-yloxy)ethlamino]-1-hydroxyethyl]-2-iodophenyl]methanesulfonamide, N'-[5-[2-[2-(9H-carbazol-2-yloxy)ethylamino]-1-hydroxyethyl]-2-fluorophenyl]-N,N-dimethylsulfamide, N'-[5-[2-[2-(9H-carbazol-2-yloxy)ethylamino]-1-hydroxyethyl]-2-chlorophenyl]-N,N-dimethylsulfamide, (R)-N-methyl-[5-[2-[2-(9H-carbazol-2-yloxy)ethylamino]-1-hydroxyethyl]-2-hydroxy]benzenesulfonamide, (R)-N-[5-[2-[2-(9H-carbazol-2-yloxy)ethylamino]-1-hydroxyethyl]-2(hydroxymethyl) phenyl]methanesulfonamide, (R)-N-[3-[2-[$^2$-(dibenzofuran-3-yloxy)ethylamino]-1-hydroxyethyl]phenyl]methanesulfonamide, N'-[5-[$^2$-[$^2$-(dibenzofuran-3-yloxy)ethylamino]-1-hydroxyethyl]-2-hydrox)phenyl]-N,N-dimethylsulfamide, (R)-N'-[5-[2-[2-(dibenzofuran-3-yloxy)ethylamino]-1-hydroxyethyl]-2-hydroxyphenyl]-N,N-dimethylsulfamide, (S)-N'-[5-[2-[2-(dibenzofuran-3-yloxy)ethylamino]-1-hydroxyethyl]-2-hydroxyphenyl]-N,N-dimethylsulfamide, N-[5-[2-[2-(dibenzefuran-3-yloxy)ethylamino]-1-hydroxyethyl]-2-fluorophenyl]methanesulfonamide, N-[5-[2-[2-(dibenzofuran-3-yloxy)ethylamino]-hydroxyethyl]-2-chlorophenyl]methanesulfonamide, N-[5-[2-[2-(dibenzothiophen-3-yloxy)ethylamino]-1-hydroxyethyl]-2-hydroxyphenyl]methanesulfonamide, N'-[5-[2-[2-(dibenzothiophen-3-yloxy)ethylamino]-1-hydroxyethyl]-2-hydroxyphenyl]-N,N-dimethylsulfamide, N-[3-[2-[2-(dibenzothiophen-3-yloxy)ethylamino]-1-hydroxyethyl]phenyl]methanesulfonamide, (R)-N-[5-[2-[2-(dibenzothiophen-3-yloxy)ethylamino]-1-hydroxyethyl]-2-hydroxyphenyl]methanesulfonamide, N-[5-[2-[2-(dibezothiophen-3-yloxy)ethylamino]-1-hydroxyethyl]-2-fluorophenyl]methanesulfonamide, N-[5-[2-[2-(dibenzothiophen-3-yloxy)ethylamino]-1-hydroxyethyl]-2-chlorophenyl]methanesulfonamide, N-[5-[2-[2-(7-aminofluoren-2-yloxy)ethylamino]-1-hydroxyethyl]-2-hydroxyphenyl]methanesulfonamide, N'-[5-[2-[2-(7-acetylaminofluoren-2-yloxy)ethylamino]-1-hydroxy,ethyl]2-hydroxyphenyl]-N,N-dimethylsulfamide, N'[5-[2-[2-(9H-carbazol-2-yloxy)ethylamino]-1-hydroxyethyl]-2-aminophenyl]-N-benzyl-N-methylsulfamide, N-[5-[2-[2-(9H-carbazol-2-yloxy)ethylamino]-1-hydroxyethyl]-2-aminophenyl]methanesulfonamide, N-[5-[2-[2-(9H-carbazol-2-yloxy)ethylamino]-1-hydroxyethyl]-2-hydroxymethylphenyl]methanesulfonamide, N-[5-[2-[2-(9H-carbazol-2-yloxy)ethylamino]-1-hydroxyethyl]-2-bromophenyl]methanesulfonamide, N'[5-[2-[2-(9H-carbazol-2-yloxy)ethylamino]-1-hydroxyethyl]-2-hydroxyphenyl]-N-benzyl-N-methylsulfamide, N'[5-[2-[2-(9H-carbazol-2-yloxy)ethylamino]-1-hydroxyethyl]-2hydroxyphenyl]-N,N-diethylsulfamide, N-[5-[2-[2-(9H-carbazol-2-yloxy)ethylamino]-1-methoxyethl]-2aminophenyl]methanesulfonamide, N-[5-[2-[2-(9H-carbazol-2-yloxy)ethylamino]-1-methoxyethyl]-2-hydrox)phenyl]methanesulfonamide and N-[5-[2-[2-(dibenzothiophen-3-yloxy)ethylamino]-1-methoxyethyl]-2-hydroxyphenyl]methanesulfonamide.

The followings are concrete examples of the compound in which both $R^1$ and $R^2$ are hydrogen.

2-[N-[2-(9H-carbazol-2-yloxy)ethyl]amino]-1-(4-hydroxyphenyl)ethanol,

2-[N-[2-(9H-carbazol-2-yloxy)ethyl]amino]-1-(2-fluorophenyl)ethanol,

2-[N-[2-(9H-carbazol-2-yloxy)ethyl]amino]-1-(2-hydroxyphenyl)ethanol, (R,R)-2-[N-[1-(9H-carbazol-2-yloxy)propan-2-yl]amino]-1-phenyl]ethanol, 2-[N-[2-(9H-carbazol-2-yloxy)ethyl]amino]-1-phenyl]ethanol, (R)-[2-[N-[2-(9H-carbazol-2-yloxy,)ethyl]amino]-1-phenyl]ethanol, (S)-[2-[N-[2-(9H-carbazol-2-yloxy)ethyl]amino]-1-phenyl]ethanol,

[2-[N-[2-(3-acetylamino-9H-carbazol-2-yloxy)ethyl]amino]-1-phenyl]ethanol,

[2-[N-[2-(3-amino-9H-carbazol-2-yloxy)ethyl]amino]-1-phenyl]ethanol,

[2-[N-[2-(3-hydroxy-9H-carbazol-2-yloxy)ethyl]amino]-1-phenyl]ethanol

[2-[N-[2-(6-amino-9H-carbazol-2-yloxy)ethyl]amino]-1-phenyl]ethanol,

[2-[N-[2-(6-acetylamino-9H-carbazol-2-yloxy)ethyl]amino]-1-phenyl]ethanol,

[2-[N-[1-(9H-carbazol-2-yloxy)propan-2-yl]amino]-1-phenyl]ethanol and

[2-[N-[2-(dibenzofuran-3-yloxy)ethyl]amino]-1-phenyl]ethanol.

Examples of the compounds in which R stands for methyl include the followings.

N-[5-[2-[2-(9H-carbazol-2-yloxy)ethylamino]-1-methoxyethyl]-2-hydroxyphenyl]methanesulfonamide, N-[5-[2-[2-(dibenzothiophen-3-yloxy)ethylamino]-1-methoxyethyl]-2-hydroxyphenyl]methanesulfonamide, N-[5-[2-[2-(9H-carbazol-2-yloxy)ethylamino]-1-methoxyethyl]-2-aminophenyl]methanesulfonamide and N-[5-[2-[2-(9H-carbazol-2-yloxy)ethylamino]-1-methoxyethyl]-2-chlorophenyl]methanesulfonamide.

The compound represented by the general formula (I) can be produced, for example, by the following method.

Production Process A

A compound represented by the general formula (II)

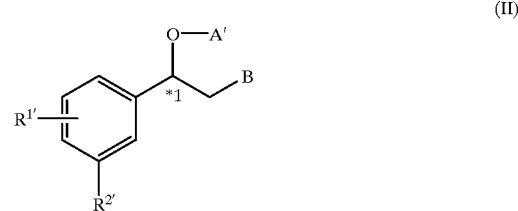

(II)

[in which $R^{1'}$ represents hydrogen atom, halogen atom, a protected hydroxyl group protected by a protecting group A, a protected amino group protected by acetyl group or a protected hydroxymethyl group protected by acetyl group, $R^{2'}$ stands for hydrogen atom, for a protected hydroxymethyl group in which the hydroxyl group is protected by a protecting group A''', for $NHR^{3'}$, for $SO_2NR^4R^{4'}$ or for nitro, wherein $R^{3'}$ represents a protecting group for the amino group, methyl, $SO_2R^5$, formyl or $CONHR^{6'}$, with $R^5$ being lower alkyl, benzyl or $NR^4R^{4'}$ and $R^{6'}$ being hydrogen atom or lower alkyl, $R^4$ and $R^{4'}$ may be identical with or different from each other and stand each for hydrogen atom, lower alky or benzyl, $R^6$ denotes hydrogen atom or lower alkyl, A' represents a protecting group for the hydroxyl group, B is bromine atom or iodine atom and *1 indicates an asymmetric carbon atom] is reacted with a compound represented by the general formula (III)

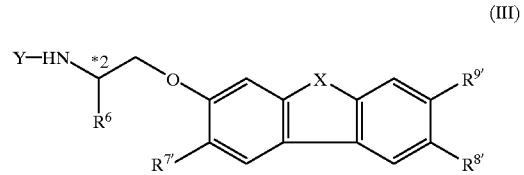

(III)

[wherein Y represents hydrogen atom, $R^6$ is hydrogen atom or lower alkly, X is secondary nitrogen atom, oxygen atom, sulfur atom or methylene and, in case X is secondary nitrogen atom, oxygen atom or sulfur atom. $R^{9'}$ is hydrogen atom and either one of $R^{7'}$ and $R^{8'}$ is hydrogen atom and the other one is hydrogen atom, acetylamino or a protected hydroxyl group protected by a protecting group A", or, in case that X is methylene, both $R^{7'}$ and $R^{8'}$ are hydrogen atom and $R^9$ stands for hydrogen atom, acetylamino or a protected hydroxyl group protected by, a protecting group A", and *2 indicates asymmetric carbon atom, when $R^6$ is lower alkyl], and the protecting groups A (proviso that in case that $R^1$ is benzyloxy and the protecting group A is benzyl, the protecting group A is not deprotected), A', A", A''' and the protecting group for amino group in $R^3$ (proviso that if is exists), or the protecting acetyl group in $R^1$ are deprotected to obtain the compound represented by the general formula (I), wherein R represents hydrogen atom, $R^1$ stands for hydrogen atom, halogen atom, hydroxy, benzyloxy, amino or hydroxymethyl, $R^2$ stands for hydrogen atom, hydroxymethyl, $NHR^3$, $SO_2NR^4R^{4'}$ or nitro, proviso that $R^3$ is hydrogen atom, methyl, $SO_2R^5$, formyl or $CONHR^{6'}$, and $R^5$ is lower alkyl, benzyl or $NR^4R^4$ and $R^4$ and $R^{4'}$ may be identical with or different from each other and are hydrogen atom, lower alkyl or benzyl group. $R^{6'}$ is represents hydrogen atom or lousier alkyl, As the protecting groups for protecting the hydroxyl groups, there is no special limitation so long as ordinary use is permitted and there may usually be used as a protecting group which can be deprotected easily and selectively, for example, benzyl or t-butyl-dimethylsilyl for the protecting group A, triethylsilyl for the protecting groups A' and A''' and methyl or benzyl for the protecting group A". For introducing a protecting group into the compound to be protected, known practice is employed and, for example, a method is used for protecting the compound by introducing therein benzyl group, in which the compound is reacted with 1.1 molar times benzyl bromide at room temperature in a reaction solvent, such as dimethylformamide, in the presence of potassium carbonate. For protecting the compound by introducing therein triethylsilyl group, the compound is reacted with 1.2–2 molar times silylating agent, such as triethylsilyl chloride, at a temperature in the range of 0 to 30° C. in a reaction solvent, such as pyridine, for 1–3 hours.

As the protecting group for protecting the amino group in the substituent $R^{3'}$, there is no special limitation so long as ordinary use as a protecting group for protecting aniline is permitted and acetyl group may usually be preferred therefor. For practising the acetylation, a reaction with acetic anhydride in a reaction solvent, such as pyridine. may be exemplified.

The coupling reaction of the compound represented by the general formula (II) with the amine represented by the general formula (III) may be realized using 1 to 1.5 moles of the amine of the general formula (III) per 1 mole of the halide of the general formula (II) in a polar solvent, such as dimethylformamide, dimethylacetamide or dimethylsulfoxide, in the presence of a proton capturing agent, for example, an amine, such as triethylamine or diisopropylethylamine, at a temperature in the range from room temperature to 90° C., preferably by heating at 60° C., for 5–10 hours.

Deprotection of the resulting product may be effected either in succession or simultaneously, while deprotection in a successive order of A", A', A''', the protecting agent for the amino group in $R^{3'}$ and at last A may be preferred. The deprotection of benzyl group for A and A" is realized by, hydrogenolysis in a solvent, such as methanol, using a catalyst. such as palladium or nickel. In the case where the substituent $R^1$ in the general formula (I) is benzyloxy, there is no need of elimination of benzyl group as the protecting group A. The deprotection of benzyl or methyl as the protecting groups A and A" may be realized by treating the product with a Lewis acid, such as boron tribromide, in a solvent, such as methylene chloride. The deprotection of acetyl-protected hydroxyl group in the substituent $R^{1'}$ may be realized by a known procedure of hydrolysis of ester. Concretely, it may be performed in an alcohol using an alkali at room temperature or by heating under reflux of the solvent. The deprotection of triethylsilyl as the protecting group A' or A''' may be realized by treating the product by adding thereto acetic acid and 3–5 molar times tetrabutylammonium fluoride in a solvent of tetrahydrofuran at room temperature for 30–5 hours. The deprotection of the protecting group, such as acetyl, for the amino group in $R^{3'}$ or of the acetyl-protected amino group in $R^{1'}$ may be realized either by treating the product with hydrochloric acid at room temperature or by heating in a solvent, such as water or methanol, with an alkali.

The compound represented by the general formula (II) can be obtained by subjecting a compound represented by the following general formula (V),

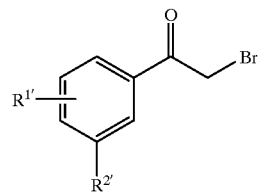

(V)

in which $R^{1'}$ and $R^{2'}$ have the same meanings as given previously, to a reduction in the manner as described below, and replacing the bromide, if the contemplated substituent group B in the general formula (II) is iodine, iodide, followed by protection of the hydroxyl group.

The reduction of the compound represented by the general formula (V) may be attained by using a reducing agent, such as a borane, when the steric configuration (*1) of the hyroxyl group of the compound represented by the general formula (II) is racemic.

In case where either R- or S-optical isomer is to be obtained as to the *1 structure in the general formula (II), the reduction can be attained by having resort to employment of a chiral assistant, such as given by the following general formula (VI).

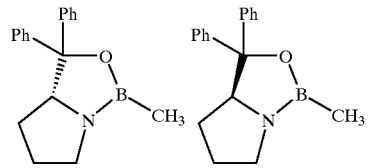

(VI)

Thus, the reduction of the compound represented by the general formula (V) is effected using a borane in the presence of the above-mentioned chiral assistant. The reduction may preferably be performed in a solvent, such as tetrahydrofuran. The preparation of such a chiral assistant and the reaction therewith may be carried out in accordance with the teachings in the literature [E. J. Corey et al, J. Org. Chem., Vol.56, 442, (1991)].

After the reduction of the compound represented by the general formula (V), the bromide thereof is, if necessary, replaced with iodide by, for example, treating the reduced compound with 3–10 times molar amount of an iodizing agent, such as sodium iodide, in a solvent, such as acetone, with heating under reflux for 1–3 hours.

The hydroxyl group of the so-treated product is then protected by the method described previously with a protecting group, such as triethylsilyl, to obtain the compound represented by the formula (II).

The compound represented by the general formula (V) is known and can be synthesized by methods given in literatures, for example, A. A. Larsen et al, J. Med. Chem., 10, 462 (1967); or C. Kaiser et al, J. Med. Chem. 17, 49 (1974).

The compound represented by the general formula (III) can be obtained by reacting a compound represented by the general formula (VII)

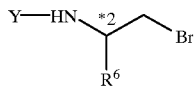

(VII)

in which Y denotes a protecting group for the amino group, $R^6$ and *2 have the same meanings as those given previously, with a compound represented by the general formula (VIII)

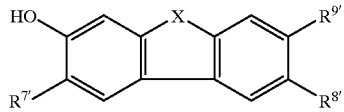

(VIII)

in which X, $R^{7'}$, $R^{8'}$ and $R^{9'}$ have the same meanings as those given previously. As the protecting group Y for protecting the amino group, there is no special limitation so long as a usual use is permitted and there may be exemplified one which can usually be deprotected easily, for example, benzyloxycarbonyl, a substituted benzyloxycarbonyl, t-butoxycarbonyl, acetyl or trifluoroacetyl.

The reaction of the compound represented by the general formula (VII) with the compound represented by the general formula (VIII) can be realized, for example, in an organic solvent usually in the presence of a base at a temperature from room temperature to the reflux temperature of the solvent employed. As the solvent, there may be employed, for example, dimethylformamide, dimethylacetamide, acetonitrile, diglym and tetrahydrofuran. As the base, there may be employed, for example, potassium carbonate, sodium carbonate, sodium hydroxide, potassium hydroxide, triethylamine, pyridine, sodium hydride or sodium methoxide, in an amount of, preferably, 1–10 moles per one mole of the compound of the general formula (VIII).

The compound represented by the general formula (III) can, in particular, if the above reaction does not proceed promptly, also be synthesized in accordance with the process described in Bull. Chem. Soc. Japan, 55, 2504 (1982) or by an improvement thereof. For example, one mole of the alcohol compound is reacted with 2–5 moles of the compound represented by the general formula (VII) in a solvent, such as dimethylformamide or acetonitrile, in the presence of 5–10 moles of 40% potassium fluoridealumina at a temperature in the range from room temperature to 90° C. In the improved process, the above reaction is realized with addition of 0.1–0.5 equivalent of potassium iodide.

Then, the protecting group Y for protecting the amino group is deprotected to obtain the amine compound represented by the general formula (III) wherein Y stands for hydrogen atom. The deprotection may be effected by a usual method, for example, by a hydrogenolysis in a solvent, such as methanol, using a catalyst, such as palladium/carbon black or by treating with hydrogen bromide/acetic acid. If the protecting group Y is acetyl or trifluoroacetyl, the deprotection may be attained by treating with an alkali in a solvent, such as methanol, to obtain the compound represented by the general formula (III) in which Y denotes hydrogen atom.

The compound represented by the general formula (VII) can be synthesized from a commercial product of an amino alcohol having the substituent $R^6$ and a stereo structure of *2 by first protecting the amino group thereof with a protecting group Y and, then, the resulting product is subjected to bromination by a usual method. If there is an easily available aminobromo compound, the contemplated compound can be obtained by, merely protecting the amino group by a protecting group Y. For example, a hydrobromide salt of a commercial 2-bromoethylamine may be reacted with benzyloxycarbonyl chloride in a solvent, such as methylene chloride, in the presence of triethylamine under cooling with ice water.

The compound represented by the general formula (VIII) in which X stands for secondary nitrogen atom, oxygen atom or sulfur atom and that in which X stands for methylene can be produced by the methods given below, respectively.

The compound of the general formula (VIII) in which X is secondary nitrogen atom, oxygen atom or sulfur atom, both $R^{8'}$ and $R^{9'}$ are hydrogen atom and $R^{7'}$ is hydrogen atom, acetylamino or a protected hydroxyl group protected by a protecting group A" can be produced in a manner as follows:

Thus, starting from a commercial product of 2-hydroxycarbazole and 3-methoxydibenzofuran or 3-hydroxydibenzothiophene which can be synthesized by method given in literature [H. Kudo et al, J. Heterocycl. Chem., 22(1), 215–218 (1985)], the compound represented by the formula (VII) is obtained. The compound of the general formula (VIII) in which $R^{7'}$ is a substituent group other than hydrogen atom can be obtained by, for example, in such a manner that the hydroxyl group of a commercial product of 2-hydroxycarbazole is protected by benzylating it, then, nitration is effected to introduce nitro group at the position of the substituent group $R^{7'}$ and this is reduced into amino group, whereupon this amino group is acetylated or is subjected to diazotization with subsequent conversion into hydroxyl group, followed by protection of the resulting hydroxyl group by a protecting group A" and subsequent deprotection of the benzyl group to build up the compound of the general formula (VIII).

For the nitration, ordinary methods given in the literatures may be employed, wherein, for example,the benzyl-protected product is subjected to nitration in acetic acid using an equivalent amount of diluted fuming nitric acid at a temperature of from room temperature to 60° C. Reduction of the resulting nitro group may be effected by a usually employed method, for example, by hydrogenation in a solvent, such as methanol, in the presence of a catalyst, such as palladium oxide at room temperature or by using hydrochloric acid with iron powder or in the presence of divalent tin at a temperature in the range from room temperature to the reflux temperature. The resulting amine may be acetylated using acetylchloride in a solvent, such as methylene chloride, at a temperature of from 0° C. to room temperature or may be converted into hydroxyl group by first diazotizing it using, for example, sodium nitrite, and, then, subjecting the resulting diazonium salt to a thermal decomposition in an acidic aqueous solution, followed by protection of the resulting hydroxyl group with a protecting group A" by the technique for protecting hydroxyl group described previously and, finally, deprotecting the benzyl group.

The compound of the general formula (VIII) in which X is secondary nitrogen atom, oxygen atom or sulfur atom, both $R^{7'}$ and $R^{9'}$ are hydrogen atom and $R^{8'}$ is hydrogen atom, acetylamino or a protected hydroxyl group protected by a protecting group A" can be produced in the manner as follows:

Thus, it can be synthesized starting from a known compound, i.e. 2-acetylcarbazole represented by the general formula (IX)

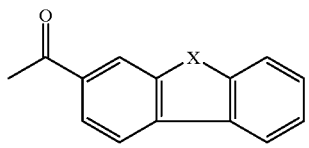

(IX)

in which X is secondary nitrogen atom, oxygen atom or sulfur atom [J. B. Kyziol et al, Tetrahedron, 36, 3017–3019 (1980)], 3-acetyldibenzofuran [M. I. Shevchuk etal, Zh. Obshch. Khim., 40 (8), 1717–1725 (1970)] or 3acetyldibenzothiophene [Phosphorus, Sulfur Silicon Relat. Elem., 72(1–4), 13–31 (1992); E. Camagine etal, J. Heterocycl. Chem., 6 (4), 517–522 (1969)]. For the compound in which $R^{8'}$ is a substituent group other than hydrogen atom, it may be processed, for example, by nitrating 2-acetylcarbazole at its position of the substituent group $R^{8'}$, followed by reduction of the resulting nitro group into amino group, whereupon the amino group is subjected to either acetylation or diazotization with subsequent conversion into hydroxyl group, which is then protected by a protecting group A" for protecting hydroxyl group.

For example, for producing the compound represented by the general formula (VIII) from the so-obtained acetyl group-containing compound, namely, for converting the acetyl group into hydroxyl group,the acetyl group at the 2-position of carbazole is oxidized by a peracid into acetyloxy which is, then, subjected to hydrolysis. Other process steps than the oxidation of the acetyl group and the hydrolysis may be accomplished in the same manner as in the case of introduction of $R^{7'}$ described above. The oxidation by a peracid can be realized using, for example, m-chloroperbenzoic acid and disodium hydrogenphosphate in a solvent, such as methylene chloride, at room temperature and the hydrolysis can be realized by, for example, using sodium hydroxide in a mixed solvent of water/ethanol.

The compound represented by the general formula (VIII) in which X is methylene (fluorene), both $R^{7'}$ and $R^{8'}$ are hydrogen atom and $R^{9'}$ is hydrogen atom or acetylamino is known and a commercial product thereof is available from, for example, the firm Sailor. In the case where $R^{9'}$ is a protected hydroxyl group protected by a protecting group A", the compound can be produced by protecting the hydroxyl group of fluorene with benzyl group, de-protecting the acetyl group in the acetylamino group, diazotizing the resulting amino group, converting it into hydroxyl group via a diazonium salt, protecting the resulting hydroxyl group by a protecting group A" for protecting hydroxyl group and finally de-protecting the benzyl group. These reaction series can be performed by the method described previously.

Alternatively, for producing the compound of the general formula (III) in which either one of $R^{7'}$, $R^{8'}$ and $R^{9'}$ is a protected hydroxyl up protected by a protecting group A", methods as given below may be incorporated.

Thus, the compound represented by the general formula (III) in which Y denotes a protecting group for protecting amino group, $R^{7'}$, $R^{8'}$ and $R^{9''}$ denote each acetyl group in accordance with X and $R^6$ and *2 have the same meanings as those given previously is subjected to hydrolysis of the acetylamino group thereof into amino group. The resulting amino group is diazotized and converted into hydroxyl group, which is then protected by a protecting group A", whereupon the protecting group Y of the amino group is deprotected to obtain the compound represented by the general formula (III) in which Y is hydrogen atom.

As a further alternative method, the compound represented by the general formula (I) in which R is hydrogen atom can be obtained using a compound represented by the general formula (IV)

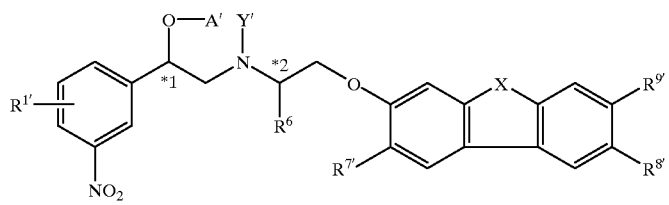

(IV)

in which Y' is hydrogen atom or a protecting group for amino group and $R^{1'}$, A', $R^6$, X, $R^{7'}$, $R^{8'}$, $R^{9'}$, *1 and *2 have the same meanings as those given previously. as an important synthesis intermediate.

For producing the compound represented by the general formula (IV), the compound represented by the general formula (II) in which $R^{2'}$ is nitro and the compound represented by the general formula (II) in which Y stands for hydrogen atom are brought into coupling reaction and, if necessary, the amino group of the reaction product is protected. The protecting group for the amino group in the substituent group Y' of the geneal formula (IV) may be the same as that for the amino group in the substituent group Y explained above and the introduction and elimination thereof may also be effected in the same manner.

For producing the compound represented by the general formula (I) using the compound represented by the general formula (IV) as a synthesis intermediate, the following techniques may be exemplified:

Thus, the compound represented by the general formula (IV) is first reduced, namely, the nitro group thereof is reduced, to obtain a compound represented by the general formula (X)

(X)

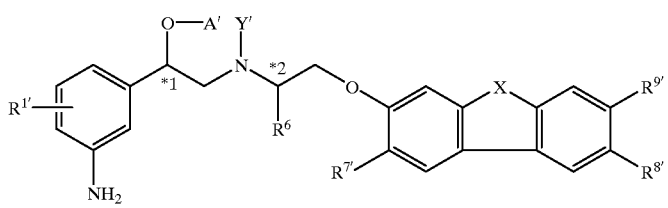

in which Y' is a protecting group for the amino group and R$^{1'}$, A', R$^{6'}$, X, R$^{7'}$, R$^{8'}$, R$^{9'}$, *1 and *2 have the same meanings as those given previously.

For the above-mentioned reduction, the amino group of the compound of the general formula (IV) may preferably have been protected by the protecting group Y' and the reduction may be performed by, for example, hydrogenating the compound in a solvent, such as methanol, in the presence of a catalyst, such as palladium oxide, or by using a system employing hydrochloric acid with iron powder or a divalent tin.

Thereafter, the resulting product is subjected to formulation, sulfonation or urearization of amine (aniline) in accordance with the requirement for providing various substituent groups for R$^3$ by, for example, a method described in the literature, C. Kaiser et al, J. Med. Chem., 17, 49 (1974), to convert it into a compound represented by the general formula (XI)

(XI)

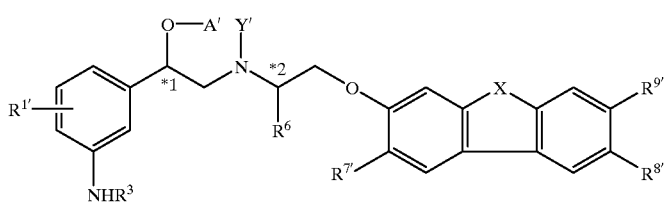

in which Y', R$^{1'}$, A', R$^3$, R$^6$, X, R$^{7'}$, R$^{8'}$, R$^{9'}$, *1 and *2 have the same meanings as those given previously, whereupon the existing protecting groups among A, A', A" and that for the amino group in Y' are de-protected by the method for deprotection described previously, to produce the compound represented by the general formula (I) in which R is hydrogen atom.

The formulation mentioned above may be effected by, for example, heating the resulting product of the general formula (X) in ethyl formate or by reacting it with a mixture of formic acid/acetic anhydride at a temperature of from cooling with ice water to room temperature. The above mentioned sulfonation may be effected by, for example, reacting the resulting compound of the general formula (X) with a sulfonyl chloride substituted by a group R$^5$ in a solvent, such as pyridine, at a temperature of from cooling with ice water to room temperature. The urearization mentioned above can be attained by, for example, reacting the resulting compound of the general formula (X) with sodium cyanate (NaOCN) at room temperature or under heating at, for example, 60° C. in a mixed solvent of water/acetic acid.

Alternatively, there is a method in which a racemic compound is obtained by a brief process step using, in the place of the compound of the general formula (II), the compound represented by the general formula (V)

(V)

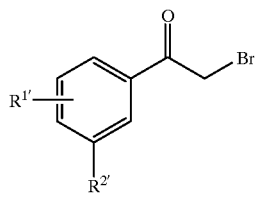

in which R$^{1'}$ and R$^{2'}$ have the same meanings as given previously.

Thus, the compound represented by the above general formula (V) is reacted with the compound represented by the general formula (III) in which Y is hydrogen atom and the resulting ketoamine compound is, then, reduced, whereupon the protecting groups A, A", A'" and that for protecting the amino group in the group R$^{3'}$ are de-protected, with the proviso that the deprotection of the protecting group A is unnecessary for the case where R$^1$ stands for benzyloxy and the protecting group A is benzyl, whereby the compound represented by the general formula (I) in which R is hydrogen atom and R$^1$, R$^2$, R$^6$, X, R$^7$, R$^8$, R$^9$, *1 and *2 have the same meanings as those given previously is obtained.

The reaction of the compound of the general formula (V) with the compound of the general formula (III) can be attained by the method disclosed in the literature, A. A. Larsen et al, J. Med. Chem., 10, 462 (1967), with an improvement in such a manner that the reaction is effected in a polar solvent, such as acetonitrile, dimethylformamide, dimethylacetamide or dimethylsulfoxide, in the presence or absence of an amine as the acidcapturing agent under cooling with ice water or with heating at a temperature up to 60° C., followed by reduction of the carbonyl group using a reducing agent, such as sodium borohydride or sodium cyanoborohydride, under cooling with ice water or at room temperature, followed by deprotection of the protecting group. By this reaction, a racemic mixture of *1 is obtained, so that an optical resolution by the method as given afterwards becomes necessary for obtaining each optical active compound.

Production Process B

As an alternative production process in which each optical active compound or racemic modification is obtained, a technique using an epoxide may be incorporated.

Thus, the compound represented by the general formula (I) in which R is hydrogen atom and $R^1$, $R^2$, $R^6$, X, $R^{7'}$, $R^{8'}$, $R^{9'}$, *1 and *2 have the same meanings as those given previously can be produced by reacting a compound represented by the general formula (XII),

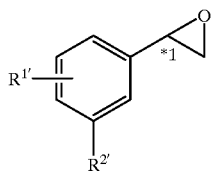

(XII)

in which R', $R^{2'}$ and *1 have the meanings as those given previously, with the compound represented by, the general formula (III) in which Y denotes hydrogen atom and X, $R^6$, $R^{7'}$, $R^8$, $R^{9'}$ and *2 have the same meanings as those defined previously, followed by deprotection of the pretecting groups A, A'', A''', that for protecting the amino group in the substituent $R^3$ and the protecting acetyl group for $R^{1'}$ by the method described in the paragraph "Production Process A", with the proviso that the deprotection of the protecting group A is unnecessary when $R^1$ is benzyloxy and the protecting group A is benzyl.

The reaction of the compound represented by the general formula (XII) with the compound represented by the general formula (III) can be carried out in a usual organic solvent, for example, dimethylsulfoxide, a straight chained or cyclic ether, dimethylformamide or dimethylacetamide. While the compound represented by the general formula (XII) and that represented by the general formula (III) are used often in an equimolar proportion, it is preferable to use an excess of the compound represented by the general formula (III) over the compound of the general formula (XII). The reaction is effected at an adequate temperature and, usually. at room temperature or the reflux temperature of the solvent employed. The reaction duration may be selected in accordance with the reaction condition and other factors and, usually, the reaction can be terminated at the point at which the yield becomes maximum.

It was reported that the yield of the reaction can be increased and the reaction duration is reduced by adding to the reaction mixture trimethylsilylacetamide (TMSA) [N,O-bis(trimethylsilylacetamide)], hexamethyldisilazane (HMDS) or bis(trimethylsilyl)urea [Tetrahedron Letters.27, 2451 (1986)] and this may adequately be incorporated herein.

The compound represented by the general formula (XII) is known and can be synthesized by an ordinary method given in chemical literatures. For example, the general formula (XII) can be produced by oxidizing styrene or a substituted styrene derivative using a peracid, such as m-chloroperbenzoic acid, or by reacting dimethylsulfonium methylideor dimethylsulfoxonium methylide with a substituted benzaldehyde having a substituent group corresponding to $R^{1'}$ or $R^{2\ '}$, as described in J. Am. Chem. Soc., 87, 1353 (1956).

An optical active compound represented by the general formula (XII) can be produced by reducing the compound represented by the general formula (II) or a substituted mandelic acid derivative in which the α-carbon atom (*1) is in a desired absolute configuration into a corresponding glycol derivative, tosylating or mesylating or halogenating, then, the resulting primary alcohol and cyclizing the resulting compound using a strong base, such as an alkali metal hydroxide, under a usual intramolecular nucleophilic substitution reaction.

Production Process C

Alternatively further, there is a method for producing a racemic modification by condensing a phenylglyoxal compound represented by the general formula (XIII)

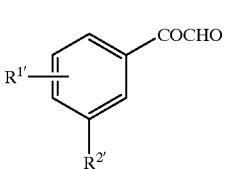

(XIII)

in which $R^{1'}$ and $R^{2'}$ have the same meanings as those given previously with an amine compound represented by the general formula (III) in which Y is hydrogen atom and X, $R^{6'}$, $R^{7'}$, $R^{8'}$, $R^{9'}$ and *2 have the same meanings as those given previously and reducing the resulting compound, with final deprotection of the protecting groups A, A'', A''' the protecting group for the amino group of $R^{3'}$ and the protecting acetyl group of $R^{1'}$ by the procedure described in the paragraph of "Production Process A", with the proviso that the deprotection of the protecting group A is unnecessary when $R^1$ is benzyloxy and the protecting group A is benzyl.

This reaction is carried out in general in a reaction solvent by reducing the Schiff base resulting from the condensation reaction using an adequate reducing agent capable of reducing the Schiff base and at the same time reducing the oxo-group into hydroxyl group. As the reducing agent, there may be employed, for example, sodium borohydride, sodium cyanoborohydride and lithium cyanoborohydride. The proportion of the phenylglyoxal compound to the amine compound is in general 1–3 moles, preferably 1–1.5 moles of the former to 1 mole of the amine compound. Reaction may be carried out at an adequate temperature and, in general, at a temperature from room temperature to the reflux temperature of the solvent employed. The reaction duration may adequately be chosen in accordance with the reaction condition and so on and may be terminated at a point at which the reaction yield becomes highest. The above reactions may be carried out in a reaction solvent based on alcohol. such as methanol or ethanol, preferably at a low temperature in the presence of sodium borohydride.

The compound of the general formula (XII) can be obtained easily by oxidizing an acetophenone derivative substituted by $R^{1'}$ and $R^{2'}$ in a reaction medium of water or an organic solvent, for example, acyclic ether, such as dioxane or tetrahydrofuran, using an oxidizing agent, such as selenium dioxide. Alternatively, it can be produced by the process described in J. Am. Chem. Soc., 79, 6562 (1957).

Production Process D

The compound represented by the general formula (I) in which R is hydrogen atom and $R^1$, $R^2$, $R^6$, X, $R^7$, $R^8$, $R^9$, *1 and *2 have the same meanings as those given previously can be obtained also by reacting an amine compound represented by the general formula (XIV),

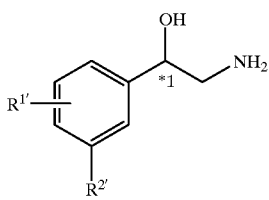

(XIV)

in which $R^{1'}$, $R^{2'}$ and *1 have the same meanings as those given previously, with a compound represented by the general formula (XV),

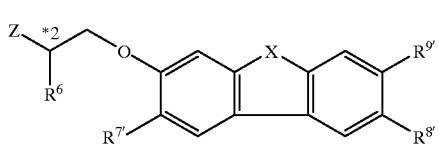

(XV)

in which $R^6$, X, $R^{7'}$, $R^{8'}$, $R^{9'}$ and *2 have the same meanings as those given previously and Z denotes an eliminable group, followed by deprotection of the protecting groups A, A", A'" that protecting the amino group in $R^{3'}$ and the protecting acetyl group in $R^{1'}$ by the method described in the paragraph "Production Process A", with the proviso that the deprotection of the protecting group A is unnecessary when $R^1$ is benzyloxy and the protecting group A is benzyl.

By effecting the coupling reaction with the amine compound in an organic solvent, if necessary, in the presence of a proton-acceptor, such as a tertiaryamine, for example, triethylamine, the compound represented by the general formula (I) is obtained. The "eliminable group" means a group which is eliminated upon the above reaction of the chloride, bromide or iodide group or mesyl or tosyl group with, for example, sulfonate or so on. The reaction may be realized, for example, using, in general, 1–10 moles of the amine compound represented by the general formula (XIV) per one mole of the compound represented by the general formula (XV).

Since this reaction proceeds at a lower velocity, the reaction may preferably be effected in an autoclave in a reaction solvent, for example, an alcohol, such as methanol, ethanol or butanol, a halogenated hydrocarbon, such as methylene chloride or chloroform, or tetrahydrofuran or dioxane. The reaction temperature is chosen, in general, in the range from 10 to 150° C., preferably from 70 to 130° C. The reaction duration is chosen, in general, in the range from 5 to 100 hours.

The compound of the general formula (XIV) can be obtained by hydrogenating a substituted mandelonitrile substituted by $R^{1'}$ and $R^{2'}$ in the presence of a catalyst, such as Raney nickel. The substituted mandelonitrile can be produced by a reaction of a substituted benzaldehyde with hydrogen cyanide or with sodium cyanate together with sodium hydrogen sulfite as a racemic compound from which each optical active isomer can easily be separated by methods and techniques employed commonly by preparing salts of the diastereomers with an optically active acid selected adequately. The optically active substituted mandelonitrile derivative can be obtained by reacting the optically active carboxylic acid resulting from hydrolysis of the optically active substituted mandelonitrile with ammonia in the presence of a commonly employed condensing agent, followed by reduction of the resulting product.

The compound of the general formula (XV) can be obtained by reacting a phenol compound represented by the general formula (VIII) with a compound represented by the general formula (XVI),

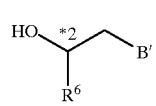

(XVI)

in which $R^6$ and *2 have the same meanings as those given previously and B' is a halogen atom, or with a compound represented by the general formula (XVII),

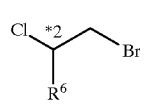

(XVII)

in which $R^6$ and *2 have the same meanings as those given previously, under the condition of synthesizing the compound represented by the general formula (III) described in the paragraph of "Production Process A", followed by tosylating or mesylating the alcohol resulting from the above reaction with the compound represented by the general formula (XVI).

Production Process E

The compound represented by the general formula (I) in which R is methyl can be produced by methylating the alcohol compound of the general formula (I) in which R is hydrogen atom produced by the "Production Process" A, B, C or D under a commonly employed acidic condition. Thus, the compound of the general formula (I) in which R is methyl can be produce by treating the compound of the general formula (I) in which R is hydrogen atom with hydrogen chloride in methanol at a temperature from room temperature to the boiling point of the reaction medium.

The compound represented by the general formula (XVIII),

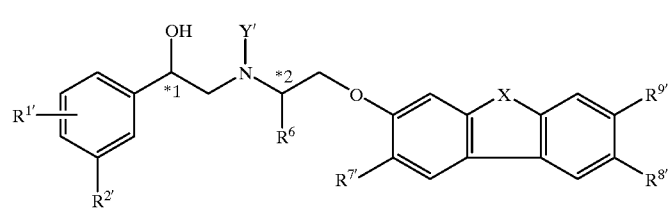

(XVIII)

which $R^{1'}$, $R^{2'}$, $R^6$, Y', X, $R^{7'}$, $R^{8'}$, $R^{9'}$, *1 and *2 have the same meanings as those given previously, which is a compound in which the amino group of the amine compound formed in the process for producing the compound represented by the general formula (I) in which R is hydrogen atom is protected by the protecting group Y' and in which a possible protecting group A' for the hydroxyl group, if present, is de-protected by the method described above, is processed by methylation of the hydroxyl group by a commonly used technique. By de-protecting the protecting group Y' for the amino group and those of A, A", A'" and that protecting the amino group in $R^{3'}$, if present, as well as the protecting acetyl group in $R^{3'}$, with the proviso that the deprotection of the protecting group A is unnecessary when $R^1$ is benzyloxy and the protecting group A is benzyl, the compound represented by the general formula (I) in which R is methyl and $R^1$, $R^2$, $R^6$, X, $R^7$, $R^8$, $R^9$, *1 and *2 have the same meanings as those given previously is obtained.

A concrete example of methylation of the hydroxyl group consists in that the compound is reacted with 1–5 equivalents of methyl iodide or methyl bromide in the presence of a base, such as potassium carbonate, triethylamine, sodium hydroxide or sodium hydride, in a solvent, such as dimethylsulfdxide, dimethylformamide, dimethoxyethane or tetrahydrofuran, at a temperature in the range from room temperature to the reflux temperature of the solvent. An alternative embodiment consists in that the compound is reacted, in a form of its alkaline solution containing sodium hydroxide or potassium hydroxide in water or in methanol, with 2–10 equivalents of dimethyl sulfate at a temperature in the range from room temperature to the reflux temperature of the solvent.

The starting compounds of the present invention may, if necessary, be purified, wherein known chromatographic techniques including column-, flush column-, thin layer- and high performance liquid chromatography may be employed therefor by taking into account of such a parameter as the Rf value given in this specification.

As described above, the compound represented by the general formula (I) may be present as four or two different isomers. The process according to the present invention can provide both the pure isomer and the racemic mixture. The reactions described above do not alter the pertaining stereo chemistry.

Therefore, starting from the compound of the general formula (V) or of the general formula (XIII) having no asymmetric carbon atom, starting from the racemic compound represented by the general formula (II), (XII) or (XIV), or starting from the racemic compound represented by the general formula (III) or (XV), isomeric mixtures (R,R), (R,S), (S,S) and (S,R) are obtained. Similarly, starting from the pure isomer of the general formula (III) or (XV) and, for example, from the R-isomer of the general formula (III), mixtures of only two isomers (R,R) and (S,R) are obtained and, if an optical active isomer of the general formula (II), (XII) or (XIV) is employed, corresponding pure isomer can be obtained.

When a mixture of the four isomers or of two isomers is obtained. the isomers can be separated by a pertinent technique, such as fractional crystallization or the like, as their addition salts with an optically active acid, such as camphor sulfonic acid, mandelic acid or a substituted mandelic acid. The fractional crystallization may be performed using an adequate solvent, preferably a lower alkanol, such as ethanol or isopropanol or a mixture of them.

Every pair of the enantiomers can be separated into each optical active isomer by, for example, forming a diastereomeric salt and chromatographic separation on an optically active column, or by other means. When one of the starting raw materials is optically active, the mixture of the diastereomers obtained as above can be divided into each pure isomer. By separating each of the optical active isomers and purifying it, it becomes possible to improve the pharmacological effect or to eliminate side effects by using only the isomer having more higher activity which is preferable as a medicament.

As the salt of the compound represented by the general formula (I) according to the present invention, there may, be exemplified salts with known acids, for example, addition salts thereof with mineral acids and organic acids, such as hydrochloric acid, hydrobromic acid, sulfuric acid, hydrogen sulfuric acid, dihydrogen phosphoric acid, citric acid, maleic acid, tartaric acid, fumaric acid, gluconic acid and methane sulfonic acid; and with optically active acids, such as camphor sulfonic acid, mandelic acid and substituted mandelic acids, wherein special preference is given to those which are medicamentally acceptable.

For preparing a salt of the compound represented by the general formula (I), the compound of the general formula (I) is dissolved in an alcohol, such as methanol or ethanol, and the acid component is added to the resulting alcoholic solution, whereby the corresponding acid addition salt can be obtained. Examples of the acids to be used therefor include mineral acids and organic acids which are medicamentally acceptable, such as hydrochloric acid, hydrobromic acid, sulfuric acid, hydrogen sulfuric acid, dihydrogen phosphoric acid, citric acid, maleic acid, tartaric acid, fumaric acid, gluconic acid and methane sulfonic acid.

The tricyclic compounds and the pharmacologically acceptable salts according to the present invention have no recognizable toxicity and are useful as medicaments and exhibit, for example, β3-activity, so that they can be utilized as medicaments for therapeutic and preventive treatments of β3-correlating diseases. The "β3-correlating diseases" is a generic expression for diseases which can be improved by a functional activity mediated β3-adrenaline receptor and include, for example, diabetes, obesity, hyperlipemia, diseasses in digestive system, such as abnormal motion and ulcer in digestive system, and depression. In particular, the compound according to the present invention serves for treating diabetes, obesity and hyperlipemia. Thus, the compound according to the present invention is effective as a medicament for preventive or therapeutic treatment of diabetes due to its function for decreasing the blood sugar value and is also effective for preventive treatment of hyperlipemia and therapeutic treatment of obesity due to its lipolytic activity.

In preparing a medicament from the compound according to the present invention, it is preferable to admix, if necessary, to an effective amount of the tricyclic compound represented by the general formula (I) or salt thereof a pharmacologically acceptable carrier to formulate a drug composition. As the pharmacologically acceptable carrier, there may be exemplified excipients, binding agents, such as carboxymethylcellulose etc., disintegrator, lubricants and various additives.

For administering the drug containing the compound according to the present invention to human, oral administration of the drug in a form of tablet, powder, granules, capsule, sugar-coated tablet, liquid drug or syrup. Drugs for parenteral administration, such as injection drugs, may also be possible. The dose amount of administration may be different in accordance with the age, body weight, significance of the disease, symptom and so on and the dose may, in general, be in an amount of 0.01–2,000 mg per day for an adult all at once or allotted in several administrations. The term for receiving such drug may in general, range from several weeks to several months with daily administration, while it is possible to increase or decrease both the term and the daily dose in accordance with the state of the disease of patient.

THE BEST MODE FOR EMBODYING THE INVENTION

Below, the present invention will further be described by way of Examples, wherein the present invention should not be understood as being restricted thereto.

For thin layer chromatography (TLC), Precoated Silica Gel 60 F254 (of the firm Merck) was employed. After development with a mixed solvent of chloroform/methanol (100/1–4/1) or ethyl acetate/n-hexane (100/0–1/10), confirmation by UV-irradiation (254 nm) and color reaction with ninhydrin was performed. The Rf values of TLC cited refer to those of the free amines. For drying the organic solvent, anhydrous magnesium sulfate or anhydrous sodium sulfate was used. A silica gel(Wako-gel C-200, a product of Wako Pure Chemical Ind., Ltd.) was used for the column chromatography and Silica Gel 60 (230–400 mesh, a product of the firm Merck) was used for the flush column chromatography. Pre-Coated Silica Gel 60 F254 (20×20 cm, 2 mm; supplied from Merck) was used for the parting thin layer chromatography. Elution was effected using a mixed developer of chloroform/methanol (1/1).

For observing the nuclear magnetic resonance spectrum (NMR), Gemini-300 (FT-NMR; of the firm Varian) was employed. As the solvent, heavy chloroform was used so long as no special mention is made. Tetramethylsilane (TMS) was used as the internal standard for the chemical shift which was recorded in terms of (δppm). The coupling constant is indicated by J(Hz). For observing mass spectrum (MS), JEOL-JMS-SX102 was employed and the observation was made by fast atom bombardment mass spectrum (FAB-MS). The results of the tests are summarized in Table 1.

EXAMPLE 1

(±)-N-[5-[2-[2-(9H-carbazol-2-yloxy)ethylamino]-1-hydroxyethyl]-2-benzyloxyphenyl] methanesulfonamide hydrochloride A. Synthesis of 2-benzyloxycarbonylamino-1-bromoethane (Intermediate 0)

To a solution of 25 g of 2-bromoethylamine hydrochloride (supplied from Tokyo Chemical Industry Co., Ltd.) and 34 ml of triethylamine in 450 ml of methylene chloride, 19 ml of benzyloxycarbonyl chloride were added dropwise over a period of 20 minutes under cooling by ice water with agitation, whereupon the agitation was continued for further 19 hours. The reaction mixture was then rinsed with water, saturated aqueous sodium bicarbonate solution and saturated aqueous sodium chloride solution successively, whereupon the organic layer was dried and the solvent was evaporated off under a reduced pressure. The residue was cooled with ice water and the crystals were filtered off and washed with hexane, whereby 29.4 g of the above-identified compound were obtained. Rf=0.58 (chloroform).

B. Synthesis of 9H-2-(2-benzyloxycarbonylaminoethoxy)-carbazole (Intermediate 1)

To a solution of 252 mg of 2-hydroxycarbazole(supplied from the firm Aldrich) and 292 mg of potassium carbonate in 4 ml of dimethylformamide, 452 mg of the above Intermediate 0 were added and the mixture was heated at 70° C. for 72 hours. To the reaction mixture, ethyl acetate and water were added to effect extraction and the organic layer was rinsed with water and dried, from which the solvent was distilled off under a reduced pressure and the residue was purified by a column chromatography (with methanol/chloroform of 1/100), whereby 184.7 mg of the above-identified compound were obtained. Rf=0.77 (methanol/chloroform of 1/10).

C. Synthesis of 2-(9H-carbazol-2-yloxy)ethylamine (Intermediate 2)

To 620 mg of Intermediate 1, 5 ml of 30% solution of hydrogen bromide in acetic acid were added and the mixture was agitated at room temperature for 1.5 hours. To the reaction mixture, diethylether was added under cooling with ice water and the deposited precipitate was isolated by filtration. Water and NaOH were added to adjust the pH of the resulting mixture at 10. whereupon the mixture was subjected to extraction with ethyl acetate. The organic layer was dried and the solvent was distilled off under a reduced pressure, whereby 311.3 mg of the above-identified compound were obtained. Rf=0.08 (methanol/chloroform of 1/10).

D. Synthesis of (±)-N-[5-[2-[2-(9H-carbazol-2-yloxy)-ethylamino]-1-hydroxyethyl]-2-benzyloxyphe methanesulfonamide hydrochloride To a solution of 500 mg of Intermediate 2 in a mixed solvent of 40 ml of anhydrous acetonitrile and 4 ml of anhydrous dimethylformamide, 670 mg of 2-bromo-1-[4-benzyloxy-3-[(methylsulfonyl)amino]phenyl]ethanone (70% purity)(fntermediate 3)[prepared by the method reported by A. A. Larsen et al, J. Med. Chem., 10, 462–472 (1967)] were added and the mixture was agitated under argon atmosphere at 0° C. for 83 minutes.

This mixture was warmed to the room temperature (ca. 22° C.) and was agitated for 79 minutes. To this mixture, a solution of 352 mg of sodium borohydride in 30 ml of anhydrous ethanol were added at room temperature. After agitation for 81 minutes, the reaction was terminated using 1.0 N hydrochloric acid (pH 4) and thereto was added 0.89 g of ethanolamine. After agitation for 10 minutes, the mixture was diluted with 100 ml of ethyl acetate and the organic layer was rinsed with saturated aqueous sodium chloride solution (three times with each 100 ml) and was dried and concentrated under a reduced pressure to obtain 1.09 g of a crude product.

This was purified by a column chromatography (ethyl acetate-1/8: methanol/chloroform), whereby 195 mg of the above-identified compound as free amine were obtained. Rf=0.41 (methanol/chloroform of 1/10). To a part of this compound, 1.1 eq. of 0.1 N HCl/ethanol were added to convert it into hydrochloride salt(the above-identified compound as free amine were obtained. Rf=0.41 (methanol/chloroform Diethyl ether was added to the residue and the deposited precipitate was isolated by filtration, washed with diethyl ether, dried under a reduced pressure at 500° C., whereby 48.5 mg of the above-identified compound were obtained as a powdery product.

EXAMPLE 2

(±)-N-[5-[2-[2-(9H-carbazol-2-yloxy)ethylamino]-1-hydroxyethyl]-2-hydroxyphenyl] methanesulfonamide hydrochloride 753 mg of hydrochloride salt of the compound of Example 1 were subjected to hydrogenolysis using 406 mg of 10% palladium/carbon black (supplied from Merck) and 85 ml of methanol under 1 atm hydrogen gas (room temperature, 2.5 hours). The catalyst was filtered off on celite and washed with chloroform and methanol. The filtrate and the washed liquor were brought together and the solvent was distilled off under a reduced pressure, whereby 520 mg of the above-identified compound were obtained as a pale yellow powdery product. Rf=0.11 (methanol/chloroform of 1/10).

EXAMPLE 3

(±)-N-[5-[2-[2-(dibenzofuran-3-yloxy)ethylamino]-1hydroxyethyl]-2-benzyloxyphenyl]methanesulfonamide A. Synthesis of 3-hydroxydibenzofuran To a solution of 1 g of 3-methoxydibenzofuran (provided from the firm SALOR) in 5 ml of methylene chloride, 10.2 ml of 1 M solution of boron tribromide in methylene chloride were added dropwise. The reaction mixture was agitated for 30 minutes under cooling with ice water and, then, warmed to room temperature and agitated further 35 minutes. Thereto were added 26 ml of water all at once and the mixture was caused to temperature elevation up to room temperature over a period of 30 minutes with vigorous agitation. The organic layer was separated off and the aqueous layer was extracted twice with methylene chloride. The united organic phase was rinsed with saturated aqueous sodium chloride solution and dried and was then concentrated under a reduced pressure to obtain 663.1 mg of the above-identified compound.

B. Synthesis of 3-(2-benzyloxycarbonylaminoethoxy)-dibenzofuran (Intermediate 4)

Following the procedures given in the step B of Example 1, 321.3 mg of 3-hydroxydibenzofuran. 541 mg of Intermediate 0 and 1, 2 g of potassium carbonate were brought into reaction in 4.5 ml of dimethylformamide. Thereto were added ethyl acetate and water to effect extraction and the organic layer was rinsed with water and dried, from which the solvent was distilled off under a reduced pressure and the residue was purified by a column chromatography (chloroform), whereby 574.2 mg of the above-identified compound were obtained. Rf=0.40 (chloroform).

C. Synthesis of 2-(dibenzofuran-3-yloxy)ethylamine (Intermediate 5)

Following the procedures of step C in Example 1, 7 ml of 30% solution of hydrogen bromide in acetic acid were added to 554.7 mg of Intermediate 4 and the mixture was agitated at room temperature for 1 hour. Thereto was added diethyl ether under cooling with ice and the deposited precipitate was isolated by filtration. Thereto were added water and NaOH to adjust the pH of the mixture at 10, whereupon the mixture was subjected to extraction with ethyl acetate. The organic layer was dried and the solvent was distilled off under a reduced pressure, whereby 224.6 mg of the above-identified compound were obtained. Rf=0.13 (methanol/chloroform of 1/10).

D. Synthesis of (±)-N-[5-[2-[2-(dibenzofuran-3-yloxy)ethylamino]-1-hydroxyethyl]-2-benzyloxyphenyl]-methanesulfonamide By a modification of the procedures described in the step D of Example 1, a solution of 227 mg of Intermediate 3 (70% purity) was added to a solution of 91.6 mg of Intermediate 5 in a mixed solvent composed of 4 ml of anhydrous acetonitrile and 1 ml of anhydrous dimethylformamide under argon atmosphere at 0° C. and thereto were further added 56.3 µl of triethylamine, whereupon the resulting mixture was warmed to the room temperature (ca. 22° C.) and was agitated for 50 minutes. To this mixture, a solution of 80 mg of sodium borohydride in 4 ml of anhydrous ethanol was added at room temperature. After agitation for 77 minutes, the reaction was terminated using 1 N hydrochloric acid (pH 4) and thereto were added 123 µl of ethanolamine. After agitation for 10 minutes, the mixture was diluted with ethyl acetate and the organic layer was rinsed thrice with saturated aqueous sodium chloride solution and was dried and concentrated under a reduced pressure to obtain a crude product. This was purified by a column chromatography (chloroform-3/100: methanol/chloroform), whereby 52.4 mg of the above-identified compound were obtained. Rf=0.37 (methanol/chloroform of 3/100).

EXAMPLE 4

(±)-N-[5-[2-[2-(dibenzofuran-3-yloxy)ethylamino]-1-hydroxyethyl]-2-hydroxyphenyl]methanesulfonamide hydrochloride Following the procedures of Example 2, 52.4 mg of the compound of Example 3 were subjected to a hydrogenolysis under 1 atm hydrogen gas using 30 mg of 10% palladium/carbon black and 6.4 ml of methanol with 4.7 µl of acetic acid (room temperature, 1 hour). The catalyst was filtered off on celite and was then washed with chloroform and methanol. The filtrate and the washed liquor were brought together, from which the solvent was distilled off. To the resulting residue, ethyl acetate and saturated aqueous sodium bicarbonate solution were added to carry out extraction and the organic layer was dried, from which the solvent was distilled off under a reduced pressure. The resulting product was converted into hydrochloride salt by adding thereto 1.1 eq. of 0.1 N hydrochloric acid/ethanol, whereby 43.3 mg of the above-identified compound were obtained as a pale orange powdery product. Rf=0.07(methanol/chloroform of 1/10).

EXAMPLE 5

(±)-N-[5-[2-[2-(9H-carbazol-2-yloxy)ethylamino]-1-hydroxyethyl]-2-fluorophenyl]methanesulfonamide hydrochloride 2-bromo-1-[4-fluoro-3-[(methylsulfonyl)aminolphenyl]ethanone was prepared in accordance with the procedures for the synthesis of Intermediate 3 (with subsequence steps A, B, C and D).

A. Synthesis of 1-(4-fluoro-3-nitrophenyl)ethanone (Intermediate 6)

13.8 g of 4'-fluoroacetophenone (provided from Tokyo Chemical Industry Co., Ltd.) were added in two portions to 100 ml of fuming nitric acid cooled to −10° C. with agitation. After the mixture was warmed to room temperature, the agitation was continued for further 4 hours. This mixture was poured into 1.0 liter of ice water and was extracted with 500 ml of ethyl acetate. The organic layer was dried and the solvent was distilled off under a reduced pressure. The residue was purified by a column chromatography (9/1–4/1: n-hexane/ethyl acetate) twice, whereby 4.16 g of the above-identified were obtained. Rf=0.50 (chloroform).

B. Synthesis of 1-(3-amino-4-fluorophenyl)ethanone (Intermediate 7)

To a solution of 4.16 g of Intermediate 6 in 305 ml of methanol which had been purged with argon, 189.7 mg of palladium oxide were added and the mixture was subjected to reduction under 1 atm hydrogen gas at room temperature. After agitation for 6 hours, the reaction system was replaced with argon and the reaction mixture was diluted with chloroform and was filtered. The solvent was evaporated off under a reduced pressure, whereby 3.52 g of the above-identified compound were obtained. Rf=0.47 (ethyl acetate/n-hexane of 1/1).

C. Synthesis of 1-[4-fluoro-3-[(methylsulfonyl)amino]-phenyl]ethanone (Intermediate 8)

To a solution of 3.48 g of the Intermediate 7 in 100 ml of pyridine, 1.93 ml of methanesulfonyl chloride were added at room temperature. After agitation for 2.5 days, the reaction mixture was poured into saturated aqueous ammonium chloride solution and was subjected to extraction with 200 ml of ethyl acetate. The organic layer was washed with saturated aqueous sodium chloride solution (three times with 100 ml) and dried and the solvent was distilled off under a reduced pressure to obtain a crude product. This was purified by a column chromatography (1/1 of n-hexane/ethyl acetate), whereby 3.9 g of the above-identified compound were obtained. Rf=0.23 (ethyl acetate/n-hexane of 1/1).

D. Synthesis of 2-bromo-1-[4-fluoro-3-[(methylsulfonyl)-amino]phenyl]ethanone (Intermediate 9)

To a solution of 3.9 g of Intermediate 8 in 50 ml of 1,4-dioxane, 2.83 g of bromine were added with agitation, the resulting mixture was warmed to 60° C. and was agitated for 1 hour. After having been cooled to room temperature, the mixture was subjected to evaporation under a reduced pressure. Water was added to the resulting residue and the deposited precipitate was crushed and was filtered off, which was washed with cold ethanol. After drying and recrystallization from ethanol, 3.69 g of the above-identified compound were obtained. Rf=0.30 (with thrice developments; ethyl acetate/n-hexane of 1/2).

E. Synthesis of (±)-N-[5-[2-[2-(9H-carbazol-2-yloxy) ethylamino]-1-hydroxyethy]-2-fluorophenyl] methanesulfonamide hydrochloride According to a modification of procedures described in the step D of Example 1, a solution of 310 mg of Intermediate 9 in 3 ml of anhydrous acetonitrile was added to a solution of 226 mg of Intermediate 2 in a mixed solvent composed of 20 ml of anhydrous acetonitrile and 2 ml of anhydrous dimethylformamide under argon atmosphere at 0° C. and thereto were added 103 µl of triethylamine, whereupon the mixture was warmed to the room temperature (ca. 22° C.) and was agitated for 50 minutes.

To this mixture was added a solution of 189 mg of sodium borohydride in 15 ml of anhydrous ethanol at room temperature. After agitation for 77 minutes, the reaction was terminated using 1 N hydrochloric acid (pH 4) and, then, 479 µl of ethanolamine were added thereto. After agitation for 10 minutes, the resulting mixture was diluted with ethyl acetate and the organic layer was rinsed with saturated aqueous sodium chloride solution three times, whereupon it was dried and subjected to evaporation under a reduced pressure to obtain a crude product. This was purified by a column chromatography (chloroform-3/100: methanol/chlroroform), whereby 239.8 mg of free amine product of the above-identified compound were obtained. To this product, 1.1 eq. of 0.1 N hydrochloric acid/ethanol were added to convert it into hydrochloride salt (the above-identified compound) and the solvent was distilled off under a reduced pressure. Diethyl ether was added to the resulting residue and the deposited precipitate was filtered off, followed by washing with hot ethanol and drying at 50° C. under reduced pressure to obtain 121.1 mg of the above-identified compound as a powdery product. Rf=0.37 (methanol/chloroform of 1/6).

EXAMPLE 6

(±)-N-[5-[2-[2-(9H-carbazol-2-yloxy)ethylamino]-1-hydroxyethyl]-2-chlorophenyl]methanesulfonamide hydrochloride 2-bromo-1-[4-chloro-3-[(methylsulfonyl)amino]phenyl] ethanone was prepared in a manner similar to the synthesis method of Intermediate 3 and in the same manner as in the steps A, B, C and D of Example 5.

A. Synthesis of 1-(4-chloro-3-nitrophenyl)ethanone (Intermediate 10)

15.5 g of 4'-chloroacetophenone (Tokyo Chemical Industry Co., Ltd.) were added in two portions to 100 ml of fuming nitric acid cooled to −10° C. with agitation. The resulting mixture was warmed to room temperature and was agitated for four hours. This mixture was poured into 1.6 liters of ice water and was then subjected to extraction with 800 ml of ethyl acetate. The organic layer was separated and dried and the solvent was evaporated off under a reduced pressure. The resulting residue was purified by a column chromatography (9/1–4/1: n-hexane/ethyl acetate), whereby 1.2 g of the above-identified compound were obtained. Rf=0.52 (chloroform).

B. Synthesis of 1-(3-amino-4-chlorophenyl)ethanone (Intermediate 11)

To a solution of 1.2 g of Intermediate 10 in 260 ml of methanol, 7.63 g of tin (II) chloride and 5.48 ml of concentrated hydrochloric acid were added and the mixture was agitated at room temperature for 3.5 hours. The mixture was concentrated and washed with saturated aqueous sodium bicarbonate solution and was then subjected to extraction with ethyl acetate. The organic layer was concentrated under a reduced pressure, whereby 970 mg of the above-identified compound were obtained. Rf=0.49 (ethyl acetate/n-hexane of 1/1).

C. Synthesis of 1-[4-chloro-3-[(methylsulfonyl)amino]-phenyl]ethanone (Intermediate 12)

To a solution of 970 mg of the Intermediate 11 in 50 ml of pyridine, 487 µl of methanesulfonyl chloride were added at room temperature. After agitation for 2.5 days. the reaction mixture was poured into saturated aqueous ammonium chloride solution and was subjected to extraction with 100 ml of ethyl acetate. The organic layer was rinsed with saturated aqueous sodium chloride solution (three times with 50 ml) and dried and concentrated under a reduced pressure to obtain a crude product. This was purified by a column chromatography (n-hexane/ethyl acetate of 3/2–1/1), whereby 890 mg of the above-identified compound were obtained. Rf=0.41 (ethyl acetate/n-hexane of 1/1).

D. Synthesis of 2-bromo-1-[4-chloro-3-[(methylsulfonyl)-amino]phenyl]ethanone (Intermediate 13)

To a solution of 890 mg of Intermediate 12 in 10 ml of 1,4-dioxane, 605 mg of bromine were added with agitation. The resulting mixture was warmed to 60° C. and was agitated for 1 hour.

After having been cooled to room temperature, the mixture was concentrated under a reduced pressure. Water was added to the resulting residue and the deposited precipitate was crushed and filtered off, which was washed with cold ethanol. After drying and recrystallization from ethanol, 620 mg of the above-identified compound were obtained. Rf=0.39 (ethyl acetate/n-hexane of 1/1).

E. Synthesis of (±)-N-[5-[2-[2-(9H-carbazol-2-yloxy) ethylamino]-1-hydroxyethy]-2-chlorophenyl] methanesulfonamide hydrochloride According to a modification of procedures described in the step D of Example 1, a solution of 327 mg of Intermediate 13 in 3 ml of anhydrous acetonitrile was added to a solution of 226 mg of Intermediate 2 in a mixed solvent composed of 20 ml of anhydrous acetonitrile and 2 ml of anhydrous dimethylformamide under argon atmosphere at 0° C. and thereto were added 103 μl of triethylamine, whereupon the mixture was warmed to the room temperature (ca. 22° C.) and was agitated for 50 minutes.

To this mixture was added a solution of 189 mg of sodium borohydride in 15 ml of absolute ethanol at room temperature. After agitation for 77 minutes, the reaction was terminated using 1 N hydrochloric acid (pH 4) and, then, 479 μl of ethanolamine were added thereto. After agitation for 10 minutes, the resulting mixture was diluted with ethyl acetate and the organic layer was rinsed with saturated aqueous sodium chloride solution three times, whereupon it was dried and subjected to evaporation under a reduced pressure to obtain a crude product. This was purified by a column chromatography (1/9–1/6: methanol/chrloroform), whereby 129.8 mg of free amine product of the above-identified compound were obtained. Rf=0.36 (methanol/chloroform of 1/6).

To this product, 1.1 eq. of 0.1 N hydrochloric acid/ethanol were added to convert it into hydrochloride salt (the above-identified compound) and the solvent was distilled off under a reduced pressure. Diethyl ether was added to the resulting residue and the deposited precipitate was filtered off, followed by washing with hot ethanol and drying at 50° C. under reduced pressure to obtain 34.1 mg of the above-identified compound as a powdery product.

EXAMPLE 7

(±)-N-[3-[2-[2-(9H-carbazol-2-yloxy)ethylamino]-1-hydroxyethyl]phenyl]methanesulfonamide hydrochloride To a solution of 219.5 mg of Intermediate 2 in a mixed solvent of 20 ml of anhydrous acetonitrile and 2 ml of anhydrous dimethylformamide, 163.6 mg of 2-bromo-1-[3-(methylsulfonyl)aminophenyl]ethanone (Intermediate 14) [prepared by the method reported by A. A. Larsen etal, J. Med. Chem., 9, 88–97 (1996)] were added the mixture was agitated under argon atmoshere at 0° C. for 83 minutes.

This mixture was warmed to the room temperature(ca. 22° C.) and was agitated for 79 minutes. To this mixture, a solution of 110 mg of sodium borohydride in 10 ml of absolute ethanol were added at room temperature. After agitation for 81 minutes, the reaction was terminated using 1.0 N hydrochloric acid (pH 4) and thereto was added 0.28 ml of ethanolamine. After agitation for 10 minutes, the mixture was diluted with 30 ml of ethyl acetate and the organic layer was rinsed with saturated aqueous sodium chloride solution three times and was dried and concentrated under a reduced pressure to obtain 399 mg of a crude product. This was purified by a PTLC (developed with methanol/chloroform of 1/8), whereby 48.3 mg of the free amine were obtained. Rf=0.32 (methanol/chloroform of 1/4).

1.1 eq. of 0.1 N HCl/ethanol were added to convert it into hydrochloride salt (the above-identified compound) and the solvent was distilled off under a reduced pressure. Diethyl ether was added to the residue and the deposited precipitate was recrystallized from diethyl ether and dried under a reduced pressure at 50° C., whereby 38.7 mg of the above-identified compound were obtained as a powdery product.

EXAMPLE 8

(±)-N-[3-[2-[2-(9H-carbazol-2-yloxy)ethylamino]-1-hydroxyethyl]phenyl]phenylmethanesulfonamide hydrochloride A. Synthesis of 1-[3-benzylsulfonylamino)phenyl]ethanone (Intermediate 15)

Following the procedures of synthesis of Intermediate 14 in Example 7, 719 mg of the above-identified compound were prepared from 300 mg of 3'-aminoacetophenone (Tokyo Chemical Industry Co., Ltd.), 427 mg of benzylsulfonylchloride (Tokyo Chemical Industry Co., Ltd.) and 3 ml of pyridine.

B. Synthesis of 2-bromo-1-[3-(benzylsulfonylamino)phenyl]ethanone (Intermediate 15-1)

Following the procedures of Example 7, 130 μl of bromine were added to a solution of 700 mg of the Intermediate 15 in 6.8 ml of 1,4-dioxane to cause reaction, whereby a fraction containing the above-identified compound (786 mg) was obtained. This showed in $^1$H-NMR (300 MHz, CDCl$_3$) a integrated ratio of 29% of the monobromide isomer, 58% of dibromide isomer and 13% of unreacted starting compound. The product was served in the form of mixture as such for the subsequent reaction.

C. Synthesis of (±)-N-[5-[2-[2-(9H-carbazol-2-yloxy)ethylamino]-1-hydroxyethyl]phenyl]phenylmethanesulfonamide hydrochloride A solution of 465 mg of Intermediate 15-1 (58% purity) in 10 ml of anhydrous acetonitrile was added to a solution of 400 mg of Intermediate 2 in a mixed solvent composed of 40 ml of anhydrous acetonitrile and 4 ml of anhydrous dimethylformamide under argon atmosphere at 0° C. and the mixture was agitated for 80 minutes.

The mixture was warmed to the room temperature (ca. 22° C.) and was agitated for further 70 minutes. To this mixture was added a solution of 244 mg of sodium borohydride in 20 ml of absolute ethanol at room temperature. After agitation for 60 minute, the reaction was terminated using 1.0 N hydrochloric acid (pH 4) and thereto was added ethanolamine. After agitation for 10 minutes, the mixture was diluted with 60 ml of ethyl acetate and was rinsed with 60 ml of water, whereupon the organic layer was washed twice with saturated aqueous sodium chloride solution and was, after drying, subjected to evaporation under a reduced pressure to obtain a crude product. This was purified by a PTLC (developed with methanol/chloroform of 1/8), whereby 66 mg of free amine compound were obtained. Rf=0.16 (methanol/chloroform of 1/10).

This was converted into hydrochloride salt (the above-identified compound) by adding 1.1 eq. of 0.1 N hydrogen chloride/ethanol, whereupon the solvent was distilled off under a reduced pressure. To the residue was added diethyl ether and the deposited precipitate was washed with diethyl ether and dried at 46° C. under a reduced pressure, whereby 60 mg of the above-identified compound were obtained as a powdery product.

EXAMPLE 9

(±)-N-[3-[2-[2-(dibenzofuran-3-yloxy)ethylamino]-1-hydroxyethyl]phenyl]methanesulfonamide hydrochloride Following the procedures of Example 7, the above-identified compound was synthesized from 224.6 mg of Intermediate 5 and 170 mg of Intermediate 14, with the proviso that the following modification was incorporated. Thus, addition of dimethylformamide was omitted and the purification of the crude product was effected twice by a chromatography (methanol/chloroform of 1/20–1/10). The free amine compound (98.4 mg) was converted into its hydrochloride salt (the above-identified compound) with 1.1 eq. of 0.1 N hydrogenchloride/ethanol, whereupon the solvent was evaporated off under a reduced pressure. To the resulting residue was added diethyl ether and the deposited precipitate was washed diethyl ether and dried under a reduced pressure at 46° C., whereby the above-identified compound was obtained as a powdery product. Rf=0.27 (methanol/chloroform of 1/10).

EXAMPLE 10

(±)-N-[3-[2-[2-(9H-7-acetylaminofluoren-2-yloxy) ethylamino]-1-hydroxyethyl]phenyl] methanesulfonamide hydrochloride A. Synthesis of N-[7-[2-[(benzyloxycarbonyl)amino] ethoxy]-9H-fluoren-2-yl]acetamide (Intermediate 16)

Following the procedures of the step B of Example 1, 300 mg of 2-acetamide-7-hydroxyfluorene (supplied from the firm SALOR), 485.5 mg of Intermediate 0 and 241.2 mg of potassium carbonate were brought into reaction in 3 ml of dimethylformamide (heated at 70° C. for 24 hours). To the reaction mixture, ethyl acetate and water were added to subject to extraction and the organic layer was rinsed with water and dried, whereupon the solvent was distilled off and the residue was purified by a column chromatography (methanol/chloroform of 1/20) to obtain 431.9 mg of the above-identified compound. Rf=0.47 (methanol/chloroform of 1/10).

B. Synthesis of N-[9H-7-(2-aminoethoxy)fluorene]-2-acetamide (Intermediate 17)

Following the procedures of step C of Example 1, 5 ml of 30% solution of hydrogen bromide in acetic acid were added to 572.9 mg of Intermediate 16 and the mixture was agitated at room temperature for 1 hour. Thereto was added diethyl ether under cooling with ice and the deposited precipitate was isolated by filtration. Water and NaOH were added to adjust the pH of the mixture at 10, whereupon the mixture was subjected to extraction with ethyl acetate. The organic layer was dried and the solvent was distilled off under a reduced pressure, whereby 256.7 mg of the above-identified compound were obtained. Rf=0.06 (methanol/chloroform of 1/5).

C. Synthesis of (±)-N-[5-[2-[2-(9H-7-acetylaminofluoren-2-yloxy)ethylamino]-1-hydroxyethyl]phenyl] methanesulfonamide hydrochloride Following the procedures of Example 7, the above-identified compound was synthesized from 253.2 mg of intermediate 17 and 154.1 mg of Intermediate 14, with the proviso that the following modification was incorporated. Thus, addition of dimethylformamide was omitted and the purification of the crude product was effected by a chromatography (methanol/chloroform of 1/10) and a PTLC (development with methanol/chloroform of 1/5). The free amine compound (52.3 mg) was converted into its hydrochloride salt (the above-identified compound) with 1.1 eq. of 0.1 N hydrogen chloride/ethanol, whereupon the solvent was evaporated off under a reduced pressure. To the resulting residue was added diethyl ether and the deposited precipitate was washed diethyl ether and dried under a reduced pressure at 46° C., whereby the above-identified compound (45.1 mg) was obtained as a powdery product. Rf=0.40 (methanol/ chloroform of 1/5).

EXAMPLE 11

(±)-N-[3-[2-[[1-(9H-carbazol-2-yloxy)propan-2R-yl] amino]-1-hydroxyethyl]phenyl]methanesulfonamide hydrochloride A. Synthesis of (R)-[1-(9H-carbazol-2-yloxy)propan-2-yl] amine (Intermediate 18)

4.82 g of (R)-(–)-2-amino-1-propanol (supplied from the firm Aldrich) were dissolved in 157 ml of tetrahydrofuran and thereto were added 13.84 g of di-tert-butyl-dicarbonate at room temperature and the mixture was agitated for 18 hours. The solvent was evaporated off under a reduced pressure to obtain 11 g of a white solid product.

10.3 g of the above white solid product were dissolved together with 17.76 g of triphenylphosphine in 147 ml of methylene chloride, whereto 9.3 g of N-chlorosuccinimide were added in small portions under ice-cooling and the mixture was agitated at room temperature for 23 hours. The reaction liquor was washed with an aqueous sodium hydroxide and saturated aqueous sodium chloride solution successively, followed by drying and distilling off of the solvent under a reduced pressure. The residue was purified by a silica gel chromatography, whereby 5.89 g of (R)-2-(N-tert-butoxycarbonyl)amino-1-chloropropane were obtained. Rf=0.89 (methanol/chloroform of 1/9).

To a solution of 734 mg of 2-hydroxycarbazole and 815.6 mg of the above compound in 9.6 ml of dimethylformamide, 1,588 mg of anhydrous potassium carbonate and 190 mg of potassium iodide were added and the reaction and the after-treatment were performed in accordance with the procedures of the synthesis method in the step B of Example 1, whereby 597 mg of (R)-2-(N-tert-butoxycarbonylamino-1-propyloxy)carbazole were obtained. Rf=0.81 (methanol/ chloroform of 1/9).

To 597 mg of the above compound were added 10 ml of 30% solution of hydrogen bromide in acetic acid and the reaction and after-treatment were effected in accordance with the procedures of the synthetic method in the step C of Example 1, whereby 258 mg of Intermediate 18 were obtained. Rf=0.06 (methanol/ethyl acetate of 1/10).

B. Synthesis of (±)-N-[3-[2-[[1-(9H-carbazol-2-yloxy) propan-2R-yl]amino]-1-hydroxyethyl]phenyl] methanesulfonamide hydrochloride The above-identified compound was synthesized in accordance with the procedures of Example 7 by performing the reaction of the Intermediate 18 (120 mg) with Intermediate 14 (190 mg) and the after-treatments, with the proviso that the following alterations were incorporated. Thus, in the coupling reaction, 72 μl (1 eq.) of triethylamine were used as the basic catalyst and the purification of the crude product was effected by a PTLC (with development with methanol/ ethyl acetate of 1/9). The free amine compound (87.5 mg) was converted into its hydrochloride salt (the above-identified compound) using 1.1 eq. of 0.1 N solution of hydrogen chloride/ethanol and the solvent was distilled off under a reduced pressure. To the residue was added diethyl ether and the deposited precipitate was washed with diethyl ether and dried at 46° C. under a reduced pressure, whereby 80.5 mg of the above-identified compound was obtained as a powdery product. Rf=0.19 (methanol/ethyl acetate of 1/10).

EXAMPLE 12

(R)-N-[5-[2-[2-(9H-carbazol-2-yloxy)ethylamino]-1-hydroxyethyl]2-hydroxyphenyl]methanesulfonamide hydrochloride A. Synthesys of (R)-2-bromo-1-[3-nitro-4-(benzyloxy)-phenyl]ethanol (Intermediate 19)

To a solution of 1.01 g of 2-bromo-1-[3-nitro-4-(benzyloxy) phenyl]ethanone (70% purity) prepared according to the method reported by C. Kaiser et al in J. Med. Chem., 17 49 (1974) and 100 mg of (R)-3, 3-diphenyl-1-methyltetrahydro-1H, 3H-pyrolo[1,2-c][1.3.2]oxazaborol [a product of Tokyo Chemical Industry Co., Ltd. referred to hereinafter as the "asymmetric catalyst"; there are (R)- and (S)-modifications] in 20 ml of anhydrous tetrahydrofuran (prepared upon use). 2.16 ml of a 2 M solution of borane/dimethylsulfide complex in tetrahydrofuran (supplied from the firm Aldrich) were added dropwise over a period of 5 minutes and the mixture was agitate at the same temperature for 2 hours.

The reaction mixture was diluted with ethyl acetate and the so-diluted mixture was washed with saturated aqueous ammonium chloride solution and saturated aqueous sodium chloride successively, followed by drying and evaporating off of the solvent under a reduced pressure. The residue was purified by a column chromatography (ethyl acetate/n-hexane of 1/2–1/1), whereby 1.015 g of the above-identified compound were obtained. Rf=0.41 (ethyl acetate/n-hexane of 1/1).

Retention time: 35.7 min. Analytical conditions: column: CHIRAL-CEL OB (4.6 mm $\phi$, 25 cm long; supplied from Daicel Chem. Ind., Ltd.). Mobile phase: n-hexane/2-propanol (7/3); flow rate : 0.5 ml/min.; detection wave length: 254 nm; temperature: 35° C.

B. Synthesis of (R)-3-nitro-4-benzyloxy-[2-iodo-1-(triethylsilyloxy)ethyl]benzene (Intermediate 20)

To a solution of 695.6 mg of Intermediate 19 in 30 ml of acetone, 2.96 g of sodium iodide (supplied from Wako Pure Chemical Ind., Ltd.) were added and the mixture was heated under reflux for 2 hours. After cooling to room temperature, the mixture was treated by filtration and the solvent in the filtrate was evaporated off under a reduced pressure. To the resulting residue, chloroform and water were added and the organic layer was rinsed with saturated aqueous sodium thiosulfate solution and was dried, whereupon the solvent was evaporated off under a reduced pressure. The resulting oily product (0.78 g), imidazole (408.5 mg) and dimethylaminopyridine (24.4 mg) were dissolved in 5 ml of dimethylformaide, whereto 452 mg of triethylsilane chloride were added under ice-cooling. Directly thereafter, the mixture was warmed to room temperature and was agitated for 1.5 hours. The resulting mixture was diluted with ethyl acetate and then rinsed with water, 2% aqueous copper sulfate solution, water and, finally, saturated aqueous sodium chloride solution successively, followed by drying and distilling off of the solvent under a reduced pressure. The residue was purified by a column chromatography (ethyl acetate/n-hexane of 1/3), whereby 915 mg of the above-identified compound were obtained. Rf=0.76(ethyl acetate/n-hexane of 1/1).

C. Synthesis of (R)-N,N-[[2-(9H-carbazol-2-yloxy)ethyl]-[2-(triethylsilyloxy)-2-[3-nitro-4-(benzyloxy)pheny]]ethyl] amine (Intermediate 21)

A solution of 289 mg of Intermediate 20, 165 mg of Intermediate 2 and 0.51 ml of Huenig base (supplied from the firm Aldrich) in 1.5 ml of dimethylacetamide was agitated for 8 hours at 60° C. To the resulting reaction mixture, 40 ml of ethyl acetate and 40 ml of water were added to effect extraction, whereupon the aqueous layer was further extracted with ethyl acetate three times. The united organic phase was dried and the solvent was distilled off under a reduced pressure. The residue was purified by a column chromatography (chloroform-methanol/chloroform=1/49), whereby 173 mg of the above-identified compound were obtained. Rf=0.60 (methanol/chloroform of 1/9).

D. Synthesis of (R)-N,N,N-[(benzyloxycarbonyl)-[2-(9H-carbazol-2-yloxy)ethyl]-[2-(triethylsilyloxy)-2-[3-nitro-4-(benzyloxy) phenyl]]ethyl]amine (Intermediate 22)

173 mg of the above amine compound were dissolved in 2 ml of methylene chloride and thereto were added 45 $\mu$l of triethylamine and the mixture was agitated under ice-cooling and thereto were added 43 $\mu$l of benzylchloroformate (supplied from the firm Aldrich). After agitation for 30 minutes, the mixture was agitated for 8 hours at room temperature. The mixture was then diluted with ethyl acetate and rinsed with water and, then, with saturated aqueous sodium chloride solution, successively, followed by drying and distilling off of the solvent under a reduced pressure. The residue was purified by a column chromatography (ethyl acetate/n-hexane=1/5–1/3), whereby 200 mg of the above-identified compound were obtained. Rf=0.55 (ethyl acetate/n-hexane of 1/2).

Retention time: 14.7 min. Analytical conditions: column: CHIRALCEL OJ-R (4.6 mm$\phi$, 15 cm long; supplied from Daicel. Chem. Ind., Ltd.): mobile phase: 0.5 M NaClO$_4$/CH$_3$CN=20/80; flow rate: 0.7 ml/min.; detection wave length: 254 mm; temperature: 30° C.

E. Synthesis of (R)-N,N,N-[(benzyloxycarbonyl)-[2-(9H-carbazol-2-yloxy)ethyl]-[2-(triethylsilyloxy)-2-[3-amino-4-(benzyloxy) phenyl]]ethyl]amine (Intermediate 23)

To a solution of 200 mg of the above nitro compound in 14 ml of methanol which had been purged by argon, 5 mg of platinum oxide (anhydrous, supplied from Wako Pure Chem. Ind., Ltd.) were added and the compound was reduced under 1 atm. hydrogen gas under ice-cooling. After agitation for 6 hours, the reaction system was replaced by argon and the reaction mixture was diluted with chloroform and filtered. The solvent was evaporated under reduced pressure, whereby 183 mg of the above-identified compound were obtained. Rf=0.32 (ethyl acetate/n-hexane of 1/3).

F. Synthesis of (R)-N-[5-[2-[benzyloxycarbonyl-[2-(9H-carbazol2-yloxy)ethyl]amino]-1-(triethylsilyloxy)ethyl]-2-(benzyloxy)phenyl]methanesulfonamide (Intermediate 24)

To a solution of 183 mg of the above amine compound in 1 ml of pyridine, 20 $\mu$l of methanesulfonyl chloride were added and the mixture was agitated for 1 hours, whereto water was added and the resulting mixture was agitated for 3 hours, before the mixture was ice-cooled and the thereby deposited precipitate was separated by filtration. The precipitate was dissolved in ethyl acetate and the organic layer was rinsed with saturated aqueous sodium chloride solution and dried, whereupon the solvent was distilled off under a reduced pressure to obtained 192 mg of the above-identified compound. Rf=0.44 (ethyl acetate/n-hexane of 1/2).

G. Synthesis of (R)-N-[5-[2-[2-(9H-carbazol-2-yloxy) ethylamino]-1-hydroxyethyl]-2-hydroxyphenyl)] methanesulfonamide hydrochloride In accordance with the procedures of the step C in Example 1, the benzyloxycarbonyl group and the triethylsilyl group were eliminated using 192 mg of the above methanesulfonamide compound with 4 ml of 30% solution of hydrogen bromide in acetic acid. Then, in accordance with the precedures of the step E in Example 1, the benzyl group was subjected to hydrogenolysis under a hydrogen atmosphere using 71 mg of 10% palladium carbon black (supplied from Merk), followed by conversion into hydrochloride salt by means of a usual technique. whereby the above-identified compound was obtained.

Retention time: 40.6 min. Analytical conditions: column: CHIRALCEL OJ-R (supplied from Daicel Chem. Ind., Ltd.): mobile phase: 0.5 M NaClO$_4$/CH$_3$CN=77/23; flow rate: 0.5 ml/min.; detection wave length: 254 nm; temperature: 40° C.

EXAMPLE 13

(S)-N-[5-[2-[2-(9H-carbazol-2-yloxy)ethylamino]-1-hydroxyethyl]-2-hydroxyphenyl] methanesulfonamide hydrochloride The reactions and the after-treatments were performed in the same manner as in Example 12, except that an asymmetric catalyst of (S)-modification (supplied from Tokyo Chemical Industry Co., Ltd.) was used.
A. Synthesis of (S)-2-bromo-1-[3-nitro-4-(benzyloxy)-phenyl]ethanol Retention time: 47.3 min. Analytical conditions: column: CHIRALCEL OB (supplied from Daicel Chem. Ind., Ltd.): mobile phase: n-hexane/2-propanol=7/3; flow rate: 0.5 ml/min.; detection wave length: 254 nm; temperature: 35° C.
D. Synthesis of (S)-N,N,N-[(benzyloxycarbonyl)-[2-(9H-carbazol-2-yloxy)ethyl]-[2-(triethylsilyloxy)-2-[3-nitro-4-(benzyloxy) phenyl]]ethyl]amine Retention time: 9.8 min. Analytical conditions: column CHIRALCEL OJ-R (supplied from Daicel Chem. Ind., Ltd.); mobile phase: 0.5 M NaClO$_4$/CH$_3$CN=2/8; flow rate: 0.7 ml/min.; detection wave length: 254 mm; temperature: 30° C.
G. Synthesis of (S)-N-[5-[2-[2-(9H-carbazol-2-yloxy) ethylamino]-1-hydroxyethyl]-2-hydroxyphenyl] methanesulfonamide hydrochloride Retention time: 47.5 min. Analytical conditions: column: CHIRALCEL OJ-R (supplied from Daicel Chem. Ind., Ltd.); mobile phase: 0.5 M NaClO$_4$/CH$_3$CN=77/23; flow rate: 0.5 ml/min.; detection wave length: 254 nm; temperature: 40° C.

EXAMPLE 14

(R)-N-[3-[2-[2-(9H-carbazol-2-yloxy)ethylamino]-1-hydroxyethyl]phenyl]methanesulfonamide hydrochloride The synthesis was performed in accordance with the procedures as given in Example 12 except that the hydrogenolysis with 10% palladium/carbon black in the step G of Example 12 was not incorporated.
A. Synthesis of (R)-2-bromo-1-(3-nitrophenyl)ethanol (Intermediate 25)

To a solution of 769 mg of 2-bromo-1-[3'-nitrophenyl] ethanone and 100 mg of the said asymmetric catalyst [(R)-modification: supplied from Tokyo Chemical Industry Co., Ltd.] in 20 ml of anhydrous tetrahydrofuran (prepared on each use), 2.16 ml of a 2 M solution of borane/dimethyl sulfide complex in tetrahydrofuran (supplied from the firm Aldrich) were added dropwise over a period of 5 minutes, whereupon the reaction and the after-treatments were performed, whereby 768 mg of the above-identified compound were obtained. Rf=0.72 (ethyl acetate/n-hexane of 1/1).

Retention time: 9.02 min. Analytical conditions: column: CHIRALCEL AD (supplied from Daicel Chem. Ind., Ltd.); mobile phase: n-hexane/2-propanol (1/1); flow rate: 0.5 ml/min.; detection wave length: 254 nm; temperature: 35° C.

B. Synthesis of (R)-3-[2-iodo-1-(triethylsilyloxy)ethyl]-nitrobenzene (Intermediate 26)

To a solution of 768 mg of Intermediate 25 in 30 ml of acetone, 2.96 g of sodium iodide (supplied from Wako Pure Chemical Ind., Ltd.) were added, followed by reaction and after-treartment. 795 mg of the resulting product, 408.5 mg of imidazole and 24.4 mg of dimethylaminopyridine were dissolved in 5 ml of dimethylformaide, whereto 452 mg of triethylsilane chloride were added under ice-cooling, followed by reaction and after-treatment, whereby 994 mg of the above-identified compound were obtained. Rf=0.43 (ethyl acetate/n-hexane of 1/3).
C. Synthesis of (R)-N,N-[[2-(9H-carbazol-2-yloxy)ethyl]-[2-(triethylsilyloxy)-2-(3-nitrophenyl)ethyl]amine (Intermediate 27)

A solution of 451 mg of Intermediate 26, 330 mg of Intermediate 2 and 1.02 ml of Hunig base (supplied from the firm Aldrich) in 2 ml of dimethylformamide was subjected to reaction and after-treatment, whereby 217 mg of the above-identified compound were obtained.
D. Synthesis of (R)-N,N,N-[(benzyloxycarbonyl)-[2-(9H-carbazol-2-yloxy)ethyl]-[2-(triethylsilyloxy)-2-(3-nitrophenyl)]ethyl]amine (Intermediate 27)

217 mg of the above amine compound were dissolved in 2 ml of methylene chloride and thereto were added 66 μl of triethylamine with subsequent agitation under ice-cooling and further addition of 63 μl of benzyl chloroformate (supplied from the firm Aldrich), followed by reaction and after-treatment, whereby 261 mg of the above-identified compound were obtained. Rf=0.32 (ethyl acetate/n-hexane of 1/2).
E. Synthesis of (R)-N,N,N-[(benzyloxycarbonyl)-[2-(9H-carbazol-2-yloxy)ethyl]-[2-(triethylsilyoxy)-2-(3-aminophenyl)]ethyl]amine To a solution of 261 mg of the above nitro compound in 5.5 ml of methanol which had been purged by argon, 5 mg of platinum oxide (anhydrous, supplied from Wako Pure Chem. Ind., Ltd.) were added to effect reduction with 1 atm. Hydrogen gas, followed by after-treatment to obtain 236 mg of the above-identified compound.
F. Synthesis of (R)-N-[3-[2-[benzyloxycarbonyl-[2-(9H-carbazol-2-yloxy)ethyl]amino]-1-(triethylsilyloxy)-ethyl] phenyl]methanesulfonamide (Intermediate 28)

To a solution of 236 mg of the above amine compound in 1 ml of pyridine, 30 μl of methanesulfonyl chloride were added to cause reaction, followed by after-treatment to obtain 253 mg of the above-identified compound. Rf=0.25 (ethyl acetate/n-hexane of 1/2).
G. Synthesis of (R)-N-[3-[2-[2-(9H-carbazol-2-yloxy) ethylamino]-1-hydroxyethyl]phenyl]methanesulfonamide hydrochloride According to the procedures of the step C in Example 1, the above methanesulfonamide compound was processed by adding to 253 mg thereof 5 ml of 30% solution of hydrogen bromide in acetic acid to cause reaction, followed by after-treatment to obtain the above-identified compound.

Retention time: 29.3 min. Analytical conditions: column: CHIRALCEL OJ-R (supplied from Daicel Chem. Ind., Ltd.); mobile phase: 0.5 M NaClO$_4$/CH$_3$CN=7/3; flow rate: 0.5 ml/min.; detection wave length: 254 nm; temperature: 30° C.

EXAMPLE 15

(S)-N-[5-[2-[2-(9H-carbazol-2-yloxy)ethylamino]-1-hydroxyethyl]2-hydroxyphenyl]methanesulfonamide hydrochloride The reactions and the after-treatments were performed in the same manner as in Example 14, except that an asymmetric catalyst of (S)-modification (supplied from Tokyo Chemical Industry Co., Ltd.) was used.

A. Synthesis of (S)-2-bromo-1-(3-nitrophenyl)ethanol

Retention time: 8.18 min. Analytical conditions: column: CHIRALCEL AD (supplied from Daicel Chem. Ind., Ltd.): mobile phase: n-hexane/ethanol=1/1; flow rate: 0.5 ml/min.; detection wave length: 254 nm; temperature: 35° C.

G. Synthesis of (S)-N-[3-[2-[2-(9H-carbazol-2-yloxy)ethylamino]-1-hydroxyethyl]phenyl]methanesulfonamide hydrochloride Retention time: 25.3 min. Analytical conditions: column: CHIRALCEL OJ-R (supplied from Daicel Chem. Ind., Ltd.); mobile phase: 0.5 M $NaClO_4/CH_3CN$=7/3: flow rate: 0.5 ml/min.; detection wave length: 254 nm; temperature: 30° C.

EXAMPLE 16

(±)-N-methyl-3-[2-[2-(9H-carbazol-2-yloxy)ethylamino]-1-hydroxyethyl]benzenesulfonamide hydrochloride A. Synthesis of N-methyl-3-acetylbenzenesulfonamide To a solution of 2 g of 3-acetylbenzenesulfonyl fluoride (supplied from the firm Across) in 20 ml of pyridine. 2,02 ml of 40% methylamine/methanol (supplied from Wako Pure Chem. Ind. Co., Ltd.) were added at room temperature and the mixture was agitated for 2 hours. There were replenished 2.02 ml of 40% methylamine/methanol and the agitation was continued for further 40 minutes. Thereto were added 5 N hydrochloric acid and about 40 ml of water to terminate the reaction (pH 4) and the product was extracted with ethyl acetate. The organic layer was separated and dried and the solvent was distilled off under a reduced pressure, whereby 996 mg of the above-identified compound were obtained. Rf=0.64 (methanol/chloroform of 1/10).

B. Synthesis of N-methyl-3-(2-bromoacetyl)benzenesulfonamide (Intermediate 29)

To a solution of 990 mg of the above-obtained compound in 15.8 ml of 1,4-dioxane, 769 mg of bromine were added and the mixture was stirred for 1 hour at 60° C. The mixture was concentrated under a reduced pressure, followed by addition of 18 ml of water to the residue, whereupon the resulting mixture was agitated vigorously under ice-cooling. The deposited precipitate was triturated and separated by filtration and was washed with water. The separated product was dried under a reduced pressure at room temperature, whereby 1.18 g of the above-identified compound were obtained. Rf=0.63 (methanol/chloroform of 1/10).

C. Synthesis of (±)-N-methyl-3-[2-[2-(9H-carbazol-2-yloxy)ethylaminol-1-hydroxyethyl]benzenesulfonamide hydrochloride According to the procedures described in the step D of Example 1, 0.59 g of the above Intermediate 29, 0.59 g of HBr-addition salt of Intermediate 2, 0.39 g of sodium borohydride and 1 ml of ethanolamine were brought into reaction, followed by after-treatment, whereby 227.8 mg of the above-identified compound were obtained,wherein the procedures were modified such that 0.56 ml (2 eq.) of triethylamine was used as the basic catalyst and the purification was effected by a column chromatography (methanol/ethyl acetate of 1/5), with subsequent PTLC (methanol/ethyl acetate of 1/5). Rf=0.28 (methanol/ethyl acetate of 1/5).

EXAMPLE 17

(±)-N-[3-[2-[2-(9H-carbazol-2-yloxy)ethylamino]-1-hydroxyethyl]phenyl]formamide hydrochloride A. Synthesis of 1-(3-formylaminophenyl)ethanone To a solution of 2 g of 1-(3-aminophenyl)ethanone (supplied from Tokyo Chemical Industry Co., Ltd.) in 15 ml of dimethylformamide, a mixture of 15 ml of formic acid and 5 ml of acetic anhydride was added and the mixture was agitated for 2.5 hours. Then, the agitation was continued for further 15 hours at room temperature and thereto was added a mixture of 3 ml of formic acid and 1 ml of acetic anhydride and agitation was continued for further 8 hours at room temperature. To this mixture, 150 ml of water and 150 ml of ethyl acetate were added to effect extraction. The organic layer was rinsed with water twice and dried, whereupon the solvent was distilled off under a reduced pressure to obtain 1.69 g of the above-identified compound. Rf=0.65 (methanol/chloroform of 1/10).

B. Synthesis of (±)-N-[3-[2-[2-(9H-carbazol-2-yloxy)ethylamino]-1-hydroxyethyl]phenyl]formamide hydrochloride To a solution of 1.6 g of the above 1-(3-formylaminophenyl) ethanone in 33.4 ml of 1,4-dioxane, 1.63 g of bromine were added and the mixture was agitated for 1 hour at 60° C. The mixture was concentrated under a reduced pressure, 40 ml of water were added to the resulting residue and the mixture was agitated vigorously under ice-cooling. To this mixture was added ethyl acetate to effect extraction and the organic layer was dried, before the solvent was distilled off under a reduced pressure. To the resulting residue, chloroform and water were added and the deposited precipitate was separated by filtration. By distilling off the solvent from the filtrate under a reduced pressure, 975 mg of a mixture containing 2-bromo-1-(3-fromylaminophenyl) ethanone were obtained.

According to the procedures as described in the step D of Example 1, 300 mg of the mixture containing the above bromo-product, 363 mg of HBr-addition salt of Intermediate 2, 239 mg of sodium borohydride and 0.6 ml of ethanolamine were brought into reaction, followed by after-treatment, whereby 73 mg of the above-identified compound were obtained, wherein, however, a modification was incorporated in such a manner that 0.34 ml (2 eq.) of triethylamine was used as a basic catalyst and the purification was effected by a PTLC (methanol/ethyl acetate of 1/3) with subsequent conversion into hydrochloride salt, followed by removal of impurities by depositing them from methanol/ethyl acetate and filtering them off. Rf=0.26 (methanol/ethyl acetate of 1/3).

EXAMPLE 18

(±)-2-[N-[2-(9H-carbazol-2-yloxy)ethyl]amino]-1-(4-hydroxy-3-nitrophenyl)]ethanol hydrochloride A. Synthesis of (±)-[2-[N-[2-(9H-carbazol-2-yloxy)ethyl]amino]-1-[3-nitro-4-(benzyloxy)phenyl]ethanol According to the procedures described in the step D of Example 1, a solution of 0.52 g (70% purity) of 2-bromo-1-[3-nitro-4-(benzyloxy) phenyl]ethanone [prepared by the method reported by Carl Kaiser et al in J.Med. Chem., 17,49–57(1974)] in a mixture of 409 μl of triethylamine and 6.4 ml of anhydrous acetonitrile and a solution of 287 mg of sodium borohydride in 13 ml of absolute ethanol were added successively to a solution of 435 mg of HBr-addition salt of Intermediate 2 in a mixed solvent composed of 25.5 ml of anhydrous acetonitrile and 20 ml of anhydrous dimethylformamide, followed by reaction and after-treatment, whereby 61.8 mg of the above-identified compound were obtained. Rf=0.24 (methanol/chloroform of 1/10).

B. Synthesis of (±)-2-[N-[2-(9H-carbazol-2-yloxy)ethyl]amino]-1-(4-hydroxy-3-nitrophenyl)ethanol hydrochloride To a solution of 127.6 mg of the compound of the above step A in 10 ml of dichloromethane, 0.69 ml of 1 M solution of boron tribromide in dichloromethane (supplied from the firm Aldrich) was added dropwise over a period of 2 minutes under cooling with dry ice/acetone coolant. The mixture was agitated as such for one hour and, then, the agitation was continued for further 5 minutes under ice-cooling. The reaction was terminated by adding 10 ml of methanol to the reaction mixture and the product was extracted therefrom with ethyl acetate after adjusting the reaction mixture at pH of 8.7 using saturated aqueous sodium bicarbonate solution. The organic layer was rinsed with saturated aqueous sodium chloride solution and dried, whereupon the solvent was distilled off under a reduced pressure. The resulting residue was triturated in ethyl acetate and the mixture was filtered to obtain 87.6 mg of free base product of the above-identified compound. This was converted into hydrochloride salt which is the above-identified compound by using 0.1 N HCl/ethanol (93.0 mg). Rf=0.33 (methanol/chloroform of 1/10).

EXAMPLE 19

(±)-2-[N-[2-(9H-carbazol-2-yloxy)ethyllamino]-1-(3-amino-4-hydroxyphenyl)ethanol·2HCl 15 mg of the compound of Example 18 were dissolved in a mixed solvent composed of I ml of methanol and 1 ml of tetrahydrofuran in accordance with the procedures described in the step E of Example 12 and thereto were added 1.1 mg of platinum oxide (anhydrous, supplied from Wako Pure Chem. Co.) under ice-cooling, followed by reaction and after-treatment, whereby 10.2 mg of the above-identified compound were obtained. Rf=0.15 (methanol/ethyl acetate of 1/3).

EXAMPLE 20

(±)-N-[5-[2-[2-(9H-carbazol-2-yloxy)ethylamino]-1-hydroxyethyl]-2-(benzyloxy)phenyl]urea hydrochloride According to the procedures described in the step D of Example 1, a solution of 0.54 g of 2-bromo-1-[4-(benzyloxy)-3-ureidphenyl]ethanone [prepared by the method reported by Carl Kaiser et al in J. Med. Chem., 17, 49–57 (1974)] in a mixture of 409 µl of triethylamine and 6.4 ml of anhydrous acetonitrile and a solution of 287 mg of sodium borohydride in 13 ml of absolute ethanol were added successively to a solution of 435 mg of HBr-addition salt of Intermediate 2 in a mixed solvent composed of 26 ml of anhydrous acetonitrile and 10 ml of anhydrous dimethylformamide, followed by reaction and after-treatment, whereby 59.3 mg of the above-identified compound were obtained. Rf=0.15 (methanol/chloroform of 1/10).

EXAMPLE 21

Synthesis of (±)-N-[5-[2-[2-(9H-carbazol-2-yloxy)ethylamino]-1-hydroxyethyl]-2-hydroxyphenyl]urea hydrochloride According to the procedures as given in Example 2, the compound of Example 20 (in a solution of 40 mg of the compound in 5.3 ml of methanol) was subjected to a hydrogenolysis using 10% palladium/carbon black (25 mg), whereby the above-identified compound (29.8 mg) was obtained. Rf=0.08 (methanol/chloroform of 1/10).

EXAMPLE 22

Synthesis of (±)-N-[5-[2-[2-(9H-carbazol-2-yloxy)ethylamino]-1-hydroxyethyl]-2-(benzyloxy)phenyl]formamide hydrochloride According to the procedures described in the step D of Example 1, a solution of 0.52 g of 2-bromo-1-[3-(formylamino)-4-(benzyloxy) phenyl]ethanone [prepared by the method reported by Carl Kaiser et al in J. Med. Chem., 17, 49–57 (1974)] in a mixture of 409 µl of triethylamine and 10 ml of anhydrous acetonitrile and a solution of 287 mg of sodium borohydride in 13 ml of absolute ethanol were added successively to a solution of 435 mg of HBr-addition salt of Intermediate 2 in a mixed solvent composed of 22 ml of anhydrous acetonitrile and 6 ml of anhydrous dimethylformamide, followed by reaction and after-treatment, whereby 57.0 mg of the above-identified compound were obtained. Rf=0.18 (methanol/chloroform of 1/10).

EXAMPLE 23

Synthesis of (±)-N-[5-[2-[2-(9H-carbazol-2-yloxy)ethylamino]-1-hydroxyethyl]-2-hydroxyphenyl]formamide hydrochloride According to the procedures as given in Example 2, the compound of Example 22 (in a solution of 40 mg of the compound in 5.8 ml of methanol) was subjected to a hydrogenolysis using 10% palladium/carbon black (27 mg), whereby the above-identified compound (28.1 mg) was obtained. Rf=0.08 (methanol/chloroform of 1/10).

EXAMPLE 24

Synthesis of (±)-N'-[5-[2-[2-(9H-carbazol-2-yloxy)ethylamino]-1-hydroxyethyl]-2-(benzyloxy)phenyl]-N,N-dimethylsulfamide hydrochloride According to the procedures described in the step D of Example 1, a solution of 0.64 g of 2-bromo-1-[4-(benzyloxy)-3-(dimethylsulfamoylamino)phenyl]ethanone [prepare by the method reported by Carl Kaiser et al in J. Med. Chem., 17, 49–57 (1974)] in a mixture of 410 µl of triethylamine and 6.5 ml of anhydrous acetonitrile and a solution of 287 mg of sodium borohydride in 15 ml of absolute ethanol were added successively to a solution of 435 mg of HBr-addition salt of Intermediate 2 in a mixed solvent composed of 26 ml of anhydrous acetonitrile and 10 ml of anhydrous dimethylformamide, followed by reaction and after-treatment, whereby 70.5 mg of the above-identified compound were obtained. Rf 0.17 (methanol/chloroform of 1/10).

EXAMPLE 25

Synthesis of (±)-N'-[5-[2-[2-(9H-carbazol-2-yloxy)ethylamino]-1-hydroxyethyl]-2-hydroxyphenyl]-N,N-dimethylsulfamide hydrochloride According to the procedures as given in Example 2, the compound of Example 24 (in a solution of 40 mg of the compound in 5.1 ml of methanol) was subjected to a hydrogenolysis using 10% palladium/carbon black (24 mg),

EXAMPLE 26

(±)-2-[N-[2-(9H-carbazol-2-yloxy)ethyl]amino]-1-
[3-(methylamino)-4-(benzyloxy)phenyl]
ethanol·2HCl According to the method reported by Carl Kaiser et al in J. Med. Chem., 17, 49–57 (1974), a solution of 500 mg of the compound of Example 22 in 1 ml of tetrahydrofuran was added dropwise to a suspension of 50 mg of lithium aluminum hydride in 2 ml of tetrahydrofuran to cause reaction, followed by after-treatment, whereby 381 mg of the above-identified compound were obtained. Rf=0.13 (methanol/chloroform of 1/10).

EXAMPLE 27

(±)-2-[N-[2-(9H-carbazol-2-yloxy)ethyl]amino]-1-
[3-(methylamino)-4-hydroxyphenyl]ethanol·2HCl According to the procedures as given in Example 2, the compound of Example 26 (in a solution of 200 mg of the compound in 25 ml of methanol) was subjected to a hydrogenolysis using 10% palladium/carbon black (100 mg), whereby the above-identified compound (153 mg) was obtained. Rf=0.09 (methanol/chloroform of 1/10).

EXAMPLE 28

(±)-2-[N-[2-(9H-carbazol-2-yloxy)ethyl]amino]-1-
(2-fluorophenyl) ethanol hydrochloride A. Synthesis of (±)-2-fluorostyrene oxide (Intermediate 30)

To a solution of 5.00 g of 2-fluorostyrene (supplied from the firm Aldrich) in 200 ml of methylene chloride, 17.7 g of metachloroperbenzoic acid (supplied from Kanto Chem. Co. Inc.) and 18.6 g of disodium phosphate were added under ice-cooling and the mixture was agitated at room temperature for 20 hours. The mixture was cooled with ice and the thereby deposited crystals were removed by twice filtrations and the filtered cake was washed with aqueous sodium thiosulfate solution (180 ml), whereupon the organic phase was dried and the solvent was distilled off under a reduced pressure, followed by purification by a column chromatography (ethyl acetate/n-hexane of 1/19), whereby 0.38 g of the above-identified compound was obtained. Rf=0.57 (ethyl acetate/n-hexane of 1/5).

B. Synthesis of (±)-2-[N-[2-(9H-carbazol-2-yloxy)ethyl]-amino]-1-(2-fluorophenyl)ethanol hydrochloride Under argon atmosphere, 1.6 ml of dimethyl sulfoxide and 1.06 ml of N,O-bis(trimethylsilyl)acetamide (25% solution in acetonitrile, supplied from Tokyo Chemical Industry Co. Ltd.) were added to 452.6 mg of Intermediate 2 and the resulting mixture was agitated at room temperature for 30 minutes. Thereto were then added 290 mg of Intermediate 30 and the agitation was continued at 70° C. for 70 hours.

The reaction mixture was cooled down to room temperature and 2 ml of 6 N hydrochloric acid were added thereto and the mixture was agitated for 5 minutes, whereupon the resulting mixture was made basic using 5 N aqueous sodium hydroxide. Then, the mixture was extracted with ethyl acetate, whereupon the organic phase was dried and the solvent was distilled off under a reduced pressure, followed by purification by a column chromatography (chloroform-methanol/chloroform of 3/100–7/100) to obtain a free amine product of the above-identified compound. Rf=0.20 (methanol/chloroform of 1/9). Using 0.1 N hydrogen chloride/ethanol, 268 mg of the above-identified compound were obtained.

whereby the above-identified compound (38.3 mg) was obtained. Rf=0.38 (methanol/ethyl acetate of 1/3).

EXAMPLE 29

(±)-2-[N-[2-(9H-carbazol-2-yloxy)ethyl]amino]-1-
(4-hydroxyphenyl) ethanol hydrochloride A. Synthesis of 2-bromo-1-(4-benzyloxy)phenylethanone (Intermediate 31)

Under argon atmosphere, 7.4 g of copper (II) bromide were suspended in 100 ml of ethyl acetate and thereto was added a solution of 5 g of 1-(4-benzyloxy)-phenylethanone (supplied from the firm Transworld) in 100 ml of chloroform with agitation while heating under reflux. After agitation for 5.5 hours, the mixture was cooled down to 62° C. and was diluted with 100 ml of chloroform, followed by filtration of the suspension and evaporation under a reduced pressure. The resulting residue was suspended in isopropyl alcohol and precipitate was removed by filtration, followed by rinsing with cold isopropyl alcohol and drying, whereby 4.52 g of the above-identified compound were obtained as pale yellow crystals.

B. Synthesis of (±)-2-[N-[2-(9H-carbazol-2-yloxy)ethyl]amino]-1-[4-(benzyloxy)phenyl]ethanol (Intermediate 32)

400 mg of Intermediate 31 and 534 mg of Intermediate 2 were subjected to reaction and after-treatment in accordance with the procedures of the step D of Example 1, whereby 120 mg of the above-identified compound were obtained. Here, however, the crude product was purified by a column chromatography (ethyl acetate/methanol of 8/1).

C. Synthesis of (±)-2-[N-[2-(9H-carbazol-2-yloxy)ethyl]amino]-1-(4-hydroxyoxyphenyl)ethanol 120 mg of Intermediate 32 were dissolved in 15 ml of dimethylformamide, whereto were added 100 μl of acetic acid and, then, 120 mg of 10% palladium/carbon black rinsed with 2 ml of dimethylformamide, whereupon the mixture was subjected to a hydrogenolysis under 1 atm for 50 minutes. After-treatments were effected in accordance with the procedures of Example 2, whereby 88 mg of the above-identified compound were obtained. Rf=0.31 (methanol/ethyl acetate of 1/3).

EXAMPLE 30

(±)-2-[N-[2-(9H-carbazol-2-yloxy)ethyl]amino]-1-
(2-hydroxyphenyl) ethanol hydrochloride A. Synthesis of 2-bromo-1-(2-benzyloxy)phenylethanone Under argon atmosphere, 14.6 g of copper (II) bromide were suspended in 175 ml of ethyl acetate and thereto was added a solution of 6.35 g of 1-(4-benzyloxy) phenylethanone (supplied from the firm Transworld) in 175 ml of chloroform with agitation while heating under reflux. By after-treatment in accordance with the procedures of the step A of Example 29, a fraction containing the above-identified compound (9.32 g) was obtained, which was served for the subsequent reaction as such without further treatment.

B. Synthesis of (±)-2-[N-[2-(9H-carbazol-2-yloxy)ethyl]amino]-1-[2-(benzyloxy)phenyl]ethanol (Intermediate 33)

442 mg of the above-obtained compound and 400 mg of Intermediate 2 were subjected to reaction and after-treatment in accordance with the procedures of the step D of Example 1, whereby 31.9 mg of the above-identified compound were obtained. Here, however, the crude product was purified by a column chromatography (methanol/chloroform of 1/20).

D. Synthesis of (±)-2-[N-[2-(9H-carbazol-2-yloxy)ethyl]-amino]-1-(2-hydroxyphenyl)ethanol acetic acid addition salt 31.9 mg of Intermediate 33 were dissolved in 4.7 ml of methanol and thereto were added 4 μl of acetic acid and the mixture was subjected to a hydrogenolysis under 1 atm hydrogen gas using 22.3 mg of 10% palladium/carbon black (room temperature, 5 hours). The catalyst was filtered off on celite and was washed with chloroform and methanol. The filtrate and the washed liquor were brought together, from which the solvent was distilled off under a reduced pressure, whereby 18.5 mg of the above-identified compound were obtained as a powdery product. Rf=0.13 (methanol/chloroform of 1/10).

EXAMPLE 31

(±)-2-[N-[2-(9H-carbazol-2-yloxy)ethyl]amino]-1-phenylethanol hydrochloride

To a solution of 140 mg of HBr addition salt of Intermediate 2 and 110 µl of triethylamine in 5 ml of methanol, 92.0 mg of phenylglyoxal were added and the mixture was heated on a water bath for 4 minutes. After cooling, 120 mg of sodium borohydride were added thereto in two portions at an interval of 10 minutes and the mixture was agitated at room temperature for 20 hours. The solvent was distilled off under a reduced pressure and thereto were added ethyl acetate and water to cause liquid separation, whereupon the organic solvent was dried and evaporated off under a reduced pressure. The resulting residue was purified by a column chromatography (methanol/chloroform of 1/25), whereby 116.3 mg of the above-identified compound were obtained. By recrystallization from ethanol, 93.8 mg were obtained as hydrochloric acid addition salt. Rf=0.34 (methanol/chloroform of 1/10).

EXAMPLE 32

(R)-2-[N-[2-(9H-carbazol-2-yloxy)ethyl]amino]-1-phenylethanol hydrochloride

To 200 mg of Intermediate 2, 0.5 ml of dimethylsulfoxide and 102 µl of (R)-(+)-styrene oxide (supplied from the firm Aldrich) were added and the resulting mixture was agitated at 70° C. for 70 hours. The mixture was made basic with addition of water and sodium hydrogen carbonate and was then subjected to extraction with ethyl acetate, followed by drying of the organic layer, whereupon the solvent was distilled off under a reduced pressure and the resulting residue was purified by a column chromatography (methanol/chloroform of 1/20) to obtain 93.4 mg of the above-identified compound. Rf=0.34 (methanol/chloroform of 1/10).

The optical purity was found to be such that it is constituted of nearly 100% of (R)-modification after high performance liquid chromatography using CHIRALCEL OD-R (4.6 mm φ×25 cm, of Daicel Chem. Ind.). The analysis was carried out with a mobile phase of 0.5 M $NaClO_4/CH_3CN$ of 1/1, a flow rate of 0.5 ml/min., a detection wave length of 254 nm, a column temperature of 25° C. with retention time of 33.2 min. for (R)-modification and 32.4 min. for (S)-modification respectively. Using an ethanolic hydrogen chloride solution, 70 mg of hydrochloric acid addition salt were obtained.

EXAMPLE 33

(S)-2-[N-[2-(9H-carbazol-2-yloxy)ethyl]amino]-1-phenylethanol hydrochloride.

To 70.4 mg of Intermediate 2, 0.3 ml of dimethyl sulfoxide and 36 µl of (S)-(−)-styrene oxide (supplied from the firm Aldrich) were added and the resulting mixture was agitated at 70° C. for 70 hours. The mixture was made basic with addition of water and sodium hydrogen carbonate and was then subjected to extraction with ethyl acetate, followed by drying of the organic layer, whereupon the solvent was distilled off under a reduced pressure and the resulting residue was purified by a PTLC (chloroform/methanol of 10/1) to obtain 22.4 mg of the above-identified compound. Rf=0.34 (methanol/chloroform of 1/10). The optical purity was found, after high performance liquid chromatography as in Example 32 with the analysis under the same condition, to be such that it is constituted of nearly 100% of (S)-modification and the retention time was found to be 32.4 min. By using an ethanolic hydrogen chloride solution, 15 mg of hydrochloric acid addition salt were obtained.

EXAMPLE 34

(±)-2-[N-[2-(dibenzofuran-2-yloxy)ethyl]amino]-1-phenylethanol hydrochloride

To a solution of 105 mg of HBr-addition salt of Intermediate 2 and 110 µl of triethylamine in 5 ml of methanol, 69 mg of phenylglyoxal were added, followed by procedures in accordance with those of the synthesis method in Example 31. whereby 63.6 mg of the above-identified compound were obtained. Rf=0.48 (methanol/chloroform of 1/10). Using an ethanolic solution of hydrogen chloride, 40 mg of hydrochloride salt were obtained.

EXAMPLE 35

(R,R)-2-[N-[1-(9H-carbazol-2-yloxy)propan-2-yl]amino]-1-phenylmethanol hydrochloride To 597 mg of 2-(N-tert-butoxycarbonylamino-1-propyloxy)-9H-carbazole synthesized according to the procedures of Example 11, 10 ml of 30% solution of hydrogen bromide in acetic acid were added and the reaction and the after-treatments were carried out in accordance with the procedures of the synthesis of Example 32, whereby 258 mg of the above-identified compound were obtained. Rf=0.47 (methanol/chloroform of 1/9). The optical purity was found by an analysis performed under the same condition as in Example 32 except that it was carried out using a high performance liquid chromatography at 30° C. to be such that the product was constituted of nearly 100% in the form of (R, R)-modification. The retention time was 27.3 minutes. The product was converted into hydrochloric acid addition salt by using 6 N hydrochloric acid (280 mg).

EXAMPLE 36

(±)-2-[N-[2-[(9H-3-aminocarbazol)-2-yloxy]ethyl]amino]-1-phenylethanol·2HCl

A. Synthesis of N-[2-(9H-carbazol-2-yloxy)ethyl]acetamide (Intermediate 34)

To a solution of 1 g of Intermediate 2 and 0.93 ml of triethylamine (supplied from Wako Pure Chemical Ind., Ltd.) in 5 ml of dichloromethane, solution of 0.4 ml of acetyl chloride (supplied from Wako Pure Chemical Ind.) in 2 ml of dichloromethane were added under ice-cooling and agitation. The mixture was agitated for 2.5 hours under ice-cooling and, then, warmed to room temperature. Thereto were added ethyl acetate and water and the organic layer was separated, which was washed with aqueous saturated aqueous sodium chloride solution and dried, whereupon the solvent was distilled off under a reduced pressure. The resulting product was dried at room temperature under a reduced pressure, whereby 1.16 g of the above-identified compound were obtained. Rf=0.47 (methanol/chloroform of 1/9).

B. Synthesis of N-[2-[(9H-3-nitrocarbazol)-2-yloxylethyl] acetamide (Intermediate 35)

To a solution of 500 mg of Intermediate 34 in 20 ml of acetic acid, 0.4 ml of 20% nitric acid at 60° C. under agitation. After 1 minute, 20 ml of ice water were added thereto and the mixture was agitated, whereupon water was further added thereto, followed by extraction with ethyl acetate. Organic layer was washed with water, adjusted at pH 8 with 5 N aqueous sodium hydroxide solution and washed with saturated aqueous sodium chloride solution. After drying, the solvent was distilled off under a reduced pressure and the resulting residue was purified by a column chromatography (methanol/chloroform of 1/50), whereby 271.2 mg of the above-identified compound were obtained. Rf=0.50 (twice developments with methanol/chloroform of 1/9).

C. Synthesis of N-2-[(9H-3-nitrocarbazol)-2-yloxy]ethyl] amine (Intermediate 36)

100 mg of Intermediate 35 were suspended in 2.5 N hydrochloric acid and the mixture was agitated at room temperature for 10 days and, then, agitation was further continued at 100° C. for 4 hours. To this mixture was added ethyl acetate and pH thereof was adjusted at 10 using 5 N aqueous sodium hydroxide to perform extraction. After drying, the solvent was distilled off under a reduced pressure, whereby 71.2 mg of the above-identified compound were obtained. Rf=0.11 (thrice developments with methanol/chloroform of 1/10).

D. Synthesis of (±)-2-[N-[2-[9H-3-nitrocarbazol)-2-yloxy] ethyl]amino]-1-phenylethanol hydrochloride (Intermediate 37)

71.2 mg of Intermediate 36, 52,8 mg of phenylglyoxal (supplied from Tokyo Chemical Industry Co.,Ltd.) and 54.8 µl of triethylamine were dissolved in 5ml of methanol and the mixture was agitated at 70° C. for 4 minutes. The mixture was then cooled with ice and thereto were added 79 mg of sodium borohydride under agitation. Agitation was continued for further 21 hours, while the temperature was allowed to rise gradually to room temperature. Ethyl acetate and water were added thereto and the mixture was agitated for 15 minutes, whereupon the organic layer was separated and dried and the solvent was distilled off under a reduced pressure. The resulting residue (112.1 mg) was purified by a column chromatography (methanol/chloroform of 1/25), whereby 17.1 mg of the above-identified compound were obtained. Rf=0.34 (methanol/chloroform of 1/10).

E. Synthesis of (±)-2-[N-[2-[(9H-3-aminocarbazol)-2-yloxy]ethyl]amino]-1-phenylethanol·2HCl To a solution of 71.8 mg of the compound of Intermediate 37 in 3.7 ml of methanol, 0.16 ml of concentrate hydrochloric acid and 68.6 mg of iron powder (supplied from Kanto Chemical Co., Inc.) were added, successively, and the mixture was agitated at room temperature for 3.5 hours and, then,agitation was continued at 40° C. for additional 5 minutes. The mixture was adjusted at pH 9 using water and 5 N aqueous sodium hydroxide solution, followed by extraction with ethyl acetate and drying, whereupon the solvent was distilled off under a reduced pressure. To the resulting residue were added 4 ml of 0.1 N hydrogen chloride/ethanol and the solvent was distilled off under a reduced pressure, whereupon recrystallization from ethanol/ethyl acetate was incorporated. The crystals were isolated by filtration and were washed with ethyl acetate and diethyl ether, successively, with subsequent drying under a reduced pressure, whereby 29 mg of the above-identified compound were obtained. Rf=0.14 (free compound, methanol/chloroform of 1/10).

EXAMPLE 37

(±)-N-[5-[2-[2-(dibenzothiophen-3-yloxy) ethylamino]-1-hydroxyethyl]-2-benzyloxyphenyl] methanesulfonamide hydrochloride A. Synthesis of 3-(2-benzyloxycarbonylaminoethoxy) dibenzothiophene (Intermediate 38)

To a solution of 370.6 mg of 3-hydroxydibenzothiophene [prepared by the method reported by H. Kudo in J. Heterocycl. Chem., 22 (1), 215–218 (1985)] and 768 mg of potassium carbonate in 4 ml of dimethylformamide, 720 mg of Intermediate 0 were added and the mixture was heated at 60° C. for 30 hours. Thereto were added ethyl acetate and water to effect extraction, whereupon the organic layer was dried and the solvent was distilled off under a reduced pressure to thereby obtain 637 mg of the above-identified compound after purification by a column chromatography (mathanol/chloroform of 1/100). Rf=0.17 (ethyl acetate/n-hexane of 1/5).

B. Synthesis of 2-(dibenzothiophen-3-yloxy)ethylamine (Intermediate 39)

To 637 mg of Intermediate 38, 12 ml of 30% solution of hydrogen bromide in acetic acid were added and the mixture was agitated at room temperature for 2.5 hours. Thereto was added diethyl ether under ice-cooling and the thereby deposited precipitate was filtered off. After adjusting the pH of the remainder to 10 by adding water and NaOH, extraction with ethyl acetate was incorporated and the organic layer was dried, before the solvent was distilled off under a reduced pressure, whereby 334.2 mg of the above-identified compound were obtained. Rf=0.10 (methanol/chloroform of 1/10).

C. Synthesis of (±)-N-[5-[2-[2-(dibenzothiophen-3-yloxy) ethylamino]-1-hydroxyethyl]-2-benzyloxyphenyl] methanesulfonamide hydrochloride To a solution of 334.2 mg of Intermediate 39 in 14 ml of anhydrous acetonitrile, a solution of 980 mg of Intermediate 3 (70% purity) in 7 ml of anhydrous acetonitrile and 210 µl of triethylamine were added under argon atmosphere at 0° C., whereupon the reaction mixture was removed from the ice bath and was agitated for 83 minutes. Thereto w,as then added a solution of 270 mg of sodium borobyride in 14 ml of absolute ethanol at room temperature. After agitation for 6.5 hours, the reaction was terminated using 1.0 N hydrochloric acid (pH 4) and thereto was added 0.7 g of ethanolamine. After agitation for 10 minutes, the mixture was diluted with ethyl acetate, organic layer was rinsed with saturated aqueous sodium chloride solution and dried and the solvent was distilled off under a reduced pressure, whereby 1.09 g of crude product were obtained. This was purified by a column chromatography (methanol/chloroform of 3/100), whereby 240.6 mg of free amine product of the above-identified compound were obtained. Rf=0.38 (methanol/chloroform of 1/10). To a part (46 mg) of the so-obtained product, 1.1 equivalent amount of 0.1 N hydrogenchloride/ethanol were added to convert it into hydrochloride salt (the above-identified compound), whereupon the solvent was distilled off under a reduced pressure. To the resulting residue, diethyl ether was added and the thereby deposited precipitate was filtered off, whereupon the filtrate was rinsed with diethyl ether and dried under a reduced pressure at 50° C., whereby 48.5 mg of the above-identified compound were obtained.

EXAMPLE 38

(±)-N-[5-[2-[2-(dibenzothiophen-3-yloxy) ethylamino]-1-hydroxyethl]-2-hydroxyphenyl] methanesulfonamide hydrochloride 43 mg of the compound of Example 37 were subjected to a hydrogenolysis under 1 atm hydrogen gas using 30 mg of 10% palladium/carbon black (supplied from the firm Merck) and 5 ml of methanol. The catalyst was filtered off and washed with chloroform, methanol and hot methanol, successively. The filtrate and the washed liquor were brought together, from which the solvent was distilled off under a reduced pressure, whereby 32.5 mg of the above-identified compound were obtained as a white powdery product. Rf=0.08 (methanol/chloroform of 1/10).

EXAMPLE 39

(±)-N'-[5-[2-[2-(dibenzothiophen-3-yloxy) ethylamino]-1-hydroxyethy]-2-benzyloxyphenyl]-N,N-dimethylsulfamide hydrochloride A. Synthesis of 2-bromo-1-[4-benzyloxy-3-[(dimethylsulfamoyl) amino]phenyl]ethanone (Intermediate 40)

In the same manner as in the case of Intermediate 3, the above was prepared from 4-hydroxyacetophenone (supplied from Tokyo Chemical Industry Co., Ltd.) in four process steps [by the method reported by A. A. Larsen et al in J. Med. Chem., 10, 462–472 (1967)], wherein however, bromination was effected in the same manner as the procedures given in the step A of Example 29. Rf=0.37 (chloroform).

B. Synthesis of (±)-N'-[5-[2-[2-(dibenzothiophen-3-yloxy) ethylamino]-1-hydroxyethyl]-2-benzyloxyphenyl]-N,N-dimethylsulfamide hydrochloride To a solution of 462 mg of Intermediate 39 in 20 ml of anhydrous acetonitrile, a solution of 470 mg of Intermediate 40 in 10 ml of anhydrous acetonitrile was added under argon atmosphere at 0° C., whereupon the reaction mixture was removed from the ice bath and was agitated for 110 minutes. Thereto was then added a solution of 215 mg of sodium borohydride in 20 ml of absolute ethanol at room temperature. After agitation for 70 minutes, the reaction was terminated using 1 N hydrochloric acid (pH 4) and the thereto was added 0.54 g of ethanolamine. After agitation for 10 minutes, the mixture was diluted with ethyl acetate, organic layer was rinsed with saturated aqueous sodium chloride solution and dried, whereupon it was evaporated under a reduced pressure, whereby a crude product was obtained. This was purified by a column chromatography (methanol/chloroform of 3/100), whereby 200.2 mg of free amine product of the above-identified compound were obtained. Rf=0.37 (methanol/chloroform of 1/10). The procedures for adding thereto 1.1 equivalent amount of 0.1 N hydrogen chloride/ethanol to convert it into hydrochloride salt (the above-identified compound), distilling off of the solvent under a reduced pressure, adding to the resulting residue diethyl ether and filtering off the thereby deposited precipitate were repeated twice, followed by drying under a reduced pressure, whereby 210.8 mg of the above-identified compound were obtained.

EXAMPLE 40

(±)-N'-[5-[2-[2-(dibenzothiophen-3-yloxy) ethylamino]-1-hydroxyethyl]-2-hydroxyphenyl]-N,N-dimethylsulfamide hydrochloride 210.8 mg of the compound of Example 39 were subjected to a hydrogenolysis under 1 atm hydrogen gas using 107 mg of 10% palladium/carbon black and 22.5 ml of methanol. The catalyst was filtered off and washed with hot methanol. The filtrate and the washed liquor were brought together, from which the solvent was distilled off under a reduced pressure, whereby 137.9 mg of the above-identified compound were obtained. Rf=0.26 (methanol/chloroform of 1/10).

EXAMPLE 41

(±)-N-[3-[2-[2-(dibenzothiophen-3-yloxy) ethylamino]-1-hydroxyethyl]phenyl] methanesulfonamide hydrochloride To a solution of 462 mg of Intermediate 39 in 20 ml of anhydrous acetonitrile, a solution of 320.2 mg of Intermediate 14 in 10 ml of anhydrous acetonitrile was added under argon atmosphere at 0° C., whereupon the reaction mixture was removed from the ice bath and was agitated for 115 minutes. To this mixture was then added a solution of 215 mg of sodium borohydride in 20 ml of absolute ethanol at room temperature. After agitation for 75 minutes. the reaction was terminated using 1 N hydrochloric acid (pH 4) and thereto was added 0.54 g of ethanolamine. After agitation for 10 minutes, the mixture was diluted with ethyl acetate, organic layer was rinsed with saturated aqueous sodium chloride solution and dried, whereupon it was evaporated under a reduced pressure. This was purified by a column chromatography (elution by methanol/ethyl acetate of 1/7), whereby 251.3 mg of fractions containing the free amine product of the above-identified compound were obtained. This was further purified by a PTLC (elution with methanol/ethyl acetate of 1/7). whereby 134.7 mg of free amine product of the above-identified compound were obtained. Rf=0.50 (methanol/ethyl acetate of 1/7). To this, 1.1 equivalent amount of 0.1 N hydrogen chloride/ethanol were added to convert it into hydrochloride salt (the above-identified compound), which was washed with ethanol, ethyl acetate and diethyl ether, successively, with subsequent drying under a reduced pressure, whereby 93.9 mg of the above-identified compound were obtained.

EXAMPLE 42

(±)-N'-[5-[2-[2-(dibenzofuran-3-yloxy)ethylamino]-1-hydroxyethyl]-2-benzyloxyphenyl]-N,N-dimethylsulfamide A. Synthesis of (±)-N-[5-(2-bromo-1-hydroxyethyl)-2-benzyloxyphenyl]-N,N-dimethylsulfamide (Intermediate 41)

To a solution of 15.1 g Intermediate 40 in 197 ml of anhydrous tetrahydrofuran under ice-cooling, a solution of 61.9 ml of 1 M borane/tetrahydrfuran complex in tetrahydrofuran (supplied from the firm Aldrich) were added all at once and the mixture was agitated at this temperature for 75 minutes. The mixture was then diluted with 500 ml of ethyl acetate and thereto was added saturated aqueous ammonium chloride solution in small portions to wash the organic layer twice. The organic layer was separated and was washed with saturated aqueous sodium chloride solution and dried over anhydrous sodium sulfate, whereupon the solvent was distilled off under a reduced pressure. The residue was further dried under a reduced pressure overnight using a vacuum pump, whereby 14.91 g of the above-identified compound were obtained. Pf=0.27(ethyl acetate/n-hexane of 1/2).

B. Synthesis of (±)-N-[5-[2-iodo-1-(triethylsilyloxy) ethyl]-2-benzyloxyphenyl]-N,N-dimethylsulfamide (Intermediate 42)

To a solution of 14.9 g of Intermediate 41 in 212.9 ml of acetone, 58.09 g of sodium iodide were added and the mixture was heated under reflux for 105 minutes. The mixture was then cooled down to room temperature and was filtered, before the solvent was distilled off under a reduced pressure. The resulting residue was subjected to a phase partition between 214 ml of dichloromethane and 240 ml of water and the organic layer was washed twice with 23.5% by weight aqueous sodium hydrogen sulfide solution and, then, with saturated aqueous sodium chloride solution, before it was dried and the solvent was distilled off under a reduced pressure. This was further dried under a reduced pressure for two hours by a vacuum pump, whereby 15.51 g of brown tar-like product (iodo-isomer) were obtained. This was dissolved in 75.6 ml of dimethylformamide and thereto were added 6.1 g of imidazole and 346 mg of 4-dimethylaminopyridine, followed by a further addition of 5.83 ml of chlorotriethylsilane. After agitation for 35 minutes, the mixture was diluted with 250 ml of ethyl acetate and 100 ml of n-heptane and, then, washed with water (125 ml), with a saturated copper sulfate solution (twice, 125 ml), with water (125 ml) and, finally, with a saturated aqueous sodium chloride solution (125 ml), successively, followed by drying, whereupon the solvent was distilled off under a reduced pressure. The resulting residue was purified by a silica gel column chromatography and the target compound was obtained (15.41 g) from n-hexane-eluted fractions as a slightly brownish solid. Rf=0.86 (ethyl acetate/n-hexane of 1/1).

C. Synthesis of (±)-N'-[5-[2-[2-(dibenzofuran-3-yloxy) ethylamino]-1-(triethylsilyloxy)ethyl]-2-benzyloxyphenyl]-N,N-dimethylsulfamide (Intermediate 43)

A solution of 150 mg of Intermediate 42, 71.6 mg of Intereemediate 5 and 0.44 ml of Hunig Base (supplied from the firm Aldrich) in 0.5 ml of dimethylacetamide was agitated at 60° C. for 12 hours. To the reaction mixture, 40 ml of ethyl acetate and 40ml of water were added to effect extraction and the aqueous phase was further extracted with ethyl acetate three times. The united organic phase was dried and the solvent was distilled off under a reduced pressure. The resulting residue was purified by a column chromatography (chloroform-methanol/chloroform=1/49), whereby 173 mg of the above-identified compound were obtained. Rf=0.74 (methanol/chloroform of 1/10).

D. Synthesis of (±)-N'-[5-[2-[2-(dibenzofuran-3-yloxy) ethylamino]-1-hydroxyethyl]-2-benzyloxyphenyl]-N,N-dimethylsulfamide To a solution of 60.1 mg of Intermediate 43 in 2.9 ml of anhydrous tetrahydrofuran, 36.8 μl of acetic acid and 574 μl of 1 M solution of tetrabutyl ammonium fluoride in tetrahydrofuran were added and the mixture was agitated at room temperature for 1 hour. The reaction mixture was diluted with ethyl acetate and was washed with saturated aqueous sodium bicarbonate solution and then with saturated aqueous sodium chloride solution, followed by drying, whereupon the solvent was distilled off under a reduced pressure. The resulting residue was purified by a silica gel chromatography,whereupon the above-identified compound (50.0 mg) was obtained from eluted fractions with methanol/chloroform (7/100). Rf=0.39 (methanol/chloroform of 1/10).

EXAMPLE 43

(±)-N'-[5-[2-[2-(dibenzofuran-3-yloxy)ethylamino]-1-hydroxyethyl]-2-hydroxyphenyl]-N,N-dimethylsulfamide hydrochloride The compound of Example 42 was dissolved in 5.9 ml of methanol and thereto were added 0.92 ml of 0.1 N hydrogen chloride/ethanol and 27.6 mg of 10% palladium/carbon black and the mixture was agitated under 1 atm hydrogen gas for 2.5 hours. The catalyst was filtered and washed with hot methanol. whereupon the solvent was distilled off under a reduced pressure. The residue was triturated with diethyl ether and was collect by filtration. By drying at 50° C. under a reduced pressure for 2 hours, the above-identified compound (24.7 mg) was obtained as a slightly brownish amorphous product. Rf=0.25 (methanol/chloroform of 1/10).

EXAMPLE 44

(±)-N'-[5-[2-[2-(9H-7-acetylaminofluoren-2-yloxy) ethylamino]1-hydroxyethyl]-2-benzyloxyphenyl]-N,N-dimethylsulfamide A. Synthesis of (±)-N'-[5-[2-[2-(9H-7-acetylaminofluoren-2-yloxy)ethylamino]-1-(triethylsilyloxy)ethyl]-2-benzyloxyphenyl]-N,N-dimethylsulfamide (Intermediate 44)

In the same manner as in the case of Intermediate 43 in the step C of Example 42, a solution of 486 mg of Intermediate 42, 290,4 mg of Intermediate 17 and 1.44 ml of Hunig Base (supplied from the firm Aldrich) in 1.3 ml of dimethylacetamide was agitated at 60° C. for 16 hours. To the reaction mixture, ethyl acetate and water were added to effect extraction and the aqueous phase was further extracted with ethyl acetate three times. The united organic phase was dried and the solvent was distilled off under a reduced pressure. The resulting residue was purified by a column chromatography (chloroform-methanol/chloroform=1/49), whereby 75.3 mg of the above-identified compound were obtained. Rf=0.51 (methanol/chloroform of 1/10).

B. Synthesis of (±)-N'-[5-[2-[2-(9H-7-acetylaminofluoren-2-yloxy)ethylamino]-1-(triethylsilyloxy)ethyl]2-benzyloxyphenyl]-N,N-dimethylsulfamide To a solution of 75.3 mg of Intermediate 44 in 3.3 ml of anhydrous tetrahydrofuran, 43 μl of acetic acid and 667 μl of 1 M solution of tetrabutyl ammonium fluoride in tetrahydrofuran were added and the mixture was agitated at room temperature for 1 hour. The reaction mixture was diluted with ethyl acetate and was washed with saturated aqueous sodium bicarbonate solution and then with saturated aqueous sodium chloride solution, followed by drying over anhydrous sodium sulfate, whereupon the solvent was distilled off under a reduced pressure. The resulting residue was triturated with ethanol, whereupon the above-identified compound (47.1 mg) was obtained as a white powdery product. Rf=0.25 (methanol/chloroform of 1/10).

EXAMPLE 45

(±)-N'-[5-[2-[2-(9H-7-acetylaminofluoren-2-yloxy) ethylamino]-1-hydroxyethyl]-2-hydroxyphenyl]-N,N-dimethylsulfamide hydrochloride The compound of Example 44 was dissolved in 4.8 ml of methanol and thereto were added 0.78 ml of 0.1 N hydrogen chloride/ethanol and 25 mg of 10% palladium/carbon black and the mixture was agitated under 1 atm hydrogen gas for 2.2 hours. The catalyst was filtered and washed with hot methanol, whereupon the solvent was distilled off under a reduced pressure. The residue was triturated with diethyl ether and was collected by filtration. By drying at 50° C. under a reduced pressure for 2 hours, the above-identified compound (40.6 mg) was obtained as a slightly brownish powdery product. Rf=0.05 (methanol/chloroform of 1/10).

EXAMPLE 46

(±)-2-[N-[2-(9H-carbazol-2-yloxy)ethyl]amino]-1-(3-nitrophenyl)]ethanol hydrochloride To a mixed solution of 678.6 mg of HBr addition salt of Intermediate 2 and 371 μl of triethylamine in 45 ml of anhydrous acetonitrile and 4.5 ml of anhydrous dimethylformamide, a solution of 539 mg of 2-bromo-1-(3-nitrophenyl)ethanone [prepared by the method reported by A. A. Larsen et al in J. bled. Chem., 9, 88–97 (1966)] in 20 ml of anhydrous acetonitrile were added under argon atmosphere at 0° C. and the mixture was agitated for 1 hour. This mixture was warmed to the room temperature (ca. 22° C.) and agitation was continued for further 2 hours. To this mixture, a solution of 434 mg of sodium borohydride in 20 ml of absolute ethanol was added at room temperature. After agitation for 1 hour, the reaction was terminated with 1.0 N hydrochloric acid (pH 4), whereupon 1.1 ml of ethanolamine were added thereto. After agitation for 10 minutes, the mixture was diluted with ethyl acetate and the organic layer was washed thrice with saturated aqueous sodium chloride solution and dried, whereupon the solvent was distilled off under a reduced pressure to obtain 0.93 g of crude product. By recrystallization from ethyl acetate/ethanol, unreacted starting amine compound was removed and the filtrate was concentrated, whereupon the resulting residue was purified by a PTLC (development with methanol/chloroform of 1/10), whereby 77.4 mg of free amine compound were obtained. Rf=0.32 (methanol/chloroform of 1/10).

By adding thereto 0.1 N hydrogen chloride/ethanol (1.1 equivalent amount), it was converted into hydrochloride salt (the above-identified compound), followed by evaporating off of the solvent under a reduced pressure. Diethyl ether was added to the resulting residue and the deposited precipitate was subjected to recrystallization from ethanol, followed by drying at 50° C. under a reduced pressure, whereby the above-identified compound was obtained as a powdery product.

EXAMPLE 47

(±)2-[N-[2-(9H-carbazol-2-yloxy)ethyl]amino]-1-(3-aminophenyl)]ethanol hydrochloride To a solution of 43.9 mg of the compound of Example 46 in 2 ml of methanol, 38.3 mg of iron powder and 90 μl of concentrated hydrochloric acid were added and the mixture was agitated at room temperature for 4 hours. The reaction mixture was diluted with water and the pH thereof was adjusted with 5 N NaOH at 10, whereupon extraction with ethyl acetate was carried out. After drying the organic layer, the solvent was distilled off under a reduced pressure, whereby 50 mg of a crude product were obtained. This was purified by a PTLC (development with methanol/ethyl acetate of 1/4), whereby 16 mg of free amine compound were obtained. Rf=0.30 (methanol/ethyl acetate of 1/4).

This was converted into hydrochloride salt (the above-identified compound) by adding 0.1 N hydrogen chloride/ethanol (1.1 equivalent amount) and the solvent was distilled off under a reduced pressure. To the resulting residue, diethyl ether was added and the deposited precipitate was recrystallized from ethanol, followed by drying at 50° C. under a reduced pressure, wherupon the above-identified compound was obtained as a powdery product.

EXAMPLE 48

(±)-N'-[3-[2-[2-(9H-carbazol-2-yloxy)ethylamino]-1-hydroxyethyl]phenyl]-N,N-dimethylsulfamide hydrochloride The reaction and the after-treatments were followed as in Example 46 except that 710 mg of 2-brom-1-[3-[(dimethylsulfamoyl)amino]phenyl]ethanone [prepared by the method reported by A. A. Larsen et al in J. Med. Chem., 9, 88–97 (1966)] were employed and the resulting residue was purified by a PTLC (development with methanol/ethyl acetate of 1/4), whereby 112.2 mg of free amine compound were obtained. Rf=0.52 (methanol/ethyl acetate of 1/3).

This was converted into hydrochloride salt (the above-identified compound) by adding 0.1 N hydrogen chloride/ethanol (1.1 equivalent amount) and the solvent was distilled off under a reduced pressure. To the resulting residue, diethyl ether was added and the deposited precipitate was recrystallized from ethanol, followed by drying at 50° C. under a reduced pressure, wherupon the above-identified compound (93.2 mg) was obtained as a powdery product.

EXAMPLE 49

(±)-N-[5-[2-[2-(9H-7-acetylaminofluoren-2-yloxy)ethylamino]-1-hydroxyethyl]-2-benzyloxyphenyl]methanesulfonamide hydrochloride According to the procedures described in Example 1, 500 mg of Intermediate 17 and 1.06 g of Intermediate 3 (70% purity) were subjected to coupling reaction and the resulting product was then subjected to reduction using 359 mg of sodium borohydride whereupon the reaction mixture was purified by a silicagel column chromatography (methanol/chloroform of 1/9), to obtain 245 mg of free amine product of the above-identified compound. Rf=0.24 (methanol/chloroform of 1/10). A part (97 mg) of it was converted into hydrochloride salt (100 mg) with 0.1 N hydrogen chloride/ethanol.

EXAMPLE 50

(±)-N-[5-[2-[2-(9H-7-acetylaminofluoren-2-yloxy)ethylamino]-1-hydroxyethyl]-2-hydroxyphenyl]methanesulfonamide hydrochloride According to the procedures described in Example 2, the compound of Example 49 (100 mg) was dissolved in 10.5 ml of methanol and subjected to a hydrogenolysis using 49.5 mg of 10% palladium/carbon black. The catalyst was filtered on celite at room temperature and washed with hot methanol. After the filtrate and the washed liquor were brought together, the solvent was distilled off under a reduced pressure, whereby above-identified compound (77.5 mg) was obtained. Rf=0.03 (methanol/chloroform of 1/10).

EXAMPLE 51

(±)-N-[5-[2-[2-(9H-7-aminofluoren-2-yloxy)ethylamino]-1-hydroxyethyl]-2-benzyloxyphenyl]methanesulfonamide hydrochloride 72.1 mg of the free amine compound of Example 49 were dissolved in 10 ml of 10% solution of hydrogen chloride/methanol and was agitated at room temperature for 41 hours. The deposited precipitate was filtered off and washed with diethyl ether, followed by drying (40 minutes) under a reduced pressure at 50° C. to obtain the above-identified compound (49 mg). Rf=0.27 (methanol/chloroform of 1/10).

EXAMPLE 52

(±)-N-[5-[2-[2-(9H-7-aminofluoren-2-yloxy)ethylamino]-1-hydroxyethyl]-2-hydroxyphenyl]methanesulfonamide hydrochloride According to the procedures described in Example 2, the compound of Example 51 (49 mg) was dissolved in 5.4 ml of methanol and subjected to a hydrogenolysis using 10%

Pd-C (25.9 mg). The catalyst was filtered on celite at room temperature and washed with hot methanol. After the filtrate and the washed liquor were brought together, the solvent was distilled off under a reduced pressure, whereby the the above-identified compound (43.1 mg) was obtained. Rf=0.22 (methanol/ethyl acetate of 1/3).

EXAMPLE 53

(±)-N-[5-[2-[2-(9H-carbazol-2-yloxy)ethylamino]-1-hydroxyethyl]-2-benzyloxyphenyl]-2-propanesulfonamide hydrochloride A. Synthesis of 2-bromo-1-[4-benzyloxy-3-[(isopropylsulfonyl)amino]phenyl]ethanone (Intermediate 45)

The above-identified Intermediate was produced (2.03 g, ca. 70% purity) in two process steps from 1-(3-amino-4-benzyloxyphenyl) ethanone (2 g) in the same manner as in the case of Intermediate 3 (though, bromination was performed according to the method described in the step A of Example 29) except that isopropylsulfonyl chloride was employed instead of methanesulfonyl chloride. Rf=0.19 (chloroform).

B. Synthesis of (±)-N-[5-[2-[2-(9H-carbazol-2-yloxy)ethylamino]-1-hydroxyethyl]-2-benzyloxyphenyl]-2-propanesulfonamide hydrochloride According to the procedures described in Example 1, 1.43 g of Intermediate 45 (70% purity) and 686 mg of Intermediate 2 were were subjected to coupling reaction and, subsequently to reduction using 650 mg of sodium borohydride, whereupon the reaction mixture was purified by a silica gel chromatography (methanol/chloroform of 11/89), to obtain 369 mg of free amine product of the above-identified compound. Rf=0.49 (methanol/chloroform of 1/5). This was converted into hydrochloride salt with 0.1 N hydrogen chloride/ethanol.

EXAMPLE 54

(±)-N-[5-[2-[2-(9H-carbazol-2-yloxy)ethylamino]-1-hydroxyethyl]2-hydroxyphenyl]-2-propanesulfonamide hydrochloride According to the procedures described in Example 2, the compound of Example 53 (369 mg) was dissolved in 39.9 ml of methanol and subjected to a hydrogenolysis using 10% Pd-C (190 mg). The catalyst was filtered on celite at room temperature and washed with hot methanol. After the filtrate and the washed liquor were brought together, the solvent was distilled off under a reduced pressure, whereby the above-identified compound (267 mg) was obtained. Rf=0.27 (methanol/ethyl acetate of 1/3).

EXAMPLE 55

(±)-N-[5-[2-[2-(dibenzofuran-3-yloxy)ethylamnio]-1-hydroxyethyl]-2-fluorophenyl]methanesulfonamide hydrochloride A. Synthesis of (±)-N-[5-[2-iodo-1-(triethylsilyloxy)ethyl]-2-fluorophenyl]methanesufonamide (Intermediate 46)

The reaction and after-treatment were performed in accordance with the procedures described in the steps A and B of Example 42, whereby the above-identified compound (10.22 g) was obtained from Intermediate 9 (7.48 g). Rf=0.36 (ethyl acetate/n-hexane of 1/3).

B. Synthesis of (±)-N-[5-[2-[2-(dibenzofuran-3-yloxy)ethylamino]-1-(triethylsilyloxy)ethyl]-2-fluorophenyl]methanesulfonamide (Intermediate 47)

The reaction and after-treatment were performed in accordance with the procedures described in the step C of Example 42, whereby the above-identified compound (648 mg) was obtained from Intermediate 46 (819 mg) and Intermediate 5 (500 mg). Rf=0.44 (methanol/chloroform of 1/10).

C. Synthesis of (±)-N-[5-[2-[2-(dibenzofuran-3-yloxy)ethylamino]-1-hydroxyethyl]-2-fluorophenyl]methanesulfonamide hydrochloride To a solution of 648 mg of Intermediate 47 in 30 ml of tetrahydrofuran, 2.15 ml of 4 N solution of hydrogen chloride/dioxane were added and the mixture was agitated at room temperature for 1 hour, whereupon 30 ml of diethyl ether were added thereto and the crystals were collected by filtration and dried under a reduced pressure to obtain 408.8 mg of the above-identified compound. Rf=0.61 (methanol/ethyl acetate of 1/3).

EXAMPLE 56

(±)-N-[5-[2-[2-(dibenzothiophen-3-yloxy)ethylamino]-1-hydroxyethl]-2-fluorophenyl]methanesulfonamide hydrochloride A. Synthesis of (±)-N-[5-[2-[2-(dibenzothiophen-3-yloxy)ethylamino]-1-(triethylsilyloxy)ethyl]-2-fluorophenyl]methanesulfonamide (Intermediate 48)

The reaction and after-treatment were performed in accordance with the procedures described in the step C of Example 42, whereby the above-identified compound (581.8 mg) was obtained from Intermediate 46 (811 mg) and Intermediate 39 (500 mg). Rf=0.52 (methanol/chloroform of 1/10).

B. Synthesis of (±)-N-[5-[2-[2-(dibenzothiophen-3-yloxy)ethylamino]-1-hydroxyethyl]-2-fluorophenyl]methanesulfonamide hydrochloride To a solution of 581.8 mg of Intermediate 48 in 30 ml of tetrahydrofuran, 1.88 ml of 4 N solution of hydrogen chloride/dioxane were added and the mixture was agitated at room temperature for 1 hour, whereupon 30 ml of diethyl ether were added thereto and the crystals were collected by filtration and dried under a reduced pressure to obtain 412 mg of the above-identified compound. Rf=0.50 (methanol/ethyl acetate of 1/3).

EXAMPLE 57

(±)-N-[5-[2-[2-(dibenzofuran-3-yloxy)ethylamino]-1-hydroxyethyl]-2-chlorophenyl]methanesulfonamide hydrochloride A. Synthesis of (±)-N-[5-[2-iodo-1-(triethylsilyloxy)ethyl]-2-chlorophenyl]methanesulfonamide (Intermediate 49)

The reaction and after-treatment were performed in accordance with the procedures described in the steps A and B of Example 42, whereby the above-identified compound (1.24 g) was obtained from Intermediate 13 (1.72 g). Rf=0.65 (ethyl acetate/n-hexane of 1/2).

B. Synthesis of (±)-N-[5-[2-[2-(dibenzofuran-3-yloxy)ethylamino]-1-(triethylsilyloxy)ethyl]-2-chlorophenyl]methanesulfonamide (Intermediate 50)

The reaction and after-treatment were performed in accordance with the procedures described in the step C of Example 42, whereby the above-identified compound (544 mg) was obtained from Intermediate 49 (873 mg) and Intermediate 5 (500 mg). Rf=0.49 (methanol/ethyl acetate of 1/10).

C. Synthesis of (±)-N-[5-[2-[2-(dibenzofuran-3-yloxy) ethylamino]-1-hydroxyethyl]-2-fluorophenyl ]methanesulfonamide hydrochloride To a solution of 544 mg of Intermediate 50 in 30 ml of tetrahydrofuran, 1.75 ml of 4 N solution of hydrogen chloride/dioxane were added and the mixture was agitated at room temperature for 1 hour, whereupon 30 ml of diethyl ether were added thereto and the crystals were collected by filtration and dried under a reduced pressure to obtain 296.8 mg of the above-identified compound. Rf=0.67 (methanol/ethyl acetate of 1/3).

EXAMPLE 58

(±)-N-[5-[2-[2-(dibenzothiophen-3-yloxy) ethylamino]-1-hydroxyethyl]-2-chlorophenyl] methanesulfonamide hydrochloride A. Synthesis of (±)-N-[5-[2-[2-(dibenzothiophen-3-yloxy) ethylamino]-1-(triethylsilyloxy)ethyl ]-2-chlorophenyl] methanesulfonamide (Intermediate 51)

The reaction and after-treatment were performed in accordance with the procedures described in the step C of Example 42, whereby the above-identified compound (122 mg) was obtained from Intermediate 49 (480 mg) and Intermediate 39 (249.8 mg). Rf=0.45 (ethyl acetate/hexane of 2/1).

B. Synthesis of (±)-N-[5-[2-[2-(dibenzothiophen-3-yloxy) ethylamino]-1-hydroxyethyl]-2-chlorophenyl] methanesulfonamide hydrochloride To a solution of 122 mg of Intermediate 51 in 6 ml of tetrahydrofuran, 0.38 ml of 4 N solution of hydrogen chloride/dioxane was added and the mixture was agitated at room temperature for 1 hour, whereupon diethyl ether was added thereto and the crystals were collected by filtration and dried under a reduced pressure to obtain 86.7 mg of the above-identified compound. Rf=0.76 (methanol/ethyl acetate of 1/3).

EXAMPLE 59

(±)-N'-[5-[2-[2-(9H-carbazol-2-yloxy)ethylamino]-1-hydroxyethyl]-2-fluorophenyl]-N,N-dimethylsulfamide hydrochloride A. Synthesis of 1-[4-fluoro-3-[(dimethylsulfamoyl)amino] phenyl]ethanone (Intermediate 52)

To a solution of 1 g of Intermediate 7 in 7.2 ml of pyridine, 708 μl of dimethylaminosulfonyl chloride were added at room temperature. After agitation for 3 days, the mixture was poured into 50 ml of water and extraction with chloroform was carried out. The organic layer was washed with saturated aqueous sodium chloride solution and dried, followed by evaporating under a reduced pressure to obtain a crude product. Then, the above reaction and after-treatment were carried out once more under the same condition and the resulting crude product was purified by a column chromatography (2/1: n-hexane/ethyl acetate), whereby 1.1 g of above-identified compound were obtained. Rf=0.21 (ethyl acetate/n-hexane of 1/2).

B. Synthesis of 2-bromo-1-[4-fluoro-3-[(dimethylsulfamoyl) amino]phenyl]ethanone (Intermediate 53)

To a solution of 1.1 g of Intermediate 52 in 10 ml of 1,4-dioxane, 229 μl of bromine were added under agitation. This mixture was warmed to 60° C. and was agitated for 2.5 hours. After cooling down to room temperature, water was added thereto and extraction with ethyl acetate was carried out,whereupon the organic layer was washed saturated aqueous sodium chloride solution and dried, followed by concentration under a reduced pressure to obtain the above-identified compound as a crude product (1.588 g). Rf=0.52 (ethyl acetate/n-hexane of 1/1).

C. Synthesis of (±)-N'-[5-[2-[2-(9H-carbazol-2-yloxy) ethylamino]-1-hydroxyethyl]-2-fluorophenyl]-N,N-dimethylsulfamide hydrochloride A modification of the procedures described in the step D of Example 1 was employed, in which a solution of 1.58 g of Intermediate 53 in 15 ml of anhydrous acetonitrile were added to a solution of 632 mg of Intermediate 2 in a mixed solvent composed of 30 ml of anhydrous acetonitrile and 15 ml of anhydrous dimethylformamide under argon atmosphere at 0° C., whereupon 824 μl of triethylamine were added thereto and the mixture was warmed to the room temperature (ca. 22° C.) and was agitated for 50 minutes.

To this mixture was then added a solution of 903 mg of sodium borohydride in 30 ml of absolute ethanol at room temperature. After agitation for 70 minutes, the reaction was terminated using 1 N hydrochloric acid (pH 4) and thereto was added 1.35 ml of ethanolamine. After agitation for 10 minutes, the mixture was diluted with 200 ml of ethyl acetate, organic layer was rinsed with saturated aqueous sodium chloride solution three times and, then, dried, whereupon it was evaporated under a reduced pressure to obtain a crude product. This was purified by a column chromatography (methanol/chloroform of 1/20), whereby 276 mg of free amine product of the above-identified compound were obtained. Rf=0.66 (10% conc. aq. ammonia-containing methanol/ethylacetate of 1/4).

To this, 1.1 equivalent amount of 0.1 N hydrogen chloride/ethanol were added to convert it into hydrochloride salt (the above-identified compound), from which the solvent was distilled off under a reduced pressure. To the resulting residue was added ethanol/ethyl acetate, the thereby deposited precipitate was isolated by filtration and was dried under a reduced pressure at 50° C., whereby 188.2 mg of the above-identified compound were obtained as a powdery product.

EXAMPLE 60

(±)-N'-[5-[2-[2-(9H-carbazol-2-yloxy)ethylamino]-1-hydroxyethyl]-2-chlorophenyl]-N,N-dimethylsufamide hydrochloride A. Synthesis of 1-[4-chloro-3-[(dimethylsulfamoyl)amino] phenyl]ethanone (Intermediate 54)

To a solution of 1 g of Intermediate 11 in 6.5 ml of pyridine, 640 μl of dimethylsulfamoyl chloride were added at room temperature and the mixture was agitated for 28 hours. After heating the mixture at 40° C. for 65 hours, this was poured into water and extraction with chloroform was carried out. The organic layer was washed with saturated aqueous sodium chloride solution and dried, followed by evaporating under a reduced pressure to obtain a crude product. This was purified by a column chromatography (n-hexane/ethyl acetate of 4/1), whereby 865 mg of the above-identified compound were obtained. Rf=0.24 (ethyl acetate/n-hexane of 1/2).

B. Synthesis of 2-bromo-1-[4-chloro-3-[(dimethylsulfamoyl) amino]phenyl]ethanone (Intermediate 55)

To a solution of 860 mg of Intermediate 54 in 9 ml of 1,4-dioxane, 168 μl of bromine were added under agitation. This mixture was warmed to 60° C. and was agitated for 1.5 hours. After cooling down to room temperature, water was added thereto and extraction with ethyl acetate was carried out,whereupon the organic layer was washed saturated aqueous sodium chloride solution and dried, followed by evaporating under a reduced pressure to obtain the above-identified compound as a crude product (1.05 g). Rf=0.55 (ethyl acetate/n-hexane of 1/1).

C. Synthesis of (±)-N'-[5-[2-[2-(9H-carbazol-2-yloxy)ethylamino]-1-hydroxyethyl]-2-chlorophenyl]-N,N-dimethylsulfamide hydrochloride According to the procedures described in the step C of Example 59, the Intermediate 2 (447 mg) was reacted with the Intermediate 55 (1.05 g), followed by after-treatment and purification by a column chromatography (methanol/chloroform of 1/20) and further by a PTLC (10% conc. aq. ammonia-containing methanol/ethyl acetate of 1/4), whereby 251.1 mg of free amine product of the above-identified compound were obtained. Rf=0.67 (10% conc. aq. ammonia-containing methanol/ethyl acetate of 1/4).

To this, 1.1 equivalent amount of 0.1 N hydrogen chloride/ethanol were added to convert it into hydrochloride salt (the above-identified compound), from which the solvent was distilled off under a reduced pressure. To the resulting residue was added ethanol/ethyl acetate and the thereby deposited precipitate was isolated by filtration and was dried under a reduced pressure at 50° C., whereby 253.9 mg of the above-identified compound were obtained as a powdery product.

EXAMPLE 61

(±)-N-[5-[2-[2-(9H-carbazol-2-yloxy)ethylamino]-1-hydroxyethyl]-3-benzyloxyphenyl] methanesulfonamide A. Synthesis of 1-(3,5-dinitrophenyl)ethanone (Intermediate 56)

To a solution of 8 ml of dimethyl malonate in 70 ml of anhydrous tetrahydrofuran, 78 ml of 0.92 M methyl magnesuim bromide/tetrahydrofuran (supplied from the firm Aldrich) were added dropwise over a period of 30 minutes at a temperature of −10° C. or lower under argon atmosphere. Agitation was continued for further 15 minutes and, then, a solution of 8.0 g of 3,5-dinitrobenzoyl chloride (supplied from Tokyo Chemical Industry Co., Ltd.) in 35 ml of chloroform was added dropwise thereto over a period of 15 minutes. The temperature of the reaction mixture was permitted to elevate to room temperature and agitation was continued for further 59 hours. The solvent was evaporated off from the reaction mixture under a reduced pressure and the resulting amorphous yellow residue (36.72 g) was dissolved in a mixture of 42 ml of acetic acid/35 ml of water, whereto 5 ml of concentrated sulfuric acid were added and the mixture was agitated with heating under reflux for 5 hours. This reaction mixture was poured into 300 ml of ice water and the deposited precipitate was separated by filtration. This was washed with water and dried (6.35 g) at room temperature under a reduced pressure and was recrystallized from ethanol (5ml), whereby 2.1 g of the above-identified compound were obtained. Rf=0.79 (ethyl acetate/n-hexane of 1/2).

B. Synthesis of 1-(3-amino-5-nitrophenyl)ethanone (Intermediate 57)

To a solution of 503 mg of Intermediate 56 in 10 ml of acetic acid, a solution of 1.43 g of stannous chloride (anhydrous) in 5 ml of concentrated hydrochloric acid were added dropwise over a period of 5 minutes with agitation under cooling with salt/icecoolant. The mixture was removed from the cooing bath and was agitated for three hours while the temperature was permitted to elevate gradually to room temperature. This reaction mixture was poured into 100 ml of saturated aqueous sodium bicarbonate solution and the pH was adjusted at 8 by adding a further amount of saturated aqueous sodium bicarbonate solution. whereupon extraction with ethyl acetate (three times with each 50 ml) was performed. The organic layer was washed with saturated aqueous sodium chloride solution and dried, followed by evaporating off of the solvent under a reduced pressure to obtain 160 mg of the above-identified compound. Rf=0.51 (ethyl acetate/n-hexane of 1/2).

C. Synthesis of 1-(3-hydroxy-5-nitrophenyl)ethanone (Intermediate 58)

350 mg of Intermediate 57 were dissolved in 10 ml of sulfuric acid solution (prepared by adding 5 ml of water to 5 ml of concentrated sulfuric acid) and the mixture was agitated under ice-cooling, whereto 5 ml of an aqueous solution of sodium nitrite (140 mg) were added dropwise over a period of 5 minutes. After agitation for further 25 minutes, 10 ml of the above sulfuric acid were added thereto and the mixture was agitated with heating at 120° C. under reflux for 30 minutes. After cooling down to room temperature, extraction with ethyl acetate (twice with each 40 ml) was performed. The organic layer was dried and the solvent was distilled off under a reduced pressure, whereby 293 mg of a crude product were obtained. This was purified by a silica gel chromatography (elution with chloroform-methanol/chloroform of 3/97–5/95), whereby 154 mg of the above-identified compound were obtained. Rf=0.40 (methanol/chloroform of 1/9).

D. Synthesis of 1-(3-benzyloxy-5-nitrophenyl)ethanone (Intermediate 59)

154 mg of Intermediate 58 were dissolved in 5 ml of anhydrous dimethylformamide and thereto were added 360 mg of anhydrous potassium carbonate, 0.22 ml of benzyl bromide and 130 mg of sodium iodide, successively, and the mixture was agitated for 11.5 hours. Then, 10 ml of water were added to the reaction mixture to terminate the reaction and thereto were added further 50 ml of water, whereupon extraction with ethyl acetate (twice with each 50 ml) was performed. Organic layer was washed with 100 ml of water and with saturatd aqueous sodium chloride solution. successively, followed by drying and distilling off of the solvent under a reduced pressure, whereby 277 mg of a crude product were obtained. This was purified by a silica gel chromatography (elution with ethyl acetate/n-hexane of 1/9), whereby 140 mg of the above-identified compound were obtained. Rf=0.91 (methanol/chloroform of 1/9).

E. Synthesis of 1-(3-amino-5-benzyloxyphenyl)ethanone (Intermediate 60)

140 mg of Intermediate 59 were dissolved-in 20 ml of methanol and thereto were added 5 mg of platinum oxide under argon atmosphere, whereupon the reaction system was replaced with hydrogen gas under ice-cooling. The mixture was agitated for 11.5 hours under ice-cooling, whereupon the reaction system was replaced with argon and 20 ml of chloroform were added thereto. After the catalyst has been removed by filtration, the solvent was distilled off from the filtrate under a reduced pressure, whereby 116 mg of the above-identified compound were obtained. Rf=0.82 (methanol/chloroform of 1/9).

F. Synthesis of 1-[3-benzyloxy-5-[(methylsulfonyl)amino]phenyl]ethanone (Intermediate 61)

According to the method reported by A. A. Larsen in J. Med. Chem., 10, 462–472 (1967), reaction and after-treatment were preformed, whereby 142 mg of the above-identified compound were obtained from 116 mg of Intermediate 60 and 40 µl of methanesulfonyl chloride through purification by silica gel chromatography (elution with methanol/chloroform of 5/95). Rf=0.47 (methanol/chloroform of 1/9).

G. Synthesis of 2-bromo-1-[3-benzyloxy-5-[(methylsulfonyl) amino]phenyl]ethanone (Intermediate 62)

In the same manner as the procedures described in the step A of Example 29, 172 mg of the above-identified compound were obtained from 140 mg of Intermediate 61 and 223 mg of cupric bromide. Rf=0.78 (ethyl acetate/n-hexane of 1/1).

H. Synthesis of (±)-N-[5-[2-[2-(9H-carbazol-2-yloxy) ethylamino]-1-hydroxyethyl]-3-benzyloxyphenyl] methanesulfonamide In accordance with the procedures described in the step D of Example 1, 55 mg of the above-identified compound were obtained from 170 mg of Intermediate 62 and 95 mg of Intermediate 2. Rf=0.28 (methanol/chloroform of 1/9).

EXAMPLE 62

(±)-N-[5-[2-[2-(9H-carbazol-2-yloxy)ethylamino]-1-hydroxyethyl]-3-hydroxyphenyl] methanesulfonamide hydrochloride In accordance with the procedured described in Example 2, 55 mg of the compound of Example 61 were subjected to a hydrogenolysis using 10% palladium/carbon black (27.5 mg), whereby 30.6 mg of the above-identified compound were obtained. Here, however, the crude product was purified in a usual manner by converting it into hydrochloride salt which was recrystallized from methanol/ethyl acetate. Rf=0.05(methanol/chloroform of 1/9).

EXAMPLE 63

(±)-N-[3-[2-[2-(9H-carbazol-2-yloxy)ethylamino]-1-hydroxyethyl]2-hydroxyphenyl]methanesulfonamide hydrochloride A. Synthesis of 1-(2-hydroxy-3-nitrophenyl)ethanone (Intermediate 63) and 1-(2-hydroxy-5-nitrophenyl)-ethanone (intermediate 64)

13.2 g of 2-hydroxyacetophenone (supplied from the firm Aldrich) were dissolved in 140 ml of concentrated sulfuric acid under ice-cooling, whereto 9.66 g of potassium nitrate were added. The mixture was agitated at 10–15° C. for 105 minutes, whereto a total of 2.8 g of potassium nitrate were further added in three portions over a period of 8 hours until the starting material has been consumed. Then the mixture was agitated for 14 hours under ice-cooling and the resulting reaction mixture was poured into two liters of ice-water mixture, followed by extraction with ethyl acetate (twice with each 500 ml), whereupon the organic layer was washed with saturated aqueous sodium chloride solution and dried, before the solvent was distilled off under a reduced pressure to obtain 19.23 g of a crude product. This was purified by a silica gel chromatography, whereby 6.0 g of Intermediate 64 were obtained from elution fractions with ethyl acetate/n-hexane of 1/9 and 9.5 g of Intermediate 63 were obtained from elution fractions with ethyl acetate/n-hexane of 1/4.

Intermediate 63: Rf=0.19 (ethyl acetate/n-hexane of 1/4)

Intermediate 64: Rf=0.49 (ethyl acetate/n-hexane of 1/4).

B. Synthesis of 1-(2-methoxy-3-nitrophenyl)ethanone (Intermediate 65)

2.29 g of Intermediate 63 were dissolved in 20 ml of anhydrous dimethylformamide and thereto were added 5.2 g of anhydrous potassium carbonate, and 1.56 ml of methyl iodide, successively, whereupon the mixture was agitated for 18 hours. Then, 50 ml of water were added to the reaction mixture to terminate the reaction, whereupon extraction with ethyl acetate (6 times with each 50 ml) was performed. The organic layer was washed with saturatd aqueous sodium chloride solution, followed by drying and distilling off of the solvent under a reduced pressure, whereby 2.29 g of a crude product were obtained. This was further dried under a reduced pressure with vacuum pump, whereby 1.87 g of the above-identified compound were obtained. Rf=0.58 (ethyl acetate/n-hexane of 1/2).

C. Synthesis of 1-(3-amino-2-methoxyphenyl)ethanone (Intermediate 66)

1.87 g of Intermediate 65 were dissolved in 150 ml of methanol and thereto were added 90 mg of platinum oxide under argon atmosphere, whereupon the reaction system was replaced with hydrogen gas under ice-cooling. The mixture was agitated at room temperature for 5 hours and the reaction system was replaced with argon gas, followed by addition of 50 ml of chloroform. The catalyst was filtered off and the solvent was distilled off from the filtrate under a reduced pressure, whereby 1.59 g of the above-identified compound were obtained. Rf=0.74 (methanol/chloroform of 1/9).

D. Synthesis of 1-[2-methoxy-3-[(methylsulfonyl)amino] phenyl]ethanone (Intermediate 67)

According to the method reported by A. A. Larsen in J. Med. Chem., 10, 462–472 (1967), the above compound was produced from Intermediate 66 (1.59 g) and methanesulfonyl chloride (750 µl). Here, however, the following alteration was incorporated in the purification step from the reaction mixture. Thus, the reaction was terminated with water (50 ml) and the mixture was agitated for 12 hours before extraction with ethyl acetate (once with 50 ml and twice with each 30 ml) with subsequent washing with 1 N hydrochloric acid (twice with each 25 ml) and with saturated aqueous sodium chloride solution, succesively, followed by distilling off of the solvent under a reduced pressure, whereby the above-identified compound was obtained (1.93 g). Rf=0.55 (methanol/chloroform of 1/19).

E. Synthesis of 1-[2-methoxy-3-[N-benzyl-N-(methylsulfonyl) amino]phenyl]ethanone (Intermediate 68)

1.93 g of Intermediate 67 were dissolved in 15 ml of anhydrous dimethylformamide and thereto were added at room temperature 3.32 g of anhydrous potassium carbonate, 1.9 ml of benzyl bromide and 1.2 g of sodium iodide, successively, and the mixture was agitated for 14 hours. Then, 50 ml of water were added to the reaction mixture to terminate the reaction, whereupon extraction with ethyl acetate (thrice with each 40 ml) was performed. Organic layer was washed with water (twice with each 50 ml) and with saturatd aqueous sodium chloride solution, successively, followed by drying and distilling off of the solvent under a reduced pressure, whereby 3.04 g of a crude product were obtained. This was purified by a silica gel chromatography (elution with ethyl acetate/n-hexane of 1/4–1/2), whereupon fractions containing the target compound were processed by evaporating and recrystallization from ethyl acetate/n-hexane to obtain the above-identified compound (2.00 g). Rf=0.75 (methanol/chloroform of 1/19).

F. Synthesis of 2-bromo-1-[2-methoxy-3-[N-benzyl-N (methylsulfonyl)amino]phenyl]ethanone (Intermediate 69)

In the same manner as the procedures described in the step A of Example 29, 438 mg of the above-identified compound were obtained from 333 mg of Intermediate 68 and 491 mg of cupric bromide. Rf=0.36 (ethyl acetate/n-hexane of 1/2).

G. Synthesis of (±)-N-benzyl-N-[3-[2-[2-(9H-carbazol2-yloxy)ethylamino]-1-hydroxyethyl]-2-methoxyphenyl] methanesulfonamide (Intermediate 70)

According to the procedures described in the step D of Example 1, the above-identified compound (150 mg) was obtained from Intermediate 69 (438 mg) and Intermediate 2 (215 mg). Rf=0.74 (methanol/chloroform of 1/9).

H. Synthesis of (±)-N-benzyl-N-[3-[2-[2-(9H-carbazol2-yloxy)ethylamino]-1-hydroxyethyl]-2-hydroxyphenyl]methanesulfonamide hydrochloride (Intermediate 71)

To a solution of 100 mg of Intermediate 70 in 10 ml of anhydrous dichloromethane, 0.60 ml of 1 M solution of boron tribromide in dichloromethane (supplied from the firm Aldrich) was added dropwise under cooling with dry ice/acetone coolant. The mixture was agitated as such for 30 minutes and, then. agitation was continued for further 30 minutes under ice-cooling. The reaction was terminated by adding saturated aqueous sodium bicarbonate solution to the reaction mixture and extraction with ethyl acetate was carried out (four times with each 30 ml). The organic layer was washed with saturated aqueous sodium chloride solution with subsequent drying, whereupon the solvent was distilled off under a reduced pressure. The resulting residue was purified by a silica gel chromatography (elution with chloroform/ethyl acetate/10% of conc. aq. ammonia-containing methanol of 16/3/1–6/3/1), whereby 69 mg of free amine product of the above-identified compound were obtained, Rf=0.47 (methanol/chloroform of 1/9).

This was converted into hydrochloride salt using 0.1 N HCl/ethanol, whereby 28 mg of the above-identified compound were obtained by recrystallization from methanol/ethyl acetate. Here, 38 mg of the above-identified compound were recovered also from the filtrate.

I. Synthesis of (±)-N-[3-[2-[2-(9H-carbazol-2-yloxy)ethylamino]-1-hydroxyethyl]-2-hydroxyphenyl]methanesulfonamide hydrochloride According to the precedures described in Example 2, the above-identified compound (17.3 mg) was obtained from Intermediate 71 and the recovered product from the filtration (total sum of 55 mg) by subjecting them to a hydrogenolysis using 10% palladium/carbon black (55 mg) for 13 hours with subsequent recrystallization of the resulting crude product (25 mg) from methanol/ethyl acetate. Rf=0.41 (methanol/chloroform of 1/9).

EXAMPLE 64

(±)-N-[5-[2-[2-(9H-carbazol-2-yloxy)ethylamino]-1-hydroxyethyl]4-hydroxyphenyl]methanesulfonamide hydrochloride A Synthesis of 1-(2-methoxy-5-nitrophenyl)ethanone (Intermediate 72)

The above-identified compound (2.50 g) was obtained by processing Intermediate 64 (2.36 g) resulting from the step A of Example 63 through reaction and after-treatment in accordance with the procedures of the step B of Example 63. Rf=0.37(ethyl acetate/n-hexane of 1/2).

B. Synthesis of 1-(5-amino-2-methoxyphenyl)ethanone (Intermediate 73)

The above-identified compound (2.13 g) was obtained by processing Intermediate 72 (2.50 g) through reaction and after-treatment in accordance with the procedures of the step C of Example 63. Rf=0.38 (methanol/chloroform of 1/19).

C. Synthesis of 1-[2-methoxy-5-[(methylsulfonylamino]phenyl]ethanone (Intermediate 74)

The above-identified compound (2.656 g) was obtained by processing Intermediate 73 (2.13 g) through reaction and after-treatment in accordance with the procedures of the step D of Example 63. Rf=0.35 (methanol/chloroform of 1/19).

D. Synthesis of 1-[2-methoxy-5-[N-benzyl-N-(methylsulfonyl) amino]phenyl]ethanone (Intermediate 75)

A crude product (4.29 g) was obtained by processing Intermediate 74 (2.65 g) through reaction and after-treatment in accordance with the procedures of the step E of Example 63. By purifying this crude product by a silica gel column chromatography (elution with ethyl acetate/n-hexane of 1/4–1/2–2/3) and processing the fractions containing the target compound by evaporating and recryatallization from ethyl acetate/n-hexane, the above-identified compound (2.553 g) was obtained. Rf=0.68 (methanol/chloroform of 1/19).

E. Synthesis of 2-bromo-1-[2-methoxy-5-[N-benzyl-N-(methylsulfonyl)amino]phenyl]ethanone (Intermediate 76)

In the same manner as the procedures described in the step A of Example 29, the above-identified compound (436 mg) was obtained from Intermediate 75 (333 mg) and cupric bromide (491 mg). Rf=0.28 (ethyl acetate/n-hexane of 1/2).

F. Synthesis of (±)-N-benzyl-N-[5-[2-[2-(9H-carbazol-2-yloxy)ethylamino]-1-hydroxyethyl]-4-methoxyphenyl]methanesulfonamide (Intermediate 77)

In accordance with the procedures described in the step D of Example 1, the above-identified compound (70 mg) was obtained from Intermediate 76 (436 mg) and Intermediate 2 (215 mg). Rf=0.52 (methanol/chloroform of 1/9).

G. Synthesis of (±)-N-benzyl-N-[5-[2-[2-(9H-carbazol-2-yloxy)ethylamino]-1-hydroxyethyl]-4-hydroxyphenyl]methanesulfonamide hydrochloride (Intermediate 78)

The free base product (39 mg) was obtained by processing Intermediate 77 (70 mg) through reaction and after-treatment in accordance with the procedures of the step H of Example 63 and purification by a silicagel chromatography (elution with chloroform/ethyl acetate/10% of conc. aq. ammonia-containing methanol of 16/3/1–6/3/1). Rf=0.50 (methanol/chloroform of 1/9). By converting this product into hydrochloride salt using 0.1 N hydrogen chloride/ethanol with subsequent recrystallization from methanol/ethyl acetate, the above-identified compound (17 mg) was obtained.

H. Synthesis of (±)-N-[5-[2-[2-(9H-carbazol-2-yloxy)ethylamino]-1-hydroxyethyl]-4-hydroxyphenyl]methanesulfonamide hydrochloride According to the procedures described in Example 2, Intermediate 78 and the recovered product from the filtration (total sum of 30 mg) were treated by subjecting them to a hydrogenolysis for 13 hours using 10% palladium/carbon black (30 mg) with subsequent trituration of the resulting crude product from methanol/ethyl acetate, whereby the above-identified compound (9 mg) was obtained. Rf=0.34 (methanol/chloroform of 1/9).

EXAMPLE 65

(±)-N-[5-[2-[2-(9H-carbazol-2-yloxy)ethylamino]-1-hydroxyethyl]2-benzyloxy]benzenesulfonamide hydrochloride A. Synthesis of N-methyl-(2-benzyloxy-4-acetylbenzene)sulfonamide (Intermediate 80)

2.41 g of 1-(3-amino-4-benzyloxyphenyl)ethanone [prepared by the method reported by A. A. Larsen et al in J. Med. Chem., 10, 462–472 (1967)] were dissolved in 5 ml of acetic acid and thereto were adde 5 ml of concentrated hydrochloric acid. To this mixture, 7 ml of an aqueous solution of sodium nitrite (1.0 g) were added over a period of 50 minutes at −10° C. with agitation. Agitation was continued further for 28 minutes under ice-cooling and thereto were added a solution of 3.5 ml of thionyl chloride in 6.5 ml of acetic acid and 3 ml of an aqueous solution of cupric chloride dihydrate (720 mg), successively, whereupon the mixture was agitated for 6 hours, while the temperature was allowed to return to room temperature. The deposited precipitate was separated by filteration and was dissolved in chloroform, followed by water washing and drying with subsequent evaporating up to a volume of 50 ml under a reduced pressure, whereby a solution of 2-benzyloxy-5-acetylbenzenesulfonylchloride (Intermediate 79) in chloroform was prepared.

Thereto was added 1.0 ml of 40% aqueous solution of methylamine and the mixture was agitated at room temperature for 16.5 hours. To this reaction mixture, 50 ml of water were added and the organic layer was separated. The aqueous layer was extracted once with chloroform (50 ml) and the extract was brought together with the above organic layer and was rinsed with saturated aqueous sodium chloride solution, followed by drying, whereupon the solvent was distilled off under a reduced pressure. Resulting residue was purified by a silica gel chromatography(chloroform-methanol/chloroform of 1/19), whereby 200 mg of the above-identified compound were obtained. Rf=0.05 (chloroform).

B. Synthesis of N-methyl-[2-benzyloxy-4-(2-bromoacetyl) benzenesulfonamide (Intermediate 81)

In the same manner as the procedures described in the step A of Example 29, the above-identified compound (248 mg) was obtained from Intermediate 80 (200 mg) and cupric bromide (310 mg). Rf=0.83 (ethyl acetate/n-hexane of 1/1).

C. Synthesis of (±)-N-methyl-[5-[2-[2-(9H-carbazol-2-yloxy) ethylamino]-1-hydroxyethyl]-2-benzyloxy] benzenesulfonamide In the same manner as in the procedures described in the step D of Example 1 except that a silicagel chromatography (methanol/ethyl acetate of 1/19–1/9) was employed for the purification of the crude product, the above-identified compound (118 mg) was obtained from Intermediate 81 (248 mg) and Intermediate 2 (136 mg). Rf=0.55 (methanol/chloroform of 1/9).

EXAMPLE 66

(±)-N-methyl-[5-[2-[2-(9H-carbazol-2-yloxy) ethylamino]-1-hydroxyethyl]-2-hydroxy] benzenesulfonamide hydrochloride In accordance with the procedured described in Example 2, the compound of Example 65 (110 mg) were subjected to a hydrogenolysis using 10% palladium/carbon black (55 mg) for 1 hour, whereby the above-identified compound (39 mg) was obtained. Rf=0.05 (methanol/chloroform of 1/9).

EXAMPLE 67

(±)-2-[N-[2-(9H-carbazol-2-yloxy)ethyl]amino]-1-[4-hydroxy-3-(hydroxymethyl)phenyl]ethanol hydrochloride A. Synthesis of 2-benzyloxy-5-acetylbenzoic acid methyl ester (Intermediate 82)

1.94 g of 5-acetylsalicylic acid methyl ester (supplied from the firm AVOCADO) were dissolved in 15 ml of anhydrous dimethylformamide and thereto were added 4.2 g of anhydrous potassium carbonate, 2.5 ml of benzyl bromide and 3.3 g of sodium iodide, successively, whereupon the mixture was agitated for 60 hours. The reaction was terminated by adding 15 ml of water to the reaction mixture and th mixture was agitated with ice-cooling. The deposited precipitate was separated by filtration, washed with water and dried under a reduced pressure at 50° C. (2.83 g). This was recrystallized from toluene/n-hexane and 2.54 g of the above-identified compound were obtained. Rf=0.32 (ethyl acetate/n-hexane of 1/2).

B. Synthesis of 2-benzyloxy-5-(2-bromoacetyl)benzoic acid methyl ester (Intermediate 83)

In the same manner as the procedures described in the step A of Example 29, the above-identified compound (566 mg) was obtained from Intermediate 82(1.42 g) and cupric bromide (151 mg). Rf=0.71 (methanol/chloroform of 1/19).

C. Synthesis of (±)-[5-[2-[2-(9H-carbazol-2-yloxy) ethylaminol-1-hydroxyethyl]-2-benzyloxy]benzoic acid methyl ester (Intermediate 84)

According to the procedures described in the step D of Example 1, the above-identified compound (80 mg) was obtained from Intermediate 2 (154 mg), triethylamine (150 µl), Intermediate 83 (191 mg) and sodium borohydride (151 mg). Rf=0.24 (methanol/chloroform of 1/9).

D. Synthesis of (±)-2-[N-[2-(9H-carbazol-2-yloxy)ethyl] amino]-1-[4-benzyloxy-3-(hydroxymethyl)phenyl]ethanol (Intermediate 85)

To a suspension of 2 mg of lithium aluminum hydride in 5 ml of anhydrous tetrahydrofuran, a solution of 34 mg of Intermediate 84 in 5 ml of anhydrous tetrahydrfuran was added. After agitation for 30 minutes, reaction was terminated by adding I ml of ethyl acetate and 1 ml of 1 N HCl and the aqueous layer was adjusted at pH 10, whereupon extraction with ethyl acetate(twice with each 20 ml) was performed. The organic layer was dried and the solvent was distilled off under a reduced pressure, whereupon the resulting residue (28 mg) was purified by a silica gel chromatography (methanol/chloroform of 1/9–1/7) to obtain 24 mg of the above-identified compound. Rf=0.05 (methanol/chloroform of 1/9).

E. Synthesis of (±)-2-[N-[2-(9H-carbazol-2-yloxy)ethyl] amino]-1-[4-hydroxy-3-(hydroxymethyl)phenyl]ethanol hydrochloride In accordance with the procedured described in Example 2, Intermediate 85 (24 mg) was added to methanol (5 ml) and was subjected to a hydrogenolysis using 10% palladium/carbon black (12 mg) for 2.5 hours, whereby the above-identified compound (8.9 mg) was obtained. Rf=0.21 (methanol/chloroform of 1/7).

EXAMPLE 68

(±)-N-[3-[2-[2-(9H-6-(acetylamino)carbazol-2-yloxy]ethylamino]-1-hydroxyethyl]phenyl] methanesulfonamide hydrochloride A. Synthesis of (±)-N-[3-(2-bromo-1-hydroxyethyl)phenyl] methanesulfonamide (Intermediate 86)

The above-identified compound (50.76 g) was obtained by processing Intermediate 14 (45 g) through reaction and after-treatment in accordance with the procedures of synthesis of Intermediate 41. Rf=0.27 (methanol/chloroform of 1/10).

B. Synthesis of (±)-N-[3-[2-iodo-1-(triethylsilyloxy)ethyl] phenyl]methanesulfonamide (Intermediate 87)

According to the method for synthesizing Intermediate 42, Intermediate 86 (50.1 g) was dissolved in dried acetone (944 ml) and thereto was added sodium iodide (257.57 g) and the mixture was agitated with heating under reflux for 2.5 hours. Then, the mixture was cooled down to room temperature and was filtered, whereupon the filtrate was evaporated to dryness under a reduced pressure. The resulting residue was subjected to extraction with 720 ml of dichloromethane and 720 ml of water, followed by washing of the organic layer with 23.5% (w/w) of aqueous sodium hydrogen sulfite solution (twice), with water and with saturated aqueous sodium chloride solution, successively, and drying, whereupon the solvent was distilled off under a reduced pressure. The residue was further dried under a reduced pressure using a vacuum pump, whereby 51.61 g of a viscous fluid product was obtained. This was dissolved in 351 ml of anhydrous dimethylformamide at room temperature, whereto 28.3 g of imidazole and 1.61 g of 4-dimethylaminopyridine and the resulting mixture was agitated for 15 minutes. Thereto were added 27.04 ml of chlorotrimethylsilane all at once and the mixture was agitated at room temperature for 40 minutes. The resulting mixture was then diluted with 840 ml of ethyl acetate and 336 ml of n-heptane and was then washed with water (420 ml), with 2% aqueous solution of copper sulfate (twice with each 420 ml), with water (420 ml) and finally with saturated aqueous sodium chloride solution (420 ml), successively, and dried, whereupon the solvent was distilled off under a reduced pressure to obtain 68.25 g of the above-identified compound. Rf=0.48 (methanol/chloroform of 1/10).

C. Synthesis of 4-acetylaminocyclohexanone (Intermediate 88)

To a suspension of 20.85 g of trans-4-acetamidecyclohexanol in 21.6 ml of water under ice-cooling, Jone's Reagent prepared from 9.28 g of cromium trioxide, 8.1 ml of concentrated sulfuric acid and 33.4 ml of water was added over a period of 8 minutes under ice-cooling. The resulting mixture was agitated for further 5 hours under ice-cooling, whereupon it it was stored in a refrigerator for 2 days. This was subjected to extraction with chloroform (10 times with each 70 ml). followed by washing with saturated aqueous sodium bicarbonate solution and drying, whereupon the solvent was distilled off under a reduced pressure. The resulting residue was further dried at room temperature under a reduced pressure, whereby 8.45 g of the above-identified compound were obtained. Rf=0.40 (methanol/chloroform of 1/10).

D. Synthesis of ($\pm$)-3-acetylamino-7-methoxy-1,2,3,4-tetrahydrocarbazole (Intermediate 89)

9.77 g of 3-methoxyphenylhydrazine hydrochloride (supplied from the firm ACROS) and 8.58 g of Intermediate 88 were dissolved in 83 ml of ethanol. whereto 35 ml of 4 N hydrogen chloride/1,4-dioxane (supplied from the firm Aldrich) were added and the mixture was heated under reflux for 3 hours. The resulting nixture was cooled down to room temperature and precipitate was filtered off and the solvent in the filtrate was distilled off under a reduced pressure. To the resulting residue, ethanol/n-heptane was added and the resulting mixture was evaporated to dryness, whereupon the residue was dissolved in a small amount of ethanol, whereto water was added and the deposited precipitate was triturated and isolated by filtration, followed by water washing and drying at 42° C. under a reduced pressure. This was then treated by trituration with small amount of ethanol, crystallization from ethyl acetate (200 ml), filtration of crystals, washing with ethyl acetate and drying under a reduced pressure at room temperature to obtain 5.188 g of the above-identified compound as primary crystals. Rf=0.45 (methanol/chloroform of 1/10).

E. Synthesis of 9H-6-acetylamino-2-methoxycarbazole (Intermediate 90)

5.188 g of Intermediate 89 and 9.459 g of 2,3-dichloro-5,6-dicyano-1,4-benzoquinone (97%) were heated under reflux in benzene for 7.5 hours under argon atmosphere. The reaction mixture was filtered with heating and the filtered cake was washed with hot benzene. The filtrate and the washed liquor were brought together, from which the solvent was distilled off under a reduced pressure. To the resulting residue, ethanol was added and the deposited product was isolated by filtration, whereby 269 mg of the above-identified compound (primary crystals) were obtained. Rf=0.39 (methanol/chloroform of 1/10).

F. Synthesis of 9H-6-acetylamino-2-hydroxycarbazole (intermediate 91)

269 mg of Intermediate 90 were added at 180° C. to pyridine hydrochloride (prepared by heating 5 ml of pyridine and 5 ml of concentrated hydrochloric acid at 180° C. for 1.5 hours to dehydrate) and the mixture was agitated with heating under reflux for 4 hours. The resulting mixture was poured into 100 ml of ice and was then subjected to extraction with ethyl acetate. The aqueous layer was adjusted at pH 7 and was treated by a further extraction with ethyl acetate. Both organic layers were brought together and are washed with saturated aqueous sodium chloride solution, followed by drying, whereupon the solvent was distilled off under a reduced pressure. The resulting residue (182.1 mg) was dissolve in pyridine (5 ml), whereto 1 ml of acetic anhydride was added and the mixture was agitated at room temperature for 12 hours. The resulting mixture was diluted with 50 ml of water and was then subjected to extraction with ethyl acetate, followed by washing with water and then with saturated aqueous sodium chloride solution with subsequent drying, whereupon the solvent was distilled off under a reduced pressure. The resulting residue was dissolved in 4 ml of methanol (MS3A grade), whereto 1 ml of water and 0.5 ml of 5 N aqueous sodium hydroxide solution were added and the mixture was agitated at room temperature for 45 minutes. Then, the mixture was diluted with 40 ml of water and adjusted at pH 3 with 1N hydrochloric acid, whereupon extraction with ethyl acetate was effected three times for this mixture. The resulting organic layers were washed with saturated aqueous sodium chloride solution with subsequent drying, followed by distilling off of the solvent under a reduced pressure, whereby 163.8 mg of the above-identified compound were obtained. Rf=0.10 (methanol/chloroform of 1/10).

G. Synthesis of 9H-6-acetylamino-2-(2-benzyloxycarbonyl-aminoethoxy)carbazole (Intermediate 92)

According to the procedures described in the step B of Example 1, 520 mg of Intermediate 0 were added to a solution of 161 mg of Intermediate 91 and 470 mg of potassium carbonate in dimethylformamide (1.7ml) and the mixture was agitated at room temperature for 11.5 hours with further agitation at 50° C. for 8 hours. Thereto were added ethyl acetate and water, followed by extraction with ethyl acetate twice and washing with water and with saturated aqueous sodium chloride solution, successively, drying and distilling off of the solvent under a reduced pressure, whereupon the resulting residue was purified by a column chromatography (methanol/chloroform of 3/100–6/100), whereby 105.8 mg of the above-identified compound were obtained. Rf=0.37 (methanol/chloroform of 1/10).

H. Synthesis of 2-(gH-6-acetylaminocarbazol-2-yloxy) ethylamine (Intermediate 93)

To 105,8 mg of Intermediate 92, 2.1 ml of 30% solution of hydrogen bromide in acetic acid were added and the mixture was agitated at room temperature for 1.5 hours. Thereto were added 50 ml of diethyl ether and the deposited precipitate was isolated by filtration. This was dissolved in water and the pH was adjusted at 10 with aqueous NaOH and was subjected to extraction with ethyl acetate. After drying the organic layer, the solvent thereof was distilled off under a reduced pressure, whereby 80.1 mg of the above-identified compound were obtained. Rf=0.05 (methanol/chloroform of 1/5).

I. Synthesis of ($\pm$)-N-[3-[2-[2-[9H-6-(acetylamino)carbazol-2yloxy]ethyamino]-1-hydroxyethyl]phenyl] methanesulfonamide hydrochloride 117.5 mg of Intermediate 87 and 80, 1 mg of Intermediate 93 were dissolved in 0.5 ml of anhydrous dimethylacetamide and thereto were added 493 $\mu$l of Hunig Base, whereupon the mixture was agitated at 60° C. for 27 hours under argon atmosphere. Then, the mixture was cooled down to room temperature and was diluted with ethyl acetate, followed by washing water (twice) and then with saturated aqueous sodium chloride solution and drying, whereupon the solvent was distilled off under a reduced pressure. The resulting residue was dissolved in ethyl acetate and the insoluble matter was filtered off, whereupon the filtrate was evaporated under a reduced pressure. The resulting residue was subjected to a primary purification by a silica gel chromatography (methanol/chlorofrom of 5/100–1/10).

Fractions containing a product which is positive to ninhydrin coloration were united and the so-united fractions were evaporated to dryness. The resulting product (49.6 mg) was dissolved in 2.7 ml of anhydrous tetrahydrofuran and thereto were added 35 μl of acetic acid and 535 μl of 1 M tetrabutylammonium fluoride/tetrahydrofuran and the resulting mixture was agitated at room temperature for 1 hour in a tightly closed vessel. The resulting mixture was diluted with ethyl acetate, followed by washing with saturated aqueous sodium bicarbonate solution and, then, with saturated aqueous sodium chloride solution with subsequent drying, whereupon the solvent was distilled off under a reduced pressure. By purifying the resulting residue, by a silica gel chromatography (with eluting off low polar impurities with methanol/chloroform of 1/10 and eluting with conc. aq. ammonia/methanol/chloroform of 1/9/50), 30.5 mg of free amine product of the above-identified compound were obtained. This was converted into hydrochloride salt by a usual technique, followed by dissolution in small amount of methanol, dilution with ethyl acetated, crystallization and collecting by filteration, 29.5 mg of the above-identified compound were obtained. Rf=0.14 (methanol/chloroform of 1/5).

EXAMPLE 69

(R)-N-[5-[2-[2-(dibenzofuran-3-yloxy)ethylamino]-1-hydroxyethyl]-2-hydroxyphenyl]methanesulfonamide hydrochloride In accordance with the procedures described in Example 12, the above-identified compound (37.6 mg) was obtained from Intermediate 19 (220 mg) and Intermediate 5 (121.7 mg).

Retention time: 36.3 min. for R-modification (41.7 min. for S-modification); Analytical condition: column: two sets, 4.6 mm×150 mm, CHIRALCEL OJ-R (supplied from Daicel Chem. Ind.): mobile phase: 0.5 M NaClO$_4$/HClO$_4$ buffer solution (pH 2.0)/acetonitrile(7/3); flow rate: 0.5 ml/min., detection: 254 nm; temperature: 40° C.

EXAMPLE 70

(R)-N-[3-[2-[2-(dibenzofuran-3-yloxy)ethylamino]-1-hydroxyethyl]phenyl]methanesulfonamide hydrochloride In accordance with the procedures described in Example 14, the above-identified compound (167.0 mg) was obtained from Intermediate 26 (815 mg) and Intermediate 5 (455 mg).

Retention time: 28.7 min. for R-modification (25.4 min. for S-modification); Analytical condition: column: two sets, 4.6 mm ID×150 mm, CHIRALCEL OJ-R(supplied from Daicel Chem. Ind.): mobile phase: 0.5 M NaClO$_4$/HClO$_4$ buffer solution (pH 2.0)/acetonitrile(7/3); flow rate: 0.5 ml/min.; detection: 254 nm; temperature: 40° C.

EXAMPLE 71

(R)-N-[3-[2-[2-(9H-7-acetylaminofluoren-2-yloxy)ethylamino]-1-hydroxyethyl]phenyl]methanesulfonamide hydrochloride In accordance with the procedures described in Example 14, the above-identified compound (55.5 mg) was obtained from Intermediate 26 (815 mg) and Intermediate 17 (564.6 mg).

Retention time: 77.6 min. for R-modification (64.7 min. for S-modification); Analytical condition: column: two sets, 4.6 mm ID×150 mm, CHIRALCEL OJ-R(supplied from Daicel Chem. Ind.); mobile phase: 0.5 M NaClO$_4$/HClO$_4$ buffer solution (pH 2.0)/acetonitrile(8/2); flow rate: 0.5 ml/min.; detection: 254 nm; temperature: 40° C.

EXAMPLE 72

(R)-N-[5-[2-[2-(dibenzothiophen-3-yloxy)ethylamino]-1-hydroxyethyl]-2-hydroxyphenyl]methanesulfonamide hydrochloride In accordance with the procedures described in Example 12, the above-identified compound (223.2 mg) was obtained from Intermediate 19 (642 mg) and Intermediate 39 (380 mg).

Retention time: 36.3 min. for R-modification (38.6 min. for S-modification); Analytical condition: column: two sets, 4.6 mm ID×150 mm, CHIRALCEL OJ-R(supplied from Daicel Chem. Ind.); mobile phase: 0.5 M NaClO$_4$/HClO$_4$ buffer solution (pH 2.0)/acetonitrile(7/3); flow rate: 0.5 ml/min.; detection: 254 nm; temperature: 40° C.

EXAMPLE 73

(R)-N'-[5-[2-[2-(9H-carbazol-2-yloxy)ethylamino]-1-hydroxyethyl]-2-hydroxyphenyl]-N,N-dimethylsulfamide hydrochloride A. Synthesis of (R)-N'-[5-(2-bromo-1-hydroxyethyl)-2benzyloxyphenyl]-N,N-dimethylsulfamide In accordance with the procedures described in the synthesis of Intermediate 19, the above-identified compound (925.7 mg) was obtained from Intermediate 40 (1.058 g).

Retention time: 19.6 min. for R-modification (17.4 min. for S-modification): Analytical condition: column: 4.6 mm ID×250 mm, CHIRALCEL OJ (supplied from Daicel Chem. Ind.); mobile phase: ethanol/n-hexane(1/1); flow rate: 0.7 ml/min.; detection: 254 nm; temperature: R.T.

B. Synthesis of (R)-N'-[5-[2-iodo-1-(triethylsilyloxy) ethyl]-2-benzyloxypheny]-N,N-dimethylsulfamide (Intermediate 94)

In the same manner as in the synthesis of Intermediate 42 (racemi), the above-identified compound(l.27 g) was obtained from above-mentioned Intermediate (925 mg) in two process steps.

C. Synthesis of (R)-N'-[5-[2-[2-(9H-carbazol-2-yloxy)ethylamino]-1-(triethylsilyloxy)ethyl]-2-benzyloxyphenyl]-N,N-dimethylsulfamide (Intermediate 95)

In the same manner as the synthesis of Intermediate 43, the above-identified compound (262.2 mg) was obtained from Intermediate 94 (590 mg) and Intermediate 2 (294 mg). Rf=0.54 (methanol/chloroform of 1/10).

D. Synthesis of (R)-N'-[5-[2-[2-(9H-carbazol-2-yloxy)ethylaminol-1-hydroxyethyll-2-benzyloxyphenyl]-N,N-dimethylsulfamide (Intermediate 96)

In accordance with the procedures described in Example 42, the above-identified compound (83.7 mg) was obtained from Intermediate 95 (120 mg).

E. Synthesis of (R)-N'-[5-[2-[2-(9H-carbazol-2-yloxy)ethylamino]-1-hydroxyethyl]-2-hydroxyphenyll-N,N-dimethylsulfamide hydrochloride The above-identified compound (75.6 mg) was obtained by reaction and after-treatment of Intermediate 96 (82 mg) in accordance with the procedures described in Example 25.

Retention time: 38.0 min. for R-modification (47.7 min. for S-modification); Analytical condition: column: two sets, 4.6 mm ID×150 mm, CHIRALCEL OJ-R(supplied from

EXAMPLE 74

(S)-N'-[5-[2-[2-(9H-carbazol-2-yloxy)ethylamino]-1-hydroxyethyl]-2-hydroxyphenyl]-N,N-dimethylsulfamide hydrochloride A. Synthesis of (S)-N'-[5-(2-bromo-1-hydroxyethyl)-2-benzyloxyphenyl]-N,N-dimethylsulfamide In accordance with the procedures of synthesis of Intermediate 19, the above-identified compound (928.1 mg) was obtained from Intermediate 40(1.05 g) using as the asymmetric catalyst an (S)-modification.

Retention time: (19.6 min. for R-modification) 17.4 min. for S-modification; Analytical condition: column: 4.6 mm ID×150 mm, CHIRALCEL DJ (supplied from Daicel Chem. Ind.): mobile phase: ethanol/n-hexane(1/1); flow rate: 0.7 ml/min.; detection: 254 nm; temperature: R.T.

B. Synthesis of (S)-N'-[5-[2-iodo-1-(triethylsilyloxy) ethyl]-2-benzyloxyphenyl]-N,N-dimethylsulfamide (Intermediate 97)

In the same manner as in the synthesis of Intermediate 42 (racemi), the above-identified compound (1.18 g) was obtained from above-mentioned Intermediate (868.1 mg) in two process steps.

C. Synthesis of (S)-N'-[5-[2-[2-(9H-carbazol-2-yloxy)ethylamino]-1-(triethylsilyloxy)ethyl]-2-benzyloxyphenyl]-N,N-dimethylsulfamide (Intermediate 98)

In the same manner as the synthesis of Intermediate 43, the above-identified compound (120.8 mg) was obtained from Intermediate 97 (300 mg) and Intermediate 2 (144 mg).

D. Synthesis of (S)-N'-[5-[2-[2-(9H-carbazol-2-yloxy)ethylamino]-1-hydroxyethyl]-2-benzyloxyphenyl]-N,N-dimethylsulfamide (Intermediate 99)

In accordance with the procedures described for the synthesis of the compound Example 42, the above-identified compound (83.7 mg) was obtained from Intermediate 98 (120.8 mg).

E. Synthesis of (S)-N'-[5-[2-[2-(9H-carbazol-2-yloxy)ethylamino]-1-hydroxyethyl]-2-hydroxyphenyl]-N,N-dimethylsulfamide hydrochloride The above-identified compound (42.3 mg) was obtained by reaction and after-treatment of Intermediate 99 (65.8 mg) in accordance with the procedures described in Example 25.

Retention time: (38.5 min. for R-modification) 47.7 min. for S-modification; Analytical condition: column: two sets, 4.6 mm ID×150 mm, CHIRALCEL OJ-R(supplied from Daicel Chem. Ind.); mobile phase: 0.5 M NaClO$_4$/HClO$_4$ buffer solution (pH 2.0)/acetonitrile (7/3); flow rate: 0.5 ml/min.; detection: 254 nm; temperature: 40° C.

EXAMPLE 75

(R)-N'-[5-[2-[2-(dibenzofuran-3-yloxy)ethylamino]-1-hydroxyethyl]-2-hydroxyphenyl]-N,N-dimethylsulfamide hydrochloride In accordance with the procedures described in Example 73, the above-identified compound (32.9 mg) was obtained from Intermediate 94 (240 mg) and Intermediate 5 (115.4 mg).

Retention time: 18.3 min. for R-modification (21.5 min. for S-modification); Analytical condition: column: two sets, 4.6 mm ID×150 mm, CHIRALCEL OJ-R(supplied from Daicel Chem. Ind.): mobile phase: 0.5 M NaClO$_4$/HClO$_4$ buffer solution (pH 2.0)/acetonitrile(6/4); flow rate: 0.5 ml/min.; detection: 254 nm; temperature: 40° C.

EXAMPLE 76

(S)-N'-[5-[2-[2-(dibenzofuran-3-yloxy)ethylamino]-1-hydroxyethyl]-2-hydroxyphenyl]-N,N-dimethylsulfamide hydrochloride In accordance with the procedures described in Example 74, the above-identified compound (39.6 mg) was obtained from Intermediate 97 (240 mg) and Intermediate 5 (114.4 mg).

Retention time: (18.3 min. for R-modification) 21.5 min. for S-modification; Analytical condition: column: two sets, 4.6 mm ID×150 mm, CHIRALCEL OJ-R(supplied from Daicel Chem. Ind.); mobile phase: 0.5 M NaClO$_4$/HClO$_4$ buffer solution (pH 2.0)/acetonitrile(6/4); flow rate: 0.5 ml/min.; detection: 254 nm; temperature: 40° C.

EXAMPLE 77

(R)-N-[5-[2-[2-(9H-carbazol-2-yloxy)ethylamino]-1-hydroxyethyl]-2-fluorophenyl]methanesulfonamide hydrochloride A. Synthesis of (R)-N-[5-(2-bromo-1-hydroxyethyl)-2fluorophenyl]methanesulfonamide (Intermediate 100)

In accordance with the procedures described in the synthesis of Intermediate 19, the above-identified compound (1.79 g) was obtained from Intermediate 9 (1.53 g) by reaction and after-treatment.

Retention time: 31.1 min. for R-modification (33.3 min. for S-modification): Analytical condition: column: 4.6 mm ID×250 mm, CHIRALPAK AD (supplied from Daicel Chem. Ind.); mobile phase: ethanol/n-hexane(1/1); flow rate: 0.3 ml/min.; detection: 254 nm; temperature: R.T.

B. Synthesis of (R)-N-[5-[2-iodo-1-[(triethylsilyl)oxy]ethyl]-2-fluorophenyl]methanesulfonamide (Intermediate 101)

In accordance with the procedures for synthesis of Intermediate 20, the above-identified compound (2.29 g) was obtained from Intermediate 100 (1.78 g) by reaction and after-treatment.

C. Synthesis of (R)-N-[5-[2-[2-(9H-carbazol-2-yloxy)ethylamino]-1-[(triethylsilyl)oxylethyl]-2-fluorophenyl]methanesulfonamide (Intermediate 102)

In accordance with the procedures for synthesis of Intermediate 21, the above-identified compound (243.0 mg) was obtained from Intermediate 101 (445 mg)and Intermediate 2 (294 mg) by reaction and after-treatment. Rf=0.50 (methanol/chloroform of 1/10).

D. Synthesis of (R)-N-[5-[2-[2-(9H-carbazol-2-yloxy)ethylamino]-1-hydroxyethyl]-2-fluorophenyl]methanesulfonamide hydrochloride Intermediate 102 (243 mg) was dissolved in anhydrous tetrahydrofuran (15 ml), whereto 4 N hydrogenchloride/1,4-dioxane (1 ml) was added and the mixture was agitated at room temperature for 1 hour. The deposited precipitate was taken out and washed with tetrahydrofuran, whereupon it was dried under a reduced pressure at 40° C., whereby the above-identified compound was obtained (96.8 mg).

Retention time: 42.1 min. for R-modification (38.5 min. for S-modification); Analytical condition: column: two sets, 4.6 mm ID×150 mm, CHIRALCEL OJ-R(supplied from Daicel Chem. Ind.): mobile phase: 0.5 M NaClO$_4$/HClO$_4$ buffer solution (pH 2.0)/acetonitrile(7/3); flow rate: 0.5 ml/min.; detection: 254 nm; temperature: 40° C.

EXAMPLE 78

(S)-N-[5-[2-[2-(9H-carbazol-2-yloxy)ethylamino]-1-hydroxyethyl]-2-fluorophenyl]methanesulfonamide hydrochloride A. Synthesis of (S)-N-[5-(2-bromo-1-hydroxyethyl)-2-fluorophenyl]methanesulfonamide (Intermediate 103)

In accordance with the procedures of synthesis of Intermediate 19, the above-identified compound (1.36 g) was obtained from Intermediate 9 (1.53 g) using as the asymmetric catalyst an (S)-modification by reaction and after-treatment.

Retention time: (31.1 min. for R-modification) 33.3 min. for S-modification; Analytical condition: column: 4.6 mm ID×250 mm, CHIRALPAK AD (supplied from Daicel Chem. Ind.); mobile phase: ethanol/n-hexane(1/1): flow rate: 0.3 ml/min.; detection: 254 nm; temperature: R.T.

B. Synthesis of (S)-N-[5-[2-iodo-1-[(triethylsilyl)oxy]ethyl]-2-fluorophenyl]methanesulfonamide (Intermediate 104)

In accordance with the procedures for synthesis of Intermediate 20, the above-identified compound (1.85 g) was obtained from Intermediate 103 (1.36 g) by reaction and after-treatment.

C. Synthesis of (S)-N-[5-[2-[2-(9H-carbazol-2-yloxy)ethylamino]-1-[(triethylsilyl)oxy]ethyl]-2-fluorophenyl]methanesulfonamide (Intermediate 105)

In accordance with the procedures for synthesis of Intermediate 21, the above-identified compound (198.2 mg) was obtained from Intermediate 104 (445 mg) and Intermediate 2 (294 mg) by reaction and after-treatment.

D. Synthesis of (S)-N-[5-[2-[2-(9H-carbazol-2-yloxy)ethylamino]-1-hydroxyethyl]-2-fluorophenyl]methanesulfonamide hydrochloride Intermediate 105 (154.8 mg) was dissolved in anhydrous tetrahydrofuran (6.8 ml), whereto 4 N hydrogenchloride/1,4-dioxane (430 μl) was added and the mixture was agitated at room temperature for 1 hour. The deposited precipitate was taken out and was washed with tetrahydrofuran, whereupon it was dried under a reduced pressure at 40° C., whereby the above-identified compound was obtained (109.0 mg).

Retention time: (42.1 min. for R-modification) 38.5 min. for S-modification; Analytical condition: column: two sets. 4.6 mm ID×150 mm, CHIRALCEL OJ-R (supplied from Daicel Chem. Ind.): mobile phase: 0.5 M NaClO$_4$/HClO$_4$ buffer solution (pH 2.0)/acetonitrile (7/3); flow rate: 0.5 ml/min.; detection: 254 nm; temperature: 40° C.

EXAMPLE 79

(R)-N-[5-[2-[2-(9H-carbazol-2-yloxy)ethylamino]-1-hydroxyethyl]-2-chlorophenyl]methanesulfonamide hydrochloride A. Synthesis of (R)-N-[5-(2-bromo-1-hydroxyethyl)-2-chlorophenyl]methanesulfonamide (Intermediate 106)

In accordance with the procedures of synthesis of Intermediate 19, the above-identified compound (880 mg) was obtained from Intermediate 13 (800 mg) by reaction and after-treatment.

Retention time: 14.1 min. for R-modification (16.8 min. for S-modification); Analytical condition: column: 4.6 mm ID×250 mm, CHIRALPAK AD (supplied from Daicel Chem. Ind.); mobile phase: ethanol/n-hexane (4/1); flow rate: 0.5 ml/min. detection: 254 nm; temperature: R.T.

B. Synthesis of (R)-N-[5-[2-iodo-1-[(triethylsilyl)oxy]ethyl]-2-chlorophenyl]methanesulfonamide (Intermediate 107)

In accordance with the procedures for synthesis of intermediate 20, the above-identified compound (1.24 g) was obtained from Intermediate 106 (880 mg) by reaction and after-treatment.

C. Synthesis of (R)-N-[5-[2-[2-(9H-carbazol-2-yloxy)ethylamino]-1-[(triethylsilyl)oxy]ethyl]-2-chlorophenyl]methanesulfonamide (Intermediate 108)

In accordance with the procedures for synthesis of Intermediate 21, the above-identified compound (135.9 mg) was obtained from Intermediate 107 (489.4 mg) and Intermediate 2 (294 mg) by reaction and after-treatment. Rf=0.57 (methanol/chloroform of 1/10).

D. Synthesis of (R)-N-[5-[2-[2-(9H-carbazol-2-yloxy)ethylamino]-1-hydroxyethyl]-2-chlorophenyl]methanesulfonamide hydrochloride Intermediate 108 (73.2 mg) was dissolved in anhydrous tetrahydrofuran (4.2ml), whereto 4 N hydrogenchloride/1,4-dioxane (240 μl) was added and the mixture was agitated at room temperature for 1 hour. The deposited precipitate was taken out and washed with tetrahydrofuran, whereupon it was dried under a reduced pressure at 40° C., whereby the above-identified compound was obtained (36.3 mg).

Retention time: 61.7 min. for R-modification (58.4 min. for S-modification); Analytical condition: column: two sets, 4.6 mm ID×150 mm, CHIRALCEL OJ-R(supplied from Daicel Chem. Ind.); mobile phase: 0.5 M NaClO$_4$/HClO$_4$ buffer solution (pH 2.0)/acetonitrile(7/3); flow rate: 0.5 ml/min.; detection: 254 nm; temperature: 40° C.

EXAMPLE 80

(S)-N-[5-[2-[2-(9H-carbazol-2-yloxy)ethylamino]-1-hydroxyethyl]-2-chlorophenyl]methanesulfonamide hydrochloride A. Synthesis of (S)-N-[5-(2-bromo-1-hydroxyethyl)-2-chlorophenyl]methanesulfonamide (Intermediate 109)

In accordance with the procedures of synthesis of Intermediate 19, the above-identified compound (753.4 mg) was obtained from Intermediate 13 (780 mg) using as the asymmetric catalyst an (S)-modification by reaction and after-treatment.

Retention time: (14.1 min. for R-modification) 16.8 min. for S-modification; Analytical condition: column: 4.6 mm ID×250 mm, CHIRALPAK AD (supplied from Daicel Chem. Ind.): mobile phase: ethanol/n-hexane(4/1); flow rate: 0.5 ml/min.; detection: 254 nm; temperature: R.T.

B. Synthesis of (S)-N-[5-[2-iodo-1-[(triethylsilyl)oxy]ethyl]-2-chlorophenyl]methanesulfonamide (Intermediate 110)

In accordance with the procedures for synthesis of Intermediate 20, the above-identified compound (1.06 g) was obtained from Intermediate 109 (753 mg) by reaction and after-treatment.

C. Synthesis of (S)-N-[5-[2-[2-(9H-carbazol-2-yloxy)ethylamino]-1-[(triethylsilyl)oxy]ethyl]-2-chlorophenyl]methanesulfonamide (Intermediate 111)

In accordance with the procedures for synthesis of Intermediate 21, the above-identified compound (111.2 mg) was obtained from Intermediate 110 (490 mg) and Intermediate 2 (294 mg) by reaction and after-treatment.

D. Synthesis of (S)-N-[5-[2-L2-(9H-carbazol-2-yloxy)ethylamino]-1-hydroxyethyl]-2-chlorophenyl]methanesulfonamide hydrochloride Intermediate 111 (111.2 mg) was dissolved in anhydrous tetrahydrofuran (6.3 ml), whereto 4 N hydrogenchloride/1, 4-dioxane (360 μl) was added and the mixture was agitated at room temperature for 1 hour. The deposited precipitate was taken out and washed with tetrahydrofuran, whereupon it was dried under a reduced pressure at 40° C., whereby the above-identified compound was obtained (70.4 mg).

Retention time: (61.7 min. for R-modification) 58.4 min. for S-modification: Analytical condition: column: two sets, 4.6 mm ID×150 mm, CHIRALCEL OJ-R (supplied from Daicel Chem. Ind.); mobile phase: 0.5 M NaClO$_4$/HClO$_4$ buffer solution (pH 2.0)/acetonitrile (7/3); flow rate: 0.5 ml/min.; detection: 254 nm: temperature: 40° C.

EXAMPLE 81

(R)-N-methyl-[5-[2-[2-(9H-carbazol-2-yloxy) ethylamino]-1-hydroxyethyl]-2-hydroxy] benzenesulfonamide hydrochloride A. Synthesis of (R)-N-methyl-[5-(2-bromo-1-hydroxyethyl)-2-benzyloxy]benzenesulfonamide (Intermediate 112)

In accordance with the procedures of synthesis of Intermediate 19, the above-identified compound (752.2 mg) was obtained from Intermediate 81 (800 mg)by reaction and after-treatment. Rf=0.15 (ethyl acetate/n-hexane of 1/2).

B. Synthesis of (R)-N-methyl-[5-[2-iodo-1-[(triethylsilyl)oxy]ethyl]-2-benzyloxy]benzenesulfonamide (Intermediate 113)

In accordance with the procedures for synthesis of Intermediate 20, the above-identified compound (587.9 mg) was obtained from Intermediate 112 (462.8 mg) by reaction and after-treatment. Rf=0.53 (ethyl acetate/n-hexane of 1/2).

C. Synthesis of (R)-N-methyl-[5-[2-[2-(9H-carbazol-2-yloxy) ethylamino]-1-((triethylsilyl)oxy]ethyl]-2-benzyloxy]benzenesulfonamide (Intermediate 114)

In accordance with the procedures for synthesis of Intermediate 21, the above-identified compound (265.3 mg) was obtained from Intermediate 113 (587.9 mg) and Intermediate 2 (295 mg) by reaction and after-treatment. Rf=0.45 (methanol/chloroform of 1/10).

D. Synthesis of (R)-N-methyl-(5-[2-(2-(9H-carbazol-2-yloxy) ethylamino]-1-hydroxyethyl]-2-benzyloxy] benzenesulfonamide (Intermediate 115)

To a solution of Intermediate 114 (265.3 mg) in 13.3 ml of anhydrous tetrahydrofuran, acetic acid (169.6 μl) and 1 M solution (2.65 ml) of tetrabutylammonium fluoride in tetrahydrofuran were added and the mixture was agitated at room temperature for 1 hour. The reaction mixture was diluted with ethyl acetate and was washed with saturated aqueous sodium bicarbonate solution and then with saturated aqueous sodium chloride solution, followed by drying over anhydrous sodium sulfate, whereupon the solvent was distilled off under a reduced pressure. The resulting residue was triturated in ethanol, whereupon the above-identified compound (111.3 mg) was obtained. On the other hand, the residue left after evaporation of the filtrate was purified by a silica gel chromatography (methanol/chloroform of 7/100), whereby the above-identified compound was obtained (59 mg).

E. Synthesis of (R)-N-methyl-[5-[2-[2-(9H-carbazol-2-yloxy) ethylamino]-1-hydroxyethyl]-2-hydroxy] benzenesulfonamide hydrochloride In accordance with the procedured described in Example 2, Intermediate 115 (166.3 ma) was treated by reaction and after-treatment, whereby the above-identified compound (136.3 mg) was obtained.

Retention time: 117.8 min. for R-modification(132.6 min. for S-modification): Analytical condition: column: two sets, 4.6 mm ID×150 mm, CHIRALCEL OJ-R (supplied from Daicel Chem. Ind.); mobile phase: 0.5 M NaClO$_4$/HClO$_4$ buffer solution (pH 2.0)/acetonitrile(78/22); flow rate: 0.5 ml/min.; detection: 254 nm; temperature: 40° C.

EXAMPLE 82

(±)-N-[5-[2-[2-(9H-carbazol-2-yloxy)ethylamino]-1-hydroxyethyl]-2-aminophenyl]methanesulfonamide hydrochloride A. Synthesis of 1-(4-acetylamino-3-nitrophenyl)ethanone (Intermediate 116)

To 4.5 ml of ice-cooled acetic anhydride, 0.5ml of fuming nitric acid was added in five allotted portions under agitation. Thereto were added dropwise a solution of 350 mg of 4-acetamide-acetophenone (supplied from the firm Lancaster) in acetic acid (1.8 ml) over a period of 7 minutes, while maintaining the temperature below 12° C. After agitation for 38 minutes at 5° C., 10 ml of water and 10 ml of ethyl acetate were added therein and the organic layer was separated. The aqueous layer was subjected extraction with 10 ml of ethyl acetate and the organic layers were united and the united organic phase was poured into 200 ml of saturated aqueous sodium bicarbonate solution and the mixture was agitated for 30 minutes. The organic layer was separated and the aqueous layer was subjected to extraction with 50 ml of ethyl acetate and the organic layers were brought together and the so-united organic phase was dried, followed by distilling off of the solvent, whereby 0.41 g of the above-identified compound was obtained. Rf=0.67 (methanol/chloroform of 1/19).

B. Synthesis of 1-(3-amino-4-acetylaminophenyl)ethanone (Intermediate 117)

To a solution of 410 mg of Intermediate 116 in 40 ml of methanol, 20 mg of platinum oxide were added under argon atmosphere and the reaction system was replaced with hydrogen gas under ice-cooling. The mixture was agitated at room temperature for 12.5 hours, whereupon the reaction system was replaced with argon gas and 20 ml of chloroform were introduced into the reaction mixture. Catalyst was separated and the solvent in the filtrate was distilled off under a reduced pressure. The resulting residue was purified by a silica gel chromatography (eluted with ethyl acetate/n-hexane of 3/7-solely with ethyl acetate), whereby 0.29 g of the above-identified compound was obtained. Rf=0.06 (methanol/chloroform of 1/19).

C. Synthesis of 1-[4-acetylamino-3-[(methylsulfonyl) amino]phenyl]ethanone (Intermediate 118)

According to the method reported by A. A. Larsen et al in J. Med. Chem., 10, 462–472 (1967), the above-identified compound was prepared from Intermediate 117 (290 mg) and methanesulfonyl chloride (118.5 μl ). Here, however, a modification in the purification of the reaction mixture was incorporated such that the reaction was terminated with addition of 10 ml of water with adjustment of pH at 4 by 1 N hydrochloric acid, before extraction with ethyl acetate (4 times each with 30 ml). The organic layer was washed with saturated aqueous sodium chloride solution and dried, whereupon the solvent was distilled off under a reduced pressure. By purifying the resulting residue by a silica gel chromatography (methanol/chloroform of 3/97), 315 mg of the above-identified compound were obtained. Rf=0.37 (methanol/chloroform of 1/19).

D. Synthesis of 2-bromo-1-[4-acetylamino-3-[(methylsulfonyl) amino]phenyl]ethanone (Intermediate 119)

In the same manner as the procedures described in the step A of Example 29 except that the purification of the compound from the reaction mixture was performed only by a silica gel chromatography (elution with ethyl acetate/n-hexane of 7/13-with ethyl acetate only), 267 mg of the above-identified compound were obtained from 310 mg of Intermediate 118 and 570 mg of cupric bromide. Rf=0.68 (ethyl acetate/n-hexane of 1/1).

E. Synthesis of (±)-N-[5-[2-[2-(9H-carbazol-2-yloxy) ethylamino]-1-hydroxyethyl]-2-acetylaminophenyl] methanesulfonamide ([intermediate 120)

In the same manner as the procedures described in the step D of Example 1 except that only a silica gel chromatography (methanol/chloroform of 5/95–15/85) was employed for purifying the crude product, the above-identified compound (53 mg) was synthesized from Intermediate 119 (147 mg) and Intermediate 2 (90.5 mg). Rf=0.17 (methanol/ chloroform of 1/9).

F. Synthesis of (±)-N-[5-[2-[2-(9H-carbazol-2-yloxy) ethylamino]-1-hydroxyethyl]-2-aminophenyl] methanesulfonamide hydrochloride 70 mg of Interemediate 120 were added to 8 ml of 1,4-dioxane and thereto were added 2 ml of concentrated hydrochloric acid, whereupon to reaction mixture was agitated for 1 hour with heating under reflux. The mixture was evaporated to dryness under a reduced pressure and the resulting residue (60 mg ) was processed by recrystallization from methanol/ethyl acetate, whereby 13 mg of the above-identified compound were obtained. Rf=0.05 (water/ methanol/chloroform of 1/15/25).

EXAMPLE 83

(±)-N-methyl-N-benzyl-[5-[2-[2-(9H-carbazol-2-yloxy)ethylamino]-1-hydroxyethyl]-2-hydroxy] benzenesulfonamide hydrochloride A. Synthesis of N-methyl-N-benzyl-(2-benzyloxy-5-acetyl) benzenesulfonamide (Intermediate 121)

In the same manner as the procedures described in the step A of Example 65, the above-identified compound was prepared from 1-(3-amino-4-benzyloxy-phenyl)ethanone. Here, however, instead of adding 40% aqueous solution of methylamine, 0.2 ml of N-methyl-benzylamine and 0.7 ml of triethylamine were reacted in 10 ml of dichloromethane for 31.5 hours. To the reaction mixture, 10 ml of water were added and the organic layer was collected. The organic layer was washed with 1 N hydrochloric acid and saturated aqueous sodium chloride solution, followed by drying, whereupon the solvent was distilled off under a reduced pressure, whereby 398 mg of the above-identified compound were obtained. Rf=0.36 (ethyl acetate/n-hexane of 1/2).

B. Synthesis of N-methyl-N-benzyl-[2-benzyloxy-5-(2-bromoacetyl)]benzenesulfonamide (Intermediate 122)

In the same manner as the procedures described in the step A of Example 29 except that the purification was effected by a silica gel chromatography (ethyl acetate/n-hexane of 1/9–1/4),the above-identified compound (228 mg) was produced from Intermediate 121 (205 mg) and cupric bromide (246 mg). Rf=0.50 (ethyl acetate/n-hexane of 1/2).

C. Synthesis of (±)-N-methyl-N-benzyl-[5-[2-[2-(9H-carbnazol-2-yloxy)ethylamino]-1-hydroxyethyl]-2-benzyloxy]benzenesulfonamide (Intermediate 123)

According to the procedures described in the step D of Example 1 except that a silica gel chromatography (elution with methanol/chloroform of 5/95 for the first and with methanol/ethyl acetate of 1/19 for the second elution) was employed for the purification of crude product, the above-identified compound (0.20 g ) was obtained from Intermediate 122 (228 mg) and Intermediate 2 (102 mg). Rf=0.25 (methanol/chloroform of 1/19).

D. Synthesis of (±)-N-methyl-N-benzyl-[5-[2-(2-(9H-carbazol-2-yloxy)ethylamino]-1-hydroxyethyl]-2-hydroxy] benzenesulfonamide hydrochloride According to the procedures described in Example 2, 0.20 g of Intermediate 123 were subjected to a hydrogenolysis for 1 hour using 100 mg of 10% palladium/carbon black, followed by conversion into hydrochloride salt and recrystallization from methanol/ethyl acetate, whereby 62 mg of the above-identified compound were obtained. Rf=0.31 (methanol/chloroform of 1/9).

EXAMPLE 84

(±)-N-[5-[2-[2-(H-carbazol-2-yloxy)ethylamino]-1-hydroxyethyl]-2-(hydroxymethyl)phenyl] methanesulfonamide A. Synthesis of 1-[4-(ethoxycarbonyl)phenyl] ethanoneethyleneacetal (Intermediate 124)

9.61 g of 4-acetylbenzoic acid ethyl ester (supplied from the firm Wako Pure Chem. Ind.) were dissolved in 200 ml of toluene and thereto were added 20 ml of ethylene glycol and 200 mg of p-toluenesulfonic acid hydrate under argon atmosphere, whereupon the mixture was heated under reflux for 24 hours on Dean-Stark apparatus while removing water. The reaction mixture was then cooled down to room temperature and the toluene layer was washed with water (twice with each 100 ml) and, then, with saturated aqueous sodium chloride solution (100 ml), followed by drying and evaporation to dryness under a reduced pressure, whereby the above-identified compound (12.76 g ) was obtained. Rf=0.58 (ethyl acetate/n-hexane of 1/2).

B. Synthesis of 1-[4-(hydroxymethyl)phenyl]ethanone (Intermediate 125)

1.90 g of lithium aluminum hydride were suspended in 120 ml of anhydrous tetrahydrofuran under argon atmosphere and thereto were added dropwise a solution of 12.76 g of Intermediate 124 in 40 ml of anhydrous tetrahydrofuran over a period of 90 minutes under ice-cooling with subsequent agitation for 90 minutes. Thereto were added 100 ml of ethyl acetate gradually over a period of 25 minutes to terminate the reaction, whereupon 100 ml of 1 N sulfuric acid were added thereto over a period of 30 minutes. The mixture was further agitated at room temperature for 45 minutes, whereupon 100 ml of water were added thereto and the organic phase was collected. The aqueous phase was subjected to extraction with ethyl acetate (twice with each 100 ml) and the organic layers were brought together and the so-united organic phase was washed with water (100 ml) and, then, with saturated aqueous sodium chloride solution (100 ml), followed by drying and distilling off of the solvent under a reduced pressure. The resulting residue (12.25 g) was dissolved in acetone (200 ml), whereto p-toluenesulfonic acid hydrate (200 mg) was added and the mixture was agitated for 20 hours at room temperature, After confirmation of termination of the reaction by $^1$H-NMR, the acetone solvent was distilled off under a reduced pressure. The residue was treated by partition between 50 ml of ethyl acetate and 50 ml of water and the organic layer was separated, which was washed with saturated aqueous sodium chloride solution and dried, before the solvent was distilled off under a reduced pressure, whereby 6.688 g of the above-identified compound were obtained. Rf=0.19 (ethyl acetate/n-hexane of 1/2).

C. Synthesis of 1-[4-(acetoxymethyl)phenyl]ethanone (Intermediate 126)

6.67 g of Intermediate 125 were dissolved in 7.3 ml of pyridine and thereto were added 6.3 ml of acetic anhydride, whereupon the mixture was agitated at room temperature for 12.5 hours. Thereto were added 300 ml of water to terminate the reaction and the mixture was subjected to extraction with 50 ml of ethyl acetate. The aqueous layer was treated by extraction with ethyl acetate (twice with each 50 ml) and the organic layers were brought together, whereupon the so-united organic phase was washed with 100 ml of water, 50 ml of 1 N hydrochloric acid and, finally, 50 ml of saturated aqueous sodium chloride solution, successively, followed by drying and evaporation of the solvent under a reduced pressure, whereby 8.27 g of the above-identified compound were obtained. Rf=0.56 (ethyl acetate/n-hexane of 1/1).

D. Synthesis of 1-[3-nitro-4-(acetoxymethyl)phenyl] ethanone (Intermediate 127)

To 80 ml of fuming nitric acid under cooling with an ice/salt coolant, 8.09 g of Intermediate 126 were added all at once. While maintaining this temperature, the mixture was agitated for 10 minutes, before it was poured into 300 ml of ice/water mixture. This was treated by extraction with ethyl acetate (three times with each 80 ml) and the organic layer was washed with water (three times with each 100 ml), with saturated aqueous sodium bicarbonate solution and with saturated aqueous sodium chloride solution, succesively, with subsequent drying, whereupon the solvent was distilled off under a reduced pressure. The resulting residue (9.70 g) was purified by a silica gel chromatography (ethyl acetate/ n-hexane of 1/2), whereby 8.41 g of the above-identified compound were obtained. Rf=0.36 (ethyl acetate/n-hexane of 1/2).

E. Synthesis of 1-[3-amino-4-(acetoxymethyl)phenyl] ethanone (Intermediate 128)

1.97 g of Intermediate 127 were dissolved in 358 ml of methanol and thereto were added 10.55 g of stannous chloride and 7.5 ml of concentrated hydrochloric acid under argon atmosphere, whereupon the mixture was agitated at room temperature for 2 hours. Thereto were added 200 ml of saturated aqueous sodium bicarbonate solution and the mixture was agitated at room temperature for 75 minutes, whereupon the inorganic salts precipitated were removed by filtering on celite and the filtrate was evaporated under a reduced pressure to a volume of about 200 ml. This was subjected to extraction with ethyl acetate (300 ml) and the extract was washed with saturated aqueous sodium chloride solution with subsequent drying, whereupon the solvent was distilled off under a reduced pressure. The resulting residue (1.32 g) was purified by a silica gel chromatography (ethyl acetate/n-hexane of 1/2), whereby 0.56 g of the above-identified compound was obtained. Rf=0.31 (ethyl acetate/ n-hexane of 1/2).

F. Synthesis of 1-[3-(methylsulfonyl)amino-4-(acetoxymethyl) phenyl]ethanone (Intermediate 129)

0.56 g of Intermediate 128 was dissolved in 3.6ml of pyridine and thereto were added 215 µl of methanesulfonyl chloride under argon atmosphere and the mixture was agitated at room temperature for 26 hours. Thereto were added 5 ml of water and the mixture was subjected to extraction with ethyl acetate (three times with each 20 ml) and the organic layer was washed with 1 N hydrochloric acid (twice with each 50 ml) and saturated aqueous sodium chloride solution, successively, with subsequent drying, whereupon the solvent was distilled off under a reduced pressure, whereby 0.58 g of the above-identified compound was obtained. Rf=0.39 (ethyl acetate/n-hexane of 1/1).

G. Synthesis of 2-bromo-1-[3-(methylsulfonyl)amino-4-(acetoxymethyl)phenyl]ethanone (intermediate 130)

In the same manner as the procedures described in the step A of Example 29, the above-identified compound (430 mg) was produced from Intermediate 129 (285 mg) and cupric bromide (491 mg, supplied from Kanto Chem. Co., Inc.). Rf=0.44 (ethyl acetate/n-hexane of 1/2).

H. Synthesis of (±)-N-[5-[2-[2-(9H-carbazol-2-yloxy)-ethylamino]-1-hydroxyethyl]-2-(acetoxymethyl)phenyl]-methanesulfonamide (Intermediate 131)

According to the procedures described in the step D of Example 1 except that a silica gel chromatography (with methanol/ethyl acetate of 1/9 -1/4 for the first and with 10% conc. aq. ammonia-containing methanol/chloroform of 2/25 for the second) was employed for the purification of the crude product, the above-identified compound (68 mg) was obtained from Intermediate 130 (405 mg) and Intermediate 2 (226 mg). Rf=0.18(10% conc. aq. ammonia-containing methanol/chloroform of 1/9).

I. Synthesis of (±)-N-[5-[2-[2-(9H-carbazol-2-yloxy)-ethylamino]-1-hydroxyethyl]-2-(hydroxymethyl)phenyl]-methanesulfonamide hydrochloride To 68 mg of Intermediate 131, 10 ml of 2 N aqueous sodium hydroxide solution were added and the mixture was agitated at room temperature for 2.5 hours. This was diluted with 30 ml of water and thereto were added 50 ml of saturated aqueous sodium chloride solution, followed by extraction with ethyl acetate(three times with each 50 ml). The organic layer was dried and the solvent was distilled off therefrom under a reduced pressure, whereupon the resulting residue was purified by a silica gel chromatography (10% conc.aq.ammonia-containing methanol/ethyl acetate of 1/9), whereby free base product of the above-identified compound was obtained. This was converted into hydrochloride salt by a usual technique, which was then treated by crystallization from methanol/ethyl acetate to obtain 22 mg of the above-identified compound. Rf=0.11 (10% conc. aq. ammonia-containing methanol/chloroform of 1/9).

EXAMPLE 85

(±)-N-[5-[2-[2-(9H-carbazol-2-yloxy)ethylamino]-1-hydroxyethyl]-2-bromophenyl]methanesulfonamide 2-bromo-1-[4-bromo-3-[(methylsulfonyl)amino]phenyl] ethanone was produced in the same manner as in the steps B, C and D of Example 6 in accordance with the procedures for the synthesis of Intermediate 13.

A. Synthesis of 1-(3-amino-4-bromophenyl)ethanone

To a solution of 5.0 g of 4-bromo-3-nitroacetophenone (supplied from the firm Lancaster) in 890 ml of methanol, 19.4 g of tin (II) chloride and 17 ml of concentrated hydrochloric acid were added and the mixture was agitated at room temperature for 3.5 hours. There to were added 470 ml of saturated aqueous sodium bicarbonate solution and the deposited precipitate was filtered off, which was subjected to extraction with ethyl acetate. The organic layer was dried and concentrated under a reduced pressure, whereby 3.97 g of the above-identified compound were obtained. Rf=0.43 (ethyl acetate/n-hexane of 1/2).

B. Synthesis of 1-[4-bromo-3-[(methylsulfonyl)amino] phenyl]ethanone (Intermediate 132)

To a solution of 3.97 g of the above compound in 21 ml of pyridine, 1.8 ml of methanesulfonyl chloride were added at room temperature and the mixture was agitated for 1 hour. The mixture was poured into 142 ml of water. After agitation overnight, the deposited precipitate was isolated by filtration and was dissolved in ethyl acetate. The organic layer was washed with saturated aqueous sodium chloride solution with subsequent drying, and concentrated under a reduced pressure to obtain a crude product (4.08 g). Rf=0.41 (ethyl acetate/n-hexane of 1/1).

C. Synthesis of 2-bromo-1-[4-bromo-3-[(methylsulfonyl) amino]phenyl]ethanone (Intermediate 133)

To a solution of 4.08 g of Intermediate 132 in 40 ml of 1,4-dioxane, 0.75 ml of bromine was added with agitation under argon atmosphere. The resulting mixture was warmed to 60° C. and was agitated for 1.5 hours. After having been cooled to room temperature, water was added. The mixture was extracted with ethyl acetate, organic layer was washed with saturated aqueous sodium chloride solution and dried. The mixture was concentrated under a reduced pressure to obtain a crude product (6.28 g). To this, a 1/1 liquid mixture of ethyl acetate/n-hexane was added and-warmed and cooled and the deposited precipitate was isolated by filtration, whereby 4.0 g of the above-identified compound were obtained. Rf=0.54 (ethyl acetate/n-hexane of 1/1).

D. Synthesis of (±)-[5-[2-[2-(9H-carbazol-2-yloxy) ethylamino]-1-hydroxyethyl]-2-bromophenyl] methanesulfonamide hydrochloride According to the procedures described in the step D of Example 1, a free amine product of the above-identified compound (191,6 mg) was produced from HBr-addition salt of Intermediate 2 (452.5 mg) and Intermediate 133 (742.1 mg) through reaction and after-treatment with subsequent purification by a PTLC (with development by methanol/chloroform of 1/10). Rf=0.58 (methanol/ethyl acetate of 1/3).

This was converted into its hydrochloride salt (the above-identified compound) by adding thereto 1.1 equivalent amount of 0.1 N hydrogen chloride/ethanol,wherefrom the solvent was distilled off under a reduced pressure. To the resulting residue, diethyl ether was added and the deposited precipitate was collected by filtration and was processed by recrystallization from ethanol, followed by drying at 50° C. under a reduced pressure, whereby the above-identified compound(112.6 mg) was obtained as a powdery product.

EXAMPLE 86

(±)-N-[5-[2-[2-(9H-carbazol-2-yloxy)ethylamino]-1-hydroxyethyl]-2-iodophenyl]methanesulfonamide 2-bromo-1-[4-iodo-3-[(methylsulfonyl)amino]phenyl] ethanone was produced in the same manner as in the steps A, B, C and D of Example 6.

A. Synthesis of 1-(4-iodo-3-nitrophenyl)ethanone (Intermediate 134)

20 g of 4'-iodoacetophenone (Tokyo Chemical Industry Co., Ltd.) were added in two portions to 130 ml of fuming nitric acid cooled with ice/salt. After agitation for 15 minutes, the resulting mixture was poured into 1 liter of ice water and was then subjected to extraction with 1 liter of ethyl acetate. The organic layer was separated and dried and the solvent was evaporated off, whereby 20.7 g of the above-identified compound were obtained. Rf=0.19 (ethyl acetate/n-hexane of 1/5).

B. Synthesis of 1-(3-amino-4-iodophenyl)ethanone (Intermediate 135)

To a solution of 14.3 g of Intermediate 134 in 2134 ml of methanol, 40.5 g of tin (II) chloride and 40.8 ml of concentrated hydrochloric acid were added and the mixture was agitated at room temperature for 4.75 hours. To this mixture, 1100 ml of saturated aqueous sodium bicarbonate solution were added and deposited precipitate was separated by filtration. Filtrate was partly concentrated and was subjected to extraction with ethyl acetate. The organic layer was dried and concentrated to dryness under a reduced pressure, whereby 11.87 g of the above-identified compound were obtained. Rf=0.67 (methanol/chloroform of 1/10).

C. Synthesis of 1-[4-iodo-3-[(methylsulfonyl) amino]phenyl]ethanone (Intermediate 136)

To a solution of 11.87 g of the Intermediate 135 in 50 ml of pyridine, 3.55 ml of methanesulfonyl chloride were added at room temperature. After agitation for 2.5 hours, the reaction mixture was poured into water (250 ml). The deposited precipitate was separated by filtration and dissolved in ethyl acetate. The organic layer was washed with saturated aqueous sodium chloride solution and dehydrated and concentrated under a reduced pressure to obtain a crude product. To this, ethyl acetate/n-hexane (1/1) was added and deposited precipitate was recovered by filtration and drying, whereby 10.44 g the above-identified compound were obtained. Rf=0.14 (ethyl acetate/n-hexane of 1/3).

D. Synthesis of 2-bromo-1-[4-iodo-3-[(methylsulfonyl) amino]phenyl]ethanone (Intermediate 137)

To a solution of 10.4 g of Intermediate 136 in 102 ml of 1,4-dioxane, 1.66 ml of bromine were added under argon atmosphere with agitation. The resulting mixture was warmed to 60° C. and was agitated for 1.5 hours. After having been cooled to room temperature, it was processed by extraction of water and ethyl acetate, washing of the organic layer, drying and evaporating under reduced pressure, whereby 11.77 g of the above-identified compound were obtained. Rf=0.25 (ethyl acetate/n-hexane of 1/2).

E. Synthesis of (±)-N-[5-[2-[2-(9H-carbazol-2-yloxy) ethylamino]-1-hydroxyethyl]-2-iodophenyl] methanesulfonamide hydrochloride According to the procedures described in the step D of Example 1, free amine product of the above-identified compound (211.5 mg) was obtained from Intermediate 2 (500 mg) and Intermediate 137 (1.385 g) by reaction and after-treatment through crude purification of the resulting residue on a column chromatography (6.3% methanol/chloroform) and fine purification by a PTLC (development with 10% conc. aq. ammonia-containing methanol/ethyl acetate of 1/4). Rf=0.49 (10% conc. aq. ammonia-containing methanol/ethylacetate of 1/4).

To this product, 1.1 equivalent amount of 0.1 N hydrochloric acid/ethanol were added to convert it into hydrochloride salt (the above-identified compound) and the solvent was distilled off under a reduced pressure. After drying at 50° C. under reduced pressure 218 mg of the above-identified compound were obtained as a powdery product.

EXAMPLE 87

(±)-N'-[5-[2-[2-(9H-carbazol-2-yloxy)ethylamino]-1-hydroxyethyl]2-hydroxyphenyl]-N-methyl-N-benzylsulfamide hydrochloride A. Synthesis of N-methyl-N-benzylsulfamoyl chloride To an ice-cooled solution of 3.0 ml of sulfuryichloride in 50 ml of dichloromethane under argon atmosphere, 6.45 ml of N-methy-N-benzylamine and 7.0 ml of triethylamine were added over a period of 15 minutes. After agitation for 15 minutes, 50 ml of water was added thereto to terminate the reaction. The organic layer was separated and washed with 50 ml of 1 N hydrochloric acid with subsequent drying, whereupon the solvent was distilled off under a reduced pressure. 100 ml of n-hexane were added to the resulting residue (8.35 g) and the mixture was cooled, whereupon the deposited precipitate was filtered off. The filtrate was evaporated to dryness under a reduced pressure, whereby 5.30 g of the above-identified compound were obtained. Rf=0.64 (ethyl acetate/n-hexane of 1/4).

B. Synthesis of 1-[4-benzyloxy-3-[(N-methyl-N-benzylsulfamoyl) amino]phenyl]ethanone (Intermediate 138)

The above-identified compound (671 mg) was produced from the above Intermediate (880 mg) and 1-(3-amino-4-benzyloxyphenyl)ethanone (482 mg) [this was carried out in accordance with the method reported by A. A. Larsen et al in J. Med. Chem., 10, 462–472(1967)]. Here, however, a mixed solvent of pyridine/dichloromethane (7 ml, 2/5) was used and there action mixture was agitated first at room temperature for 66 hours and, then, agitated with heating under reflux for further 2 hours. The purification was performed by extraction with 20 ml of water and 50 ml of ethyl acetate and washing the organic layer with 30 ml of 1 N hydrochloric acid. The united aqueous phase was extracted further with ethyl acetate (twice with each 30 ml), whereupon the united organic phase was washed with saturated aqueous sodium chloride solution with subsequent drying, whereupon the solvent was distilled off under a reduced pressure. The resulting residue was purified by a silica gel chromatography (ethyl acetate/n-hexane of 1/3). Rf=0.47 (methanol/chloroform of 1/19).

C. Synthesis of 2-bromo-1-[4-benzyloxy-3-[(N-methyl-N-benzylsulfamoyl)aminolphenyl]ethanone (Interemediate 139)

In the same manner as the procedures described in the step A of Example 29, the above-identified compound (810 mg, ca. 80% purity) was produced from Intermediate 138 (670 mg) and cupric bromide (780 mg). Rf=0.41 (ethyl acetate/n-hexane of 1/2).

D. Synthesis of (±)-N'-[5-[2-[2-(9H-carbazol-2-yloxy)-ethylamino]-1-hydroxyethyl]-2-(benzyloxy)phenyl]-N-methyl-N-benzylsulfamide (Intermediate 140)

The above-identified compound (251 mg) was produced through reaction and after-treatment in accordance with the procedures described in the step D of Example 1 from Intermediate 2 (400 mg), triethylamine (280 μl) and Intermediate 139 (805 mg) via purification by a silica gel chromatography (elution with methanol/ethyl acetate of 1/9). Rf=0.47 (methanol/chloroform of 1/9).

E. Synthesis of (±)-N'-[5-[2-[2-(9H-carbazol-2-yloxy)-ethylaminol-1-hydroxyethyl]-2-hydroxyphenyl]-N-methyl-N-benzylsulfamide hydrochloride The above-identified compound (46 mg) was produced in accordance with the procedures described in Example 2. by adding 250 mg of Intermediate 140 to 50ml of methanol and effecting a hydrogenolysis using 122 mg of 10% palladium/carbon black with subsequent conversion into hydrochloride salt by a usual method and recrystallization from methanol/ethyl acetate. Rf=0.33 (methanol/chloroform of 1/9).

EXAMPLE 88

(±)-N'-[5-[2-[2-(9H-carbazol-2-yloxy)ethylamino]-1-hydroxyethyl]-2-hydroxyphenyl]-N,N-diethylsulfamide hydrochloride A. Synthesis of N,N-diethylsulfamoyl chloride In accordance with the procedures described in the step A of Example 87, 2.07 ml of N,N-diethylamine and 2.8 ml of triethylamine were added to an ice-cooled solution of 1.6 ml of sulfuryl chloride in 20 ml of dichloromethane, over a period of 2 hours under argon atmosphere. After agitation for 1 hour, 20 ml of water was added thereto to terminate the reaction. The organic layer was separated and washed with 20 ml of 1 N hydrochloric acid with subsequent drying, whereupon the solvent was distilled off under a reduced pressure. 30 ml of n-hexane were added to the resulting residue and the mixture was cooled, whereupon the deposited precipitate was filtered off. The filtrate was evaporated to dryness under a reduced pressure, whereby 2.19 g of the above-identified compound were obtained. Rf=0.59 (ethyl acetate/n-hexane of 1/4).

B. Synthesis of 1-[4-benzyloxy-3-[(N,N-diethylsulfamoyl) amino]phenyl]ethanone (intermediate 141)

The above-identified compound (513 mg) was produced from the above Interemediate (686 mg) and 1-(3-amino-4-benzyloxyphenyl)ethanone (482 mg) [this was carried out in accordance with the method reported by A. A. Larsen et al in J. Med. Chem., 10, 462–472(1967)]. Here, however, a mixed solvent of pyridine/dichloromethane (7 ml, 2/5) was used and the reaction mixture was agitated first at room temperature for 66 hours and, then, agitated with heating under reflux for further 2 hours. The purification was performed by extraction with 20 ml of water and 20 ml of ethyl acetate and washing the organic layer with 30 ml of 1 N hydrochloric acid. The united aqueous phase was extracted further with ethyl acetate (twice with each 30 ml), whereupon the united organic phase was washed with saturated aqueous sodium chloride solution with subsequent drying, whereupon the solvent was distilled off under a reduced pressure. The resulting residue was purified by a silica gel chromatography (ethyl acetate/n-hexane of 1/3). Rf=0.42 (ethyl acetate/n-hexane of 1/2).

C. Synthesis of 2-bromo-1-[4-benzyloxy-3-[(N,N-diethylsulfamoyl)amino]phenyl]ethanone (Interemediate 142)

In the same manner as the procedures described in the step A of Example 29, the above-identified compound (693 mg, ca. 70% purity) was produced from Intermediate 141 (500 mg) and cupric bromide (670 mg). Rf=0.64 (ethyl acetate/n-hexane of 1/2).

D. Synthesis of (±)-N'-[5-[2-[2-(9H-carbazol-2-yloxy) ethylamino]-1-hydroxyethyl]-2-(benzyloxy)phenyl]-N,N-diethylsulfamide (Intermediate 143)

The above-identified compound (256 mg) was produced through reaction and after-treatment in accordance with the procedures described in the step D of Example 1 from Intermediate 2 (390 mg), triethylamine (280 μl) and Intermediate 142 (673 mg) via purification by a silica gel chromatography (elution with methanol/ethyl acetate of 1/9). Rf=0.46 (methanol/chloroform of 1/9).

E. Synthesis of (±)-N'-[5-[2-[2-(9H-carbazol-2-yloxy)-ethylamino]-1-hydroxyethyl]-2-hydroxyphenyl]-N,N-diethylsulfamide hydrochloride The above-identified compound (85 mg) was produced in accordance with the procedures described in Example 2, by adding 250 mg of Intermediate 143 to 50 ml of methanol and effecting a hydrogenolysis using 120 mg of 10% palladium/carbon black with subsequent conversion into hydrochloride salt by a usual method and recrystallization from methanol/ethyl acetate. Rf=0.32 (methanol/chloroform of 1/9).

EXAMPLE 89

(±)-N,N-dimethyl-[5-[2-[2-(9H-carbazol-2-yloxy) ethylamino]-1-hydroxyethyl]-2-hydroxy] benzenesulfonamide hydrochloride A. Synthesis of N,N-dimethyl-[2-benzyloxy-5-(2-bromoacetyl) benzene]sulfonamide (Intermediate 144)

In the same manner as the procedures described in the steps A and B of Example 83, the above-identified compound (705 mg) was prepared from 1-(3-amino-4-benzyloxyphenyl)ethanone [prepared by the method reported by A. A. Larsen et al in J. Med. Chem., 10, 462–472 (1967)]. Here, however, instead of adding N-methylbenzylamine, N,N-dimethylamine was reacted. Rf=0.33 (ethyl acetate/n-hexane of 1/2).

B. Synthesis of N,N-dimethyl-[2-benzyloxy-5-[2-iodo-1-[(triethylsilyl)oxy]ethyl]]benzenesulfonamide (Intermediate 145)

In the same manner as the procedures for the synthesis of Intermediate 42, 700 mg of Intermediate 144 were treated by reaction and after-treatment, whereby 407 mg of the above-identified compound were obtained. Rf=0.74 (ethyl acetate/n-hexane of 1/1).

C. Synthesis of (±)-N,N-dimethyl-[5-[2-[2-(9H-carbazol-2-yloxy)ethylamino]-1-[(triethylsilyl)oxy]ethyl]-2-benzyloxy]benzenesulfonamide (Intermediate 146)

According to the procedures for the synthesis of Intermediate 43 except that a silica gel chromatography (elution with methanol/chloroform of 1/25) was employed for the purification of crude product, the above-identified compound (138 mg) was obtained from Intermediate 145 (398 mg) and Intermediate 2 (193 mg). Rf=0.43(methanol/chloroform of 1/10).

D. Synthesis of (±)-N,N-dimethyl-[5-[2-[2-(9H-carbazol-2-yloxy)ethylamino]-1-hydroxyethyl]-2-benzyloxy]-benzenesulfonamide (intermediate 147)

135 mg of Intermediate 146 were dissolved in 7 ml of anhydrous tetrahydrofuran, whereto 38.2 μl of acetic acid and 314 μl of 1 M solution of tetrabutylammonium fluoride/tetrahydrofuran were added and the mixture was agitated at room temperature for 14.5 hours. Then, the mixture was diluted with ethyl acetate, followed by rinsing with saturated aqueous sodium chloride solution and dried, whereupon the solvent was distilled off under a reduced pressure. The residue was purified by a PTLC (development with methanol/chloroform of 1/10), whereby 4.9 mg of the above-identified compound were obtained. Rf=0.23 (methanol/chloroform of 1/10). By a usual technique, it was converted into hydrochloride salt (7.7 mg).

E. Synthesis of (±)-N,N-dimethyl-[5-[2-[2-(9H-carbazol-2-yloxy)ethylamino]-1-hydroxyethyl]-2-hydroxy]-benzenesulfonamide hydrochloride The above-identified compound (5.0 mg) was produced in accordance with the procedures described in Example 2, by performing a hydrogenolysis of Intermediate 147 (7.7 mg) using of 10% palladium/carbon black(4 mg) for 2 hours, followed by filtering off the catalyst and distilling off the solvent under a reduced pressure. Rf=0.31 (methanol/chloroform of 1/9).

EXAMPLE 90

(±)-N-[5-[2-[2-(9H-carbazol-2-yloxy)ethylamino]-1-methoxyethyl]-2-hydroxyphenyl]methaneesulfonamide hydrochloride A. Synthesis of (±)-N-[5-[2-[2-(9H-carbazol-2-yloxy)ethylamino]-1-methoxyethyl]-2-benzyloxyphenyl]methanesulfonamide (Intermediate 148)

120 mg of the compound of Example 1 were agitated with heating under reflux in 10 ml of 10% hydrogen chloride/methanol for 24 hours. Then, the mixture was further agitated for 3 days at room temperature. The reaction mixture was evaporated to dryness under a reduced pressure, whereto saturated aqueous sodium bicarbonate solution was added and extraction with ethyl acetate was performed (twice with each 20 ml). After drying, evaporation was carried out and the residue was purified by a silica gel chromatography (methanol/chloroform of 1/19), whereby 72 mg of the above-identified compound were obtained. Rf=0.55 (methanol/chloroform of 1/9).

B. Synthesis of (±)-N-[5-[2-[2-(9H-carbazol-2-yloxy)ethylamino]-1-methoxyethyl]-2-hydroxyphenyl]methanesulfonamide hydrochloride In accordance with the procedures described in Example 2, 70 mg of Intermediate 148 were subjected to hydrogenolysis using 30 mg of 10% palladium/carbon black for 1 hour, whereupon conversion into hydrochloride salt was effected with subsequent evaporation to dryness and trituration from diethyl ether, whereby 60 mg of the above-identified compound were obtained. Rf=0.40 (methanol/chloroform of 1/9).

EXAMPLE 91

(±)-N-[5-[2-[2-(dibenzothiophen-3-yloxy)ethylamino]-1-methoxyethyl]-2-hydroxyphenyl]methanesulfonamide hydrochloride 28 mg of the compound of Example 38 were suspended in 3 ml of 10% hydrogen chloride/methanol and the mixture was agitated for 3 days with heating under reflux. Then, 10 ml of 10% hydrogen chloride/methanol were replenished thereto and the mixture was further agitated for 2 days. The reaction mixture was evaporated to dryness under a reduced pressure and the residue was dissolved in methanol and purified by a PTLC (developemnt with methanol/chloroform of 1/10). From this, by triturating in diethyl ether and filtration, 11.8 mg of the above-identified compound were obtained. Rf=0.38 (methanol/chloroform of 1/10).

EXAMPLE 92

(±)-N-[5-[2-[2-(9H-carbazol-2-yloxy)ethylamino]-1-methoxyethyl]-2-aminophenyl]methanesulfonamide hydrochloride Intermediate 120 (35 mg) was added to 10% hydrogen chloride/methanol (5 ml) and the mixture was agitated for 2 hours with heating under reflux. By evaporating to dryness, the above-identified compound (37 mg) was obtained. Rf=0.29 (methanol/chloroform of 1/9).

TEST EXAMPLE 1

Human β3-agonist Activity:

Human β3-agonist activity was examined using CHO cells (chinese hamster ovarian cells) to which pcDNA3 (in vitrogen) cells inserted human β3 gene was transfected. Human β3 fragment was obtained by PCR using human fat tissue cDNA (supplied from Clontech) with a β3 primer [Krief et al, J. Clin. Invest., Vol. 91, p344–349 (1993)], And then full length of human β3 gene was cloned using this fragment as a probe.

The cells were cultured in a HAM F-12 medium containing 10% of fetal bovine serum. 400 μg/ml of Geneticin (Gibco BRL), 100 U/ml penicillin and 100 μg/ml streptomycin. $5 \times 10^5$ cells were placed on a 6-well plate and cultured for 24 hours, after which the medium was changed to a HAMf F-12 medium without serum and was kept for 2 hours. Each test compound was first dissolved in DNMSO, and then diluted with a HAM F-12 medium containing 1 mM isobutylmethyl xanthine and 1 mM ascorbic acid. A 10-fold dilution in the range of $10^{-5}$ to $10^{-12}$ M was added into the cell.

After culturing for 30 minutes, culture medium was withdrawn, 0.5 ml of 1 N NaOH was added and was kept for 20 minutes. And then 0.5 ml of 1 N acetic acid was added with subsequent agitation and centrifugation. Finally the concentration of cAMP were analyzed using cAMP EIA KIT (Cayman). Intrinsic activities and $ED_{50}$ of 65 compounds in Example 1–92 are shown in Table 2. BRL37344 was synthesized by the method given in "Drugs of the future", Vol. 16, p 797–800 (1991). CL316, 243 was synthesized by the method given in J. Med. Che., Vol. 35, p 3081–3084. Isoprotelenol was purchased from Research Biochimicals International. As seen in Table 2, the activities of these compounds were found to be higher than BRL 37344 and CL316,243.

TEST EXAMPLE 2

Effect on Heart:

The hearts of male guinea pigs having body weights in the range of 180–250 g were excised and each right atrium specimen was prepared which was set in an organ bath filled with aerated Krebs solution. The automaticity was measured using an isometric transducer (TB-611T of the firm Nippon Koden) connected to a polygraph (MR-6000 of the firm Nippon Koden). The $ED_{50}$ values for the inventive compounds in Examples were higher than that of β3 and these compounds have almost no contribution to increase in the cardiac rate, so that they are selective and are expected to have lower side effects.

TEST EXAMPLE 3

Lipolytic Activity in Canine Fatty Cell:

Adipose tissues in the omentum were collected from dogs and minced and washed. Krebs-Ringer buffer solution containing 1 mg/ml Collagenase (Sigma) and 1% of bovine serum albumin was added in an amount of 3 ml per one gram of the tissue. These cells were then incubated at 37° C. for 30 minutes with shaking and then undigested tissues were removed with a nylon filter. The resulting adipocytes were washed four times with Krebs-Ringer buffer, and then the concentration of cells was diluted to $2\times10^5$/ml with Krebs-Ringer buffer solution containing 4% of bovine serum albumin. These cells were transfered to Eppendorf tubes each in an amount of 300 μl.

Each 300 μl of a culture medium containing the test compounds were added to these tubes and was held at 37° C. for 1 hour with shaking. Stimulation was stoped by cooling with ice. After centrifugation, the adipocytes were taken off with an aspirator, whereupon the glycerol was determined using F-KIT GLTCEROL (Behringer-Mlanheim). A shown in Table 3, the compounds of inventive Examples exhibited in vitro lipolytic activities and, therefore, it was expected that they may be effective also in vivo lipolysis.

TEST EXAMPLE 4

Blood Sugar Decreasing Effect and Lipolytic Effect:

Male ddy mice (supplied from the firm Nippon Charles Liver) of 6 weeks age were subcutaneously administered with glucose in a dose of 2 g/kg. The animals were also treated with either one of test compounds via oral or intraperitoneal administration in a dose of 0.1 ml per 10 grams of body weight. After one hour, blood sample was taken from abdominal aorta, from which serum was separated and served as the sample.

Blood Sugar Decreasing Effect:

The samples prepared as above were analyzed for the serum glucose concentration by Auto analyzer (SUPER Z of the firm M.C. Medical). For the analyzer kit, Glucose II HA TEST WAKO (of the firm Wako Pure Chemical) was used.

% decrease in blood sugar=$[(A-B)/(A-C)]\times100$ in which A represents the glucose concentration upon being loaded with glucose, B represents the glucose concentration after administration of the compound and C is the usual level of the glucose concentration.

The compound of Example 31 exhibited a blood sugar reduction as high as 34.5% by oral adminstration and the compound of Example 2 showed a 77.1% reduction of blood sugar by intraperitoneal administration. Therefore, it was proven that the compound according to the present invention is effective as a medicament for therapuetic and preventive treatment of diabetes.

Lipolytic Effect:

Amount of free fatty acid in the samples was determined using NEFA HA TEST WAKO (of the firm Wako Pure Chemical). The compounds of Examples 31 and 7 have shown that they increased 32.4% and 47.7% by an oral administration of 30 and 100 mg/kg, respectively. The compound of Example 2 showed an increase of 67.2% by an intraperitoneal administration of 10 mg/kg. This shows that these compounds have lypolytic activity. Therefore, it was shown that they are useful as medicament for preventive and therapeutic treatment of hyperlipemia and for therapeutic treatment of obesity.

TEST EXAMPLE 5

Toxicity Test:

The compounds of Examples 7 and 31 were administered to 6 week age male ddy mice (supplied from the firm Nippon Charles Liver) at a dose of 100 mg/kg. For all 8 mice. no fatal case was found, which was the case for other compounds, so that the compound according to the present intention exhibits-low toxicity.

Effect of the Invention

The compounds according to the present invention are novel and are useful for use in drug composition for therapuetic and preventive treatment of β3-correlating diseases, such as diabetes, obesity and hyperlipemia.

TABLE 1

| Compound No. | 1H-NMR (CDCl$_3$): δ (ppm), J (Hz) | MS m/z |
|---|---|---|
| Intermed. 0 | 3.47(2H, t, J=6.0), 3.61(2H, q, J=6.0), 5.11(1H, s), 5.29(1H brs), 7.30~7.38(5H, m) | |
| Intermed. 1 | (DMSO-d6): 3.44(2H, b t), 4.08 (2H, t, J=5.7), 5.05(2H, s), 6.76 (1H, dd, J=2.1, 8.7), 6.9 6(1H, bd, J=2.1), 7.10(1H, dd, J=73), 7.24~7.38(6H, m), 7.41 (1H, d, J=8.1), 7.52(1H, bt), 7.95 (1H, d, J=8.7), 7.97(1H, d, J=7.5), 11.08(1H, s) | 361 (MH+) |
| Intemed. 2 | (DMSO-d6): 1.8~2.1(2H, brs), 2.93(2H, t, J=5.8), 4.00(2H, t J=5.8), 6.7 4(1H, *dd, J=2.2, 8.5), 6.9 6(1H, d, J=2.2), 7.10 (1H, dd), 7.27(1H, dd), 7.41(1H d, J=8.0), 7.95(1H, d, J=8. 5) 7.9 7(1H, d, J=7.7), 11.08(1H, s) | 227 (MH+) |
| Example 1 | (DMSO-d6): 2.69(d, 2H, J=5.7) 2.89(s, 3H), 2.96(t, 2H, J=5.2), 4.09(t, 2H, J=5.2), 4.59(m 1H) 5.15(s, 2H) 5.31(bs, 1H), 6.76(dd, 1H, J=8.5, 2.2), 6.9 6(d, 1H, J=1.9), 7.05~7.17(m, 8H), 7.25~7.42(m, 6H), 7.54(d 2H, J=6.6), 7.96(t, 2H, J=8.5), 11.08(s, 1H) | 546 (MH+) |
| Example 2 | (DMSO-d6): 2.75(m, 2H), 2.93 (s, 8H), 3.04(m, 2H), 4.14(t, 2 H, J=5.2) 4.60(m, 1H), 6.77(d d, 1H, J=8.8, 2.2), 6.85(d, 1H, J=8.2), 6.97(d, 1H, J=1.9), 7.04(dd, 1H, J=8.2, 1.9) 7.10(m, | 456 (MH+) |

TABLE 1-continued

| Compound No. | 1H-NMR (CDCl₃): δ (ppm), J (Hz) | MS m/z |
|---|---|---|
| | 1H), 7.2 1(d, 1H, J=1.9) 7.28 (dt, 1H, J=8.0, 1.1), 7.41(d, 1H, J=8.0), 7.97(m, 2H), 11.10 (s, 1H) | |
| Intermed. 4 | 3.6 6(q, 2H, J=5.2) 4.12(t, 2H, J=5.2), 5.13(s, 2H), 5.27(bs 1H), 6.91(dd, 1H, J=8.5, 2.2), 7.0 6(d, 1H, J=2.2), 7.2 6~7.41 (m, 7H), 7.52(dd, 1H, J=8.2, 0.8), 7.80(d, 1H, J=8.5), 7.85 (m, 1H) | 362 (MH+) |
| Intermed. 5 | 3.14(t, 2H, J=5.2), 4.09(t, 2H, J=5.2), 6.96(dd, 1H, J=8.5, 2.2), 7.10(d, 1H, J=2.2), 7.28~7.41(m, 2H), 7.52(m, 1H), 7.81 (d, 1H, J=8.5), 7.86(m, 1H) | 228 (MH+) |
| Example 3 | (DMSO-d6): 2.71(d, 2H, J=5.5), 2.94(s, 3H), 2.98(m, 2H), 4.1 4(m, 2H), 4.60(m, 1H), 5.13(bs, 1H), 5.16(s, 2H), 5.31(bs,1H), 7.00(dd, 1H, J=8.5, 2.4), 7.07 (d, 1H, J=8.5), 7.15(dd, 1H, J=8.5, 2.2), 7.26~7.48(m, 7H), 7.54(m, 2H), 7.64(dd, 1H, J=7.4, 0.8), 8.00(d, 1H, J=8.5), 8.04 (m, 1H) | 547 (MH+) |
| Example 4 | (DMSO-d6): 2.68(d, 2H, J=6.3), 2.92(s, 3H), 2.96(t, 2H, J=5.5), 4.13(t, 2H, J=5.5), 4.54(m 1H), 6.83(d, 1H, J=8.2), 7.01 (septet, 2H), 7.19(d, 1H, J=2.2), 7.30(d, 1H, J=2.2), 7.35 (dt, 1H, J=7.4, 1.1), 7.42(dt, 1H, J=7.4, 1.4), 7.64(d, 1H, J=8.0), 8.00(d, 1H, J=8.8), 8.03 (d, 1H, J=7.4) | 457 (MH+) |
| Intermed. 6 | 2.68(s, 3H), 7.42(dd, 1H, J=10.2, 8.4), 8.26(ddd, 1H, J=8.4, 4.2, 2.1), 8.65(dd, 1H, J=7.2, 2.1) | |
| Intermed. 7 | 2.55(s, 3H), 3.88(bs, 2H), 7.04 4(ddd, 1H, J=10.5, 8.4, 0.6) 7.28~7.35(m, 1H), 7.41(ddd, 1H, J=8.7, 2.1, 0.6) | |
| Intermed. 8 | 2.61(s, 3H), 3.09(s, 3H), 6.69 (bs, 1H), 7.25(dd, 1H, J=9.9, 9.6), 7.82(ddd, 1H, J=8.4, 4.8, 2.1), 8.17(dd, 1H, J=7.5, 2.1) | |
| Intermed. 9 | 3.16(s, 3H), 4.41(s, 2H), 6.62 (bs, 1H), 7.28(t, 1H, J=9.0), 7.86 (ddd, 1H, J=8.7, 4.8, 2.1) 8.21(dd, 1H, J=7.5, 2.1) | |
| Example 5 | (DMSO-d6; HCl): 3.05(s, 3H), 3.13 (m, 1H), 3.31(m, 1H), 3.49 (m, 2H), 4.38(m, 2H), 4.99(m, 2H), 6.31(d, 1H, J=4.2) 6.84(dd, 1H, J=8.4, 2.4), 7.03(d, 1H, J=1.8), 7.12(m, 1H), 7.26~7.38 (m, 3H), 7.42~7.50(m, 2H), 8.01 (m, 2H), 8.97(bs, 2H), 9.71 (m, 1H), 11.19(s, 1H) | 458 (MH+) |
| Intermed. 10 | 2.65(s, 3H), 7.68(d, 1H, J=8.4), 8.09(dd, 1H, J=8.7, 2.1), 8.43 (d, 1H, J=2.1) | |
| Intermed. 11 | 2.55(s, 3H), 4.19(bs, 2H), 7.23~7.37(m, 3H) | |
| Intermed. 12 | 2.61(s, 3H), 3.07(s, 3H), 6.86 (bs, 1H), 7.54(d, 1H, J=8.4), 7.75 (dd, 1H, J=8.4, 2.1), 8.21 (d, 1H, J=2.1) | |
| Intermed. 13 | 3.10(s, 3H), 4.41(s, 2H), 6.90 (bs, 1H), 7.58(d, 1H, J=8.4), 7.78(dd, 1H, J=8.4, 2.1), 8.24 (d, 1H, J=2.1) | |
| Example 6 | (DMSO-d6;HCl): 3.06(s, 3H), 3,17 (m, 1H), 3.27(m, 1H), 3.48 | 474 (NH+) |
| | (m, 2H), 4.38(m, 2H), 5.00(m, 1H), 6.35(d, 1H, J=4.2) 6.84(dd, 1H, J=8.4, 2.7), 7.02(d, 1H, J=2.1), 7.12(m, 1H), 7.27~7.34 (m, 2H), 7.44(d, 1H, J=7.8), 7.52~7.59(m, 2H), 8.01(m, 2H), 8.91(bs, 2H), 9.55(m, 1H), 11.17 (s, 1H) | |
| Example 7 | (DMSO-d6): 2.72(m, 2H), 2.96 (s, 3H), 2.98(m, 2H), 4.11(t, 2H, J=5.7), 4.35(bs, 1H), 4.65(m, 1H), 5.40(bs, 1H), 6.76(dd, 1H, J=8.5, 2.2), 6.96(d, 1H, J=1.9), 7.07~7.13(m, 3H), 7.24~7.32 (m, 3H), 7.41(d, 1H, J=8.2) 7.9 6(m, 2H), 11.09(s, 1H) | 440 (NH+) |
| Intermed. 15 | 2.58(s, 3H), 4.36(s, 2H), 7.15 (bs, 1H), 7.22~7.48(m, 6H) 7.62~7.75(m, 2H), 8.57(m, 1H) | |
| Example 8 | (DMSO-d6): 2.73(m, 2H), 2.98 (m, 2H), 4.10(m, 2H), 4.42(s, 2H), 4.64(m, 1H) 5.38(m, 1H), 6.76 (d, 1H, J=8.8), 6.96(s, 1H) 7.06~7.13(m, 3H), 7.20·7.46 (m, 9H), 7.96(m, 2H), 11.09(s, 1H) | 516 (NH+) |
| Example 9 | (DMSO-d6): 2.71(m, 2H), 2.96 (s, 3H), 2.97(m, 2H), 4.1 4(m, 2H), 4.63(m, 1H), 5.39(bs, 1H), 7.00(dd, 1H, J=8.5, 2.2), 7.09 (m, 2H), 7.23·7.46(m, 5H), 7.64 (d, 1H, J=7.4), 8.02(m, 2H) | 441 (NH+) |
| Intermed. 17 | 2.20(s, 3H), 3.11(t, 2H, J=5.2), 3.84(s, 2H), 4.04(t, 2H, J=5.2), 6.92(m, 1H), 7.08 (m, 1H) 7.24~7.38(m, 3H), 7.58(d, 1H, J=2.2), 7.61(d, 1H, J=2.5), 7.83(s, 1H) | |
| Example 10 | (DMSO-d6): 2.05(s, 3H), 2.71 (m, 2H), 2.94(s, 2H), 2.96(m, 3H), 3.84(s, 2H), 4.07(m, 2H) 4.63(bs, 1H), 5.39(m, 1H), 6.9 2(dd, 1H, J=8.5, 2.2), 7.06~7.15 (m, 3H), 7.24(s, 1H), 7.27(t, 1H, J=8.2), 7.46(d, 1H, J=8.2), 7.65(d, 1H, J=2.7), 7.68(d, 1H, J=2.7), 7.86(s, 1H), 9.95 (s, 1H) | 496 (NH+) |
| Intermed. 18 | (DMSO-d6): 1.10(d, 3H, J=6.3), 1.74(bs, 2H), 3.19(m, 1H), 3.80 (m, 2H), 6.7 8(dd, 1H, J=8.5, 2.2), 6.9 7(d, 1H, J=1.9), 7.10 (t, 1H, J=7.4), 7.28(t, 1H, J=7.4), 7.42(d, 1H, J=8.0), 7.94 (d, 1H, J=8.5), 7.97(d, 1H, J=8.5), 11.16(s, 1H) | |
| Example 11 | (DMSO-d6): 1.10(m, 3H), 2.63 (m, 1H), 2.78(m, 1H), 2.93(s, 3/2H), 2.94(s, 3/2H), 3.06(m, 1H), 3.90(m, 2H), 4.60(m, 1H) 6.75(m, 1H), 6.96(dd, 1H, J=8.2, 1.9), 7.08(m, 3H), 7.26(m, 3H), 7.42(d, 1H, J=8.0), 7.96 (m, 2H), 11.19(s, 1H) | 454 (MH+) |
| Intermed. 19 | 2.70(d, 1H, J=3.3), 3.56(dd, 1H, J=10.4, 8.5), 3.63(dd, 1H, J= 10.4, 3.3), 4.92(m, 1H), 5.25 (s, 2H), 7.13(d, 1H, J=8.5), 7.30~7.48(m, 5H), 7.53(dd, 1H, J= 8.8, 2.5), 7.91(d, 1H, J=2.5) | |
| Intermed. 20 | 0.53~0.62(m, 6H), 0.91(t, 9H, J=7.7), 3.31(m, 2H) 4.75(t, 1H, J=5.8), 5.24(s, 2H), 7.13(d 1H, J=8.8), 7.31~7.52(m, 6H) 7.87(d, 1H, J=2.2) | |

TABLE 1-continued

| Compound No. | 1H-NMR (CDCl₃): δ (ppm), J (Hz) | MS m/z |
|---|---|---|
| Intermed. 21 | 0.51~0.60(m, 6H), 0.89(t, 9H, J=7.7), 2.78(dd, 1H, J=11.8, 4.4), 2.89(dd, 1H, J=11.8, 7.7) 3.04(m, 2H), 4.12(m, 2H), 4.84 (dd,1H, J=7.7, 4.4), 5.19(s, 2H), 6.80~6.86(m, 2H), 7.05(d 1H, J=8.5), 7.20(m, 1H), 7.30~ 7.52(m, 7H), 7.86~8.09(m, 5H) | |
| Intermed. 22 | 0.39~0.57(m, 6H), 0.77~0.91 (m, 9H), 3.40~3.52(m, 1H), 3.49 (d, 2H, J=5.2), 3.5 5~3.68(m, 1H), 3.75(m, 1H) 3.88~4.17(m, 2H), 5.10(s, 2H), 5.14(d, 2H, J= 10.2), 6.70~6.83(m, 2H), 7.00 (dd, 1H, J=18.1, 8.8), 7.20(dd, 1H, J=8.0, 4.7), 7.27~7.50 (m, 12H), 7.80~8.00(m, 4H) | 745 (M+) |
| Intermed. 23 | 0.40~0.58(m, 6H), 0.79~0.92 (m, 9H), 3.42~3.50(m, 3H), 3.49 (d, 2H, J=7.7), 3.55~3.66(m, 1H), 3.71(m, 1H), 3.86~4.16(m, 2H), 5.03(d, 2H, J=2.5), 5.18 (d, 2H, J=16.5), 6.71~6.85(m, 2H), 7.16~7.45(m, 16H), 7.88 (m, 1H), 7.96(d, 1H, J=7.1) | |
| Intermed. 24 | 0.40~0.58(m, 6H), 0.79~0.92 (m, 9H), 2.98(s, 3H), 3.42~3.50 (m, 1H), 3.49(d, 2H, J=7.7), 3.55~3.66(m, 1H), 3.17(m, 1H), 3.86~4.16(m, 2H), 5.03(d, 2H, J=2.5), 5.18(d, 2H, J=16.5), 6.71~6.85(m, 2H), 7.16~7.45(m, 16H), 7.88(m, 1H), 7.96(d, 1H, J=7.1) | |
| Intermed. 25 | 2.86(d, 1H, J=3.6), 3.56(dd, 1H, J=10.7, 8.5), 3.70(dd, 1H, J= 10.7, 3.6), 5.06(dt, 1H, J=8.5, 3.6), 7.58(t, 1H, J=7.7), 7.75 (ddd, 1H, J=7.7, 1.1, 0.5), 8.20 (m, 1H), 8.30(dd, 1H, J=2.2, 1.6) | |
| Intermed. 28 | (DMSO-d6): 0.50(m, 6H), 0.83 (m, 9H), 2.72(m, 2H), 2.96(s, 3H), 2.98(m, 2H), 4.08(m, 2H), 4.75 (m, 1H), 5.04(s, 2H), 6.76(dd, 1H, J=8.8, 2.2), 6.96(d, 1H, J=1.9), 7.07~7.13(m, 3H), 7.24~ 7.32(m, 3H), 7.41(d, 1H, J=8.2), 7.96(m, 2H), 11.09(s, 1H) | |
| Intermed. 29 | 2.72(s, 3/2H), 2.73(s, 3/2H), 4.46(s, 2H), 7.70(dd, 1H, J=7.8, 7.8), 8.11(ddd, 1H, J=7.8, 1.8), 8.21(ddd, 1H, J=7.8, 1.8) 8.45(dd, 1H, J=1.8, 1.8) | 1.8), |
| Example 16 | (DMSO-d6; HCl): 2.41(d, 3H), 3.16 (m, 1H), 3.35(m, 1H), 3.49 (m, 2H), 4.42(m, 2H), 5.21(d, 1H J=10.4), 6.48(bs, 1H), 6.84 (d, 1H, J=8.2), 7.04(d, 1H, J=1.9) 17.11(t, 1H, J=7.4), 7.29(m, 1H), 7.44(d, 2H, J=8.0Hz), 7.50~7.78(m, 4H), 7.88(s, 1H), 8.00(d, 2H, J=8.0), 9.22(bs, 1H), 9.56(bs, 1H), 11.29(s, 1H) | 440 (MH+) |
| Example 17 | (DMSO-d6; HCl): 3.16(m, 1H), 3.28(m, 1H), 3.50(m, 1H), 4.41 (m, 2H), 5.08(m, 1H), 6.84(dd, 1H, J=8.2, 2.2), 7.03(d, 1H, J=1.9), 7.11(t, 1H, J=7.4), 7.15~ 7.55(m, 7H), 7.74(m, 1H), 8.01 (m, 2H), 9.09(bs, 1H), 9.38(bs, 1H), 11.25(s, 1H) | 390 (MH+) |
| Example 18 | (DMSO-d6): 2.77(m, 2H), 3.00 (t, 2H, J=5.5), 4.12(t, 2H, J=5.5) 4.68(m, 1H) 5.17(br.s, 1H), 6.76(dd, 1H, J=8.5, 2.2), 6.96 (d, 1H, J=2.2), 7.09(m, 2H) 7.28(m, 1H), 7.41(d, 1H, J=8.0 7.53(dd, 1H, J=8.8; 2.2), 7.87 (d, 1H, J=2.2), 7.97(m, 2H), 11.10(s, 1H) | 408 (MH+) |
| Example 19 | (DMSO-d6; 2HCl): 3.06(1H, m), 3.20(1H, m), 3.49(2H, m), 4.39 (2H, m), 4.95(1H, m), 6.19(1H, br.s), 6.84(1H, dd, J=8.5, 2.2), 17.00(1H, d, J=8.5), 7.03(1H, d, J=2.2), 7.12(2H, m), 7.30 (2H, m), 8.01(2H, m), 8.96(1H, br. s), 9.19(1H, br.s), 10.60(1H, br.s), 11.21(1H, s) | 378 (MH+) |
| Example 20 | (CD3 OD): 3.20~3.29(2H, m), 3.53 (2H, t, J=4.7), 4.38(2H, t, J= 4.7), 4.90(1H, m), 5.07(2H, s), 6.82(1H, d, J=8.2), 6.87(1H, dd, J=8.5, 2.2), 6.95(1H, dd, J=8.2, 1.9), 7.05(1H, d, J=1.1), 7.12(1H, dd, J=7.1, 1.1), 7.18~ 7.46(7H, m), 7.86(1H, d, J= 1.9), 7.94(2H, d, J=8.5) | 505 (MH+) |
| Example 21 | (DMSO-d6): 3.00(1H, m), 3.11 (1H, m), 3.39(2H, m), 4.33(2H, m), 4.80(1H, m), 5.86(1H, m), 6.25(2H, s), 6.79(2H, s), 6.83 (1H, dd, J=8.5, 2.2), 7.02(1H, d, J=2.5), 7.12(1H, m) 7.30(1H, m), 7.44(1H, d, J=8.2), 7.90~8.02 (3H, m), 8.08(1H, s), 8.60 (1H, br.s), 10.02(1H, s), 11.17 (1H, s) | 415 (MH+) |
| Example 22 | (CD3 OD): 2.92(1H, m), 3.04(1H, m), 3.63(2H, m), 4.18(2H, m), 4.82(1H, m), 5.11(2H, s), 6.73 (1H, dd, J=8.5, 2.2), 6.80(1H, d, J=8.2), 6.88(1H, m), 6.93(1H, d, J=1.9), 7.10(1H, dd, J=8.2), 7.24~7.52(8H, m), 7.86~7.95 (2H, m) | 490 (MH+) |
| Example 23 | (DMSO-d6; HCl): 2.82~3.00(2H, m), 3.44(2H, m), 4.34(2H, m), 4.46(1H, m), 6.83(2H, s), 6.86 (1H, m), 7.04(1H, d, J=2.2), 7.12 (1H, dd, J=6.6, 7.7), 7.30(1H, dd. J=6.6, 7.7), 7.44(1H, d, J=8.5), 7.72(1H, m), 8.02(2H, d, J= 8.2), 8.91(1H, br.s), 9.28 (1H, br.s), 9.76(1H, s), 11.18(1H, s) | 400 (MH+) |
| Example 24 | (DMSO-d6): 2.61(6H, s), 2.73 2H, m), 3.00(2H, m), 4.11(2H, m), 4.61(1H, m), 5.16(2H, s), 5.38(1H, m), 6.76(1H, m), 6.96 (1H, s), 7.02(1H, d, J=8.8), 7.10 (2H, m), 7.24~7.46(6H, m), 7.56 (2H, m), 7.97(2H, m), 11.00 (1H, m) | 575 (MH+) |
| Example 25 | (DMSO-d6; HCl): 2.67(6H, s), 3.04 (1H, m), 3.18(1H, m), 3.45 (2H, m), 4.39(2H, m), 4.93(1H, m), 6.11(1H, br.s), 6.83(1H, dd, J=8.8, 2.2), 6.91(1H, m), 7.03 (2H, m), 7.11(1H, m), 7.30(1H, m), 7.35(1H, d, J=2.2), 7.44 (1H, d, J=7.7), 8.00(2H, m), 8.72 (1H, s), 8.99(1H, br.s), 9.28 (1H, br.s), 10.07(1H, s), 11.25 (1H, s) | 485 (MH+) |
| Example 26 | (DMSO-d6; 2HCl): 2.81(s, 3H), 3.17(m, 1H), 3.27(m, 1H), 3.48 (m, 2H), 4.38(m, 2H), 5.00(m, 2H), 6.35(d, 1H, J=4.2), 6.84(dd, 1H, J=8.4, 2.7), 7.02(d, 1H, J=2.1), 7.12(m, 1H), 7.27~7.34 | 482 (MH+) |

TABLE 1-continued

| Compound No. | 1H-NMR (CDCl$_3$): δ (ppm), J (Hz) | MS m/z |
|---|---|---|
| | (m, 2H), 7.44(d, 1H, J=7.8), 7.52~7.59(m, 2H), 8.01(m, 2H), 8.91(bs. 2H), 10.21(bs. 2H), 11.17(s, 1H) | |
| Example 27 | (DMSO-d6; 2HCl): 2.80(s, 3H), 3.17(m, 1H), 3.27(m, 1H), 3.48(m, 2H), 4.38(m, 2H), 5.00(m, 2H), 6.35(d, 1H, J=4.2), 6.84(dd, 1H, J=8.4, 2.7), 7.02 (d, 1H, J=2.1) 7.12(m, 1H), 7.27~7.34(m, 2H), 7.44(d, 1H, J=7.8), 7.52~7.59(m, 2H), 8.01(m, 2H), 8.91(bs, 2H), 9.55(m, 1H), 10.21(bs, 2H), 11.17(s, 1H) | 392 (MH+) |
| Intermed. 30 | 2.79(dd, 1H, J=5.7, 2.7), 3.17(dd, 1H, J=5.7, 4.2), 4.15(m, 1H), 7.01~7.31(m, 4H), | |
| Example 28 | (DMSO-d6; HCl): 3.19(m, 1H), 3.32(m, 1H), 3.49(m, 2H), 4.40(t, 2H, J=5.1), 5.32(m, 1H), 6.34(d, 1H, J=3.9), 6.84(dd, 1H, J=8.7, 2.4), 7.03(d, 1H, J=2.2) 7.12(m, 1H), 7.19~7.34(m, 3H), 7.36~7.46(m, 2H), 7.59(dt, 2H, J=7.5, 1.8), 8.01(d, 2H, J=8.4) | 365 (MH+) |
| Intermed. 31 | 4.39(s, 2H), 5.15(s, 2H), 7.04(m, 2H), 7.32~7.46(m, 5H), 7.97(m, 2H) | |
| Intermed. 32 | (DMSO-d6): 2.72(m, 2H), 2.97(t, 2H, J=5.4), 4.10(t, 2H, J=5.4), 4.61(m, 1H), 5.26(bs, 1H) 6.76(dd, 1H, J=8.7, 2.1), 6.93~6.98(m, 3H), 7.09(m, 1H), 7.24~7.46(m, 9H), 7.95(t, 2H, J=8.4), 11.07(s, 1H) | |
| Example 29 | (DMSO-d6): 2.69(m, 2H), 2.96(m, 2H), 4.10(m, 2H), 4.58(m, 1H), 5.12(bs, 1H), 6.67~6.78(m, 3H), 6.96(d, 1H, J=1.2), 7.06~7.18(m, 3H), 7.27(m, 1H), 7.41(d, 1H, J=8.1), 7.95(m, 2H), 9.21(bs, 1H), 11.06(s, 1H) | 363 (MH+) |
| Intermed. 33 | (DMSO-d6): 2.62(dd, 1H, J=12.1, 8.5), 2.83(m, 1H), 2.94(m, 2H), 4.07(m, 2H), 5.10(m, 1H), 5.23(bs, 1H), 6.76(dd, 1H, J=8.5, 2.2), 6.96(m, 2H), 7.03(d, 1H, J=8.2), 7.11(m, 1H), 7.20(m, 1H), 7.25~7.33(m, 2H), 7.34~7.42(m, 3H), 7.94~7.97(m, 3H) 7.97(m, 2H), 11.11(s, 1H) | |
| Example 30 | (DMSO-d6; AcOH): 1.89(s, 3H), 2.69(m, 1H), 2.85(m, 1H), 2.99(m.2H), 4.13(t, 2H, J=5.2), 4.91(m, 1H), 6.77(m, 3H), 6.96~7.14(m, 5H), 7.24~7.33(m, 2H), 7.41(d, 1H, J=8.0), 7.97(m, 2H), 11.10(s, 1H) | 363 (MH+) |
| Example 31 | (DMSO-d6): 2.6~2.67(2H, m), 2.97(2H, bt), 4.11(2H, bt), 4.66(1H, bt), 5.33(1H, brs), 6.76(1H, dd, J=2.1, 8.4), 6.96(1H, d, J=2.1), 7.10(1H, dd, J=8.0) 7.2~7.38(6H, m), 7.41(1H, d, J=7.8), 7.95(1H, d, J=8.7), 7.97(1H, d, J=7.5), 11.08(1H, s) | 347 (MH+) |
| Example 34 | 2.83(1H, dd, J=9, 12.3), 3.04(1H, dd, J=3.6, 12.3), 3.1~3.16(2H, m), 4.19(2H, t, J=5.1), 4.78(1H, dd, J=3.6, 9), 7.04(1H, dd, J=2.7, 9.0), 7.26~7.48(9H, m), 7.55(1H, bd, J=8.4), 7.90(1H, bd) | 348 (MH+) |
| Example 35 | (DMSO-d6): 1.12(3H, d, J=6.3), 2.77(2H, d, J=6.0), 3.07(1H, q, J=6.3), 3.42(2H, t, J=6.0), 4.49~4.56(1H, m), 4.60~4.66(1H, m) 4.71(1H, t, J=5.8), 5.32(1H, bd), 6.73(1H, dd, J=2.2, 6.3), 6.94(1H, d, J=2.2), 7.10(1H, dd), 7.20~7.39(8H, m), 7.42(1H, d, J=8.0), 7.95(1H, d, J=8.8), 7.98(1H, d, J=9.0), 11.08(1H, s) | 361 (MH+) |
| Intermed. 34 | (DMSO-d6): 1.85(s, 3H), 3.45(q, 2H, J=5.8), 4.06(t, 2H, J=5.8), 6.77(dd, 1H, J=8.5, 2.2), 6.97(d, 1H, J=2.2), 7.10(m, 1H), 7.28(m, 1H), 7.41(d, 1H, J=8.0), 7.97(m, 2H), 8.15(m, 1H), 11.11(s, 1H) | |
| Intermed. 35 | 1.85(s, 3H), 3.49(q, 2H, J=5.8), 4.23(t, 2H, J=5.8), 7.22(m, 2H), 7.41(m, 1H), 7.52(d, 1H, J=8.0), 8.10(m, 1H), 8.18(d, 1H, J=8.2), 8.81(s, 1H), 11.74(bs, 1H) | |
| Intermed. 37 | (DMSO-d6): 2.75(m, 2H), 3.02(t, 2H, J=5.5), 4.27(t, 2H, J=4.7), 4.66(m, 1H), 5.31(d, 1H, J=4.1), 7.18~7.26(m, 3H), 7.27~7.45(m, 5H), 7.52(d, 1H, J=8.0), 8.19(d, 1H, J=8.0), 8.83(s, 1H), 11.71(s, 1H) | 392 (MH+) |
| Example 36 | (DMSO-d6): 2.73(m, 2H), 3.03(t, 2H, J=5.6), 4.27(t, 2H, J=4.8), 4.65(m, 1H), 5.31(d, 1H, J=4.1), 7.16~7.25(m, 3H), 7.27~7.46(m, 5H), 7.52(d, 1H, J=8.0), 8.18(d, 1H, J=8.0), 8.83(s, 1H), 11.71(s, 1H) | 378 (MH+) |
| Intermed. 38 | (CDCl3): 3.66(2H, m), 4.13(2H, m), 5.12(2H, s), 5.26(1H, br.s), 7.01(1H, dd, J=8.8, 2.2), 7.23~7.50(8H, m), 7.80(1H, m) 7.99~8.60(2H, m) | 378 (MH+) |
| Intermed. 39 | (DMSO-d6): 2.93(2H, t, J=5.8), 4.04(2H, t, J=8.8, 2.5), 7.39~7.49(2H, m), 7.61(1H, d, J=2.5), 7.95(1H, dd, J=6.9, 1.9), 8.23(2H, m) | 244 (MH+) |
| Example 37 | (CDCl3): 2.82~2.95(2H, m), 2.91(3H, s), 3.09(2H, m), 3.95(3H, br.s), 4.18(2H, t, J=5.2), 4.75(1H, m), 5.11(2H, s), 6.99(1H, d, J=8.5), 7.05(1H, dd, J=8.5, 2.2), 7.18(1H, dd, J=8.5, 2.2), 7.34(1H, d, J=2.5), 7.35~7.46(7H, m) 7.51(1H, d, J=1.9), 7.80(1H, m), 8.03(1H, d, J=8.8), 8.05(1H, dd, J=6.3, 1.4) | 563 (MH+) |
| Example 38 | (DMSO-d6; HCl): 2.95(3H, s), 3.08(1H, m), 3.22(1H, m), 3.47(2H, m), 4.44(2H, m), 4.92(1H, m), 6.12(1H, d, J=3.8), 6.94(1H d, J=8.2), 7.09(1H, dd, J=8.2, 1.9), 7.17(1H, dd, J=8.5, 2.2), 7.27(1H, d, J=1.9), 7.46(2H, m), 7.69(1H, d, J=2.2), 7.98(1H, m), 8.27(2H, m), 8.82(1H, br.s), 9.06(2H, br.s), 10.06(1H, s) | 473 (MH+) |
| Intermed. 40 | (CDCl3): 2.87(6H, s), 4.39(2H, s) 5.20(2H, s), 6.89(1H, br.s), 7.03(1H, dd, J=8.5, 2.7), 7.35~7.46(5H, m), 7.74(1H, dd, J=8.5, 2.2), 8.10(1H, d, J=2.2) | 427 (M+) |
| Example 39 | (DMSO-d6): 2.61(6H, m), 2.67(2H, d, J=6.6), 2.95(2H, m), 4.13(2H, m), 4.56(1H, m), 5.16(2H, s), 5.28(1H, d, J=4.1), 7.01 | 592 (MH+) |

TABLE 1-continued

| Compound No. | 1H-NMR (CDCl$_3$): δ (ppm), J (Hz) | MS m/z |
|---|---|---|
| | (1H, d, J=8.5), 7.09(2H, dd, J=8.5, 2.2), 7.33(1H, d, J=7.4), 7.35~7.40(3H, m), 7.44(2H, m) 7.55(2H, m), 7.60(1H, d, J=2.5), 7.96(1H, m), 8.23(2H, m) | |
| Example 40 | (DMSO-d6; HCl): 2.67(6H, s), 2.99(1H, m), 3.12(1H, m), 3.12 (1H, m), 3.35(1H, s), 3.39(2H, m), 4.84(1H, m), 5.98(1H, br.s), 6.88(1H, d, J=8.2), 7.02(1H, dd, J=8.2, 1.9), 7.15(1H, dd, J=8.5, 2.2) 17.34(1H, d, J=1.9) 7.46(2H, m), 7.67(1H, d, J=2.2), 7.98(1H, m), 8.27(2H, m), 8.61(2H, br.s), 10.01(1H, br.s) | 502 (MH+) |
| Example 41 | (DMSO-d6; HCl): 3.00(3H, s) 3.08(1H, m), 3.26(1H, m), 3.47 (2H, m), 4.43(2H, m), 5.00(1H, m), 6.25(1H, m), 7.12~7.20(3H, m), 7.30~7.40(2H, m), 7.40~7.51 (2H, m), 7.69(1H, d, J=2.2), 7.98(1H, m), 8.27(2H, m), 9.05 (2H, br), 9.87(1H, br) | 457 (MH+) |
| Intermed. 41 | (CDCl3): 2.71(1H, br.s), 2.79 (6H, s), 3.51(1H, dd, J=10.2, 8.5), 3.59(1H, dd, J=10.4, 3.6), 4.48(1H, dd, J=8.5, 3.6), 5.12 (2H, s), 6.89(4H, br.s), 6.95 (1H, d, J=8.2), 7.09(1H, dd, J=8.5, 1.6), 7.33~7.45(5H, m), 7.52(1H, d, J=1.9) | 430 (MH+) |
| Intermed. 42 | (CDCl3): 0.52~0.63(6H, m), 0.87~0.94(9H, m), 2.77(6H, s), 3.28~3.33(2H, m), 4.71(1H, m), 5.10(2H, s), 6.83(1H, br.s), 6.93(1H, dd, J=8.5, 5.2), 7.05 (1H, dd, J=8.5, 2.2), 7.37~7.43 (5H, m), 7.50(1H, d, J=2.2) | |
| Intermed. 43 | (CDCl3): 0.50~0.59(6H, m), 0.89(9H, m), 2.76(6H, s), 2.71~2.79 (1H, m), 2.89(1H, dd, J=11.8, 8.2), 3.06(2H, t, J=5.2), 4.15 (2H, t, J=5.2), 4.80(1H, dd, J=8.2, 4.1), 5.09(2H, s), 6.90 (1H, d, J=8.2), 6.93(1H, dd, J=8.5, 2.2), 7.05(1H, dd, J=8.5, 2.2), 7.07(1H, d, J=2.2), 7.29 (1H, dd, J=7.4, 1.1), 7.34(1H, dd, J=5.2, 1.6), 7.36~7.45(5H, m), 7.49~7.54(2H, m), 7.80(1H, d, J=8.5), 7.85(1H, m) | 690 (MH+) |
| Example 42 | (CDCl3): 2.78(6H, s), 2.72~ 2.78(1H, m) 2.99(1H, dd, J=11.8, 3.6), 3.11(2H, m), 4.17(2H, m), 4.68(1H, m), 5.11(2H, s), 6.93 (1H, d, J=8.5), 6.94(1H, dd, J=8.5, 1.9), 7.08~7.12(2H, m), 7.30(1H, m), 7.34(1H, m), 7.36~ 7.42(5H, m), 7.52(2H, m), 7.81 (1H, d, J=8.5), 7.86(1H, m) | 576 (MH+) |
| Example 43 | (DMSO-d6; HCl): 2.67(6H, s), 3.06(1H, m), 3.19(1H, m), 3.48 (2H, m), 4.42(2H, m), 4.88(1H, m), 6.11(1H, d, J=3.3), 6.88(1H, d, J=8.2), 7.03(1H, dd, J=8.2, 1.9), 7.07(1H, dd, J=8.8, 2.2), 7.41~7.50(4H, m), 7.66(1H, d, J=8.2), 8.06(2H, m), 8.71(1H, s), 8.88(1H, br.s), 9.04 (1H, br.s), 10.01(1H, s) | 486 (MH+) |
| Intermed. 44 | (CDCl3): 0.50~0.59(6H, m), 0.88(9H, m), 2.17(3H, s), 2.74 (H, m), 2.76(6H, s), 2.87(1H, dd, J=11.8, 8.2), 3.02(2H, t, J=4.9), 3.77(2H, s), 4.08(2H, t, J=4.9), 4.80(1H, dd, J=8.0, 3.8), | 745 (MH+) |

TABLE 1-continued

| Compound No. | 1H-NMR (CDCl$_3$): δ (ppm), J (Hz) | MS m/z |
|---|---|---|
| | 5.08(2H, s), 6.86(1H, dd, J=8.5, 2.2), 6.90(1H, d, J=8.5), 7.01(1H, d, J=1.9), 7.04(1H, dd, J=8.5, 1.9), 7.31(1H, dd, J=8.2, 1.6), 7.35~7.44(5H, m), 7.51~7.58(3H, m), 7.78(2H, m) | |
| Example 44 | (CDCl3): 2.18(3H, s), 2.78(6H, s), 2.72~2.78(1H, m), 2.97 (1H, dd, J=11.8, 3.6), 3.07(2H, m), 3.77(2H, s), 4.10(2H, m), 4.68(1H, m), 5.10(2H, s), 6.89(1H, dd, J=8.5, 2.2), 6.91(1H, d, J=8.5), 7.02(1H, d, J=1.9), 7.04(1H, dd, J=8.5, 1.9), 7.32 (1H, dd, J=8.2, 1.7), 7.35~7.41 (5H, m), 7.51~7.57(3H, m), 7.79 (2H, m) | 631 (MH+) |
| Example 45 | (DMSO-d6; HCl): 2.06(3H, s), 2.67 (6H, s), 2.86~3.10(2H, m), 3.26(2H, m), 3.86(2H, s), 4.24 (2H, m), 4.76(1H, m) 5.80(1H, br.s), 6.85(1H, d, J=8.2), 6.99 (2H, m) 7.18(1H, d, J=2.1), 7.32(1H, d, J=2.1), 7.48(1H, d, J=8.0), 7.70(2H, m), 7.88(1H, s), 10.01(1H, s) | 541 (MH+) |
| Example 46 | (DMSO-d6): 2.7~2.8 6(2H, m) 2.95~3.11(2H, m), 4.07~4.13(2H, m), 4.84(1H, br.s), 5.69(1H, br.s), 6.76(1H, dd, J=8.5, 2.2), 6.96(1H, d, J=2.2), 7.10 (1H, dd, J=8.0, 8.0), 7.27(1H, dd, J=8.0, 8.0), 7.41(1H, d, J=8.0), 7.62(1H, d, J=8.0, 8.0), 7.84 (1H, d, J=8.0), 7.95(1H, d, J=8.5), 7.98(1H, d, J=8.0), 8.10 (1H, m), 8.25(1H, br.s), 11.09 (1H, s) | 392 (MH+) |
| Example 47 | (DMSO-d6): 2.68(2H, d, J=6.3) 2.96(2H, br. t, J=5.5), 4.10 (2H, br. t, J=5.5), 4.50(1H, br. t), 4.96(2H, s), 5.14(1H, br.s), 6.42(1H, d, J=7.7), 6.48(1H, d, J=7.7), 6.59(1H, br.s), 6.76 (1H, dd, J=8.5, 2.2), 6.94(1H, dd, J=7.7, 7.7), 6.96(1H, d, J=2.2), 7.10(1H, dd, J=8.0, J=8.0), 7.27(1H, dd, J=8.0, 8.0) 7.41(1H, d, J=8.0), 7.95(1H, d, J=8.5), 7.7(1H, d, J=8.0), 11.08(1H, s) | 362 (MH+) |
| Example 48 | (DMSO-d6): 2.89(6H, s), 2.94~ 3.02(2H, m), 3.29~3.36(2H, m), 4.10(2H, br.t), 4.63(1H, br.s), 5.41(1H, br.s), 6.76(1H, d, J=8.8), 6.95(1H, s), 7.0~7.13 (3H, m), 7.2~7.3(3H, m), 7.92~ 8.0(2H, m), 11.09(~H, s) | 469 (MH+) |
| Example 49 | (DMSO-d6): 2.06(3H, s), 2.68 (2H, d, J=6.0), 2.89(3H, s), 2.93 (2H, m), 3.83(2H, s), 4.06(2H, m), 4.58(1H, m), 5.16(2H, s) 5.30(1H, br.s), 6.92(1H, dd, J=8.2, 1.9), 7.07(1H, d, J=8.5) 7.15(2H, m), 7.26~7.50(5H, m), 7.53(2H, m), 7.67(1H, m), 7.85 (1H, s), 9.95(1H, s) | 602 (MH+) |
| Example 50 | (DMSO-d6; HCl): 2.06(3H, s) 2.95(3H, s), 3.05(1H, m), 3.20 (1H, m), 3.42(2H, m), 3.87(2H, s), 4.34(2H, m), 4.89(1H, m), 6.08 (1H, s), 6.93(1H, d, J=8.5), 6.99(1H, m), 7.08(1H, d, J=9.6), 7.20(1H, s), 7.26(1H, s), 7.48 (1H, d, J=8.5), 7.70(2H, m), 7.89(1H, s), 8.86(2H, br.s), | 512 (MH+) |

TABLE 1-continued

| Compound No. | 1H-NMR (CDCl$_3$): δ (ppm), J (Hz) | MS m/z |
|---|---|---|
| Example 51 | 10.03(2H, br) (DMSO-d6): 2.73(1H, dd, J=12.1, 9.6), 2.90(3H, s), 2.99(1H, dd, J=12.1, 3.6), 3.07(2H, q, J=4.9), 3.49(1H, s), 3.77(2H, s), 4.11(2H, t, J=4.9), 4.67(1H, dd, J=9.6, 3.6), 5.10(2H, s), 6.69(1H, dd, J=8.2, 2.2), 6.86(2H, m), 6.97(1H, d, J=8.5), 7.04(1H, m), 7.18(1H, dd, J=8.8, 1.9), 7.32~7.50(7H, m), 7.53(1H, m) | 560 (MH+) |
| Example 52 | (DMSO-d6; 2HCl): 2.95(3H, s), 3.07(1H, m), 3.17(1H, m), 3.43(2H, m), 3.94(2H, s), 4.37(2H, m), 4.91(1H, m), 6.09(1H, br.s), 6.94(1H, d, J=8.5), 7.05(2H, m), 7.25(3H, m), 7.45(1H, s) 7.83(2H, m), 8.82(1H, s), 8.94(1H, br.s), 9.22(1H, br.s), 9.80(1H, br), 10.06(1H, s), 10.03(2H, br.s) | 470 (MH+) |
| Intermed. 45 | (CDCl3): 1.36(6H, d, J=9.6), 3.29(1H, m), 4.40(2H, s), 5.20(2H, s), 6.79(1H, s), 7.05(1H, d, J=8.5), 7.35~7.47(5H, m), 7.78(1H, dd, J=8.5, 2.2), 8.21(1H, d, J=2.2) | |
| Example 53 | (DMSO-d6): 1.16(6H, d, J=6.9), 2.69(2H, d, J=6.3), 2.96(2H, t, J=5.2), 3.12(1H, m), 4.10(2H, t, J=5.2), 4.58(1H, m), 5.14(2H, s), 5.31(1H, s), 6.76(1H, dd, J=8.8, 1.7), 6.96(1H, d, J=1.9), 7.02~7.15(3H, m), 7.25~7.44(6H, m), 7.54(2H, m), 7.97(2H, m), 11.10(1H, s) | 574 (MH+) |
| Example 54 | (DMSO-d6; HCl): 1.27(6H, d, J=6.9), 2.95~3.28(3H, m), 3.47(2H, m), 4.39(2H, m), 4.91(1H, m), 6.11(1H, br.s), 6.84(1H, dd, J=8.5, 2.2), 6.92(1H, m), 7.05(2H, m), 7.12(1H, t, J=7.4), 7.30(2H, m), 7.44(1H, d, J=8.2) 8.00(2H, m), 8.73(1H, s), 8.94(1H, m), 9.18(1H, br.s), 10.07(1H, s), 11.23(1H, s) | 484 (MH+) |
| Intermed. 46 | (CDCl3): 0.52~0.62(6H, m), 0.87~0.94(9H, m), 3.03(3H, s), 3.3~3.34(2H, m), 4.74(1H, m), 6.54(1H, br.s), 7.08~7.2(2H, m), 7.57(1H, dd, J=7.6, 2.2) | |
| Intermed. 47 | (CDCl3): 0.51~0.6(6H, m), 0.85~0.92(9H, m), 2.78(1H, dd, J=11.8, 4.0), 2.87(1H, dd, J=11.8, 8.0), 3.00(3H, s), 3.06(2H, t, J=5.2), 4.16(2H, t, J=5.2), 4.84(1H, dd, J=8.0, 4.0), 6.93(1H, dd, J=8.5, 2.2), 7.08(1H, d, J=2.2), 7.10(1H, m), 7.15~7.21(1H, m), 7.31(1H, m), 7.38(1H, m), 7.52(1H, d, J=8.2), 7.59(1H, dd, J=8.0, 2.2), 7.81(1H, d, J=8.5), 7.86(1H, m) | |
| Example 55 | (DMSO-d6; HCl): 3.05(3H, s), 3.12(1H, m), 3.29(1H, m), 3.48(2H, m), 4.43(2H, m), 5.01(1H, m), 6.31(1H, d, J=4.4), 7.08(1H, dd, J=8.5, 2.2), 7.29(1H, m) 7.32~7.50(6H, m), 7.66(1H, d, J=8.0), 8.07(2H, m), 8.96(2H, m), 9.711(1H, s) | 459 (MH+) |
| Intermed. 48 | (CDCl3): 0.55~0.61(6H, m), 0.85~0.92(9H, m), 2.77(1H, dd, J=11.8, 4.1) 2.88(1H, dd, J=11.8, 7.8) 2.99(3H, s), 3.06(2H, t, J=5.2), 4.16(2H, t, J=5.2) 4.83(1H, dd, J=7.8, 4.1), 7.04(1H, dd, J=8.8, 2.5), 7.10(1H, m), 7.15~7.21(1H, m), 7.32(1H, d, J=2.2), 7.35~7.46(2H, m), 7.58(1H, dd, J=7.7, 2.1), 7.80(1H, m), 8.03(1H, d, J=8.8), 8.04(1H, m) | |
| Example 56 | (DMSO-d6; HCl): 3.05(3H, s), 3.11(1H, m), 3.32(1H, m), 3.49(2H, m), 4.42(2H, m), 4.98(1H, m), 6.31(1H, d, J=3.3), 7.17(1H, dd, J=8.8, 2.5), 7.27~7.37(2H, m), 7.43~7.52(3H, m), 7.69(1H, d, J=2.5), 7.98(1H, m), 8.28(2H, m), 8.95(2H, br.s), 9.71(1H, s) | 475 (MH+) |
| Intermed. 49 | (CDCl3): 0.54~0.63(6H, m), 0.87~0.95(9H, m), 3.02(3H, s), 3.28~3.34(2H, m), 4.74(1H, m) 6.81(1H, br.s), 7.16(1H, dd, J=8.2, 2.2), 7.40(1H, d, J=8.2) 7.65(1H, d, J=2.2) | |
| Intermed. 50 | (CDCl3): 0.52~0.62(6H, m), 0.86~0.93(9H, m), 2.80(1H, dd, J=12.0, 4.2), 2.88(1H, dd, J=12.0, 8.0), 2.98(3H, s), 8.08(2H, t, J=5.2), 4.15(2H, t, J=5.2), 4.85(1H, dd, J=8.0, 4.2), 6.92(1H, dd, J=8.5, 2.2), 7.08(1H, d, J=2.2), 7.17(1H, dd, J=8.2, 1.9), 7.28~7.41(3H, m), 7.5~7.56(1H, m), 7.67(1H, d, J=2.2), 7.81(1H, d, J=8.2), 7.86(1H, m) | |
| Example 57 | (DMSO-d6; HCl): 3.06(3H, s), 3.12(1H, m), 3.29(1H, m), 3.48(2H, m), 4.42(2H, m), 5.01(1H, m), 6.34(1H, m), 7.07(1H, dd, J=8.8, 2.2), 7.31(1H, dd, J=8.2, 2.2), 7.34~7.41(2H, m), 7.45(1H, m), 7.52(1H, d, J=1.9), 7.57(1H, d, J=8.2), 7.66(1H, m), 8.06(2H, m), 9.02(2H, br.s) | 475 (MH+) |
| Intermed. 51 | (CDCl3): 0.52~0.62(6H, m), 0.86~0.92(9H, m), 2.79(1H, dd, J=12.1, 4.1), 2.87(1H, dd, J=12.1, 7.7), 2.97(3H, s), 3.05(2H, br. t), 4.15(2H, br. t) 4.84(1H, dd, J=7.7, 4.1), 7.03(1H, d, J=8.7, 2.5), 7.16(1H, dd, J=8.7, 2.2), 7.31(1H, d, J=2.5), 7.35~7.46(3H, m), 7.66(1H, d, J=2.2), 7.80(1H, m), 8.02(1H, d, J=8.4), 8.04(1H, m) | |
| Example 58 | (DMSO-d6; HCl): 3.06(3H, s), 3.08~3.15(1H, m), 3.27~3.35(1H, m), 3.44~3.53(2H, m), 4.40~4.48(2H, m), 5.0~5.09(1H, m), 6.37(1H, br.s), 7.17(1H, dd, J=8.6, 2.2), 7.31(1H, dd, J=8.2 J=1.9), 7.46~7.57(2H, m), 7.53(1H, d, J=1.9), 7.56(1H, d, J=8.2), 7.68(1H, d, J=2.5), 7.95~7.99(1H, m), 8.23~8.3(2H, m), 9.02(1H, br.s), 9.18(1H, brs), 9.55(1H, s) | 491 (MH+) |
| Intermed. 52 | (CDCl3): 2.60(3H, s), 2.90(6H, s), 6.58(1H, br.s), 7.19(1H, dd, J=8.5, 7.7), 7.73(1H, m), 8.14(1H, dd, J=7.7, 2.2) | |
| Intermed. 53 | (CDCl3): 2.90(6H, s), 4.41(2H, s), 6.69(1H, br. s), 7.23(1H, dd, J=9.9, 8.8), 7.77(1H, ddd, J=7.0, 4.9, 2.2), 8.17(1H, dd, 7.4, 2.2) | |

TABLE 1-continued

| Compound No. | 1H-NMR (CDCl₃): δ (ppm), J (Hz) | MS m/z |
|---|---|---|
| Example 59 | (DMSO-d6; HCl): 2.71(6H, s), 3.0~3.14(1H, br. s), 3.22~3.84 (1H, br. s), 3.43~3.53(2H, m), 4.33~4.46(2H, m), 5.02(1H, m) 6.34(1H, br. s), 6.83(1H, dd, J=8.5, 2.2), 7.03(1H, d, J=2.2), 7.12(1H, dd, J=7.7, 7.7), 7.2~7.3 8(3H, m), 7.44(1H, d, J=8.0), 7.52(1H, dd, J=7.7, 2.0) 8.00(2H, d, J=8.5), 8.94~9.10 (1H, br. s), 9.14~9.30(1H, br. s), 9.71(1H, s), 11.22(1H, s) | 487 (MH+) |
| Intermed. 54 | (CDCl3): 2.60(3H, s), 2.89(6H, s), 6.85(1H, br. s), 7.48(1H, d, J=8.2), 7.65(1H, dd, J=8.2, 1.9), 8.17(1H, d, 1.9) | |
| Intermed. 55 | (CDCl3): 2.90(6H, s), 4.41(2H, s), 6.90(1H, br. s), 7.52(1H, d, J=8.5), 7.68(1H, dd, J=8.5, 1.9), 8.20(1H, d, J=1.9) | |
| Intermed. 56 | (CDCl3): 2.79(3H, s), 9.08(2H, d, J=2.2), 9.25(1H, dd, J=2.2) | |
| Intermed. 57 | (CDCl3): 2.63(3H, s), 4.19(2H, br. s), 7.53(1H, dd, J=2.2), 7.67(1H, dd, J=2.2), 8.10(1H, dd, J=2.2) | |
| Intermed. 58 | (CDCl3): 2.68(3H, s), 6.34(1H, br. s) 7.79(1H, dd, J=2.5), 7.92(1H, dd, J=2.2), 8.34(1H, dd, J=1.9) | |
| Intermed. 59 | (CDCl3): 2.66(3H, s), 5.20(2H, s) 7.30~7.48(5H, m), 7.88 (1H, dd, J=2.5), 8.01(1H, dd, J= 2.5, 1.9), 8.36(1H, dd, J=1.9) | |
| Intermed. 60 | (CDCl3): 2.53(3H, s), 3.80(2H, br. s) 5.07(2H, s), 6.50(1H, dd, J=1.9), 6.89(1H, dd, J=1.9), 6.98(1H, dd, J=2.2), 7.30~ 7.48(5H, m) | |
| Example 60 | (DMSO-d6; HCl): 2.73(6H, s), 3.0~3.15(1H, m), 3.2 4~3.3 6(1H, m), 3.4~3.54(2H, m), 4.35~ 4.46(2H, m), 5.05(1H, m), 6.38(1H, br. s), 6.84(1H, dd, J=8.5, 2.2), 7.03(1H, d, J=2.2), 7.12 (1H, dd, J=8.0, 8.0), 7.23~7.34 (2H, m), 7.44(1H, d, J=8.0), 7.52(1H, d, J=8.2), 7.61(1H, d, J= 1.9), 8.01(2H, d, J=8.5), 8.94~ 9.08(1H, br. s), 9.15~9.28 (1H, br. s), 9.46(1H, s), 11.22 (1H, s) | 503 (MH+) |
| Intermed. 61 | (CDCl3): 2.58(3H, s), 3.00(3H, s), 5.12(2H, s), 6.88(1H, bs), 7.15(1H, d, J=2.2), 7.27~7.47 (7H, m) | |
| Intermed. 62 | (CDCl3): 3.02(3H, s), 4.40(2H, s), 5.13(2H, s), 6.95(1H, br. s), 7.15~7.18(1H, m), 7.31~7.50 (7H, m) | |
| Example 61 | (CDCl3): 2.74(2H, m), 2.86(3H, s), 2.96(2H, m), 4.00(2H, m), 4.68(1H, d, J=5.5), 4.94(2H, s), 6.74(4H, m), 6.84(1H, s), 7.18 (1H, m), 7.27~7.39(7H, m), 7.85(1H, d, J=8.5), 7.92(1H, d, J=7.4), 8.26(1H, br. s) | 546 (MH+) |
| Example 62 | (DMSO-d6): 2.98(3H, s), 3.23 (2H, m), 3.47(2H, m), 4.39(2H, t, J=4.7), 4.91(1H, d, J=10.4) 6.19(1H, d, J=3.6), 6.57(1H, s), 6.64(1H, dd, J=1.9), 6.73(1H, s), 6.84(1H, dd, J=8.8, 2.5) 7.03(1H, d, J=2.2), 7.12(1H, dd, J=7.4), 7.30(1H, dd, J=7.1), 7.44(1H, d, J=8.0) | 456 (MH+) |
| Intermed. 63 | (CDCl3): 2.73(3H, s), 7.05(1H, dd, J=8.0), 8.06(1H, d, J=8.0), 8.20(1H, d, J=8.2) | |
| Intermed. 64 | (CDCl3): 2.75(3H, s), 7.10(1H, d, J=9.3), 8.36(1H, dd, J=9.3 2.8), 8.72(1H, d, J=2.8) | |
| Intermed. 65 | (CDCl3): 2.66(3H, s), 3.95(3H, s), 7.30(1H, d, J=8.0), 7.82 (1H, dd, J=8.0, 1.9), 7.93(1H, dd, J=8.0, 1.9) | |
| Intermed. 66 | (CDCl3): 2.62(3H, s), 3.78(3H, s), 3.92(2H, br. s), 6.89(1H, dd, J=7.1, 2.5), 6.97(1H, d, J= 6.9), 6.98(1H, d, J=2.5) | |
| Intermed. 67 | (CDCl3): 2.63(3H, s), 3.08(3H, s), 3.82(3H, s), 7.05(1H, br. s), 7.19(1H, dd, J=8.0), 7.38 (1H, dd, J=8.0, 1.7), 7.71(1H, dd, J=8.2, 1.7) | |
| Intermed. 68 | (CDCl3): 2.61(3H, s), 3.01(3H, s), 3.83(3H, s), 4.82(2H, s), 7.06(1H, dd, J=8.0, 7.8), 7.19~ 7.30(6H, m), 7.52(1H, dd, J=8.0, 1.9) | |
| Intermed. 69 | (CDCl3): 3.01(3H, s), 3.87(3H, s), 4.49(2H, s), 4.83(2H, s), 7.11(1H, dd, J=8.0, 7.8) 7.19~ 7.31(6H, m), 7.57(1H, dd, J=8.0, 1.9) | |
| Intermed. 70 | (CDCl3): 2.74(1H, d, J=8.8), 2.93(3H, s), 2.98~3.14(3H, m), 3.80(3H, s), 4.15(2H, m), 4.81 (2H, m), 5.04(1H, d, J=8.8), 6.84(1H, d, J=8.5), 6.87(1H, br. s), 7.01(1H, d, J=8.0), 7.06 (1H, dd, J=7.4), 7.17~7.40(8H, m), 7.50(1H, d, J=7.4), 7.91(1H, d, J=8.2), 7.96(1H, d, J=7.7) 8.12(1H, br. s) | |
| Intermed. 71 | (DMSO-d6): 2.9~3.1(2H, m), 3.12(3H, s), 3.15~3.30(2H, m), 4.34~4.44(2H, m), 14.76(2H, m), 5.30(1H, d, J=9.6), 6.2~6.4 (1H, br. s), 6.78~6.98(2H, m), 7.02~7.38(10H, m), 7.44(2H, d, J=8.0), 7.95(1H, dd, J=7.7, 8.2), 8.01(2H, d, J=8.2) | |
| Example 63 | (CD3 OD): 2.85(3H, s), 2.96~3.20 (4H, m), 4.21(2H, t, J=5.0), 4.98(1H, m), 6.77(1H, dd, J=7.7), 6.81(1H, d, J=8.9, 2.2), 6.99(1H, d, J=2.2), 7.07~7.14 (2H, m), 17.23~7.30(2H, m), 7.38 (1H, d, J=8.2), 7.91(2H, dd, J= 8.2) | 456 (MH+) |
| Intermed. 72 | (CDCl3): 2.65(3H, s), 4.05(3H, s), 7.08(1H, d, J=9.1), 8.36 (1H, dd, J=9.1, 3.0), 8.63(1H, d, J=2.8) | |
| Intermed. 73 | (CDCl3): 2.60(3H, s), 3.50(2H, br. s), 3.84(3H, s), 6.82(2H, m), 7.08(1H, m). | |
| Intermed. 74 | (CDCl3): 2.63(3H, s), 2.97(3H, s), 3.93(3H, s), 6.39(1H, br. s), 7.01(1H, d, J=9.1), 7.51~7.57 (2H, m) | |
| Intermed. 75 | (CDCl3): 2.59(3H, s), 2.95(3H, s), 3.88(3H, s), 4.81(2H, s), 6.87(1H, d, J=9.1), 7.22~7.28 (5H, m), 7.30(1H, dd, J=8.8, 2.8), 7.71(1H, d, J=3.0) | |
| Intermed. 76 | (CDCl3): 2.96(3H, s), 3.92(3H, s), 4.56(2H, s), 4.81(2H, s), 6.90(1H, d, J=8.8), 7.22~7.28 (5H, m), 7.37(1H, dd, J=9.1, 3.0), 7.77(1H, d, J=2.8) | |

TABLE 1-continued

| Compound No. | 1H-NMR (CDCl$_3$): δ (ppm), J (Hz) | MS m/z |
|---|---|---|
| Intermed. 77 | (CDCl3): 2.6~3.0(2H, m), 2.94 (3H, s), 3.04~3.08(2H, m), 3.70 (3H, s), 4.14(2H, t, J=5.8), 4.79(2H, d, J=9.9), 4.99(1H, m), 6.60(1H, d), 6.80~6.86(2H, m), 7.03(1H, dd, J=8.5, 3.0), 7.18~7.42(8H, m), 7.88~8.00 (3H, m), 8.07(1H, m) | |
| Intermed. 78 | (CD3 OD): 3.01(3H, s), 3.31(2H, m), 3.54(2H, m), 4.38(2H, t, J= 5.0), 4.78~4.82(2H, m), 5.27 (1H, m), 6.72~6.95(2H, m), 7.05 (1H, d, J=1.9) 7.08~7.48 (1H, m), 7.95(2H, d, J=7.1) | |
| Example 64 | (CD3 OD): 2.88(3H, s), 3.19(2H, m), 8.62(2H, m), 4.22(2H, m), 5.24(1H, m), 6.72~7.48(9H, m), 7.85~7.95(2H, m) | 456 (MH+) |
| Intermed. 79 | (CDCl3): 2.61(3H, s), 5.45(2H, s), 7.22(1H, d, J=8.8), 7.34~ 7.55(5H, m), 8.26(1H, dd, J=8.8, 2.2), 8.55(1H, d, J=2.5) | |
| Intermed. 79' | (CDCl3): 2.57(3H, d, J=5.2), 2.61(3H, s), 4.70(1H, q, J=5.5), 5.32(2H, s), 7.17(1H, d, J=8.8), 7.24~7.51(5H, m), 8.18(1H, dd, J=8.8, 2.2)8.50(1H, d, J= 2.2) | |
| Intermed. 80 | (CDCl3): 2.58(3H, s), 4.43(2H, s), 4.74(1H, s), 5.34(2H, s), 7.20(1H, d, J=8.8), 7.36~7.51 (5H, m), 8.20(1H, dd, J=8.8, 2.2), 8.52(1H, d, J=2.2) | |
| Example 65 | (DMSO-d6): 2.42(3H, d, J=5.0), 2.71(2H, d, J=6.0), 2.95(2H, t, J=5.2), 4.08(2H, t, J=5.5), 4.64(1H, m), 5.33(2H, s), 5.42 (1H, d, J=4.1), 6.75(1H, dd, J= 8.5, 2.2), 6.93~7.00(2H, m), 7.10(1H, dd, J=7.7, 7.4), 7.15 (1H, d, J=8.8), 7.24~7.54(8H, m), 7.76(1H, d, J=2.2), 7.92~8.00 (2H, m), 11.08(1H, s) | 546 (MH+) |
| Example 66 | (DMSO-d6; HCl): 2.41(3H, d, J= 5.0), 3.03~3.35(2H, m), 3.47 (2H, m), 4.39(2H, m), 5.00(1H, d, J=10.4), 6.21(1H, br. s), 6.8 4(1H, dd, J=8.5, 2.2), 6.88(1H, d, J=5.2), 7.03(1H, d, J=2.2), 7.08(1H, d, J=8.2), 7.13(1H, d, J=8.0), 7.30(1H, ddd, J=8.2 1.1), 7.44(1H, d, J=8.0), 7.47 (1H, dd, J=8.8, 2.2), 7.71(1H, d, J=2.2), 8.01(2H, d, J=8.5) 8.90~9.05(1H, br. s), 9.10~9.25 (1H, br.s), 10.8.9(1H, s), 1 1.2 1(1H, s) | 456 (MH+) |
| Intermed. 82 | (CDCl3): 2.58(3H, s), 3.94(3H, s), 5.28(2H, s), 7.07(1H, d, J= 8.8), 7.30~7.52(5H, m), 8.08 (1H, dd, J=8.8, 2.5), 8.44(1H, d, J=2.2) | |
| Intermed. 83 | (CDCl3): 3.94(3H, s), 4.42(2H, s), 5.29(2H, s), 7.10(1H, d, J= 8.8), 7.34~7.50(5H, m), 8.11 (1H, dd, J=8.8, 2.5) 8.47(1H, d, J=2.2) | |
| Intermed. 84 | (CDCl3): 2.77(1H, d, J=12.3), 2.99(1H, d, J=12.3), 3.08(2H, m), 3.89(3H, s), 4.13(2H, t, J= 5.1), 4.72(1H, d, J=8.7), 5.14 (2H, s), 6.83(2H, m), 6.95(1H, d, J=8.5), 7.20(1H, m), 7.30~ 7.48(8H, m), 7.84(1H, d, J=2.2) 7.91(1H, d, J=9.3), 7.96(1H, d, J=7.7) 8.12(1H, br. s) | 511 (MH+) |
| Intermed. 85 | (CDCl3): 2.81(1H, d, J=11.8), 2.99(1H, d, J=12.1), 3.10(2H, m), 4.17(2H, t, J=5.0), 4.71(1H, m), 4.75(2H, s), 5.12(2H, s), 6.85(1H, d, J=8.5), 6.88(1H, s), 6.94(1H, d, J=8.2), 7.20~7.42 (9H, m), 7.93(1H, d, J=8.8), 7.97(1H, d, J=7.7), 8.20(1H, br. s) | 411 (MH+) |
| Example 67 | (DMSO-d6; HCl): 3.71(1H, br. s), 3.19(1H, br. s), 3.48(2H, br. s), 4.38(1H, m), 4.49(2H, s), 4.90(1H, d, J=10.2), 5.04(1H, br. s), 6.03(1H, d, J=3.3), 6.78 (1H, d, J=8.2), 6.84(1H, dd, J= 8.2, 2.2), 7.02(1H, d, J=2.2), 7.07(1H, d, J=7.4), 7.12(1H, dd, J=7.4, 7.4), 7.30(1H, dd, J= 8.0, 8.0), 7.36(1H, s), 7.44 (1H, d, J=7.7), 8.01(2H, d, J=8.5) | 393 (MH+) |
| Intermed. 86 | (CDCl3): 2.73(1H, br. s), 3.03 (3H, s), 3.53(1H, dd, J=10.44, 8.8), 3.66(1H, dd, J=10.44, 3.3), 4.94(1H, dd, J=8.8, 3.6), 6.57(1H, br. s), 7.17~7.24(2H, m), 7.26(1H, m), 7.38(1H, m) | |
| Intermed. 87 | (CDCl3): 0.47~0.68(6H, m), 0.91(9H, t, J=7.7), 3.01(3H, s), 3.33(2H, d, J=5.8), 4.75(1H, t, J=5.8), 6.49(1H, br. s), 7.13~ 7.19(2H, m), 7.22(1H, m), 7.33 (1H, t, J=7.7) | |
| Intermed. 88 | (CDCl3): 1.58~1.73(2H, m), 2.00 (3H, s), 2.20~2.32(2H, m), 2.35~2.55(4H, m), 4.25(1H, m), 5.48(1H, br, s) | |
| Intermed. 89 | (DMSO-d6): 1.75(1H, m), 1.82 (3H, s), 1.94(1H, m), 2.42(1H, dd, J=14.6, 8.5), 3.73(3H, s), 4.01(1H, m), 6.57(1H, dd, J=8.2, 2.2), 6.75(1H, d, J=2.2), 7.18 (1H, d, J=8.5), 7.93(1H, d, J= 8.0), 10.50(1H, s) | |
| Intermed. 90 | (DMSO-d6): 2.05(3H, s), 3.83 (3H, s), 6.74(1H, dd, J=8.5, 2.2), 7.30~ 6.93(1H, d, J=2.2), 7.86(1H, d, J=8.8), 8.21(1H, d, J=1.9), 9.85(1H, s), 11.00(1H, s) | |
| Intermed. 91 | (DMSO-d6): 2.05(3H, s), 6.60 (1H, dd, J=8.5, 1.9), 6.77(1H, d, J=1.6), 7.26(1H, d, J=8.5), 7.34(1H, dd, J=8.5, 1.6), 7.74 (1H, d, J=8.5), 8.15(1H, s), 9.38 (1H, s), 9.82(1H, s), 10.83 (1H, s) | |
| Intermed. 92 | (DMSO-d6): 2.06(3H, s), 3.43 (2H, m), 4.07(2H, m), 5.05(2H, s), 6.74(1H, dd, J=8.5, 1.9), 6.94(1H, s), 7.25~7.50(7H, m), 7.54(1H, t, J=5.5), 7.86(1H, d, J=8.5), 8.22(1H, s), 9.86(1H, s), 11.02(1H, s) | |
| Intermed. 93 | (DMSO-d6): 1.8~2.1(2H, br. s), 2.05(3H, s), 2.93(2H, t, J=5.8), 4.00(2H, t, J=5.8), 6.74(1H, dd, J=8.5, 2.2), 6.93(1H, d, J=2.2), 7.30~7.40(2H, m), 7.86 (1H, d, J=8.8), 8.21(1H, d, J= 1.9), 9.85(1H, s), 11.00(1H, s) | |
| Example 68 | (DMSO-d6; HCl): 2.06(3H, s), 3.00(3H, s), 3.17(1H, m), 3.27 (1H, m), 3.48(2H, m), 4.37(2H, m), 4.97(1H, m), 6.26(1H, m) 6.82(1H, m), 6.99(1H, m), 7.15(2H, | 497 (M+) |

TABLE 1-continued

| Compound No. | 1H-NMR (CDCl$_3$): δ (ppm), J (Hz) | MS m/z |
|---|---|---|
| | m), 7.30~7.40(4H, m), 7.92 (1H, d, J=8.8), 8.27(1H, s), 8.91 (2H, m), 9.86(1H, s), 9.89(1H, s), 11.09(1H, s) | |
| Intermed. 95 | (CDCl3): 0.49~0.58(6H, m), 0.88(9H, m), 2.75(6H, s), 2.72~2.79(1H, m) 2.81~2.94(1H, m), 3.01(2H, m), 4.12(2H, m), 4.80 (1H, dd, J=7.7, 4.1), 5.07(2H, s), 6.82(1H, dd, J=8.5, 2.2), 6.93(1H, dd, J=8.5, 2.2), 7.05 (1H, dd, J=8.5, 2.2), 7.07(1H, d, J=2.2), 7.29(1H, dd, J=7.4, 1.1), 7.34(1H, dd, J=5.2, 1.6), 7.36~7.45(5H, m), 7.49~7.54 (2H, m), 7.80(1H, d, J=8.5), 7.85(1H, m) | 689 (MH+) |
| Intermed. 102 | (CDCl3): 0.51~0.60(6H; m), 0.88(9H, m), 2.78(1H, dd, J=11.8, 4.1), 2.89(1H, dd, J=11.8, 7.7), 2.99(3H, s), 3.05(2H, t, J=4.9), 14.15(2H, t, J=4.9), 4.83 (1H, dd, J=7.7, 4.1), 6.82(1H, dd, J=8.5, 2.2), 6.91(1H, d, J=2.2), 7.05~7.28(3H, m), 7.31~7.42(2H, m), 7.59(1H, dd, J=8.0, 1.9), 7.90~8.00(2H, m), 8.12 (1H, br. s) | |
| Intermed. 108 | (CDCl3): 0.52~0.61(6H, m), 0.89(9H, m), 2.79(1H, dd, J=12.1, 4.4), 2.89(1H, dd, J=12.1, 7.7), 2.96(3H, s), 3.04(2H, m), 4.15(2H, m), 4.84(1H, m), 6.82 (1H, dd, J=8.5, 2.2), 6.92(1H, d, J=1.9), 7.17(1H, dd, J=8.8, 1.9), 7.21(1H, d, J=8.2, 1.4), 7.30~7.42(3H, m), 7.67(1H, d, J=2.2), 7.90~7.99(2H, m), 8.14 (1H, br. s) | |
| Intermed. 112 | (CDCl3): 2.49(3H, d, J=5.2), 3.28(1H, d, J=3.0), 3.47(1H, dd, J=10.7, 8.0), 3.56(1H, dd, J=10.7, 4.1), 4.83(1H, q, J=5.5), 4.88(1H, m), 5.22(2H, s), 7.09 (1H, d, J=8.8), 7.30~7.48(5H, m), 7.55(1H, dd, J=8.8, 2.5), 7.88(1H, d, J=2.2) | |
| Intermed. 113 | (CDCl3): 0.47~0.66(6H, m), 0.85~0.95(9H, m), 2.52(3H, d, J=5.5), 3.28~3.35(2H, m), 4.66 (1H, m), 4.77(1H, m), 5.23(2H, s), 7.09(1H, d, J=8.5), 7.34~7.52(5H, m), 7.55(1H, dd, J=8.5, 2.5), 7.91(1H, d, J=2.2) | |
| Intermed. 114 | (CDCl3): 0.48~0.58(6H, m), 0.87(9H, m), 2.50(3H, d, J=5.5), 2.80(1H, dd, J=11.8, 4.4), 2.91 (1H, dd, J=11.8, 7.4), 4.07(2H, m), 4.69(1H, q, J=5.5), 4.86 (1H, dd, J=7.4, 4.4), 5.15(2H, s), 6.77(1H, d, J=1.9), 6.82(1H, dd, J=6.3, 2.2), 7.01(1H, d, J=8.5), 7.20(1H, m), 7.30~7.48 (7H, m), 7.52(1H, dd, J=8.5, 2.2), 7.89~8.00(2H, m), 8.19(1H, s) | |
| Intermed. 116 | (CDCl3): 2.34(3H, s), 2.84(3H, s), 8.21(1H, dd, J=9.1, 2.2), 8.81(1H, d, J=2.2), 8.95(1H, d, J=9.1) | |
| Intermed. 117 | (CDCl3): 2.25(3H, s), 2.56(3H, s), 7.44(2H, m), 7.50(1H, m) | |
| Intermed. 118 | (CDCl3): 2.26(3H, s), 2.60(3H, s), 3.05(3H, s), 6.79(1H, s), 7.90(2H, m), 8.24(1H, dd, J=8.1, 2.5), 8.5 5(1H, br. s) | |
| Intermed. 119 | (CDCl3): 2.27(3H, s), 3.08(3H, s), 4.41(2H, s), 6.73(1H, br. s), 7.87~8.09(2H, m), 8.31(1H, dd, J=8.8), 8.58(1H, d, J=10.2) | |
| Intermed. 120 | (DMSO-d6; HCl): 2.10(3H, s), 2.94(3H, s), 3.15(2H, d, J=8.2) 3.48(2H, m), 4.39(2H, m), 5.01 (1H, m), 6.26(1H, m), 6.84(1H, d, J=8.5), 7.03(1H, s), 7.12 (1H, dd, J=7.1, 6.9), 7.24~7.33 (2H, m), 7.44(2H, d, J=8.5), 7.56 (1H, m), 8.01(2H, d, J=6.9), 8.8~9.1(2H, m), 9.62(1H, m), 11.18(1H, s) | 497 (MH+) |
| Example 82 | (DMSO-d6; 2HCl): 3.02(3H, s), 3.2~3.5(4H, m), 4.26(2H, m), 4.84(1H, d, J=9.3), 6.8~7.5(8H, m), 7.64(1H, s), 7.87(1H, d, J=7.7), 8.01(1H, d, J=8.2) 9.0~9.6(3H, br. s), 11.3(1H, s) | 455 (MH+) |
| Intermed. 121 | (CDCl3): 2.61(3H, s), 2.62(3H, s), 4.18(2H, s), 5.27(2H, s), 7.15(3H, m), 7.35~7.44(3H, m), 7.47(2H, d, J=8.0), 8.16(1H, dd, J=8.8, 2.2), 8.57(1H, d, J=2.2) | |
| Intermed. 122 | (CDCl3): 2.62(3H, s), 4.19(2H, s), 4.43(2H, s), 5.28(2H, s), 7.12~7.20(2H, m), 7.18(1H, d, J=8.52), 7.24~7.50(8H, m), 8.20(1H, dd, J=8.5, 2.2) 8.59(1H, d, J=2.2) | |
| Intermed. 123 | (CDCl3): 2.59(3H, s), 2.72~2.82 (1H, m), 3.00~3.08(1H, m), 3.10(2H, m), 4.13~4.20(4H, m), 4.72~4.77(1H, m), 5.16(2H, s), 6.84(1H, dd, J=8.2, 2.2), 6.91 (1H, d, J=2.2), 7.05(1H, d, J=8.5), 7.13~7.49(13H, m), 7.57 (1H, d, J=8.2), 7.93(1H, d, J=8.5), 7.97(1H, d, J=7.7), 8.01 (1H, d, J=1.7) | 636 (MH+) |
| Example 83 | (DMSO-d6; HCl): 2.64(3H, s), 3.14(2H, m), 3.48(2H, m, 4.31 (2H, s), 4.39(2H, m), 5.00(1H, m), 6.23(1H, br. s), 6.83(1H, dd, J=8.8, 2.2), 7.02(1H, d, J=1.9), 7.08 ~7.15(3H, m), 7.26~7.40 (6H, m), 7.43(1H, d, J=8.5), 7.51(1H, dd, J=8.8, 1.9), 7.80 (1H, d, J=1.9), 7.99(1H, d, J=8.8), 8.80~9.10(2H, br), 10.96 (1H, s), 11.18(1H, s) | 546 (MH+) |
| Intermed. 124 | (CDCl3): 1.39(3H, t, J=7.1), 1.66(3H, s), 3.76(2H, m), 4.05 (2H, m), 4.38(2H, q, J=7.1), 7.56 (2H, d, J=8.5), 8.03(2H, d, J=8.5) | |
| Intermed. 125 | (CDCl3): 2.61(3H, s), 4.79(2H, s), 7.46(2H, d, J=8.0), 7.96 (2H, d, J=8.2) | |
| Intermed. 126 | (CDCl3): 2.14(3H, s), 2.61(3H, s), 5.17(2H, s), 7.45(2H, d, J=8.5), 7.96(2H, d, J=8.5) | |
| Intermed. 127 | (CDCl3): 2.20(3H, s), 2.68(3H, s), 5.57(2H, s), 7.73(1H, d, J=8.2), 8.22(1H, dd, J=8.2, 1.6), 8.65(1H, d, J=1.6) | |
| Intermed. 128 | (CDCl3): 2.10(3H, s), 2.56(3H, s), 4.18(2H, br. s), 5.12(2H, s), 7.27~7.31(3H, m) | |
| Intermed. 129 | (CDCl3): 2.11(3H, s), 2.62(3H, s), 3.12(3H, s), 5.18(2H, s), 7.52(1H, d, J=8.0), 7.74(1H, br. s), 7.79(1H, dd, J=8.0, 1.6), 8.08(1H, d, J=1.6) | |

TABLE 1-continued

| Compound No. | 1H-NMR (CDCl₃): δ (ppm), J (Hz) | MS m/z |
|---|---|---|
| Intermed. 130 | (CDCl3): 2.12(3H, s), 3.14(3H, s), 4.43(2H, s), 5.18(2H, s), 7.55(1H, d, J=8.0), 7.80(1H, b s), 7.83(1H, dd, J=8.0, 1.7), 8.12(1H, d, J=1.7) | |
| Intermed. 131 | (DMSO-d6): 2.05(3H, s), 2.96 (3H, s), 2.92~3.00(2H, m), 3.28~3.32(2H, m), 4.08~4.13(2H, m), 4.67(1H, br. s), 5.15(2H, s), 5.44(1H, m), 6.76(1H, dd, J=8.2, 1.9), 6.96(1H, d, J=1.9), 7.07~7.13(1H, m), 7.24~7.44 (4H, m), 7.93~8.00(3H, m) | 500 (MH+) |
| Example 84 | (DMSO-d6; HCl): 3.02(3H, s), 3.25~3.35(2H, m), 3.43~3.53 (2H, m), 4.36~4.43(2H, m), 4.62 (2H, s), 5.03(1H, d, J=9.1), 6.26 (1H, bs), 6.84(1H, dd, J=8.5, 2.2), 7.03(1H, d, J=1.9), 7.12 (1H, dd, J=7.1), 7.24~7.35(2H, m), 7.38(1H, s), 7.44(1H, d, J=8.0), 7.47(1H, d, J=8.0), 8.01 (1H, d, J=8.2), 9.06(1H, s), 8.90~9.25(2H, br), 11.21(1H, s) | 470 (MH+) |
| Intermed. 132 | (CDCl3): 2.61(3H, s), 3.06(3H, s), 7.66(1H, dd, J=8.5, 2.2) 7.71(1H, d, J=8.5), 8.20(1H, d, J=2.2) | |
| Intermed. 133 | (CDCl3): 3.09(3H, s), 4.42(2H, s), 7.68(1H, dd, J=8.4, 1.8), 7.75(1H, d, J=8.4), 8.21(1H, d J=1.8) | |
| Example 85 | (DMSO-d6; HCl): 3.07(3H, s), 2.98~3.16(2H, m), 3.43~3.55 (2H, m), 435~4.44(2H, m), 5.0~5.08 (1H, m), 6.3 8(1H, br. s), 6.84 (1H, dd, J=8.5, 2.2), 7.03 (1H, d, J=2.2), 7.12(1H, dd, J=8.0, 8.0), 7.24(1H, dd, J=8.0, 1.9), 7.30(1H, dd, J=8.0, 8.0), 7.44(1H, d, J=8.0), 7.52(1H, d, J=1.9), 7.72(1H, d, J=8.0), 8.00(2H, d, J=8.5), 8.95~9.08 (1H, m), 9.10~9.25(1H, m), 9.47 (1H, s), 11.20(1H, s) | 520 (M+2)+ |
| Intermed. 134 | (CDCl3): 2.64(3H, s), 7.80(1H, dd, J=8.2, 2.2), 8.19(1H, d, J=8.2), 8.36(1H, d, J=2.2) | |
| Intermed. 135 | (CDCl3): 2.54(3H, s), 4.25(2H, br. s), 7.01(1H, dd, J=8.2, 1.9), 7.29(1H, d, J=1.9), 7.74(1H, d, J=8.2) | |
| Intermed. 136 | (CDCl3): 2.60(3H, s), 3.06(3H, s), 7.51(1H, dd, J=8.2, 1.9), 7.96(1H, d, J=8.2), 8.16(1H, d, J=1.9) | |
| Intermed. 137 | (CDCl3): 3.09(3H, s), 4.41(2H, s), 6.76(1H, br. s), 7.53(1H, dd, J=8.2, 2.2), 8.00(1H, d, J=8.2), 8.18(1H, d, J=2.2) | |
| Example 86 | (DMSO-d6; HCl): 3.08(3H, s), 3.0~3.1(2H, m), 3.45~3.54(2H, m), 4.38~4.47(2H, m), 4.9 8~5.08 (1H, m), 6.37(1H, br. s), 6.84 (1H, dd, J=8.5, 2.2), 7.03(1H, d, J=2.2), 7.06~7.16(2H, m) 7.30(1H, dd, J=8.2, 8.2), 7.44 (1H, d, J=8.2), 7.46(1H, d, J=2.2), 7.94(1H, d, J=8.2), 8.01 (2H, d, J=8.5), 8.94~9.06(1H, br), 9.10~9.24(1H, br), 9.36(1H, s), 11.21(1H, s) | 566 (MH+) |
| Intermed. 138 | (CDCl3): 2.55(3H, s), 2.70(3H, s), 4.31(2H, s), 5.17(2H, s), 6.95(1H, s), 7.02(1H, d, J=8.5), 7.15~7.21(2H, m), 7.23~7.31 (2H, m), 7.33~7.44(6H, m), 7.74(1H, dd, J=8.5, 2.2), 8.14 (1H, d, J=2.8) | |
| Intermed. 139 | (CDCl3): 2.72(3H, s), 4.33(2H, s), 4.37(2H, s), 5.18(2H, s), 6.98(1H, s), 7.04(1H, d, J=8.5), 7.16~7.22(2H, m), 7.25~7.32 (2H, m), 7.34~7.43(6H, m), 7.77(1H, dd, J=8.8, 1.9), 8.14 (1H, d, J=2.2) | |
| Intermed. 140 | (DMSO-d6): 2.51(3H, s), 2.69 (2H, m), 2.94(2H, m), 4.07(2H, m), 4.11(2H, m), 4.60(1H, m), 5.15 (2H, s), 6.74(1H, d, J=10.7), 6.94(1H, m), 7.03~7.58(16H, m), 7.91~8.00(3H, m), 11.08 (1H, s) | 651 (MH+) |
| Example 87 | (DMSO-d6; HCl): 2.57(3H, s), 3.00~3.30(2H, m), 3.47(2H, m), 4.18(2H, m), 4.37(2H, m), 4.92 (1H, d, J=9.6), 6.14(1H, br. s), 6.82(1H, dd, J=8.5, 2.2), 6.91 (1H, d, J=8.2), 7.02~7.12(3H, m), 7.18~7.21(2H, m), 7.25~7.35(4H, m), 7.41(1H, d, J=2.2), 7.43(1H, d, J=8.0), 7.97~8.02 (2H, m) | 561 (MH+) |
| Intermed. 141 | (CDCl3): 1.09(6H, t, J=7.1), 2.55(3H, s), 3.30(4H, q, J=7.1), 5.17(2H, s), 6.91(1H, bs), 6.99 (1H, d, J=8.5), 7.36~7.44 (5H, m), 7.69(1H, dd, J=8.5, 2.2), 8.02(1H, d, J=2.2) | |
| Intermed. 142 | (CDCl3): 1.10(6H, t, J=7.4), 3.31(4H, q, J=7.4), 4.39(2H, s), 5.19(2H, s), 6.94(1H, bs) 7.02(1H, d, J=8.8), 7.36~7.44 (5H, m), 7.72(1H, dd, J=8.8), 8.03 (1H, d, J=2.2) | |
| Intermed. 143 | (DMSO-d6): 0.88(6H, t, J=7.1), 2.68(2H, d, J=5.8), 2.95(2H, m), 3.07(4H, q, J=7.1), 4.09 (2H, m), 4.58(1H, m), 5.13(2H, s), 6.76(1H, d, J=6.6), 6.92~7.14 (4H, m), 7.24~7.44(7H, m), 7.54(2H, d, J=6.9), 7.90~8.02 (2H, m) | 603 (MH+) |
| Example 88 | (DMSO-d6; HCl): 0.95(6H, t, J=7.1), 3.13(4H, q, J=7.1), 2.95~3.25(2H, m), 3.48(2H, m), 4.37 (2H, m), 4.88(1H, d, J=10.2), 6.11(1H, br. s), 6.8 0~6.8 8(2H, m), 6.95~7.04(2H, m), 7.12 (1H, dd, J=8.0, 0.8), 7.27~7.34 (2H, m), 7.44(1H, d, J=8.0), 8.01 (2H, d, J=8.5), 8.54(1H, s), 8.6~9.1(2H, br), 9.85(1H, s), 11.19(1H, s) | 513 (MH+) |
| Intermed. 144 | (CDCl3): 2.75(6H, s), 4.41(2H, s), 5.29(2H, s), 7.15(1H, d, J=8.8), 7.35~7.4 5(3H, m), 7.47~7.52(2H, m), 8.17(1H, dd, J=8.8, 2.2), 8.54(1H, d, J=2.2) | |
| Intermed. 145 | (CDCl3): 0.52~0.62(6H, m), 0.85~0.94(9H, m), 2.71(6H, s), 3.26~3.35(2H, m), 4.76(1H, t, J=6.2), 5.19(2H, s), 7.05(1H, d, J=8.5), 7.32~7.44(3H, m), 7.46~7.55(3H, m), 7.90(1H, d, J=2.2) | |
| Intermed. 146 | (CDCl3): 0.48~0.58(6H, m), 0.87(9H, t, J=7.8), 2.71(6H, s), 2.74~2.82(1H, m), 2.85~2.91 (1H, m), 3.04(2H, m), 4.13(2H, m), 4.8~4.86(1H, m), 5.16(2H, s), | |

TABLE 1-continued

| Compound No. | 1H-NMR (CDCl$_3$): δ (ppm), J (Hz) | MS m/z |
|---|---|---|
| | 6.82(1H, dd, J=8.5, 2.2), 6.88(1H, d, J=2.2), 7.01(1H, d, J=8.5), 7.20(1H, m), 7.29~7.42 (6H, m), 7.45~7.52(2H, m), 7.91 (1H, d, J=8.5), 7.96~7.98(2H, m), 8.20(1H, br. s) | |
| Intermed. 147 | (DMSO-d6): 2.62(2H, m), 2.71~2.75(2H, m), 2.95(2H, m), 4.08 (2H, m), 4.65~4.72(1H, m), 5.24 (2H, s), 5.46(1H, br. s), 6.75 (1H, dd, J=8.5, 2.2), 6.95(1H, d, J=2.2), 7.10(1H, dd, J=7.7, 7.7), 7.24~7.44(6H, m) 7.48~7.54(2H, m), 7.57(1H, dd, J=8.5, 2.2), 7.78(1H, d, J=2.2), 7.95 (1H, d, J=8.5), 7.98(1H, d, J=8.2), 11.10(1H, s) | 560 (MH+) |
| Example 89 | (DMSO-d6; HCl): 2.71(6H, s), 2.76~2.82(2H, m), 3.02(2H, m), 4.13(2H, m), 4.64~4.70(1H, m), 6.76(1H, dd, J=8.5, 2.2), 6.96 (1H, d, J=2.2), 7.01(1H, d, J=8.2), 7.10(1H, dd, J=8.0, 8.0), 7.28(1H, dd, J=8.0, 8.0), 7.38~7.45(2H, m), 7.65(1H, d, J=2.2), 7.96(1H, d, J=8.5), 7.98 (1H, d, J=8.0), 8.28(1H, br. s), 11.15(1H, s) | 470 (MH+) |
| Intermed. 148 | (CDCl3): 2.70(1H, d, J=8.5), 2.81(1H, d, J=8.5), 2.90(3H, s), 3.04(2H, m), 3.25(3H, s), 4.12 (2H, t, J=4.7), 4.32(1H, dd, J=8.5, 4.7) 15.07(2H, s), 6.82 (1H, dd, J=8.5, 2.2), 6.88(1H, s), 6.96(1H, d, J=8.2), 7.09(1H, dd, J=8.5, 1.7), 7.19(1H, dd, J=8.8, 1.4), 7.29~7.45(7H, m), 7.51(1H, d, J=1.9), 7.90(1H, d, J=8.5), 7.96(1H, d, J=7.7), 8.29(1H, m) | 560 (MH+) |
| Example 90 | (DMSO-d6; HCl): 2.96(3H, s), 3.19(3H, s), 3.23(2H, d, J=6.6) 3.46(2H, m), 4.37(2H, m), 4.54 (1H, t, J=6.6), 6.84(1H, dd, J=8.5, 1.9), 6.96(1H, d, J=8.5), 7.01~7.08(2H, m), 7.12(1H, dd, J=7.4, 7.4), 7.23(1H, m) 7.30(1H, m), 7.44(1H, d, J=8.0), 8.01(2H, d, J=8.2), 8.85(1H, s), 8.9 6(1H, br. s), 10.15(1H, s | 470 (MH+) |
| Example 91 | (DMSO-d6; HCl): 2.96(3H, s), 3.18 (3H, s), 3.18(1H, m), 3.31 (1H, m), 3.40(2H, m), 4.38(2H, m), 4.48(1H, m), 6.95(1H, d, J=8.0), 7.05(1H, m), 7.16(1H, dd, J=8.5, 2.2), 7.22(1H, d, J=2.2), 7.46(2H, m), 7.68(1H, d, J=2.2), 7.98(1H, m), 8.27(2H, m), 8.82(1H, br. s), 10.12(1H, br. s) | 487 (MH+) |
| Example 92 | (DMSO-d6; 2HCl): 2.94(3H, s), 3.17(3H, s), 3.22(2H, m), 3.46 (2H, m), 4.38(2H, m), 4.51(1H, m), 6.81~6.90(2H, m), 7.03(2H, dd, J=6.3, 2.2), 7.12(2H, dd, J=7.4, 7.4), 7.27~7.33(1H, m), 7.44(1H, d, J=8.0), 8.01(2H, d, J=8.5), 8.8~9.2(3H, br), 11.20(1H, s) | 469 (MH+) |

TABLE 2

| Compound | * Intrinsic activity (%) | ED$_{50}$ (nM) |
|---|---|---|
| Isoproterenol | 100 | 140 |
| BRL 37344 | 29 | 104 |
| CL 316, 243 | 9 | 1700 |
| Example 1 | 80 | 340 |
| Example 2 | 120 | 0.18 |
| Example 4 | 80 | 0.52 |
| Example 5 | 114 | 66 |
| Example 6 | 119 | 33 |
| Example 7 | 95 | 18 |
| Example 8 | 47 | 720 |
| Example 9 | 85 | 750 |
| Example 10 | 47 | 150 |
| Example 11 | 95 | 26 |
| Example 12 | 113 | 0.14 |
| Example 13 | 110 | 2.7 |
| Example 14 | 97 | 2.8 |
| Example 15 | 88 | 110 |
| Example 16 | 99 | 30 |
| Example 17 | 53 | 910 |
| Example 18 | 90 | 32 |
| Example 25 | 95 | 2.1 |
| Example 28 | 97 | 1000 |
| Example 29 | 120 | 250 |
| Example 30 | 110 | 1700 |
| Example 31 | 100 | 2200 |
| Example 32 | 98 | 1600 |
| Example 34 | 37 | 4600 |
| Example 35 | 90 | 520 |
| Example 38 | 76 | 0.006 |
| Example 40 | 97 | 200 |
| Example 41 | 63 | 600 |
| Example 43 | 104 | 85 |
| Example 45 | 89 | 17 |
| Example 47 | 86 | 2000 |
| Example 48 | 73 | 220 |
| Example 50 | 85 | 0.94 |
| Example 52 | 76 | 2.6 |
| Example 54 | 109 | 8.4 |
| Example 55 | 78 | 230 |
| Example 56 | 97 | 630 |
| Example 57 | 68 | 230 |
| Example 58 | 91 | 550 |
| Example 62 | 106 | 210 |
| Example 66 | 106 | 72 |
| Example 67 | 109 | 28 |
| Example 68 | 92 | 38 |
| Example 69 | 94 | 0.016 |
| Example 70 | 76 | 300 |
| Example 71 | 97 | 180 |
| Example 72 | 80 | 0.00003 |
| Example 73 | 102 | 0.038 |
| Example 74 | 114 | 0.74 |
| Example 75 | 105 | 88 |
| Example 76 | 131 | 520 |
| Example 77 | 100 | 21 |
| Example 78 | 110 | 51 |
| Example 79 | 107 | 1.2 |
| Example 80 | 110 | 57 |
| Example 81 | 98 | 6.2 |
| Example 82 | 130 | 2800 |
| Example 83 | 79 | 740 |
| Example 84 | 71 | 58 |
| Example 85 | 70 | 56 |
| Example 87 | 138 | 84 |
| Example 88 | 86 | 390 |
| Example 89 | 73 | 350 |
| Example 90 | 102 | 190 |
| Example 92 | 81 | 280 |

* Relative activity for isoproterenol

TABLE 3

| Compound | * Intrinsic activity (%) | $ED_{50}$ (nM) |
| --- | --- | --- |
| Isoproterenol | 100 | 1.7 |
| Example 2 | 82 | 56 |
| Example 4 | 88 | 0.7 |
| Example 7 | 90 | 1200 |
| Example 9 | 106 | 250 |
| Example 25 | 70 | 510 |
| Example 31 | 103 | 7700 |
| Example 32 | 94 | 290 |
| Example 38 | 103 | 2.6 |
| Example 40 | 92 | 13 |
| Example 41 | 109 | 240 |
| Example 43 | 77 | 4 |
| Example 50 | 112 | 0.19 |
| Example 52 | 100 | 0.38 |
| Example 54 | 118 | 25 |
| Example 67 | 94 | 54 |
| Example 69 | 107 | 0.65 |
| Example 71 | 88 | 110 |
| Example 72 | 96 | 0.54 |
| Example 92 | 126 | 1900 |

* Relative activity for isoproterenol

What is claimed is:

1. A compound represented by the general formula (I) or a salt thereof:

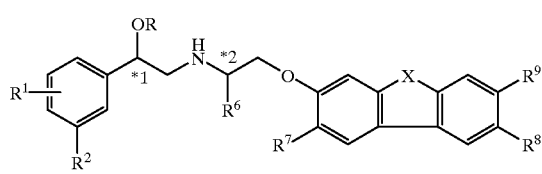

(I)

in which R represents hydrogen atom or methyl, $R^1$ stands for hydrogen atom, halogen atom, hydroxy, benzyloxy, amino or hydroxymethyl, $R^2$ stands for hydrogen atom, hydroxymethyl, $NHR^3$, $SO_4NR^4R^{4'}$ stand for hydrogen atom, methyl, $SO_2R^5$, formyl or $CONHR^{6'}$, with $R^5$ being lower alkyl, benzyl or $NR^4R^{4'}$ and $R^{6'}$ being hydrogen atom or lower alkyl, and $R^4$ and $R^{4'}$ may be identical with or different from each other and stand each for hydrogen atom, lower alkyl or benzyl, $R^6$ represents hydrogen atom or lower alkyl, X is oxygen atom or sulfur atom, $R^9$ stands for hydrogen atom and either one of $R^7$ and $R^8$ is hydrogen atom, and the other one is hydrogen atom, amino, acetyl amino or hydroxy, and *1 indicate an asymmetric carbon atom and *2 indicates that the carbon atom is asymmetric provided that $R^6$ is lower alkyl.

2. A compound represented by the general formula (I) or a salt thereof as claimed in claim 1;

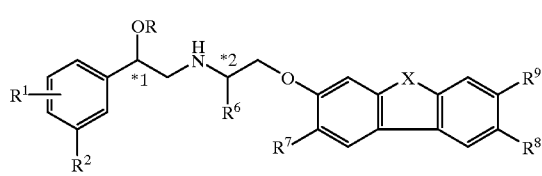

(I)

in which R represents hydrogen atom, $R^1$ stands for hydrogen atom, halogen atom, hydroxy, benzyloxy, amino or hydroxymethyl, $R^2$ stands for hydrogen atom, hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or $NR^4R^{4'}$ and $R^{6'}$ being hydrogen atom or lower alkyl, and $R^4$ and $R^{4'}$ may be identical with or different from each other and stand each for hydrogen atom, lower alkyl or benzyl, $R^6$ represents hydrogen atom or lower alkyl, X is oxygen atom or sulfur atom, $R^9$ stands for hydrogen atom and either one of $R^7$ and $R^8$ is hydrogen atom and the other one is hydogen atom, amino, acetylamino or hydroxy, and *1 indicates an asymmetric carbon atom and *2 indicates that the carbon atom is asymmetric provided that $R^6$ is lower alkyl.

3. A compound represented by the general formula (I) or a salt thereof as claimed in claim 2;

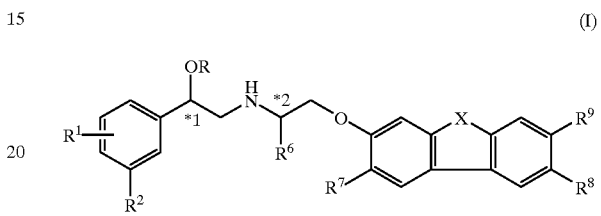

(I)

in which R represents hydrogen atom, $R^1$ stands for hydrogen atom, fluorine atom, chlorine atom, hydroxy or benzyloxy, $R^2$ stands for hydrogen atom, hydroxymethyl, $NHR^3$ $SO_2NR^4R^{4'}$ or nitro, wherein $R^3$ is hydrogen atom, methyl, $SO_2R^5$, formyl or $CONHR^{6'}$ and either one of $R^4$ and $R^{4'}$ is hydrogen atom and the other one is hydrogen atom, lower alkyl or benzyl, with $R^4$ being lower alkyl, benzyl or dimethylamino and $R^{6'}$ being hydrogen atom or lower alkyl, $R^5$ represents hydrogen atom or lower alkyl, X is oxygen atom or sulfur atom, $R^9$ stands for hydrogen atom and either one of $R^7$ and $R^8$ is hydrogen atom and the other one is hydrogen atom, amino, acetylamino or hydroxy, and *1 indicates an asymmetric carbon atom and *2 indicates that the carbon atom is asymmetric provided that $R^6$ is lower alkyl.

4. A compound represented by the general formula (I) or a salt thereof as claimed in claim 2;

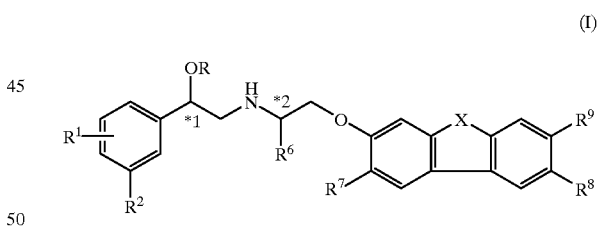

(I)

in which R represents hydrogen atom, $R^1$ stands for hydrogen atom, halogen atom, hydroxy or benzyloxy, $R^2$ stands for hydroxymethyl, $NHR^3$, $SO_2NR^4R^{4'}$ or nitro, wherein $R^3$ is hydrogen atom, methyl, $SO_2R^5$, formyl or $CONHR^{6'}$ and $R^4$ and $R^{4'}$ may be identical with or different from each other and stand each for hydrogen atom, lower alkyl or benzyl, with $R^5$ being lower alkyl, benzyl or $NR^4R^{4'}$ and $R^{6'}$ being hydrogen atom or lower alkyl, $R^6$ represents hydrogen atom or lower alkyl, X is oxygen atom or sulfur atom, $R^9$ stands for hydrogen atom and either one of $R^7$ and $R^8$ is hydrogen atom and the other one is hydrogen atom, amino acetylamino or hydroxy, and *1 indicates an asymmetric carbon atom and *2 indicates that the carbon atom is asymmetric provided that $R^6$ is lower alkyl.

5. A compound or a salt thereof as claimed in claim 2, wherein, in the general formula (I), both R and $R^1$ represent hydrogen atom, $R^2$ stands for hydroxymethyl, $NHR^3$ or $SO_2NR^4R^{4'}$, wherein $R^3$ is hydrogen atom, methyl, $SO_2R^5$, formyl or $CONHR^{6'}$ and $R^4$ and $R^{4'}$ may be identical with or different from each other and stand each for hydrogen atom, lower alkyl or benzyl, with $R^5$ being lower alkyl, benzyl or $NR^4R^{4'}$.

6. A compound or a salt thereof as claimed in claim 2, wherein, in the general formula (I), R denotes hydrogen atom, $R^1$ stands for halogen atom or hydroxy, $R^2$ stands for $NHSO_2R^5$ or $SO_2NR^4R^{4'}$, wherein $R^5$ is lower alkyl, benzyl or $NR^4R^{4'}$ and $R^4$ and $R^{4'}$ may be identical with or different from each other and stand each for hydrogen atom, lower alkyl or benzyl.

7. A compound represented by the general formula (I) or a salt thereof as claimed in claim 2;

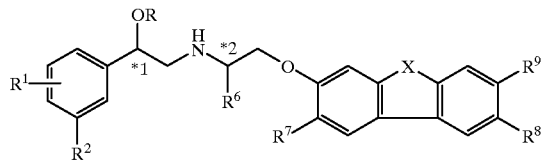

(I)

wherein R represents hydrogen atom, $R^1$ stands for hydrogen atom, halogen atom or hydroxy, $R^2$ stands for hydrogen atom, $R^6$ represents hydrogen atom or lower alkyl, X is oxygen atom or sulfur atom, $R^9$ stands for hydrogen atom and either one of $R^7$ and $R^8$ is hydrogen atom and the other one is hydrogen atom, amino, acetylamino or hydroxy, and *1 indicates an asymmetric carbon atom and *2 indicates that the carbon atom is asymmetric provided that $R^6$ is lower alkyl.

8. A compound represented by the general formula (I) or a salt thereof as claimed in claim 1:

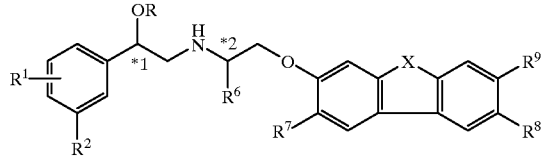

(I)

wherein R represents methyl, $R^1$ stands for hydrogen atom, halogen atom, hydroxy, amino or hydroxymethyl, $R^2$ stands for $NHR^3$ or $SO_2NR^4R^{4'}$, wherein $R^3$ represents $SO_2R^5$, with $R^5$ being lower alkyl, benzyl or $NR^4R^{4'}$, and $R^4$ and $R^{4'}$ may be identical with or different from each other and stand each for hydrogen atom, lower alkyl or benzyl, $R^6$ represents hydrogen atom or lower alkyl, X is oxygen atom or sulfur atom, $R^9$ stands for hydrogen atom and either one of $R^7$ and $R^8$ is hydrogen atom and the other one is hydrogen atom, amino, acetylamino or hydroxy, and *1 indicates an asymmetric carbon atom and *2 indicates that the carbon atom is asymmetric provided that $R^6$ is lower alkyl.

9. A pharmaceutical composition comprising as an effective component, a compound or a salt thereof as claimed in claim 1, in a physiologically or pharmacologically acceptable carrier.

10. A pharmaceutical composition as claimed in claim 9, in the form of a drug suitable for therapeutic treatment or preventive treatment of one of diabetes, obesity and hyperlipemia.

11. A method for producing a compound represented by the general formula (I)

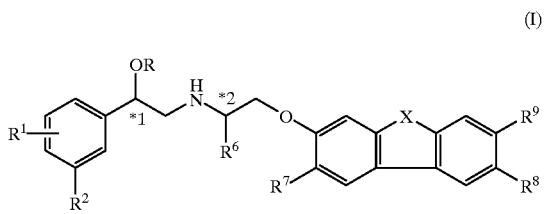

(I)

in which R represents hydrogen atom, $R^1$ stands for hydrogen atom, halogen atom, hydroxy, benzyloxy, amino or hydroxymethyl, $R^2$ stands for hydrogen atom, hydroxymethyl, $NHR^3$, $SO_2NR^4R^{4'}$ or nitro, wherein $R^3$ is hydrogen atom, methyl, $SO_2R^5$, formyl or $CONHR^{6'}$, with $R^5$ being lower alkyl, benzyl or $NR^4$ and $R^{4'}$ being hydrogen atom or lower alkyl, and $R^4$ and $R^{4'}$ may be identical with or different from each other and stand each for hydrogen atom, lower alkyl or benzyl, $R^6$ represents hydrogen atom or lower alkyl, X is oxygen atom or sulfur atom, $R^9$ stands for hydrogen atom and either one of $R^7$ and $R^8$ is hydrogen atom and the other one is hydrogen atom, amino, acetylamino or hydroxy, and *1 indicates an asymmetric carbon atom and *2 indicates that the carbon atom is asymmetric provided that $R^6$ is lower alkyl, comprising the step of reacting a compound represented by general formula (II)

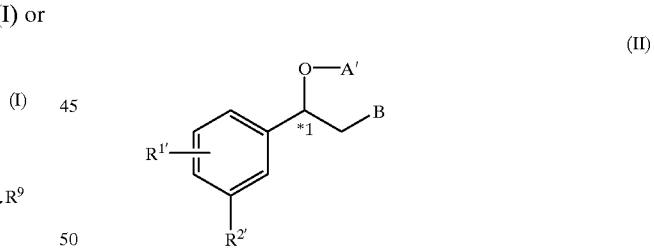

(II)

in which $R^1$ represent hydrogen atom, halogen atom, a protected hydroxyl group protected by a protecting group A, a protected amino group protected by acetyl group or a protected hydroxymethyl group protected by acetyl group, $R^{2'}$ stands for hydrogen atom, for a protected hydroxymethyl group in which the hydroxyl group is protected by a protecting group A''' for $NHR^{3'}$, for $SO_2NR^4R^{4'}$ or for nitro, wherein $R^{3'}$ represents a protecting group for the amino group, methyl, $SO_2R^5$, formyl or $CONHR^{6'}$, with $R^5$ being lower alkyl, benzyl or $NR^4R^{4'}$ and $R^{6'}$ being hydrogen atom or lower alkyl, $R^4$ and $R^{4'}$ may be identical with or different from each other and stand each for hydrogen atom, lower alkyl or benzyl, $R^6$ denotes hydrogen atom or lower alkyl, A' represents a protecting group for the hydroxyl group, B is bromine atom or iodine atom and *1 indicates an asymmetric carbon atom with a compound represented by the general formula (III)

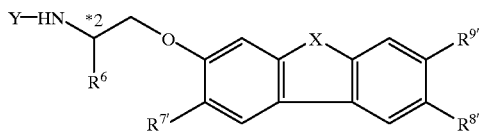

(III)

in which Y represents hydrogen atom, R⁶ is hydrogen atom or lower alkyl, X is oxygen atom or sulfur atom, R⁹' is hydrogen atom and either one of R⁷' and R⁸' is hydrogen atom and the other one is hydrogen atom, acetylamino or a protected hydroxyl group protected by A protecting group A''', and *2 indicates that the carbon atom is asymmetric provided that R⁶ is lower alkyl, wherein the protecting groups A, A', A'', and A''' as well as the protecting group for the amino group in R³' and the protecting acetyl group in R¹' are eliminated for protection with the proviso that the protecting group A is not eliminated if A is benzyl and R¹ is benzyloxy.

12. A compound represented by the general formula (III)

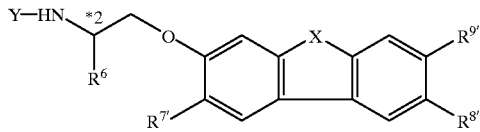

(III)

in which Y represents hydrogen atom or a protecting group for the amino group, R⁶ is hydrogen atom or lower alkyl, X is oxygen atom or sulfur atom, R³' is hydrogen atom and either one of R⁷' and R⁸' is hydrogen atom and the other one is hydrogen atom, acetylamino or a protected hydroxyl group protected by a protecting group A'', and *2 indicates that the carbon atom is asymmetric provided that R⁶ is lower alkyl.

13. A compound represented by the general formula (IV)

the amino group, X is oxygen atom or sulfur atom, R⁹' is hydrogen atom and either one of R⁷' and R⁸' is hydrogen atom and the other one is acetylamino or a protected hydroxyl group protected by a protecting group A'', A' represents a protecting group for the hydroxyl group, *1 indicates an asymmetric carbon atom and *2 indicates that the carbon atom is asymmetric provided that R⁶ lower alkyl.

14. A compound or a salt thereof as claimed in claim 2, wherein the compound is selected from the group consisting of (R)-N[5-[2-[2-(dibenzofuran-2-yloxy)ethylamino]-1-hydroxyethyl]2 hydroxyphenyl]methanesulfonamide; (S)-N-[5-[2-[2-(dibenzofuran-3-yloxy)ethylamino]-2-hydroxyethyl]-1-hydroxyphenyl]methanesulfonamide;N-[S-[2-[2-(dibenzofuran-3-yloxy) ethylamino]-1-hydroxyethyl]-2-hydroxyphenyl]methanesulfonamide; N-[3-[2-[2-(dibenzofuran-3-yloxy) ethylamino]-1-hydroxyethyl]-phenyl]methanesulfonamide; (R)-N-[3-[2-[2-(dibenzofuran-3-yloxy)ethylamino]-1-hydroxyethyl]phenyl]methanesulfonamide; N'-[5-[2-[2-(dibenzofuran-3-yloxy)ethylamino]1 hydroxyethyl]-2-hydroxyphenyl]-N,N-dimethylsulfamide; (R)-N'-[5-[2-[2-(dibenzofuran-3-yloxy) ethylamino]-1-hydroxyethyl]-2-hydroxyphenyl]-N,N-dimethylsulfamide; (S)-N'-[5-[2-[2-(dibenzofuran-3-yloxy) ethylamino]-1-hydroxyethyl]-2-hydroxyphenyl]-N,N-dimethylsulfamide; N-[5-[2-[2-(dibenzofuran-3-yloxy) ethylamino]-1-hydroxyethyl]-2-fluorophenyl] methanesulfonamide; N-[5-[2-[2-(dibenzofuran-3-yloxy) ethylamino]-1-hydroxyethyl]2-chorophenyl] methanesulfonamide;N-[5-[2-[2-(dibenzothiophen-3-yloxy) ethylamino]-1-hydroxyethyl]-2-hydroxyphenyl] methanesulfonamide, N'-[5-[2-[2-(dibenzothiophen-3-yloxy) ethylamino]-1-hydroxyethyl]2 hydroxyphenyl]-N,N-dimethylsulfamide; N-[3-[2-[2-(dibenzothiophen-3-yloxy) ethylamino]-1-hydroxyethyl]phenyl[methanesulfonamide, (R)-N-[5-[2-[2-(dibenzozhiophen-3-yloxy) ethylamino]-1-hydroxyethyl]-2-hydroxyphenyl]methanesulfonamide; N-[5-[2-[2-(dibezothiophen-3-yloxy)ethylamino]-1-hydroxyethyl]-2-flurophenyl]methanesulfonamide; N-[5-[2-[2-(dibenzothiophen-3-yloxy)ethylamino]-1-hydroxyethyl]-2-chlorophenyl]methanesulfonamide; N-[5-[2-[2-(7-aminofluoren-2-yloxy)ethylamino]-1-hydroxyethyl]2-hydroxyphenyl]methanesulfonamide; N' [5-[2-[2-(7-acetylaminofluoren-2-yloxy)ethylamino]-1-hydroxyethyl]-2-hydroxyphenyl]-N,N-dimethylsulfamide.

15. A compound or a salt thereof as claimed in claim 8, wherein the compound is 2-[N-[2-(dibenzofuran-3-yloxy) ethyl]amino]-1-phenylethanol.

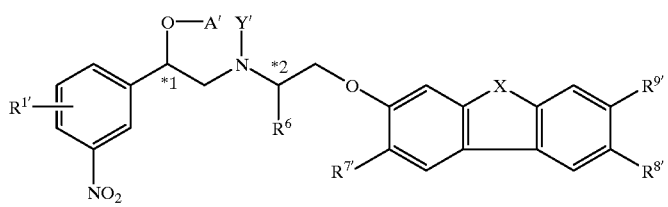

(IV)

in which R¹' reprsents hydrogen atom, halogen atom, a protected hydroxyl group protected by a protecting group A, a protected amino group protected by acetyl group or a protected hydroxymethyl group in which the hydroxyl group is protected by acetyl group, R⁶ stands for hydrogen atom or lower alkyl, Y' is hydrogen atom or a proctecting group for 16. A compound or a salt thereof as claimed in claim 10, wherein the compound is selected from the group consisting of N-[5-[2-[2-(dibenzothiophen-3-yloxy)ethylamino]-1-methoxyethyl]-2-hydroxyphenyl]methanesulfonamide.

* * * * *

UNITED STATES PATENT AND TRADEMARK OFFICE
CERTIFICATE OF CORRECTION

PATENT NO. : 6,187,809 B1
DATED : February 13, 2001
INVENTOR(S) : Shiro Miyoshi and Kohei Ogawa It is certified that error appears in the above-identified patent and that said Letters Patent is hereby corrected as shown below:

Column 111,
Line 40, change "$SO_4NR^4R^{4'}$ stand for" to -- $SO_2NR^4R^{4'}$ or nitro, wherein $R^3$ is --.
Line 51, change "*1 indicate" to -- *1 indicates --.

Column 112,
Line 31, change "with $R^4$" to -- with $R^5$ --.
Line 33, change "alkyl, $R^5$" to -- alkyl, $R^6$ --.
Line 62, change "amino acetylamino" to -- amino, acetylamino --.

Column 113,
Line 57, change "$SO_2NR^4R^4$" to -- $SO_2NR^4R^{4'}$ --.

Column 114,
Line 30, change "$NR^4$ and $R^{4'}$" to -- $NR^4 R^{4'}$ and $R^{6'}$ --.
Line 53, change "represent" to -- represents --.

Column 115,
Line 19, change "by A protecting" to -- by a protecting --.
Line 40, change "atom, $R^{3'}$" to -- atom, $R^{9'}$ --.
Line 62, change "$R^{1'}$ reprsents" to -- $R^{1'}$ represents --.

UNITED STATES PATENT AND TRADEMARK OFFICE
CERTIFICATE OF CORRECTION

PATENT NO.   : 6,187,809 B1
DATED        : February 13, 2001
INVENTOR(S)  : Shiro Miyoshi and Kohei Ogawa It is certified that error appears in the above-identified patent and that said Letters Patent is hereby corrected as shown below:

<u>Column 116,</u>
Line 7, change "$R^6$ lower" to -- $R^6$ is lower --.
Line 12, change "N-[5-[2-[2-(dibenzofuran-3-yloxy)ethylamino-2-" to
-- N-[5-[2-[2-(dibenzofuran-3-yloxy)ethylamino-1- --.
Line 13, change "hydroxyethyl]-1-" to -- hydroxyethyl]-2- --.
Line 14, change "[S-[2-[2-" to -- [5-[2-[2- --.
Line 19, change "yloxy)ethylamino]1" to -- yloxy)ethylamino]-1- --.
Line 27, change "ethylamino]-1-hydroxyethyl]2-" to
-- ethylamino]-1-hydroxyethyl]-2- --.
Line 30, change "methanesulfonamide," to -- methanesulfonamide; --.
Line 31, change "yloxy)ethylamino]-1-hydroxyethyl]2" to
-- yloxy)ethylamino]-1-hydroxyethyl]-2- --.
Line 34, change "(R)-N-[5-[2-[2-(dibenzozhiophen-3-yloxy)" to
-- (R)-N-[5-[2-[2-(dibenzothiophen-3-yloxy) --.

Signed and Sealed this

Seventeenth Day of June, 2003

JAMES E. ROGAN
*Director of the United States Patent and Trademark Office*